(12) United States Patent
Erion et al.

(10) Patent No.: US 7,351,399 B2
(45) Date of Patent: *Apr. 1, 2008

(54) PRODRUGS FOR PHOSPHORUS-CONTAINING COMPOUNDS

(75) Inventors: Mark D. Erion, Del Mar, CA (US); K. Raja Reddy, San Diego, CA (US); Edward D. Robinson, San Diego, CA (US); Bheemarao G. Ugarkar, San Diego, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/145,194

(22) Filed: Jun. 3, 2005

(65) Prior Publication Data

US 2005/0288240 A1    Dec. 29, 2005

Related U.S. Application Data

(63) Continuation of application No. 09/978,454, filed on Oct. 15, 2001, now Pat. No. 6,946,115, which is a continuation of application No. 09/392,352, filed on Sep. 8, 1999, now Pat. No. 6,312,662, which is a continuation-in-part of application No. 09/263,976, filed on Mar. 5, 1999, now abandoned.

(60) Provisional application No. 60/077,164, filed on Mar. 6, 1998, provisional application No. 60/077,165, filed on Mar. 6, 1998.

(51) Int. Cl.
*A61K 51/00* (2006.01)
*A61M 36/14* (2006.01)

(52) U.S. Cl. .................... 424/1.77; 424/1.11; 424/1.65; 514/7; 549/200; 568/8

(58) Field of Classification Search ............. 424/1.11, 424/1.65, 1.73, 1.77, 9.1, 9.2, 600, 601, 603; 514/7; 549/200; 568/8
See application file for complete search history.

(56) References Cited

U.S. PATENT DOCUMENTS

| | | | |
|---|---|---|---|
| 3,018,302 A | 1/1962 | Bielefeld et al. | |
| 4,952,740 A | 8/1990 | Juge et al. | |
| 5,130,303 A | 7/1992 | Akiyama et al. | |
| 5,658,889 A | 8/1997 | Gruber et al. | |
| 5,663,159 A | 9/1997 | Starrett, Jr. et al. | |
| 5,962,522 A | 10/1999 | Wacher et al. | |
| 6,004,927 A | 12/1999 | Benet et al. | |
| 6,028,054 A | 2/2000 | Benet et al. | |
| 6,054,587 A | 4/2000 | Reddy et al. | |
| 6,110,903 A | 8/2000 | Kasibhatla et al. | |
| 6,284,748 B1 | 9/2001 | Dang et al. | |
| 6,294,672 B1 | 9/2001 | Reddy et al. | |
| 6,312,662 B1 * | 11/2001 | Erion et al. ........... | 424/9.1 |
| 6,399,782 B1 | 6/2002 | Kasibhatla et al. | |
| 6,489,476 B1 | 12/2002 | Dang et al. | |
| 6,752,981 B1 | 6/2004 | Erion et al. | |
| 6,946,115 B2 * | 9/2005 | Erion et al. ........... | 424/1.73 |
| 2003/0225277 A1 | 12/2003 | Kopcho et al. | |
| 2003/0229225 A1 | 12/2003 | Reddy et al. | |
| 2004/0092476 A1 | 5/2004 | Boyer et al. | |
| 2004/0192651 A1 | 9/2004 | Reddy et al. | |
| 2005/0101775 A1 | 5/2005 | Erion et al. | |
| 2005/0282782 A1 | 12/2005 | Martin | |

FOREIGN PATENT DOCUMENTS

| | | |
|---|---|---|
| DE | 3 512 781 A1 | 4/1985 |
| EP | 0 161 955 A1 | 11/1985 |
| EP | 0 180 276 A1 | 7/1986 |
| EP | 0 338 372 A2 | 10/1989 |
| EP | 0 353 692 B1 | 2/1990 |
| EP | 0 481 214 B1 | 4/1992 |
| WO | WO 90/08155 | 7/1990 |
| WO | WO 90/09163 A2 | 8/1990 |
| WO | WO 90/10636 | 9/1990 |
| WO | WO 91/19721 A1 | 12/1991 |
| WO | WO 96/01267 A1 | 1/1996 |

(Continued)

OTHER PUBLICATIONS

Ayral-Kaloustian, S., et al., "Synthesis of Partially-Protected D-Frutofuranoses and D-Fructose-6-Phosphates", *Carbohydrate Research* 214: 187-192, Elsevier Science Publishers B.V., Amsterdam (1991).

Bentrude, Wesley G., et al. "Conformation of Saturated Six-Membered-Ring Phosphorus Heterocycles. 2-Aryl-1,3,2$\lambda^5$-oxazaphosphorinanes" *J. Am. Chem Soc.* 110: 7119-7127 (1988).

Bentrude, Wesley G., et al. "Conformations of Saturated Six-Membered-Ring Phosphorus Heterocycles Related to Cyclophosphamide. NMR, X-ray, and Infrared Studies of 2-Methoxy-2-oxo-1,3,2-oxazaphosphorinane and 2-Thio-1,3,2-oxazaphosphorinane" *J. Am. Chem Soc.* 108: 6696-6675 (1986).

Denmark, Scott E., et al., "Asymmetric Electrophilic Amination of Chiral Phosphorus-Stabilized Anions" *Tetrahedron* 48/11: 2191-2208 Pergamon Press plc (1992).

Erion, M., et al., "Liver-Targeted Drug Delivery Using HepDirect Prodrugs" *J. Pharmacol. Exper. Ther.* 312:554-560, American Society for Pharmacology and Experimental Therapeutics (Feb. 2005).

(Continued)

*Primary Examiner*—Dameron L. Jones
(74) *Attorney, Agent, or Firm*—Sterne, Kessler Goldstein & Fox P.L.L.C.

(57) ABSTRACT

Prodrugs of formula I, their uses, their intermediates, and their method of manufacture are described:

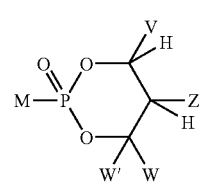

I and pharmaceutically acceptable prodrugs and salts thereof.

9 Claims, 1 Drawing Sheet

FOREIGN PATENT DOCUMENTS

| WO | WO 97/03679 A1 | 2/1997 |
| --- | --- | --- |
| WO | WO 98/09668 | 3/1998 |
| WO | WO 98/39342 A1 | 9/1998 |
| WO | WO 98/39343 A1 | 9/1998 |
| WO | WO 98/39344 A1 | 9/1998 |
| WO | WO 99/47549 A1 | 9/1999 |
| WO | WO 00/14095 A1 | 3/2000 |
| WO | WO 00/38666 A2 | 7/2000 |
| WO | WO 00/52015 | 9/2000 |
| WO | WO 01/18013 | 3/2001 |
| WO | WO 02/00673 A1 | 1/2002 |
| WO | WO 03/095665 | 11/2003 |
| WO | WO 2004/037161 | 5/2004 |
| WO | WO 2004/041834 | 5/2004 |
| WO | WO 2004/041837 | 5/2004 |

OTHER PUBLICATIONS

Erion, M. et al. "HepDirect Prodrugs for Targeting Nucleotide-Based Antiviral Drugs to the Liver" *Current Opinion in Investigational Drugs* 7/2:109-117, The Thomson Corporation (2006).

Erion, M., et al., "Design, Synthesis, and Characterization of a Series of Cytochrome $P_{450}$ 3A-Activated Prodrugs (HepDirect Prodrugs) Useful for Targeting Phosph(on)ate-Based Drugs to the Liver," *J. Am. Chem. Soc.* 126:5154-5163, American Chemical Society (Apr. 2004).

Fang, C., et al. "Liver-Targeting Prodrug of PMEA Induces a Much More Favorable Kidney and Liver Toxicological Gene Expression-in Rats Compared to BisPOM-PMEA" Abstract #1274, 42nd Annual Meeting of the Society of Toxicology, Salt Lake City, UT (Mar. 9-13, 2003).

Fang, C., et al., "Renal Toxicological Gene Response to Anti-Hepatitis B Prodrugs Hepavir B and Hepsera in Rats" Abstract #1472, 43rd Annual Meeting of the Society of Toxicology, Baltimore, MD (Mar. 21-25, 2004).

Freeman, Sally, et al., "Prodrug Design for Phosphates and Phosphonates" Chapter 3 in *Progress in Medicinal Chemistry*, 34 111-147 Elsevier Sciences BV (1997).

Hong, Z. and Lin, C.-C., "Clinical Update of Remofovir (Hepavir B): a Liver-targeting Prodrug of PMEA for the Treatment of Hepatitis B," Presented at the *SRI-Antiviral Drug Discovery & Development Summit*, Mar. 30, 2004.

Hong, Z., "Hepavir B: a Safer and Liver-Targeting Prodrug of PMEA," Presented at the *SRI-Antiviral Drug Discovery & Development Summit*, Ribopharm Inc., Mar. 27, 2003.

Lin, C.-C., et al. "Comparative Disposition and Metabolic Profiles of [$^{14}$C]Remofovir and [$^{14}$C]Adefovir Dipivoxil in Rat Liver and Kidney" Abstracts of the 40th Annual Meeting of the European Association for the Study of the Liver, Paris, France, *J. Hepatology* 42/2 Abstract #405 Elsevier (Apr. 2005).

Lin, C.-C., et al. "Single-Dose Pharmacokinetics and Metabolism of [$^{14}$C]Remofovir in Rats and Cynomolgus Monkeys" *Antimicrobial Agents and Chemotherapy* 49/3: 925-930, American Society for Microbiology (Mar. 2005).

Lin, C.-C., et al., "Pradefovir is a Substrate, but Neither an Inhibitor nor an Inducer for Cytochrome P450," AASLD Abstracts, *Hepatology* 514A:Abstract No. 811, John Wiley & Sons, Inc. (Oct. 2005).

Lin, C.-C., et al., "Remofovir Mesylate: a Prodrug of PMEA with Improved LIver-Targeting and Safety in Rats and Monkeys," *Antiviral Chem. Chemother.* 15:307-316, International Medical Press (2004).

Mackenna, D., et al., "MB07133: A HepDirect™ Prodrug of Cytarabine Monophosphate for Use in Hepatocellular Carcinoma," *Hepatology* 38(*Suppl. 1*):411A, AASLD Abstract No. 524, John Wiley & Sons, Inc. (Oct. 2003).

Meier, Chris, et al. "ADA-Bypass by Lipophilic CycloSal-ddAMP Pro-Nucleotides. A Second Example of the Efficiency of the cycloSal-Concept" *Bioorganic & Medicinal Chemistry Letters* 7/12: 1577-1582 Elsevier Science Ltd. (1997).

Reddy, K.R., et al., "Stereoselective Synthesis of Nucleoside Monophosphate HepDirect™ Prodrugs," *Tetrahedron Lett.* 46:4321-4324, Elsevier Ltd. (2005).

Reddy, M.R. et al., Development of a Quantum Mechanics-Based Free-Energy Perturbation Method: Use in the Calculation of Relative Solvation Free Energies, *J. Am. Chem. Soc.* 126, 6224-6225 (2004).

Shih, Y-E, et al. Studies on Potential Antitumor Agents (III). Synthesis of 4-Arylcyclophosphamides. *Heterocycles* 9/9 1277-1285 (1978).

Ten Hoeve, W. and Wynberg, H. "The Design of Resolving Agents. Chiral Cyclic Phosphoric Acids" *J. Org. Chem.* 50: 4508-4514, American Chemical Society (1985).

Vitarella, D. et al. "Hepavir B, A CYP3A4-Activated Prodrug of PMEA, Showed Better Safety then Hepsera in Pre-Clinical Studies" Abstract #995 of the 43rd Annual Meeting of the Society of Toxicology, Baltimore, MD (Mar. 2004).

Xu, C.R., et al., "Toxicokinetics of Remofovir in Mice, Rats and Monkeys After Repeated Oral Administrations" Abstract #PB-P008 of the 64th International Congress FIP World Congress of Pharmacy and Pharmaceutical Science, New Orleans, LA (Sep. 2004).

Xu, C.R., et al. "Toxicokinetics of Adefovir Dipivoxil and Remofovir in 28-Day Toxicity Studies" Abstract #PB-P009 of the 64th International Congress FIP World Congress of Pharmacy and Pharmaceutical Science, New Orleans, LA (Sep. 2004).

Alexander, P., et al., "Preparation of 9-(2-Phosphonomethoxyethyl) Adenine Esters as Potential Prodrugs," *Collect. Czech. Chem. Commun.* 59:1853-1869, Nakladatelstvi Ceskoslovenski Akademie Ved. (1994).

Amin, D., et al., "1-Hydroxy-3-(methylpentylamino)-propylidene-1,1-bisphosphonic Acid as a Potent Inhibitor of Squalene Synthase," *Arzneim.-Forsch/Drug Res.* 46:759-762, Blackwell Publishing, Inc. (1996).

Atiq, O., et al., "Treatment of Unresectable Primary Liver Cancer with Intrahepatic Fluorodeoxyuridine and Mitomycin C Through an Implantable Pump," *Cancer* 69:920-924, John Wiley and Sons, Inc. (1992).

Auberson, Y., et al., "N-Phosphonoalkyl-5-Aminomethylquinoxaline-2,3-Diones: In Vivo Active AMPA and NMDA-(Glycine) Antagonists," *Bioorg. Med. Chem. Lett.* 9:249-254, Elsevier Science Ltd. (Jan. 1999).

Balthazor, T. and Grabiak, R.C., "Nickel-Catalyzed Arbuzov Reaction: Mechanistic Observations," *J. Org. Chem.* 45:5425-5426, American Chemical Society (1980).

Beaucage, S.L. and Iyer, R.P., "The Synthesis of Modified Oligonucleotides by the Phosphoramidite Approach and Their Applications," *Tetrahedron* 49:6123-6194, Pergamon Press Ltd. (1993).

Bespalov, A., et al., "Prolongation of morphine analgesia by competitive NMDA receptor antagonist D-CPPene (SDZ EAA 494) in rats," *Eur. J. Pharmacol.* 351:299-305, Elsevier Science B.V. (Jun. 1998).

Bijsterbosch, M.K., et al., "Disposition of the Acyclic Nucleoside Phosphonate (S)-9-(3-Hydroxy-2-Phosphonylmethoxypropyl)Adenine," *Antimicro. Agents Chemother.* 42:1146-1150, American Society for Microbiology (May 1998).

Bird, J., et al., "Synthesis of Novel *N*-Phosphonoalkyl Dipeptide Inhibitors of Human Collagenase," *J. Med. Chem.* 37:158-169, American Chemical Society (1994).

Borch, R.F. and Millard, J.A., "The Mechanism of Activation of 4-Hydroxycyclophosphamide," *J. Med. Chem.* 30:427-431, American Chemical Society (1987).

Brill, T. and Landon, S.J., "Arbuzov-like Dealkylation Reactions of Transition-Metal-Phosphite Complexes," *Chem. Rev.* 84 :577-585, American Chemical Society (1984).

Campagne, J.-M., et al., "Synthesis of Mixed Phosphate Diester Analogues of Dipeptides using BOP or PyBOP Reagents," *Tetrahedron Lett.* 34:6743-6744, Pergamon Press Ltd. (1993).

Campbell, D.A., "The Synthesis of Phosphonate Esters, an Extension of the Mitsunobu Reaction," *J. Org. Chem.* 52:6331-6335, American Chemical Society (1992).

Casara, P.J., et al., "Synthesis of Acid Stable 5'-Fluoromethyl Phosphonates of Nucleosides. Evaluation as Inhibitors of Reverse Transcriptase," *Bioorg. Med. Chem. Lett.* 2:145-148, Pergamon Press Ltd. (1992).

Castel, D. and Peri, S.P., "Steric and Electronic Effects in the Aryl Phosphate to Arylphosphonate Reaarangement," *Synthesis* (9):691-693, Georg Thieme Verlag KG (1991).

Chen, L. and Waxman, D.J., "Intratumoral Activation and Enhanced Chemotherapeutic Effect of Oxazaphosphorines following Cytochrome P-450 Gene Transfer: Development of a Combined Chemotherapy/Cancer Gene Therapy Strategy," *Cancer Res.* 55:581-589, The American Association for Cancer Research (1995).

Chen, L., et al., "Sensitization of Human Breast Cancer Cells to Cyclophosphamide and Ifosfamide by Transfer of a Liver Cytochrome P450 Gene," *Cancer Res.* 56:1331-1340, The American Association for Cancer Research (1996).

Cooper, D.B., et al., "Use of Carbohydrate Derivatives for Studies of Phosphorus Stereo-chemistry. Part II. Synthesis and Configurational Assignments of 1,-3,2-Oxathiaphosphorinan-2-ones and 1,3,2-Dioxaphosphorinan-2-thiones," *J. Chem. Soc. Perkin I* 3/2422:1049-1052, Royal Society of Chemistry (1974).

De Clercq, E., et al., "A novel selective broad-spectrum anti-DNA virus agent," *Nature* 323:464-467, Nature Publishing Group (1986).

De Lombaert, S., et al., "*N*-Phosphomomethyl Dipeptides and Their Phosphonate Prodrugs, a New Generation of Neutral Endopeptidase (NEP, EC 3.4.24.11) Inhibitors," *J. Med. Chem.* 37:498-511, American Chemical Society (1994).

De Lombaert, S., et al., "Pharmacological Profile of a Non-Peptidic Dual Inhibitor of Neutral Endopeptidase 24.11 and Endothelin-Converting Enzyme," *Biochem. Biophys. Res. Commun.* 204:407-412, Academic Press, Inc. (1994).

De Waziers, I., et al., "Cytochrome P 450 Isoenzymes, Epoxide Hydrolase and Glutathione Transferases in Rat and Human Hepatic and Extrahepatic Tissues," *J. Pharm. Exp. Ther.* 253:387-394, American Society for Pharmacology and Experimental Therapeutics (1990).

Dearfield, K., et al., "Analysis of the genotoxicity of nine acrylate/methacrylate compounds in L5178Y mouse lymphoma cells," *Mutagenesis* 4:381-383, Oxford University Press (1989).

Desos, P., et al., "Structure-Activity Relationships in a Series of 2(1*H*)Quinolones Bearing Different Acidic Function in the 3-Position: 6,7-Dichloro-2(1*H*)-oxoquinoline-3-phosphonic Acid, a New Potent and Selective AMPA/Kainate Antagonist with Neuroprotective Properties," *J. Med. Chem.* 39:197-206, American Chemical Society (1996).

Dickson, J.K., et al., "Orally Active Squalene Synthase Inhibitors: Bis((acyloxy)alkyl) Prodrugs of the α-Phosphonosulfonic Acid Moiety," *J. Med. Chem.* 39:661-664, American Chemical Society (1996).

Edmundson, R.S., et al., "Cyclic Organophosphorous Compounds. Part 23. Configurational Assignments in the 4-Phenyl-1,3,2λ-dioxaphosphoriane Series. *X*-Ray Molecular Structures of cis-2-Benzylamino-4-phenyl-1,3,2-dioxaphosphorinane 2-Oxide," *J. Chem. Research (S)*, 122-123, Science Reviews Ltd. (1989).

Enriquez, P., et al., "Conjugation of Adenine Arabinoside 5'-Monophosphate to Arabinogalactan: Synthesis, Characterization, and Antiviral Activity," *Bioconjugate Chem.* 6:195-202, American Chemical Society (1995).

Farquhar, D., et al., "Biologically Reversible Phosphate-Protective Groups," *J. Pharm. Sci.* 72:324-325, American Chemical Society (1983).

Farquhar, D., et al., "Synthesis and Biological Evaluation of Neutral Derivatives of 5-Fluoro-2'-deoxyuridine 5'-Phosphate," *J. Med. Chem.* 26:1153-1158, American Chemical Society (1983).

Farquhar, D. and Smith, R., "Synthesis and Biological Evaluation of 9-[5'-(2-Oxo-1,3,2-oxazaphosphorinan-2-yl)β-D-arabinosyl]adenine and 9-[5-(2-Oxo-1,3,2-dioxazaphosphorinan-2-yl)-β-D-arabinosyl]adenine: Potential Neutral Precursors of 9-[β-D-Arabinofuranosyl]adenine 5'-Monophosphate," *J. Med. Chem.* 28:1358-1361, American Chemical Society (1985).

Farquhar, D., et al., "Synthesis and Antitumor Evaluation of Bis[(pivaloyloxy) methyl]2'-Deoxy-5-fluorouridine 5'-Monophosphate (FdUMP): A Strategy to Introduce Nucleotides into Cells," *J. Med. Chem.* 37:3902-3909, American Chemical Society (1994).

Farquhar, D., et al., "5'-4-(Pivaloyloxy)-1,3,2-dioxaphosphorinan-2-yl-]2'-deoxy-5-fluorouridine: A Membrane-Permeating Prodrug of 5-Fluoro-2'-deoxyuridylic Acid (FdUMP)," *J. Med. Chem.* 38:488-495, American Chemical Society (1995).

Farquhar, D., et al., "Biologically-Cleavable Phosphate Protective Groups: 4-Acyloxy-1,3,2-Dioxaphosphorinanes as Neutral Latent Precursors of Dianionic Phosphates," *Tetrahedron Lett.* 36:655-658, Elsevier Science Ltd. (1995).

Fiume, L., et al., "Inhibition of Hepatitis B Virus Replication by Vidarabine Monophosphate Conjugated with Lactosaminated Serum Albumin," *The Lancet* 2:13-15, The Lancet Publishing Group (1988).

Freed, J.J., et al., "Evidence for Acyloxymethyl Esters of Pyrimidine 5'-Deoxyribonucleotides as Extracellular Sources of Active 5'-Deoxyribonucleotides in Cultured Cells," *Biochem. Pharm.* 38:3193-3198, Elsevier Inc. (1989).

Friis, G.J. and Bundgaard, H., "Prodrugs of phosphates and phosphonates: Novel lipophilic β-acyloxyalkyl ester derivatives of phosphate- or phosphonate containing drugs masking the negative charges of these groups," *Euro. J. Pharm. Sci.* 4:49-59, Elsevier Science B.V. (1996).

Guida, W.C., et al., "Structure-Based Design of Inhibitors of Purine Nucleoside Phosphorylase. 4. A Study of Phosphate Mimics," *J. Med. Chem.* 37:1109-1114, American Chemical Society (1994).

Harada, et al., "Resolution of 1,3-alkanediols Via Chiral Spiroketals Derived from t-Menthone," *Tetrahedron* 28:4843-4846, Peragmon Press (1987).

He, K., et al., "Inactivation of Cytochrome P450 3A4 by Bergamottin, a Component of Grapefruit Juice," *Chem. Res. Toxicol.* 11:252-259, American Chemical Society (Apr. 1998).

Hillers, S., et al., "Analogs of pyrimidinemono-and polynucleotides. VI. Phosphates of 1-(1,4-dihydroxy-2-pentyl)thymine and 1-(1,3-dihydroxy-2-propyl) uracil," *Chemical Abstracts* 89(17), Chemical Abstracts Service (1978).

Hirayama, N., et al., "Structure and conformation of a novel inhibitor of angiotensin I converting enzyme—a tripeptide containing phosphonic acid," *Int. J. Pept. Protein Res.* 38:20-24, Blackwell Publishing (1991).

Hunston, R., et al., "Synthesis and Biological Properties of Some Cyclic Phosphotriesters Derived from 2'-Deoxy-5-fluorouridine," *J. Med. Chem.* 27:440-444, American Chemical Society (1984).

Keenan, R., et al., "Pathology Reevaluation of the Kociba et al. (1978) Bioassay of 2,3,7,8-TCDD: Implications for Risk Assessment," *J. Tox. Envir. Health* 34:279-296, Hemisphere Publishing Corporation (1991).

Kelley, J.L., et al., "[[(Guaninylalkyl)phosphinico]methyl]phosphonic Acids. Multisubstrate Analogue Inhibitors of Human Erythrocyte Purine Nucleoside Phosphorylase," *J. Med. Chem.* 38:1005-1014, American Chemical Society (1995).

Khamnei, S. and Torrence, P.F., "Neighboring Group Catalysis in the Design of Nucleotide Prodrugs," *J. Med. Chem.* 39:4109-4115, American Chemical Society (1996).

Khorana, H.G., et al., "Cyclic Phosphates. III. Some General Observations on the Formation and Properties of Five-, Six- and Seven-membered Cyclic Phosphate Esters," *J. Am. Chem. Soc.* 79:430-436, American Chemical Society (1957).

Korba, B.A., et al., "Liver-Targeted Antiviral Nucleotides: Enhanced Antiviral Activity of Phosphatidyl-Dideoxyguanosine Versus Dideoxyguanosine in Woodchuck Hepatitis Virus Infection in Vivo," *Hepatology* 25:958-963, John Wiley & Sons, Inc. (1996).

Kryuchkov, A.A., et al., "Influence of Solvent on the Strength of Cyclic Oxygen-Containing Phosphorus Acids," *Bull. Acad. Sci. USSR, A translation of Izvestiya Akademii Nauk SSSR, Ser. Khim.* 36:1145-1148, Consultants Bureau (1987).

Lefebvre, I., et al., "Mononucleoside Phosphotriester Derivatives with *S*-Acyl-2-thioethyl Bioreversible Phosphate-Protecting Groups: Intracellular Delivery of 3'-Azido-2',3'-dideoxythymidine 5'-Monophosphate," *J. Med. Chem.* 38:3941-3950, American Chemical Society (1995).

Lok, A.S.F., et al., "Neurotoxicity associated with adenine arabinoside monophosphate in the treatment of chronic hepatitis B virus infection," *J. Antimicrob. Chemotherap.* 14:93-99, Oxford University Press (1984).

Lu, X. and Zhu, J., "Palladium-Catalyzed Reaction of Aryl Polyfluoroalkanesulfonates with O,O-Dialkyl Phosphonates," *Synthesis* (8):726-727, Georg Thieme Verlag (1987).

Ludeman, S.M., et al., "Synthesis and Antitumor Activity of Cyclophosphamide Analogues. 4. Preparation, Kinetic Studies, and Anticancer Screening of "Phenylketophosphamide" and Similar Compounds Related to the Cyclophosphamide Metabolic Aldophosphamide," *J. Med. Chem.* 29:716-727, American Chemical Society (1986).

McGuigan, C., et al., "Intracellular Delivery of Bioactive AZT Nucleotides by Aryl Phosphate Derivatives of AZT," *J. Med. Chem.* 36:1048-1052, American Chemical Society (1993).

McGuigan, C., et al., "Kinase Bypass: A New Strategy for Anti-HIV Drug Design," *Bioorg. Med. Chem. Lett.* 3:1207-1210, Pergamon Press Ltd. (1993).

Meier, C., et al., "Cyclic Saligenyl Phosphotriesters of 2',3'-Dideoxy-2',3'-didehydrothymidine (d4T)—A New Pro-Nucleotide Approach—" *Bioorg. Med. Chem. Lett.* 7:99-104, Elsevier Science Ltd. (Jan. 1997).

Meijer, D.K.F., et al., "Covalent and Noncovalent Protein Binding of Drugs: Implications for Hepatic Clearance, Storage, and Cell-Specific Drug Delivery," *Pharm. Res.* 6:105-118, Plenum Publishing Corporation (1989).

Melvin, L.S., "An Efficient Synthesis of 2-Hydroxyphenylphosphonates," *Tetrahedron Lett.* 22:3375-3376, Pergamon Press Ltd. (1981).

Meyer, R., et al., "2'-O-Acyl-6-thioinosine Cyclic 3',5'-Phosphates as Prodrugs of Thioinosinic Acid," *J. Med. Chem.* 22:811-815, American Chemical Society (1979).

Mitchell, A., et al., "Bioreversible Protection for the Phospho Group: Bioactivation of the Di(4-acyloxybenzyl) and Mono(4-acyloxybenzyl) Phosphoesters of Methylphosphonate and Phosphonacetate," *J. Chem. Soc. Perkin Trans. I*, 2345-2353, Royal Society of Chemistry (1992).

Mitsunobu, O., "The Use of Diethyl Azodicarboxylate and Triphenylphosphine in Synthesis and Transformation of Natural Products," *Synthesis I*, pp. 1-28, Georg Thieme Verlag (1981).

Moore, M., et al., "Comparison of mutagenicity results for nine compounds evaluated at the *hgprt* locus in the standard and suspension CHO assays," *Mutagenesis* 6:77-85, Oxford University Press (1991).

Mosbo, J.A. and Verkade, J.G., "Dipole Moment, Nuclear Magnetic Resonance, and Infrared Studies of Phosphorus Configurations and Equilibria in 2-R-2-Oxo-1,3,2-dioxaphosphorinanes," *J. Org. Chem.* 42:1549-1555, American Chemical Society (1977).

Murray, G., et al., "Cytochrome P450 Expression Is a Common Molecular Event in Soft Tissue Sarcomas," *J. Pathology* 171:49-52, John Wiley & Sons, Ltd. (1993).

Murray, G., et al., "Cytochrome P450 CYP3A in human renal cell cancer," *Brit. J. Cancer* 79:1836-1842, Nature Publishing Group (Apr. 1999).

Nakayama, K. and Thompson, W.J., "A Highly Enantioselective Synthesis of Phosphate Triesters," *J. Am. Chem. Soc.* 112:6936-6942, American Chemical Society (1990).

Neidlein, R., et al., "Mild Preparation of I-Benzyloxyiminoalkylphosphonic Dichlorides: Application to the Synthesis of Cyclic Phosphonic Diesters and Cyclic Monoester Amides," *Heterocycles* 35:1185-1203, Elsevier Science (1993).

Nifantyev, E.E., et al., "Synthesis and Structure of Some Stable Phospholane-Phospholanes," *Phosphorus, Sulfur and Silicon and Related Elements* 113:1-13, Taylor & Francis (1996).

Ogg, M., et al., "A reporter gene assay to assess the molecular mechanisms of xenobiotic-dependent induction of the human CYP3A4 gene in vitro," *Xenobiotica* 29:269-279, Taylor & Francis Ltd. (Mar. 1999).

Ohashi, K., et al., "Synthesis of Phosphonosphingoglycolipid Found in Marine Snail *Turbo Cornutus*," *Tetrahedron Lett.* 29:1189-1192, Pergamon Press Ltd. (1988).

Petrakis, K. and Nagabhushan, T.L., "Palladium-Catalyzed Substitutions of Triflates Derived from Tyrosine-Containing Peptides and Simpler Hydroxyarenes Forming 4-(Diethoxyphosphinyl)phenylalanines and Diethyl Arylphosphonates," *J. Am. Chem. Soc.* 109:2831-2833, American Chemical Society (1987).

Predvoditelev, D.A., et al., "Glycero-2-Hydroxymethylene Phosphates," *J. Org. Chem. USSR, A Translation of Zhur. Org. Khim.* 13:1489-1492, Plenum Publishing Corporation (1977).

Predvoditelev, D.A., et al., "Synthesis of Lipids and Their Models on the Basis of Glycerol Alkylene Phosphites. V. Cyclic Phosphatidylglycerol and Phosphatidylhydroxyhomocholine," *J. Org. Chem. USSR, A Translation of Zhur. Org. Khim.* 17:1156-1165, Plenum Publishing Corporation (1981).

Redmore, D., "Phosphate Derivatives of Nitrogen Heterocycles. 2. Pyridinephosphonic Acid Derivatives," *J. Org. Chem.* 35:4114-4117, American Chemical Society (1970).

Ramachandran, et al., "Efficient General Synthesis of 1,2- and 1,3-diols in High Enantiometric Excess via the Intramolecular Asymmetric Reduction of Corresponding Ketoalkyl Diisopinocampheylborinate Intermediates," *Tetrahedron Lett.* 38:761-764, Pergamon Press Ltd. (Feb. 1997).

Shaw, J.-P. and Cundy, K.C., "Biological Screens of PMEA Prodrugs," *Pharm. Res.* 10:S-294, Kluwer Academic Publishers B.V., Abstract No. PDD 7480 (1993).

Shih, Y.-E., et al., "Preparation and Structures of 2-Dimethylamino-4-phenyl-1,3,2-dioxaphosphoronane-2-oxides," *Bull. Inst. Chem. Acad. Sin.* 41:9-16, Academia Sinica, Nankang, Taipei, Taiwan (1994).

Starrett, J.E., Jr., et al., "Synthesis, Oral Bioavailability Determination, and in Vitro Evaluation of Prodrugs of the Antiviral Agent 9-[2-(Phosphonomethoxy)ethyl]adenine (PMEA)," *J. Med. Chem.* 37:1857-1864, American Chemical Society (1994).

Thomson, W., et al., "Synthesis, Bioactivation and Anti-HIV Activity of the Bis(4-acyloxybenzyl) and Mono(4-acyloxybenzyl) Esters of the 5'-monophosphate of AZT," *J. Chem. Soc. Perk. Trans. I*, 1239-1245, Royal Society of Chemistry (1993).

Turner, "A General Approach to the Synthesis of 1,6-, 1-7-and 1,8-Naphthyridines," *J. Org. Chem.* 55:4744-4750, American Chemical Society (1990).

Venook, A., "Treatment of Hepatocellular Carcinoma: Too Many Options?," *J. Clin. Oncol.* 12:1323-1334, American Society of Clinical Oncology (1994).

Vo-Quang, Y., et al., "(1-Amino-2-propenyl)phosphonic Acid, an Inhibitor of Alanine Racemase and D-Alanine:D-Alanine Ligase," *J. Med. Chem.* 29:579-581, American Chemical Society (1986).

Wagner, A., et al., "Direct Conversion of Tetrahydropyranylated Alcohols to the Corresponding Bromides," *Tetrahedron Lett.* 30:557-558, Pergamon Press plc (1989).

Wallace, E.M., et al., "Design and Synthesis of Potent, Selective Inhibitors of Endothelin-Converting Enzyme," *J. Med. Chem.* 41:1513-1523, American Chemical Society (Apr. 1998).

Walsh, E., et al., "Phenoxymethylphosphonic Acids and Phosphonic Acid Ion-exchange Resins," *Phenoxymethylphosphonic Acid Ion-Exchange Resins* 78:4455-4458, American Chemical Society (1956).

Watkins, P., "Noninvasive tests of CYP3A enzymes," *Pharmacogenetics* 4:171-184, Lippincott Williams & Wilkins (1994).

Weber, G.F. and Waxman, D.J., "Activation of the Anti-cancer Drug Ifosphamide by Rat Liver Microsomal P450 Enzymes," *Biochem. Pharm.* 45:1685-1694, Pregamon Press Ltd. (1993).

Weibel, M., et al., "Potentiating Effect of {2-[2-[(2-Amino-1,6-Dihydro-6-Oxo-9H-Purin-9-yl)Methyl]-Phenyl] Ethenyl}-Phosphonic Acid (MDL 74,428), A Potent Inhibitor of Purine Nucleoside Phosphorylase, on the Antiretroviral Activities of 2',3'-Dideoxyinosine Combined to Ribavirin in Mice," *Biochem. Pharmacol.* 48:245-252, Elsevier Science Ltd. (1994).

Wileman, T., et al., "Receptor-mediated endocytosis," *Biochem. J.* 232:1-14, Portland Press (1985).

Yu, L. J., et al., "In vivo Modulation of Alternative Pathways of P-450-Catalyzed Cyclophosphamide Metabolism: Impact on Pharmacokinetics and Antitumor Activity," *J. Pharmacol. Exp.*

Ther. 288:928-937, The American Society for Pharmacology and Experimental Therapeutics (Mar. 1999).

Zon, G., "Cyclophosphamide Analogues" in *Progress in Medicinal Chemistry*, Ellis, G.P., et al., eds., Elsevier Biomedical Press, New York, Chapter 4, pp. 205-246 (1982).

Zon, G., et al., "NMR Spectroscopic Studies of Intermediary Metabolites of Cyclophosphamide. A Comprehensive Kinetic Analysis of the Interconversion of *cis*-and *trans*-4-Hydroxycyclophosphamide with Aldophosphamide and the Concomitant Partitioning of Aldophosphamide between Irreversible Fragmentation and Reversible Conjugation Pathways," *J. Med. Chem.* 27:466-485, American Chemical Society (1984).

Dialog File 351, Accession No. 4429221, WPI English language abstract for DE 3 512 781 A1, (date not available).

Co-Pending U.S. Appl. No. 09/518,501, inventors Erion, M., et al., filed Mar. 3, 2000, entitled, "Novel Phosphorus-Containing Prodrugs" (not published).

Arner, E.S.J. and Eriksson, S., "Mammalian Deoxyribonucleoside Kinases," *Pharmac. Ther.* 67(2): 155-186, Elsevier Science Ltd. (1995).

Elliott, R.L. et al., "Synthesis and Biological Evaluation of Phosphonamidate Peptide Inhibitors of Enkephalinase and Angiotensin-Converting Enzyme," *J. Med. Chem.* 28:1208-1216, American Chemical Society (1985).

Gorenstein, D.G. et al., "Stereoelectronic Effects in the Reactions of Epimeric 2-Aryloxy-2-oxy-1,3,2-dioxaphosphorinanes and Oxazaphosphorinanes," *J. Am. Chem. Soc.* 102: 5077-5081, American Chemical Society (1980).

Hulst, R. et al., "A New $^{31}$P NMR Method for the Enantiomeric Excess Determination of Alcohols, Amines and Amino Acid Esters," *Tetrahedron Letters* 34(8): 1339-1342, Pergamon Press Ltd. (1993).

Lorey, M. and Meier, C., "A New Cyclic Phosphoramidate D4T Prodrug Approach *Cyclo*Amb-D4T-Phosphoramidates," *Nucleosides & Nucleotides* 18(4&5): 947-948, Marcel Dekker, Inc. (1999).

Merckling, F.A. and Rüedi, P., "Diasteroselectivity in Nucleophilic Displacement Reactions at Phosphorus; Isolation and Characterization of a Pentacoordinated Intermediate," *Tetrahedron Letters* 37(13): 2217-2220, Elsevier Science Ltd. (1996).

\* cited by examiner

US 7,351,399 B2

PRODRUGS FOR PHOSPHORUS-CONTAINING COMPOUNDS

RELATED APPLICATION

This application is a continuation of U.S. application Ser. No. 09/978,454, filed Oct. 15, 2001, now U.S. Pat. No. 6,946,115 which is a continuation of U.S. application Ser. No. 09/392,352, now U.S. Pat. No. 6,312,662, filed Sep. 8, 1999, which is a continuation-in-part of U.S. application Ser. No. 09/263,976, filed Mar. 5, 1999, now abandoned which claims benefit of U.S. Provisional Application Ser. Nos. 60/077,164 and 60/077,165 both filed on Mar. 6, 1998, all of which are incorporated by reference in their entirety.

FIELD OF THE INVENTION

The present invention is directed towards novel prodrugs of phosphate, phosphonate, and phosphoramidate compounds which in their active form have a phosphate, phosphonate, or phosphoramidate group, to their preparation, to their synthetic intermediates, and to their uses. More specifically, the invention relates to the area of substituted cyclic 1,3-propanyl phosphate, phosphonate and phosphoramidate esters.

BACKGROUND OF THE INVENTION

The following description of the background of the invention is provided to aid in understanding the invention, but is not admitted to be, or to describe, prior art to the invention. All publications are incorporated by reference in their entirety.

Free phosphorus and phosphonic acids and their salts are highly charged at physiological pH and therefore frequently exhibit poor oral bioavailability, poor cell penetration and limited tissue distribution (e.g. CNS). In addition, these acids are also commonly associated with several other properties that hinder their use as drugs, including short plasma half-life due to rapid renal clearance, as well as toxicities (e.g. renal, gastrointestinal, etc.) (e.g. *Antimicrob Agents Chemother* May 1998; 42(5): 1146-50). Phosphates have an additional limitation in that they are not stable in plasma as well as most tissues since they undergo rapid hydrolysis via the action of phosphatases (e.g. alkaline phosphatase, nucleotidases). Accordingly, phosphate esters are frequently used as a prodrug strategy, especially for water insoluble compounds, since the phosphate group enables high water solubility and thereby enables delivery of the drug parenterally.

Prodrugs of phosphorus-containing compounds have been sought primarily to improve the limited oral absorption and poor cell penetration. In contrast to carboxylic acid proesters, many phosphonate and phosphate esters fail to hydrolyze in vivo, including simple alkyl esters. The most commonly used prodrug class is the acyloxyalkyl ester, which was first applied to phosphate and phosphonate compounds in 1983 by Farquhar et al. *J. Pharm. Sci.* 72(3): 324 (1983). The strategy entails cleavage of a carboxylic ester by esterases to generate an unstable hydroxyalkyl intermediate which subsequently breaks down to generate the drug and an aldehyde. In some cases this biproduct (e.g., formaldehyde), can be toxic. This strategy is used to enhance the bioavailability for several drugs. For example, the bis (pivoyloxymethyl) prodrug of the antiviral phosphonate 9-(2-phosphonylmethoxyethyl)adenine (PMEA) has been studied clinically for the treatment of CMV infection and the bis(pivaloyloxymethyl) prodrug of the squalene synthetase inhibitor BMS187745 is undergoing clinical evaluation for the treatment of hypercholesterolemia and associated cardiovascular diseases. The marketed antihypertensive, fosinopril, is a phosphinic acid angiotensin converting enzyme inhibitor that requires the use of an isobutryloxyethyl group for oral absorption.

Several other esters have been used as prodrugs of phosphorus-containing compounds. For example, aryl esters, especially phenyl esters, are another prodrug class reported to be useful for the delivery of phosphorus-containing compounds. DeLambert et al., *J. Med. Chem.* 37: 498 (1994). Phenyl esters containing a carboxylic ester ortho to the phosphate have also been described. Khamnei and Torrence, *J. Med. Chem.*; 39:4109-4115 (1996).

Benzyl esters are reported to generate the parent phosphonic acid. In some cases using substituents at the ortho- or para-position can accelerate the hydrolysis. Benzyl analogs with an acylated phenol or an alkylated phenol can generate the phenolic compound through the action of enzymes, e.g. esterases, oxidases, etc., which in turn undergoes cleavage at the benzylic C—O bond to generate the phosphonic acid and the potentially toxic quinone methide intermediate. Examples of this class of prodrugs are described by Mitchell et al., *J. Chem. Soc. Perkin Trans.* I 2345 (1992); Brook, et al. WO 91/12721. Still other benzylic prodrugs have been described containing a carboxylic ester-containing group attached to the benzylic methylene. Glazier et al. WO 91/19721.

Cyclic phosphonate esters have also been described for phosphorus-containing compounds. In some cases, these compounds have been investigated as potential phosphate or phosphonate prodrugs. Hunston et al., *J. Med. Chem.* 27: 440-444 (1984). The numbering for these cyclic esters is shown below:

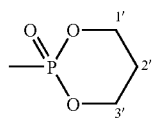

The cyclic 2',2'-difluoro-1',3'-propane ester is reported to be hydrolytically unstable with rapid generation of the ring-opened monoester. Starrett et al. *J. Med. Chem.* 37: 1857-1864 (1994).

Cyclic 3',5'-phosphate esters of araA, araC and thioinosine have been synthesized. Meier et al. *J. Med. Chem.* 22: 811-815 (1979). These compounds are ring-opened through the action of phosphodiesterases which usually require one negative charge.

Cyclic 1',3'-propanyl phosphonate and phosphate esters are reported containing a fused aryl ring, i.e. the cyclosaligenyl ester, Meier et al., *Bioorg. Med. Chem. Lett.* 7: 99-104 (1997). These prodrugs are reported to generate the phosphate by a "controlled, non-enzymatic mechanism[s] at physiological pH according to the designed tandem-reaction in two coupled steps". The strategy was purportedly used to deliver d4-T monophosphate to CEM cells and CEM cells deficient in thymidine kinase infected with HIV-1 and HIV-2.

Unsubstituted cyclic 1',3'-propanyl esters of the monophosphates of 5-fluoro-2'-deoxy-uridine (Farquhar et al., *J. Med. Chem.* 26: 1153 (1983)) and ara-A (Farquhar et al., *J. Med. Chem.* 28: 1358 (1985)) were prepared but showed no in vivo activity. In addition, cyclic 1',3'-propanyl esters substituted with a pivaloyloxy methyloxy group at C-1' was prepared for 5-fluoro-2'-deoxy-uridine monophosphate (5-FdUMP; (Freed et al., *Biochem. Pharmac.* 38: 3193 (1989); and postulated as potentially useful prodrugs by others (Biller et al., U.S. Pat. No. 5,157,027). In cells, the acyl group of these prodrugs underwent cleavage by esterases to generate an unstable hydroxyl intermediate which rapidly broke down to the free phosphate and acrolein following a β-elimination reaction as well as formaldehyde and pivalic acid.

Cyclic phosphoramidates are known to cleave in vivo by an oxidative mechanism. For example, cyclophosphoramide is thought to undergo oxidation at C-1' to form the hydroxylated intermediate, which like the 1'-substituted cyclic 1',3'-propane esters described above, breaks down to acrolein and the corresponding phosphoramidate. Cyclophosphoramidates were also prepared as potential prodrugs of both 5-FdUMP and araAMP and shown to have modest activity in vivo.

A variety of substituted 1',3' propanyl cyclic phosphoramidates, wherein 1' represents the carbon alpha to the nitrogen were prepared as cyclophosphamide analogs (Zon, Progress in Med. Chem. 19, 1205 (1982)). For example, a number of 2'- and 3'-substituted proesters were prepared in order to decrease the propensity of the α,β-unsubstituted carbonyl bi-product to undergo to a Michael reaction. 2'-Substituents included methyl, dimethyl, bromo, trifluoromethyl, chloro, hydroxy, and methoxy whereas a variety of groups were used at the 3'-position including phenyl, methyl, trifluoromethyl, ethyl, propyl, i-propyl, and cyclohexyl. Analogs with a 3'-aryl group underwent oxidation alpha to the nitrogen and accordingly exhibited anticancer activity in the mouse L1210 assay. A variety of 1'-substituted analogs were also prepared. In general these compounds were designed to be "pre-activated" cyclophosphamide analogs that bypass the oxidation step by already existing as a 1'-substituted analog capable of producing the final compound, e.g. hydroperoxide and thioether. A series of 1'-aryl analogs were also prepared in order to enhance the oxidation potential. In contrast to the 1'-hydroperoxy analogs, the 1'-aryl compounds exhibited either no activity or very poor activity in the standard anticancer in vivo screen assay, i.e. the mouse L1210 assay. The lack of activity was postulated to arise from the steric hinderance of the phenyl and therefore the limited oxidation of the prodrug. Support for this postulate was the potent activity of the acyclic phenyl keto analog which exhibited activity similar to cyclophosphamide.

Cyclic esters of phosphorus-containing compounds are reported in the chemical literature, however they were not tested as prodrugs in biological systems. These cyclic esters include:

[1] di and tri esters of phosphoric acids as reported in Nifantyev et al., *Phosphorus, Sulfur Silicon and Related Eelements*, 113: 1 (1996); Wijnberg et al., EP-180276 A1;

[2] phosphorus (III) acid esters. Kryuchkov et al., *Izv. Akad. Nauk SSSR, Ser. Khim.* 6: 1244 (1987). Some of the compounds were claimed to be useful for the asymmetric synthesis of L-Dopa precursors. Sylvain et al., DE3512781 A1;

[3] phosphoramidates. Shih et al., *Bull. Inst. Chem. Acad. Sin*, 41: 9 (1994); Edmundson et al., *J. Chem. Res. Synop.* 5: 122 (1989); and

[4] phosphonates. Neidlein et al., *Heterocycles* 35: 1185 (1993).

Numerous phosphorus-containing compounds are known to exhibit pharmacological activity but remain far from optimal due to one or more of the above-described limitations. Some of the activities described include phosphonic acids that are useful as antihypertensives and therapy for heart failure via inhibition of NEP 24.11, phosphonic acids that are useful for treating a variety of CNS conditions (stroke, epilepsy, brain and spinal cord trauma, etc.) via binding to excitory amino acid receptors (e.g. NMDA receptor), bisphosphonic acids that are useful for treating osteoporosis, phosphonic acids that are useful as lipid lowering agents (e.g. squalene synthase inhibitors), phosphonates that are useful in treating inflammation (e.g. collagenase inhibitors), phosphonates and phosphates that are useful in treating diabetes, cancer and parasitic and viral infections.

Phosphates and phosphonates that are known to be particularly useful in glucose lowering activity and therefore are anticipated to be useful in treating diabetes are compounds that bind to the AMP site of fructose 1,6-bisphosphatase (FBPase) as described by U.S. Pat. No. 5,658,889, WO 98/39344, WO 98/39343, and WO 98/39342. Other examples of phosphorus-containing drugs include squalene synthetase inhibitors (e.g. BMS 188494).

A large class of drugs known to be active against hepatitis are generally nucleoside or nucleotide analogs that are phosphorylated inside cells to produce the biologically active triphosphate. Examples include Lamivudine (3TC) and Vidarabine (araA). In each case, the drug interferes with viral replication via the triphosphate form through either inhibition of the viral DNA polymerases or DNA chain termination. Some specificity for virus-infected cells is gained by both preferential phosphorylation of the drug by virally-encoded kinases as well as by specific inhibition of viral DNA polymerases. Nevertheless many of the nucleoside-based drugs are associated with significant non-hepatic toxicity. For example, araA frequently produces neurological toxicity (40%) with many patients showing myalgia or a sensory neuropathy with distressing pain and abnormalities in nerve conduction and a few showing tremor, dysarthria, confusion or even coma. Lok et al., *J. Antimicrob. Chemotherap.* 14: 93-99 (1984).

Phosphonic acids also show antiviral activity. In some cases the compounds are antivirals themselves (e.g. phosphonoformic acid), whereas in other cases they require phosphorylation to the disphosphate, e.g. 9-(2-phosphonyl-methoxyethyl)adenine (PMEA, Adefovir). Frequently, these compounds are reported to exhibit enhanced activity due to either poor substrate activity of the corresponding nucleoside with viral kinases or because the viral nucleoside kinase which is required to convert the nucleoside to the monophosphate is down regulated viral resistance. Monophosphates and phosphonic acids, however, are difficult to deliver to virally-infected cells after oral administration due to their high charge and in the case of the monophosphate instability in plasma. In addition, these compounds often have short half-lives (e.g. PMEA, Adefovir) due in most cases to high renal clearance. In some cases, the high renal clearance can lead to nephrotoxicities or be a major limitation in diseases such as diabetes where renal function is often compromised.

Liver cancer is poorly treated with current therapies. In general, liver tumors are resistant to radiotherapy, respond poorly to chemotherapy and are characterized by a high degree of cell heterogeneity. Similar compounds as those described for hepatitis are also compounds that are useful for cancer (e.g. 2-Fluoroarabinosyladenosine (F-ara-A, Fludarabine), 2'2'-difluorodeoxycytidine (dFdC, Gemcitabine) and 5-fluorouracil or 5-fluoro-2'-deoxy uridine.

Hepatitis and liver cancer remain poorly treated with current therapies due to dose-limiting extrahepatic side effects or inadequate delivery of chemotherapeutic agents to the target tissue. Efforts to deliver drugs to the liver with relatively high organ specificity have primarily focused on strategies involving receptor mediated endocytosis (RME). RME transport systems are common to normal macrophages, hepatocytes, fibroblasts and reticulocytes. Macromolecules internalized via RME include asialoglycoproteins, LDL, transferrin and insulin. Another strategy for drug delivery to the liver uses colloids or liposomes both of which are subject to phagocytosis by the macrophage (Kupffer cells in liver) and localization in tissues of the reticuloendothelial system (e.g. liver, spleen and bone). Of these possible approaches, most of the attention has focused on the use of glycoprotein and oligosaccharide drug conjugates as a method for organ specific delivery. Natural desialylated glycoproteins, e.g. asialoorosomucoid and asialofetuin, neoglycoproteins, e.g. mannosylated and lactosylated albumin, and polysacharrides such as arabinogalactan have been used to successfully deliver drugs to the liver.

Conjugates of several drug classes have been reported, including the antiviral drug araAMP. For example, araAMP conjugated to lactosaminated serum albumin was effective in treating chronic type B hepatitis without signs of neurotoxicity. Fiume et al., *The Lancet* 13 (1988). Because conjugation of drugs to plasma proteins may have several limitations, including uptake by scavenger receptors on non-hepatocytes, immunogenicity and instability of the protein to conjugation conditions, and in vivo metabolism, efforts have focused on the use of oligosaccharide conjugates. One such approach uses arabinogalactan conjugate. The araAMP conjugate is reported to have good activity in woodchucks carrying the hepatitis virus. Enriquez et al., *Bioconj. Chem.* 6: 195-202 (1995).

Limitations in approaches described above include drug loading capacity, complexity of the manufacture and characterization of the conjugate, and receptor down regulation. Thus, there is still a need for prodrugs of phosphorus containing drugs.

SUMMARY OF THE INVENTION

Figure 1:
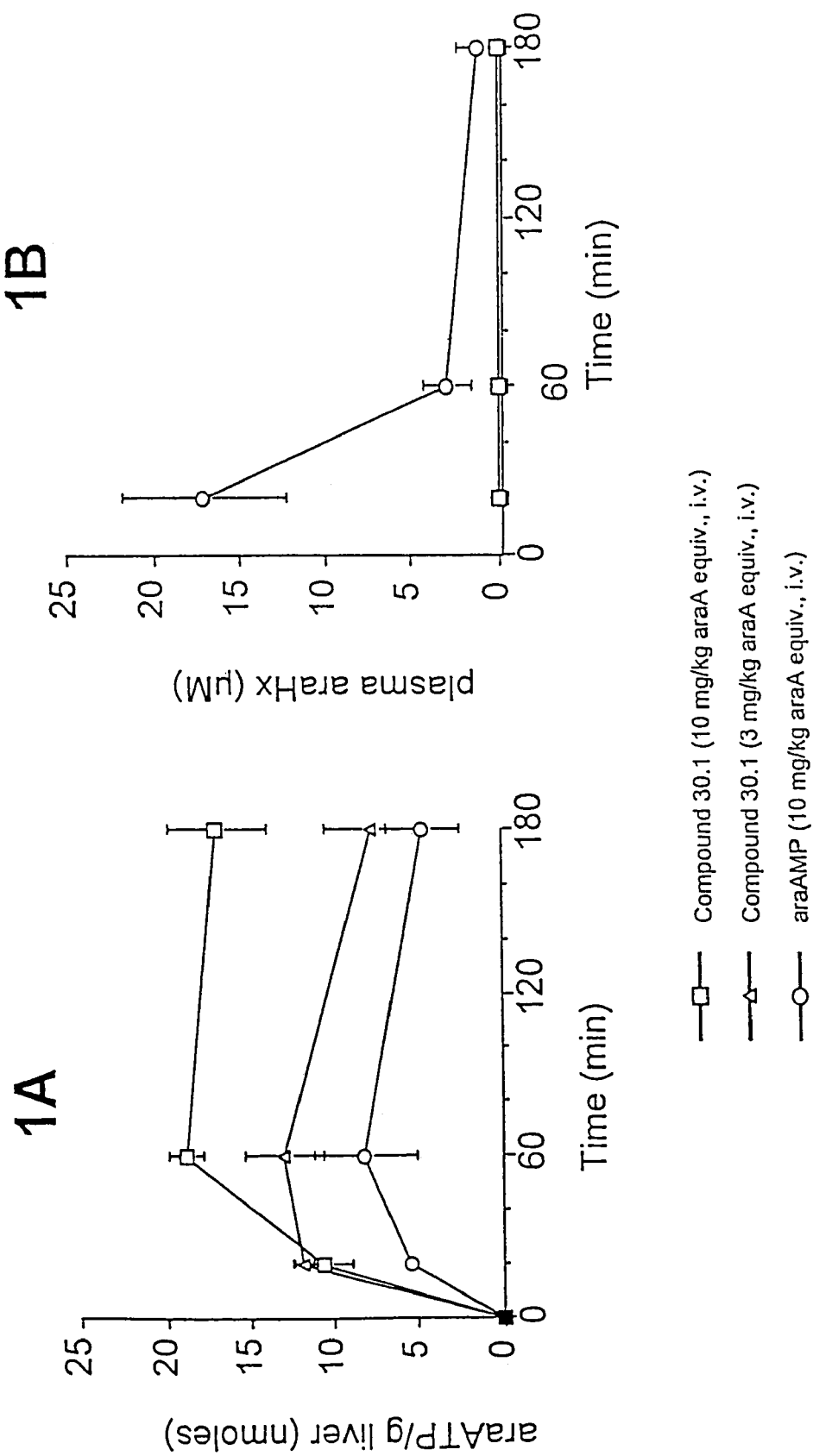
FIG. 1A depicts the amount of araATP in nmoles per gram of liver found over time after i.v. administration of compound 30.1 at 10 mg/kg and 3 mg/kg and after i.v. administration of 10 mg/kg araAMP. Significantly higher liver levels of the biologically active araATP was found after administration of prodrug 30.1.
FIG. 1B depicts the amount of araH found in the plasma over time after i.v. administration of prodrug 30.1 at 10 mg/kg and 3 mg/kg and after i.v. administration of 10 mg/kg araAMP. In contrast to an AMP, no araH (a toxic metabolite) was detected in the blood after administration of prodrug 30.1.

The present invention is directed towards novel prodrugs of phosphate, phosphonate, and phosphoramidate compounds, their preparation, their synthetic intermediates, and their uses. In one aspect, the invention is directed towards the use of the prodrugs to enhance oral drug delivery. Another aspect of the invention is the use of the prodrugs to treat diseases that benefit from enhanced drug distribution to the liver and like tissues and cells, including hepatitis, cancer, liver fibrosis, malaria, other viral and parasitic infections, and metabolic diseases where the liver is responsible for the overproduction of the biochemical end product, e.g. glucose (diabetes); cholesterol, fatty acids and triglycerides (hyperlipidemia) (atherosclerosis) (obesity). In another aspect, the prodrugs are used to prolong pharmacodynamic half-life of the drug. In addition, the prodrug methodology of the current invention is used to achieve sustained delivery of the parent drug. In another aspect, the prodrugs are used to increase the therapeutic index of the drug. In another aspect of the invention, a method of making these prodrugs is described. A further aspect is the novel intermediates to these prodrugs. In another aspect, the prodrugs are also useful in the delivery of diagnostic imaging agents to the liver.

One aspect of the present invention concerns compounds that are converted in vitro or in vivo to the corresponding $M-PO_3^{2-}$, $M-P_2O_6^{3-}$ and $MP_3O_3^{4-}$ and are of formula I

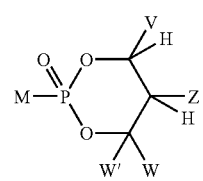

I wherein:

together V and Z are connected via an additional 3-5 atoms to form a cyclic group containing 5-7 atoms, optionally 1 heteroatom, substituted with hydroxy, acyloxy, alkoxycarbonyloxy, or aryloxycarbonyloxy attached to a carbon atom that is three atoms from both O groups attached to the phosphorus; or together V and Z are connected via an additional 3-5 atoms to form a cyclic group, optionally containing 1 heteroatom, that is fused to an aryl group at the beta and gamma position to the O attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from an O attached to the phosphorus;

together Z and W are connected via an additional 3-5 atoms to form a cyclic group, optionally containing one heteroatom, and V must be aryl, substituted aryl, heteroaryl, or substituted heteroaryl;

together W and W' are connected via an additional 2-5 atoms to form a cyclic group, optionally containing 0-2 heteroatoms, and V must be aryl, substituted aryl, heteroaryl, or substituted heteroaryl;

Z is selected from the group consisting of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂) OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)_p—OR¹², and —(CH₂)_p—SR¹²;

p is an integer 2 or 3;

with the provisos that:

a) V, Z, W, W' are not all —H; and b) when Z is —$R^2$, then at least one of V, W, and W' is not —H, alkyl, aralkyl, or alicyclic;

$R^2$ is selected from the group consisting of $R^3$ and —H;

$R^3$ is selected from the group consisting of alkyl, aryl, alicyclic, and aralkyl;

$R^{12}$ is selected from the group consisting of —H, and lower acyl;

M is selected from the group that attached to $PO_3^{2-}$, $P_2O_6^{3-}$, or $P_3O_9^{4-}$ is the biologically active agent, and that is attached to the phosphorus in formula I via a carbon, oxygen, sulfur or nitrogen atom;

and pharmaceutically acceptable prodrugs and salts thereof.

The present invention provides several novel methods of making the prodrugs. One method relies on the reaction of the following novel P(III) reagent:

M'—G'H + [cyclic phosphite with L—P, V, H, Z, H, W, W'] → [cyclic phosphite with M'—G'—P, V, H, Z, H, W, W']

G'=O, NH L=leaving groups such as —$NR^1_2$, halogen

The resulting phosphite is then oxidized to the cyclic phosphate ester.

A second method relies on the reaction of a novel P(V) reagent:

M'—G'—H + [cyclic with L'—P(=O), V, H, Z, H, W, W'] → [cyclic with M'—G'—P(=O), V, H, Z, H, W, W']

G'=O, NH L'=leaving groups such as —$NR_2$, —O-aryl, halogen

A third method relies on reacting another novel P(V) compound with a diol:

M'—G"—P(=O)(OH)(OH) → M'—G"—P(=O)(L")(L") +

G" = O, NH, CH   L" = halogen diol → [cyclic M'—G"—P(=O), V, O, Z, O, W, W']

Since these compounds have asymmetric centers, the present invention is directed not only to racemic and diastereomeric mixtures of these compounds, but also to individual stereoisomers. The present invention also includes pharmaceutically acceptable and/or useful salts of the compounds of formula I, including acid addition salts. The present inventions also encompass prodrugs of compounds of formula I.

Definitions

In accordance with the present invention and as used herein, the following terms are defined with the following meanings, unless explicitly stated otherwise.

The term "aryl" refers to aromatic groups which have 5-14 ring atoms and at least one ring having a conjugated pi electron system and includes carbocyclic aryl, heterocyclic aryl and biaryl groups, all of which may be optionally substituted. Suitable aryl groups, include phenyl and furan-2,5-diyl.

Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups having from 1 to 4 heteroatoms as ring atoms in the aromatic ring and the remainder of the ring atoms being carbon atoms. Suitable heteroatoms include oxygen, sulfur, nitrogen, and selendum. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups containing more than one aromatic ring including both fused ring systems and aryl groups substituted with other aryl groups. Such groups may be optionally substituted. Suitable biaryl groups include naphthyl and biphenyl.

The term "alicyclic" means compounds which combine the properties of aliphatic and cyclic compounds. Such cyclic compounds include but are not limited to, aromatic, cycloalkyl and bridged cycloalkyl compounds. The cyclic compound includes heterocycles. Cyclohexenylethyl and cyclohexylethyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl. "Substituted aryl" and "substituted heteroaryl" preferably refers to aryl and heteroaryl groups substituted with 1-3 substituents. Preferably these substituents are selected from the group consisting of lower alkyl, lower alkoxy, lower perhaloalkyl, halo, hydroxy, and amino.

The term "-aralkyl" refers to an alkylene group substituted with an aryl group. Suitable aralkyl groups include benzyl, picolyl, and the like, and may be optionally substituted. "Heteroarylalkyl" refers to an alkylene group substituted with a heteroaryl group.

The term "-alkylaryl" refers to an aryl group substituted with an alkyl group. "Lower -alkylaryl" refers to such groups where alkyl is lower alkyl.

The term "lower" referred to herein in connection with organic radicals or compounds respectively defines such as with up to and including 10, preferably up to and including 6, and advantageously one to four carbon atoms. Such groups may be straight chain, branched, or cyclic.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl and aryl.

The term "carboxy esters" refers to —C(O)OR where R is alkyl, aryl, aralkyl, and alicyclic, all optionally substituted.

The term "carboxyl" refers to —C(O)OH.

The term "oxo" refers to =O in an alkyl group.

The term "amino" refers to —NRR' where R and R' are independently selected from hydrogen, alkyl, aryl, aralkyl and alicyclic, all except H are optionally substituted; and R and $R^1$ can form a cyclic ring system.

The term "-carboxylamido" refers to —$CONR_2$ where each R is independently hydrogen or alkyl.

The term "halogen" or "halo" refers to —F, —Cl, —Br and —I.

The term "alkylaminoalkylcarboxy" refers to the group alkyl-NR-alk-C(O)—O— where "alk" is an alkylene group, and R is a H or lower alkyl.

The term "alkyl" refers to saturated aliphatic groups including straight-chain, branched chain and cyclic groups. Alkyl groups may be optionally substituted. Suitable alkyl groups include methyl, isopropyl, and cyclopropyl.

The term "cyclic alkyl" or "cycloalkyl" refers to alkyl groups that are cyclic of 3 to 10 atoms, more preferably 3 to 6 atoms. Suitable cyclic groups include norbornyl and cyclopropyl. Such groups may be substituted.

The term "heterocyclic" and "heterocyclic alkyl" refer to cyclic groups of 3 to 10 atoms, more preferably 3 to 6 atoms, containing at least one heteroatom, preferably 1 to 3 heteroatoms. Suitable heteroatoms include oxygen, sulfur, and nitrogen. Heterocyclic groups may be attached through a nitrogen or through a carbon atom in the ring. The heterocyclic alkyl groups include unsaturated cyclic, fused cyclic and spirocyclic groups. Suitable heterocyclic groups include pyrrolidinyl, morpholino, morpholinoethyl, and pyridyl.

The term "phosphono" refers to —$PO_3R_2$, where R is selected from the group consisting of —H, alkyl, aryl, aralkyl, and alicyclic.

The term "sulphonyl" or "sulfonyl" refers to —$SO_3R$, where R is H, alkyl, aryl, aralkyl, and alicyclic.

The term "alkenyl" refers to unsaturated groups which contain at least one carbon-carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g. it is a W substituent attached to the cyclic phosph(oramid)ate, it is attached at the first carbon.

The term "alkynyl" refers to unsaturated groups which contain at least one carbon-carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g. it is a W substituent attached to the cyclic phosph (oramid)ate, it is attached at the first carbon.

The term "alkylene" refers to a divalent straight chain, branched chain or cyclic saturated aliphatic group.

The term "acyloxy" refers to the ester group —O—C(O) R, where R is H, alkyl, alkenyl, alkynyl, aryl, aralkyl, or alicyclic.

The term "aminoalkyl-" refers to the group $NR_2$-alk-wherein "alk" is an alkylene group and R is selected from H, alkyl, aryl, aralkyl, and alicyclic.

The term "alkylaminoalkyl-" refers to the group alkyl-NR-alk- wherein each "alk" is an independently selected alkylene, and R is H or lower alkyl. "Lower alkylaminoalkyl-" refers to groups where each alkylene group is lower alkylene.

The term "arylaminoalkyl-" refers to the group aryl-NR-alk- wherein "alk" is an alkylene group and R is H, alkyl, aryl, aralkyl, and alicyclic. In "lower arylaminoalkyl-", the alkylene group is lower alkylene.

The term "alkylaminoaryl-" refers to the group alkyl-NR-aryl- wherein "aryl" is a divalent group and R is H, alkyl, aralkyl, and alicyclic. In "lower alkylaminoaryl-", the alkylene group is lower alkyl.

The term "alkoxyaryl-" refers to an aryl group substituted with an alkyloxy group. In "lower alkyloxyaryl-", the alkyl group is lower alkyl.

The, term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "alkoxy-" or "alkyloxy-" refers to the group alkyl-O—.

The term "alkoxyalkyl-" or "alkyloxyalkyl-" refer to the group alkyl-O-alk- wherein "alk" is an alkylene group. In "lower alkoxyalkyl-", each alkyl and alkylene is lower alkylene.

The terms "alkylthio-" and "alkylthio-" refer to the groups alkyl-S—.

The term "alkylthioalkyl-" refers to the group alkyl-S-alk-wherein "alk" is an alkylene group. In "lower alkylthioalkyl-" each alkyl and alkylene is lower alkylene.

The term "alkoxycarbonyloxy-" refers to alkyl-O—C (O)—O—.

The term "aryloxycarbonyloxy-" refers to aryl-O—C (O)—O—.

The term "alkylthiocarbonyloxy-" refers to alkyl-S—C (O)—O—.

The terms "amido" or "carboxamido" refer to $NR_2$—C (O)— and RC(O)—$NR^1$—, where R and $R^1$ include H, alkyl, aryl, aralkyl, and alicyclic. The term does not include urea, —NR—C(O)—NR—.

The term "carboxamidoalkylaryl" and "carboxamidoaryl" refers to an aryl-alk-$NR^1$—C(O), and ar-$NR^1$—C(O)-alk-, respectively where "ar" is aryl, "alk" is alkylene, $R^1$ and R include H, alkyl, aryl, aralkyl, and alicyclic.

The term "hydroxyalkyl" refers to an alkyl group substituted with one —OH.

The term "haloalkyl" refers to an alkyl group substituted with one halo.

The term "cyano" refers to —C≡N.

The term "nitro" refers to —$NO_2$.

The term "acylalkyl" refers to an alkyl-C(O)-alk-, where "alk" is alkylene.

The term "aminocarboxamidoalkyl-" refers to the group $NR_2$—C(O)—N(R)-alk- wherein R is an alkyl group or H and "alk" is an alkylene group. "Lower aminocarboxamidoalkyl-" refers to such groups wherein "alk" is lower alkylene.

The term "heteroarylalkyl" refers to an alkyl group substituted with a heteroaryl group.

The term "perhalo" refers to groups wherein every C—H bond has been replaced with a C-halo bond on an aliphatic or aryl group. Suitable perhaloalkyl groups include —$CF_3$ and —$CFCl_2$.

The term "guanidino" refers to both —NR—C(NR)—$NR_2$ as well as —N=C($NR_2$)$_2$ where each R group is independently selected from the group of —H, alkyl, alkenyl, alkynyl, aryl, and alicyclic, all except —H are optionally substituted.

The term "amidino" refers to —C(NR)—$NR_2$ where each R group is independently selected from the group of —H, alkyl, alkenyl, alkynyl, aryl, and alicyclic, all except —H are optionally substituted.

The term "pharmaceutically acceptable salt" includes salts of compounds of formula I and its prodrugs derived from the combination of a compound of this invention and an organic or inorganic acid or base. Suitable acids include HCl.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, $R_2$N—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of formula I, fall within the scope of the present invention. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. The biologically active compounds include, for example, anticancer agents, antiviral agents, and antibiotic agents.

The term "bidentate" refers to an alkyl group that is attached by its terminal ends to the same atom to form a cyclic group. For example, propylene imine contains a bidentate propylene group.

The structure

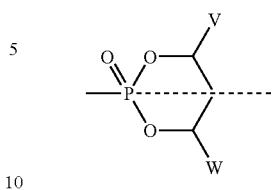

has a plane of symmetry running through the phosphorus-oxygen double bond when V=W, W'=H, and V and W are either both pointing up or both pointing down.

The term "cyclic 1',3'-propane ester", "cyclic 1,3-propane ester", "cyclic 1',3'-propanyl ester", and "cyclic 1,3-propanyl ester" refers to the following:

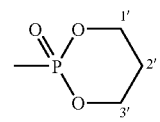

The phrase "together V and Z are connected via an additional 3-5 atoms to form a cyclic group containing 5-7 atoms, optionally containing 1 heteroatom, substituted with hydroxy, acyloxy, alkoxycarbonyloxy, or aryloxycarbonyloxy attached to a carbon atom that is three atoms from both O groups attached to the phosphorus" includes the following:

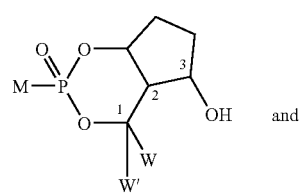

The structure shown above (left) has an additional 3 carbon atoms that forms a five member cyclic group. Such cyclic groups must possess the listed substitution to be oxidized.

The phrase "together V and Z are connected via an additional 3-5 atoms to form a cyclic group, optionally containing one heteroatom, that is fused to an aryl group attached at the beta and gamma position to the O attached to the phosphorus" includes the following:

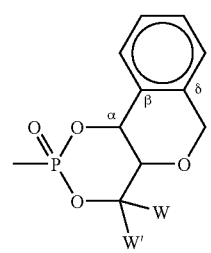

The phrase "together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a O attached to the phosphorus" includes the following:

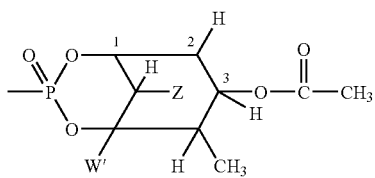

The structure above has an acyloxy substituent that is three carbon atoms from a O, and an optional substituent, —CH₃, on the new 6-membered ring. There has to be at least one hydrogen at each of the following positions: the carbon attached to Z; both carbons alpha to the carbon labelled "3"; and the carbon attached to "OC(O)CH₃" above.

The phrase "together W and W' are connected via an additional 2-5 atoms to form a cyclic group, optionally containing 0-2 heteroatoms, and V must be aryl, substituted aryl, heteroaryl, or substituted heteroaryl" includes the following:

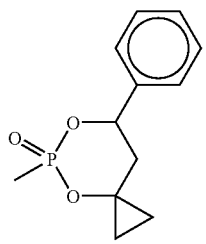

The structure above has V=aryl, and a spiro-fused cyclopropyl group for W and W'.

The term "phosph(oramid)ite" refers to carbon phosphites, phosphites, thiophosphites, and phosphoramidites which are compounds attached via C, O, S, or N, respectively, to the phosphorus in —P(OR)(OR) including cyclic forms.

The term "phosph(oramid)ate" refers to phosphonates, phosphates, thiophosphates, and phosphoramidates which are compounds attached via C, O, S, or N, respectively, to the phosphorus in —P(O)(OR)(OR), including cyclic forms.

The term "cyclic phosph(oramid)ate" refers to phosph(oramid)ates where —P(O)(OR)(OR is

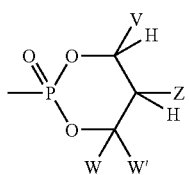

The carbon attached to V must have a C—H bond. The carbon attached to Z must also have a C—H bond.

The term "carbocyclic sugar" refers to sugar analogs that contain a carbon in place of the oxygen normally found in the sugar ring. It includes 5-membered rings such as ribofuranosyl and arabinofuranosyl sugars wherein the ring oxygen is replaced by carbon.

The term "acyclic sugar" refers to sugars that lack a ring, e.g. ribofuranosyl ring. An example is 2-hydroxyethoxymethyl in place of the ribofuranosyl ring.

The term "L-nucleoside" refers to enantiomer of the natural B-D-nucleoside analogs.

The term "arabinofuranosyl nucleoside" refers to nucleoside analogs containing an arabinofuranosyl sugar, i.e. where the 2'-hydroxyl of ribofuranosyl sugars is on the opposite face of the sugar ring.

The term "dioxolane sugar" refers to sugars that contain an oxygen atom in place of the 3' carbon of the ribofuranosyl sugar.

The term "fluorinated sugars" refers to sugars that have 1-3 carbon-fluorine atoms.

The term "nucleoside" refers to a purine or pyrimidine base, or analogs thereof, connected to a sugar, including heterocyclic and carbocyclic analogs thereof.

The term "liver" refers to liver and to like tissues and cells that contain the CYP3A4 isozyme or any other P450 isozyme found to oxidize the phosph(oramid)ates of the invention. Based on Example F, we have found that prodrugs of formula VI and VIII are selectively oxidized by the cytochrome P450 isoenzyme CYP3A4. According to DeWaziers et al (J. Pharm. Exp. Ther., 253, 387-394 (1990)), CYP3A4 is located in humans in the following tissues (determined by immunoblotting and enzyme measurements):

| Tissues | % of liver activity |
|---|---|
| Liver | 100 |
| Duodenum | 50 |
| jejunum | 30 |
| ileum | 10 |
| colon | <5 |
| | (only P450 isoenzyme found) |
| stomach | <5 |
| esophagus | <5 |
| kidney | not detectable |

Thus, "liver" more preferably refers to the liver, duodenum, jejunum, ileum, colon, stomach, and esophagus. Most preferably, liver refers to the liver organ.

The term "enhancing" refers to increasing or improving a specific property.

The term "liver specificity" refers to the ratio:

$$\frac{[\text{parent drug or a drug metabolite in liver tissue}]}{[\text{parent drug or a drug metabolite in blood, urine or another non-hepatic tissue}]}$$

as measured in animals treated with the drug or a prodrug. The ratio can be determined by measuring tissue levels of the parent drug, or drug metabolite(s) including the biologically active drug metabolite, or both at a specific time or may represent an AUC based on values measured at three or more time points.

The term "increased or enhanced liver specificity" refers to an increase in the liver specificity ratio in animals treated with the prodrug relative to animals treated with the parent drug.

The term "enhanced oral bioavailability" refers to an increase of at least 50% of the absorption of the dose of the parent drug or prodrug (not of this invention) from the gastrointestinal tract. More preferably it is at least 100%. Measurement of oral bioavailability usually refers to measurements of the prodrug, drug, or drug metabolite in blood, tissues, or urine following oral administration compared to measurements following systemic administration.

The term "drug metabolite" refers to any compound produced in vivo or in vitro from the parent drug, or its prodrugs.

The term "pharmacodynamic half-life" refers to the time after administration of the drug or prodrug to observe a diminution of one half of the measured pharmacological response. Pharmacodynamic half-life is enhanced when the half-life is increased by preferably at least 50%.

The term "pharmacokinetic half-life" refers to the time after administration of the drug or prodrug to observe a diminution of one half of the drug concentration in plasma or tissues.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The term "bypassing drug resistance" refers to the loss or partial loss of therapeutic effectiveness of a drug (drug resistance) due to changes in the biochemical pathways and cellular activities important for producing and maintaining the biologically active form of the drug at the desired site in the body and to the ability of an agent to bypass this resistance through the use of alternative pathways and cellular activities.

The term "therapeutically effective amount" refers to an amount that has any beneficial effect in treating a disease or condition.

The term "phosph(on)ate" refers to compounds attached via C, O, S or N to $PO_3^{2-}$.

The term "phosphonate" refers to —C—$PO_3R_2$.
The term "phosphate" refers to —O—$PO_3R_2$.
The term "thiophosphate" refers to —S—$PO_3R_2$.
The term "phosphoramidate" refers to —N—$PO_3R_2$.

X group nomenclature as used herein in formulae II-V describes the group attached to the phosphonate and ends with the group attached to the heteroaromatic ring. For example, when X is alkylamino, the following structure is intended:

(heteroaromatic ring)-NR-alk-P(O)(OR)₂

Likewise, Y, A, B, C, and D groups and other substituents of the heteroaromatic ring are described in such a way that the term ends with the group attached to the heteroaromatic ring. Generally, substituents are named such that the term ends with the group at the point of attachment.

The term "parent drug" refers to MH for phosph(oramid)ates where M is connected to —P(O)(OR)(OR) via oxygen, sulfur, or nitrogen, and to M-$PO_3^{2-}$ when M is connected to —P(O)(OR)(OR) via carbon. For example, AZT can be thought of as a parent drug in the form of MH. In the body AZT is first phosphorylated to AZT-$PO_3^{2-}$ and then further phosphorylated to form AZT-triphosphate, which is the biologically active form. The parent drug form MH only applies when M is attached via N, S, or O. In the case of PMEA, the parent drug form is M-$PO_3^{2-}$.

The term "biologically active drug or agent" refers to the chemical entity that produces the biological effect. In this invention, biolgically active agents refers to M-$PO_3^{2-}$, $MP_2O_6^{3-}$, or $MP_3O_9^{4-}$ where M can be the same M as in the parent drug or a metabolite.

The following well known drugs are referred to in the specification and the claims.

Abbreviations and common names are also provided.
   araA; 9-b-D-arabinofuranosyladenine (Vidarabine)
   AZT; 3'-azido-2',3'-dideoxythymdine (Zidovudine)
   d4T; 2',3'-didehydro-3'-deoxythymidine (Stavudine)
   ddI; 2',3'-dideoxyinosine (Didanosine)
   ddA; 2',3'-dideoxyadenosine
   ddC; 2',3'-dideoxycytidine (Zalcitabine)
   L-ddC; L-2',3'-dideoxycytidine
   L-FddC; L-2',3'-dideoxy-5-fluorocytidine
   L-d4C, L-3'-deoxy-2',3'-didehydrocytidine
   L-Fd4C; L-3'-deoxy-2',3'-didehydro-5-fluorocytidine
   3TC; (−)-2',3'-dideoxy-3'-thiacytidine; 2'R,5'S(−)-1-[2-(hydroxymethyl)oxathiolan-5-yl]cytosine (Lamivudine)
   1b-D-ribofuranosyl-1,2,4-triazole-3-carboxamide (Ribavirin)
   FIAU; 1-(2-deoxy-2-fluoro-b-D-arabinofuranosyl)-5-iodouridine
   FIAC; 1-(2-deoxy-2-fluoro-b-D-arabinofuranosyl)-5-iodocytosine
   BHCG; (±)-(1a,2b,3a)-9-[2,3-bis(hydroxymethyl)cyclobutyl]guanine
   FMAU; 2'-Fluoro-5-methyl-b-L-arabino-furanosyluracil
   BvaraU; 1-b-D-arabinofuranosyl-E-5-(2-bromovinyl)uracil (Sorivudine)
   E-5-(2-bromovinyl)-2'-deoxyuridine
   TFT; Trifluorothymidine (Trifluorothymidine)
   5-propynyl-1-arabinosyluracil (Zonavir)
   CDG; carbocyclic 2'-deoxyguanosine
   DAPD; (−)-B-D-2,6-diaminopurine dioxolane
   FDOC; (−)-B-D-5-fluoro-1-[2-(hydroxymethyl)-1,3-dioxolane]cytosine
   d4C; 3'-deoxy-2',3'-didehydrocytidine
   DXG; dioxolane guanosine
   FEAU; 2'-deoxy-2'-fluoro-1-b-D-arabinofuranosyl-5-ethyluracil
   FLG; 2',3'-dideoxy-3'-fluoroguanosine
   FLT; 3'-deoxy-3'-fluorothymidine
   FTC; (−)-cis-5-fluoro-1-[2-(hydroxymethyl)-1,3-oxathiolan-5-yl]cytosine
   5-yl-carbocyclic 2'-deoxyguanosine (BMS200,475)
   [1-(4'-hydroxy-1',2'-butadienyl)cytosine] (Cytallene)
   Oxetanocin A; 9-(2-deoxy-2-hydroxymethyl-beta-D-erythro-oxetanosyl)adenine
   Oxetanocin G; 9-(2-deoxy-2-hydroxymethyl-beta-D-erythro-oxetanosyl)guanine
   ddAPR: 2,6-diaminopurine-2',3'-dideoxyriboside
   3TC; (−)-2',3'-dideoxy-3'thiacytidine; (2R, 5S) 1-[2-(hydroxymethyl)-1,3-oxathiolane-5-yl]cytosine (Lamivudine)
   Cyclobut A; (±)-9-[(1 beta,2 alpha,3 beta)-2,3-bis(hydroxymethyl)-1-cyclobutyl]adenine
   Cyclobut G; (±)-9-[(1 beta,2 alpha,3 beta)-2,3-bis(hydroxymethyl)-1-cyclobutyl]guanine (Lobucavir)
   5-fluoro-2'-deoxyuridine (Floxuridine)
   dFdC; 2',2'-difluorodeoxycytidine (Gemcitabine)
   araC; arabinosylcytosine (Cytarabine)
   bromodeoxyuridine IDU; 5-iodo-2'-deoxyuridine (Idoxuridine)
CdA; 2-chlorodeoxyadenosine (Cladribine)
F-ara-A; fluoroarabinosyladenosine (Fludarabine)
ACV; 9-(2-hydroxyethoxylmethyl)guanine (Acyclovir)
GCV; 9-(1,3-dihydroxy-2-propoxymethyl)guanine (gancyclovir)
9-(4-hydroxy-3-hydroxymethylbut-1-yl)guanine (Penciclovir)
(R)-9-(3,4-dihydroxybutyl)guanine (Buciclovir)
phosphonoformic acid (Foscarnet)
PPA; phosphonoacetic acid
PMEA; 9-(2-phosphonylmethoxyethyl)adenine (Adefovir)
PMEDAP; 9-(2-phosphonylmethoxyethyl)-2,6-diaminopurine
HPMPC; (S)-9-(3-hydroxy-2-phosphonylmethoxypropyl)cytosine (Cidofovir)
HPMPA; (S)-9-(3-hydroxy-2-phosphonylmethoxypropyl)adenine
FPMPA; 9-(3-fluoro-2-phosphonylmethoxypropyl)adenine
PMPA; (R)9-(2-phosphonylmethoxypropyl)adenine
araT; 9-b-D-arabinofuranosylthymidine
FMdC; (E)-2'-deoxy-2'(fluoromethylene)cytidine
AICAR; 5-aminoimidazole-4-carboxamido-1-ribofuranosyl

DETAILED DESCRIPTION OF THE INVENTION

The invention is directed to the use of new cyclic phosph (on)ate ester methodology which allows compounds to be efficiently converted to phosph(on)ate containing compounds by p450 enzymes found in large amounts in the liver and other tissues containing these specific enzymes. This methodology can be applied to various drugs and to diagnostic imaging agents. More specifically, the invention is directed to the use of prodrug-esters of highly charged phosphate, phosphoramidate, and phosphonate containing drugs that undergo non-esterase-mediated hydrolysis reactions to produce the phosphate, phosphoramidate, and phosph(on)ate containing compounds. Because highly charged phosph(on)ate containing compounds are not readily absorbed in the gastrointestinal tract, this prodrug methodology can be used to enhance absorption after oral administration.

In another aspect of the invention, this prodrug methodology can also be used to enhance the pharmacodynamic half-life relative to the parent drug because the cyclic phosph(on)ates of the invention can avoid metabolism by enzymes which metabolize the parent drug. Similarly, prodrugs of the invention can enhance the pharmacodynamic half-life of the phosph(on)ate-containing compound because the prodrug avoids clearance pathways used to clear negatively-charged compounds from the bloodstream.

In another aspect of the invention, this prodrug methodology can also be used to achieve sustained delivery of the parent drug because oxidation of the novel prodrugs proceeds in the liver at different rates and therefore selection of prodrugs that oxidize slowly but at a rate suitable for maintaining therapeutically effective levels will produce a sustained therapeutic effect.

The novel cyclic phosphonate methodology of the present invention may also be used to increase the distribution of a particular drug or imaging agent to the liver which contains abundant amounts of the p450 isozymes responsible for oxidizing the cyclic phosphonate of the present invention so that the free phosphonate or phosphate is ultimately produced. Accordingly, this prodrug technology should prove useful in the treatment of liver diseases or diseases where the liver is responsible for the overproduction of the biochemical end product such a glucose, cholesterol, fatty acids and triglycerides. Such diseases include viral and parasitic infections, liver cancer, liver fibrosis, diabetes, hyperlipidemia, and obesity. In addition the liver specificity of the prodrugs should also prove useful in the delivery of diagnostic agents to the liver.

These specific p450 enzymes are also found in other specific tissues and cells, and thus this methodology may also be used to increase the delivery of these agents to those tissues.

In another aspect of the invention, the characteristic that most of the cyclic phosph(on)ates of the present invention are metabolized in the liver to produce the phosph(on)ate drug can enable the use of the prodrug methodology of the present invention to increase the therapeutic index of various drugs which tend to have side effects related to the amount of the drug or its metabolites which are distributed in extrahepatic tissues. Increased therapeutic index can also result from increased liver levels of the biologically active agent and therefore greater efficacy relative to the parent drug administered at similar doses.

In yet another aspect of the invention, the cyclic phosph (oramid)ates of the present invention can achieve enhanced efficacy by bypassing drug resistance caused by decreased transport into the target cells, increased drug export by transporters, increased drug metabolism, or decreased precursor metabolism to the active drug.

In another aspect of the invention, novel phosph(oramid) ite and phosph(oramid)nate intermediates are described.

In another aspect, methods of preparing the cyclic phosph (oramid)ate prodrugs are described.

Theses aspects are described in greater detail below.

Enhancing Oral Bioavailability

The invention pertains to certain cyclic phosph(oramid) ates and the use of these esters to deliver, most preferably via oral administration, a therapeutically effective amount of the corresponding phosph(on)ate compounds, preferably to an animal in need thereof. The active drug may be M-$PO_3^{2-}$. Alternatively, M-$PO_3^{2-}$ may instead undergo further phosphorylation by kinases to form M-$P_2O_6^{3-}$ and/or M-$P_3O_9^{4-}$ as the active drug substance.

Compounds containing a free phosphonic acid or a phosphoric acid group generally exhibit poor (<2%) oral bioavailability since these groups are highly charged at physiological pH. Charged groups on compounds with molecular weights greater than 250 Daltons impede passive diffusion across cell membranes as well as absorption across the gut epithelial cell layer. Neutral prodrugs of these compounds have therefore been studied since these compounds would be more lipophilic and therefore more likely to exhibit improved intestinal permeability. Although many prodrug classes have been reported, few have been found that exhibit properties suitable for drug development.

The most common prodrug class, and the class almost exclusively used for clinical candidates, is the acyloxyalkyl esters. These prodrugs, however, often exhibit only a modest improvement in oral bioavailability due to poor aqueous stability, poor stability to acidic/basic pH and rapid degradation by esterases in the gastrointestinal tract (Shaw & Cundy, *Pharm. Res.* 10, (Suppl), S294 (1993). Another class of prodrugs are the bis-aryl prodrugs (e.g. DeLombert et al. *J. Med. Chem.* 37, 498 (1994)) which have shown in a few isolated cases to provide good to modest improvements in oral bioavailability. The major limitation with this class of compounds is that the prodrug ester often is degraded to the monoacid rapidly in vivo but conversion to the parent drug occurs only slowly (sometimes over days) if at all.

The prodrugs of the invention exhibit improved properties that lead to enhanced oral bioavailability relative to the parent drug. Several characteristics of the present cyclic phosph(oramid)ate prodrugs may contibute to their ability to enhance oral bioavailabilty. First, the prodrugs exhibit good stability in aqueous solutions across a wide range of pHs. In Example A, 30.1 was found to be stable for at least seven days in 100 mM potassium phosphate buffer solutions at pH 3, 7, and 9. This pH stability prevents immediate hydrolysis in the mouth and GI tract prior to absorption. The pH stability can also be beneficial during formulation of the product.

Second, the prodrugs are resistant to esterases and phosphatases which are abundant in the gastrointestinal tract. The resistance to esterases and phosphatases can be assayed according to Example B. In addition, Example C demonstrated that 30.1, 1.1, and 1.2 were not degraded by esterases found in fresh rat plasma. Because much of the administered dose remains intact in the G.I. tract, the compound remains less highly charged than a free phosph(on)ate which means more of the drug can be absorbed by passive diffusion and enter the blood stream.

Last, the prodrug can limit metabolism at other sites on the molecule. For example, the prodrugs of the invention eliminate metabolism of the purine base of araA by adenosine deaminase which is also abundant in the GI tract. In Example C, the cyclic 1'-(4-pyridyl)-3' propanyl phosphate ester prodrug of araA was not susceptible to deamination by adenosine deaminase found in rat plasma. The amine of araA which is normally deaminated by the enzyme is protected by the cyclic phosphate moiety. Reduced metabolism at other sites of the molecule enables more of the drug to circulate in the blood stream. Although not all of these properties will be applicable to every prodrug of every drug, each of these properties can enable more drug to survive the GI tract and be available for absorption.

The novel prodrug strategy of the invention will be useful for the oral delivery of drugs that act in the liver as well as certain drugs that act on targets located in the vascular system or extrahepatic tissues. Because the highest concentration of CYP3A4 (the enzyme responsible for activating the novel prodrugs is in the liver, the biologically active drug has a high concentration in the liver, relative to other tissues. In one aspect, parent drugs which act in the liver are preferred.

However; some of the phosph(on)ates are exported by organic anion transporters in the liver and enter the blood stream. Many phosph(on)ates in the blood stream are cleared quickly by the kidneys. Examples of such compounds are the FBPase inhibitors described herein and PMEA. Such compounds probably will not reach therapeutic levels in extrahepatic tissues. However, there are some phosph(on) ates and phosphates that are able to remain in circulation because they are not rapidly cleared by the kidneys (e.g. NEP inhibitors). Such compounds are able to achieve therapeutically effective levels in blood and extrahepatic tissues. Thus, in another aspect, oral delivery to extrahepatic tissues of phosph(on)ates which are not cleared by the kidneys is preferred. Thus, such parent drugs that act at sites accessible to the free phosph(on)ic acid such as targets within the vasculature system, or enzyme or receptor targets that are located on cell membranes which are exposed to the blood or fluid in the intrastitial space are preferred. Targets suitable for this aspect of the invention would be targets in which the phosphonic acid administered parenterally (e.g. via i.v. injection) produces a pharmacological or biochemical response expected to be useful for treating a disease condition.

For example, phosph(on)ic acids that inhibit neutral endopeptidase 24.11 ("NEP inhibitors") are known to inhibit the degradation of atrial natriuretic factor in vivo and to produce an associated antihypertensive and diuretic effect (DeLambert et al., J. Med. Chem. 37, 498 (1994)) which may be useful for the treatment of hypertension and congestive heart failure. Since the inhibitors exhibit poor oral bioavailability (<2%), prodrugs of the type described in this invention could enhance the oral bioavailability and produce the phosphonic acid following prodrug cleavage in the liver. Suitable circulating drug levels are expected after prodrug cleavage in the liver, since the liver is known to excrete phosphonic acids into the circulation. For example, phosphonic acids that inhibit FBPase are exported out of hepatocytes in vitro presumably by an organic anion transporter.

Oral bioavailability can also be calculated by comparing the area under the curve of prodrug, parent drug, and/or metabolite concentration over time in plasma, liver, or other tissue or fluid of interest following oral and i.v. administration. In Example M, prodrug 30.1 demonstrated an oral bioavailability of 17.4% by analysis of hepatic levels of the phosphorylated parent compound, ara-ATP, following oral and i.v. administration.

For example, for drugs excreted renally in large amounts, oral bioavailability can also be measured by comparing the amount of the parent drug or metabolite excreted in the urine, for example, after oral and i.v. administration of the prodrug. A lower limit of oral bioavailability can be estimated by comparison with the amount of parent drug excreted in the urine after administration of the i.v. parent drug. Analysis of prodrugs of FBPase inhibitors in Example M shows that these compounds exhibit improved oral bioavailability across a wide spectrum of prodrugs, with many showing a 2.5-25-fold increase in oral bioavailability.

Preferably, oral bioavailability is enhanced by at least 50% compared to the parent drug. More preferably, oral bioavailability is enhanced by 100%.

Agents are known that inhibit CYP3A4 in the gastrointestinal tract. For example, grapefruit juice is known to decrease the activity putatively via a component in the grapefruit juice (e.g. Bergamottin; Chem Res Toxicol 1998, 11, 252-259) which results in the inactivation and/or down regulation of the enzyme. Since only GI CYP3A4 is affected, the oral absorption of the prodrugs of this invention should be enhanced. A combination of agents that inhibit, inactivate, or downregulate P450s that metabolize the prodrugs will have the effect of enhancing their absorption and thereby making more prodrug available for metabolism in the liver. The net effect of the combination would therefore be to deliver more drug to the liver after oral absorption.

Sustained Delivery

Drugs that undergo rapid elimination in vivo often require multiple administrations of the drug to achieve therapeutically-effective blood levels over a significant period of time. Other methods are also available including sustained release formulations and devices. Prodrugs that breakdown over time can also provide a method for achieving sustained drug levels. In general, this property has been not been possible with the known phosph(on)ate prodrugs since either they undergo rapid hydrolysis in vivo (e.g. acyloxyalkyl esters) or very slow conversion (e.g. di-aryl prodrugs).

The cyclic phosph(oramid)ates of the invention are capable of providing sustained drug release by providing a steady release of the drug over time. For example, most phosphates undergo dephosphorylation in vivo within minutes after systemic administration via the action of phosphatases present in the blood. Similarly, acyloxyalkyl esters of these phosphates undergo rapid esterase-mediated hydrolysis to the phosphate which then is rapidly dephosphorylated. Some prodrugs of the current invention may enable prolonged drug delivery since many of the present prodrugs are oxidized slowly over time to the phosph(on)ate in the livers.

Sustained delivery of the drugs is achievable by selecting the prodrugs of formula I that are hydrolyzed in vivo at a rate capable of maintaining therapeutically effective drug levels over a period of time. The cleavage rate of the drug may depend on a variety of factors, including the rate of the p450 oxidation, which is dependent on both the substituents on the prodrug moiety, the stereochemistry of these substituents and the drug itself. Moreover, sustained drug production will depend on the rate of elimination of the intermediate generated after oxidation and the rate and availability of the prodrug to the liver, which is the major site of oxidation. Identification of the prodrug with the desired properties is readily achieved by screening the prodrugs in an assay that monitors the rate of drug production in the presence of the major p450 enzyme involved in the metabolism, in the presence of liver microsomes or in the presence of hepatocytes. These assays are illustrated in Examples G, D, and E, and I, respectively.

It is contemplated that prodrugs of the present invention could be combined to include, for example, one prodrug which produces the active agent rapidly to achieve a therapeutic level quickly, and another prodrug which would release the active agent more slowly over time.

Examples of drugs with different rates of cleavage are shown in Example S. As indicated in this example, the rate of a drug release depends on the prodrug stereochemistry.

Improved Pharmacodynamic Half-Life

The pharmacodynamic half-life of a drug can be extended by the novel prodrug methodology as a result of both its ability to produce drug over a sustained period and in some cases the longer pharmacokinetic half-life of the prodrug. Both properties can individually enable therapeutic drug levels to be maintained over an extended period resulting in an improvement in the pharmacodynamic half-life. The pharmacodynamic half-life can be extended by impeding the metabolism or elimination pathways followed by the parent drug. For some drugs, the prodrugs of the present invention are able to impede the metabolism or elimination pathways followed by the parent drug and thereby exist for extended periods in an animal.

An example of the ability of the prodrug class to impede metabolic pathways associated with the parent drug is shown by the araAMP prodrug (30.1). In comparison to araAMP, 30.1 shows no ara-hypoxanthine ("araH") which is the known metabolic byproduct of araA produced in e.g. plasma and the gastrointestinal tract after oral or i.v./administration (Example O). AraAMP on the other hand is rapidly and nearly completely converted to araH, which is produced by first dephosphorylation to araA via phosphatases followed by deamination of the base via adenosine deaminase. The prodrug moiety prevents both dephosphorylation and deamination from occurring, as shown in Examples B and C.

A common route of elimination of phosph(on)ate drugs is via the kidneys and a transporter that recognizes anionic compounds. Complete elimination of phosphonate and phosphate containing drugs from the circulation often occurs only minutes after drug administration (e.g. PMEA). The prodrugs of this invention slow the elimination of the drug by removing the negative charge until after oxidation and hydrolysis in liver and like tissues.

The prodrug of PMEA 28.4 results in high PMEA disphosphate levels in the liver. Moreover, minor amounts of the parent drug is eliminated via the kidneys (Examples O and Q). In contrast, PMEA the bis POM prodrug of PMEA result in high levels of PMEA in the urine. Thus, prodrugs of the invention can improve the pharmacodynamic half-life by reducing the amount eliminated by the kidneys.

Enhanced Selective Delivery of Agents to the Liver and Like Tissues

Delivery of a drug to the liver with high selectivity is desirable in order to treat liver diseases or diseases associated with the abnormal liver properties (e.g. diabetes, hyperlipidemia) with minimal side effects. Efforts to deliver drugs to the liver with relatively high organ specificity have primarily focused on strategies involving receptor mediated endocytosis (RME). RME transport systems are common to normal macrophages, hepatocytes, fibroblasts and reticulocytes [Wileman et al., *Biochem. J.* 232, 1-14 (1985)]. Macromolecules internalized via RME include asialoglycoproteins, LDL, transferrin and insulin. Another strategy for drug delivery to the liver uses colloids or liposomes both of which are subject to phagocytosis by the macrophage (Kupffer cells in liver) and localized in tissues of the reticuloendothelial system (e.g. liver, spleen and bone). Of these possible approaches, most of the attention has focused on the use of glycoprotein and oligosaccharide drug conjugates as a method for organ specific delivery [Meijer, D. K. F. and van der Sluijs, P. *Pharm. Res.*, 6 105-118 (1989)]. Natural desialylated glycoproteins, e.g. asialoorosomucoid and asialofetuin, and neoglycoproteins, e.g. mannosylated and lactosylated albumin, and polysacharrides such as arabinogalactan have been used to successfully deliver drugs to the liver.

Conjugates of several drug classes have been reported, including the antiviral drug araAMP. For example, araA-MP conjugated to lactosaminated serum albumin was effective in treating chronic type B hepatitis without signs of neurotoxicity [Fiume et al., *The Lancet* 13 (1988)]. Because conjugation of drugs to plasma proteins may have several limitations, including uptake by scavenger receptors on non-hepatocytes, immunogenicity, instability of the protein to conjugation conditions, and in vivo metabolism, efforts have focused on the use of oligosaccharide conjugates. One promising approach uses arabinogalactan conjugates. The araAMP conjugate is reported to have good activity in woodchucks carrying the hepatitis virus [Enriquez, P. M., Jung, C., Josephson, L. *Bioconj. Chem.* 6, 195-202 (1995)]. Limitations in approaches described above include drug loading capacity, complexity of the manufacture and characterization of the conjugate, receptor downregulation, etc.

The prodrugs of the current invention circumvent these limitations since they represent simple, low molecular weight modifications of the drug which enable liver-selective drug delivery on the basis of the their sensitivity to liver-abundant enzymes. The prodrug cleavage mechanism was identified through studies shown in Example L. As shown in Example A, prodrugs are stable to aqueous solution across a broad pH range and therefore do not undergo a chemical cleavage process to produce the parent drug. In addition the prodrugs are stable to esterases and blood proteins (Examples B and C). In contrast to the parent drug, the prodrugs are rapidly cleaved in the presence of liver microsomes from rats (Example D) and humans (Example E). The drug is also produced in freshly isolated rat hepatocytes where it is detected as the parent drug (Example I) or as a further metabolite generated by phosphoryation of the drug (Example K). Moreover, when the parent drug is an FBPase inhibitor, the production of the drug is supported by the ability of the prodrug to result in potent gluconeogenesis inhibition (Example J).

Possible specific enzymes involved in the cleavage process were evaluated through the use of known cytochrome p450 inhibitors (Example F). The studies indicate that the isoenzyme cytochrome CYP3A4 is responsible based on ketoconozole inhibition of drug formation. Moreover, the recombinant form of CYP3A4 was shown to catalyze prodrug cleavage (Example G).

Analysis of the tissue distribution of CYP3A4 indicates that it is largely expressed in the liver (DeWaziers et al., J. Pharm. Exp. Ther. 253: 387 (1990)). Moreover, analysis of tissue homogenates in the presence of prodrugs indicates that only the liver homogenate cleaves the prodrug and to a lesser degree homogenates from tissues in the upper GI. Kidney, brain, heart, stomach, spleen, muscle, lung, and testes showed no appreciable cleavage of the prodrug.

Evidence of the liver specificity was also shown in vivo after both oral and i.v. administration of the prodrugs. Administration of a prodrug of araAMP (30.1) i.v. gave liver levels of the bioactive drug araATP 2-5-fold greater than achieved by an equivalent dose of either araA or araAMP (Example O). In contrast, the prodrug failed to produce detectable amounts of the araA bi-product araH, which, as reported in the literature, was readily detected after either araA or araAMP administration (Example O). Similarly, the prodrug 30.1 achieved high liver levels without production of the metabolite araH after oral administration. Since the prodrugs are cleaved by liver abundant enzymes, oral administration may enable even higher liver specificity via a first pass effect. Example P demonstrates the liver specificity for the prodrug 28.4 of PMEA compared to PMEA and the bisPOM of PMEA (28.3) (Example Q). Administration of these compounds i.v. led to detection of the active metabolite PMEA diphosphate in the liver. In contrast to both PMEA and bisPOM PMEA, prodrug 28.4, showed no detectable PMEA in either the blood or urine supporting its high liver specificity (Example Q).

Agents that induce P450 activity, e.g. CYP3A4 activity, are known. For example, rifampicin, glucocorticoids, phenobarbital, erythromycin are known to enhance CYP3A4 activity in rat and human livers following. P450 activity can be monitored in humans by non-invasive methods e.g. via [14C] erythromycin breath test. These studies are useful in the identification of agents that activate CYP3A4 in humans. Accordingly, for prodrugs where drug delivery is limited by prodrug metabolism rate (e.g. rate of clearance of prodrug is fast relative to rate of prodrug cleavage), agents such as rifampicin can be used in combination or as adjuncts or pre-treatments to enhance CYP3A activity in the liver and thereby to increase liver drug levels.

The biologically active agent is detected in the liver following administration of drugs of formulae VI-VIII, shown below:

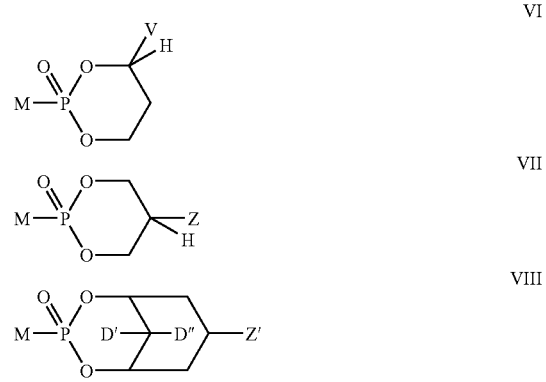

Prodrugs of formulae VI, VII, and VIII are particularly preferred.

The mechanism of cleavage could proceed by the following mechanisms. Further evidence for these mechanisms is indicated by analysis of the bi-products of cleavage. Prodrugs of formula VI generate phenyl vinyl ketone whereas prodrugs of formula VIII were shown to generate phenol (Example L).

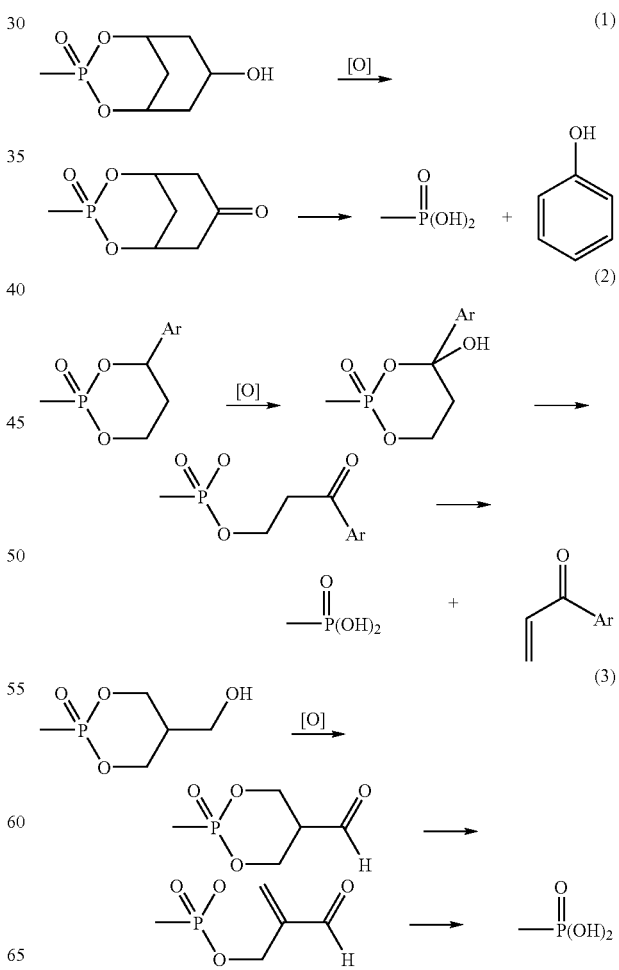

Although the esters in the invention are not limited by the above mechanisms, in general, each ester contains a group or atom susceptible to microsomal oxidation (e.g. alchohol, benzylic methine proton), which in turn generates an intermediate that breaks down to the parent compound in aqueous solution via β-elimination of the phosph(on)ate diacid.

Increased Therapeutic Index

The prodrugs of this invention can significantly increase the therapeutic index ("TI") of certain drugs. In many cases, the increased TI is a result of the high liver specificity. For example, araA and araAMP are known to produce significant systemic side effects and these side effects are associated with blood levels of the araA byproduct araH. Presumably the side effects are a result of toxicities of araH or araA in extrahepatic tissues (e.g. nerves) which produce e.g. the neuropathies associated with the drug in man (>40% of patients receiving araA). As indicated in Example O, prodrug 30.1 showed a substantial shift in the liver (araATP)/urine (araH) ratio in comparison with araAMP.

Renal toxicity is a common toxicity associated with phosphonic acids. The toxicity results from transport, e.g. via the organic anion transporters located on the basolateral membrane of the renal proximal tubule, of the negatively charged drug into e.g. tubular cells which then accumulate the drug to high concentrations unless there is an equally efficient transport of the drug out of the cell via luminal transport mechanisms (e.g. anion-exchange or facilitated diffusion). Many examples have been reported in the literature of nephrotoxic phosphonic acids, e.g. PMEA and HPMPA. The novel prodrug of PMEA showed only small amounts of PMEA in the urine relative to either PMEA or bisPOM PMEA at doses that achieved comparable liver drug levels (Examples O and Q).

Another common toxicity associated with phosphonic acid drugs is gastrointestinal toxicity via in some cases GI erosions. Prodrugs of the current invention can decrease GI toxicities, especially toxicities produced by direct action of the drug on the GI tract after oral administration. Similar to the kidney, gut epithelial cells have organic anion transporters which can result in high intracellular drug levels and cytotoxicity. Since the negatively charged phosph(on)ate is not revealed until after absorption and cleavage in the liver, prodrugs of this invention reduce gut toxicity.

Several toxicities are also associated with nearly all anticancer agents. In an effort to decrease these toxicities during treatment of primary or secondary liver cancers, drugs are sometimes administered directly into the portal artery in order to increase liver drug exposure. Since oncolytic drugs typically are associated with significant side effects, local administration enables greater hepatic uptake and thereby decreased extrahepatic toxicities. To further increase liver uptake, chemoembolization is sometimes used in conjunction with hepatic artery drug infusion. The high liver specificity of the prodrugs in the current invention suggest that systemic side effects will be similarly minimized by the novel prodrug approach.

Moreover, primary and secondary liver cancers are particularly resistant to both chemotherapy and radiotherapy. Although the mechanism for the resistance is not completely understood, it may arise from increased liver gene products that lead to rapid metabolism and/or export of chemotherapeutic agents. In addition, the liver, which is generally associated with xenobiotic metabolism and generation of cytotoxic intermediates, is equipped by nature with multiple protective mechanism so that damage from these intermediates are minimized. For example, the intracellular concentration of glutathione is very high in the liver relative to other tissues presumably so that intermediates capable of alkylating proteins and DNA are detoxified through a rapid intracellular reaction. Consequently, the liver may be resistant to chemotherapeutic agents because of these mechanisms and therefore require higher than normal concentrations of the oncolytic agent to achieve success. Higher liver concentrations require higher doses of the drug which commonly result in extrahepatic toxicities.

Prodrugs of the current invention achieve similar improvement in the response rate relative to extra-hepatic toxicities. This improvement in the therapeutic index provides an alternative strategy for the treatment of liver diseases, e.g. primary and secondary liver cancers.

The high liver specificity of prodrug cleavage implies that the by-product of prodrug cleavage is also primarily produced in the liver. Accordingly, toxicities associated with the by-product are minimized since the by-product frequently undergoes rapid detoxification reactions that either eliminate or minimize by-product toxicity. For example, reactions between the by-product and compounds and/or proteins present in the hepatocytes (e.g. glutathione and the α,β-unsaturated olefin generated by prodrugs of formulae VI and VII). Moreover, enzymes present in the liver may also further transform the by-product into a non-toxic compound (e.g. oxidation and/or sulfation of phenol, or reduction of the α,β-unsaturated ketone, etc.). In addition, intramolecular reactions that involve cyclization reactions between a reactive group and the α,β-unsaturated carbonyl-containing compound generated by prodrugs of formulae VI and VII can minimize by-product toxicity.

The cytotoxicity of the prodrugs are readily evaluated using cell lines that lack P450 activity (e.g. CYP3A4 activity).

Increased TI can also be achieved by delivery of greater amounts of the biologically active agent to the liver relative to the equivalent doses of the parent drug. Increased liver levels of the biologically active agent is achieved by administration of prodrugs together with agents that induce P450 activity, e.g. CYP3A4 activity (e.g. rifampicin, glucocorticoids, phenobarbital, erythromycin).

In some cases, prodrugs of phosphoramidates that undergo cleavage by liver microsomes have been described (e.g. cyclophosphamide). These drugs, however, are not used for liver diseases and are thought to diffuse out of the liver after the initial oxidation and then undergo a slow base catalyzed elimination in other tissues and cells to generate the biologically active agent. The prodrugs described in this invention can be tailored such that the oxidation, but especially the elimination step, are fast and therefore occur primarily in the liver. For example, cyclophosphamide after oxidation in the liver and before the β-elimination reaction exists as a mixture of the hydroxylated compound and the ring-opened aldehyde. Only the latter compound is converted to the phosphonic acid and acrolein. The conversion is slow due to the high propensity of the aldehyde to hydrate, undergo recyclization or undergo further oxidation. In fact, the aldehyde exists only as a minor component in solution (<5%). Prodrugs of formula VI-VII do not readily recyclize, since the carbonyl product is a ketone except when Z=CH2OR in formula VII. Ketones do not hydrate to a great extent (<2%) nor do they undergo the same metabolism associated with the aldehyde.

Non-Mutagenic Prodrugs

Prodrugs of the invention are generated by a postulated mechanism involving an initial oxidation followed by a β-elimination reaction. In some cases, e.g. certain prodrugs of formula VI and formula VII, the biproduct of the reaction is an α,β-unsaturated carbonyl compound, e.g. vinyl phenyl ketone for prodrugs where V=Ph, Z, W and W'=H. Compounds can act as Michael acceptors and react with nucleophiles via a Michael addition. Mutagenesis is observed with some α,β-unsaturated ketones and certain toxicities arise from Michael addition adducts (e.g. acrolein produces bladder toxicities). The degree to which these activities limit the use of compounds of Formula VI is dependent on the severity of the toxicity and the indicated disease.

Prodrugs that produce non-toxic and non-mutagenic biproducts are especially preferred for the treatment of chronic diseases (e.g. diabetes). Frequently, it is difficult to predict the mutagenic properties of a compound. For example, a number of acrylates have been shown to produce positive mutagenic responses as indicated by increased chromosome aberrations and micronucleus frequencies in cultured L5179Y mouse lymphoma cells (Dearfield et al., Mutagenesis 4, 381-393 (1989)). Other acrylates, however, are negative in this test (J. Tox. Envir. Health, 34, 279-296 (1991)) as well as in the Ames test and the CHO assay which measures newly induced mutations at the hypoxanthine-guanine phosphoribosyltransferase (hgprt) locus (Mutagenesis 6, 77-85 (1991)). Phenyl vinyl ketone lacks teratogenic activity in rat embryos in culture suggesting that it may not be mutagenic nor highly toxic (Teratology 39, 31-37 (1989)).

Since mutagenicity and toxicity are not highly predictable properties, non-mutagenic prodrugs of formula I and their associated bi-products can be readily identified by conducting well known in vitro and in vivo assays. For example, compounds can be tested in non-mammalian cell assays such as the Ames test, a fluctuation test in *Kl. pneumoniae*, a forward mutation assay with *S. typhimurium*, a chromosome loss assay in *Saccharomyces cerevisiae*, or a D3 recombinogenicity assay in *Saccharomyces cerevisiae*. Compounds can also be tested in mammalian cell assays such as the mouse lymphoma cells assay (TK+/− heterozygotes of L5178Y mouse lymphoma cells), assays in Chinese hamster ovary cells (e.g. CHO/HGPRT assay), and an assay in rat liver cell lines (e.g. RL1 or RL4). Each of these assays can be conducted in the presence of activators (e.g. liver microsomes) which may be of particular importance to these prodrugs. By conducting these assays in the presence of the liver microsomes, for example, the prodrug produces products, such as phenol or vinyl ketone. The mutagencity of the by-product is measured either directly or as a prodrug where the results are compared to the parent drug alone. Assays in liver cell lines are a preferred aspect of the invention since these cells have higher glutathione levels, which can protect the cell from damage caused by a Michael acceptor, as well as greater levels of intracellular enzymes used to detoxify compounds. For example, the liver contains reductases that with some bi-products might result in reduction of the carbonyl.

A variety of end points are monitored including cell growth, colony size, gene mutations, micronuclei formation, mitotic chromosome loss, unscheduled DNA synthesis, DNA elongation, DNA breaks, morphological transformations, and relative mitotic activity.

In vivo assays are also known that assess the mutagenicity and carcinogenicicty of compounds. For example, a non-mammalian in vivo assay is the *Drosophila* sex-linked recessive lethal assay. Examples of mammalian in vivo assays include the rat bone marrow cytogenetic assay, a rat embryo assay, as well as animal teratology and carcinogenicity assays.

Resistance Bypass

Drug resistance following prolonged treatment is a common finding for anticancer drugs and antiviral drugs used to treat hepatitis. The mechanisms for the drug resistance have been identified in many cases and involve both decreased drug transport into cancer cells, increased drug export, increased drug metabolism and decreased precursor conversion to the active drug. Many of the drugs used to treat these diseases are drugs that are converted to the corresponding triphosphate, which in turn acts as a DNA chain terminator, inhibitor of DNA polymerase or inhibitor of reverse transcriptase. In some cases, drug resistance results from a decrease in activity of the enzymes responsible for synthesis of a nucleoside mono-phosphate (e.g. kinases such as thymidylate kinase or enzymes in the biosynthesis pathway of 5-fluoro-2'-deoxy UMP). In other cases nucleoside transporters are downregulated leading to lower intracellular nucleoside drug concentration and therefore less nucleoside is available for phosphorylation. Similarly, increased expression of multidrug resistant gene product is postulated to increase the export of nucleotides from cancer cells. Administration of the prodrug generates the monophosphate by a different pathway avoiding the pathways that cause the resistance to the parent drug. Thus, the prodrugs of the present invention can achieve a therapeutic effect in cells resistant to the parent drug.

Some drugs as the mono- or triphosphate analogs are highly potent inhibitors of the target enzyme (e.g. HBV polymerase) but are poorly effective in cells or in vivo due to poor phosphorylation. These drugs are especially preferred drugs since the prodrug strategy delivers the monophosphate. Frequently, the first phosphorylation of the nucleoside is the rate-limiting step whereas phosphorylation of the monophosphate to the triphosphate by mammalian kinases is rapid and relatively insensitive to structural variations.

Types of Parent Drugs

Various kinds of parents drugs can benefit from the prodrug methodology of the present invention. Parent drugs of the form MH, which are phosphorylated to become the biologically active drug are well suited for use in the prodrug methodology of the present invention. There are many well known parent drugs of the form MH which become biologically active via phosphorylation. For example, it is well known that antitumor and antiviral nucleosides are activiated through phosphorylation. These compounds include araA; AZT; d4T; ddI; ddA; ddC; L-ddC; L FddC; L-d4C; L-Fd4C; 3TC; ribavirin; 5-fluoro 2'deoxyuridine; FIAU; FIAC; BHCG; L FMAU; BvaraU; E-5-(2-bromovinyl-2' deoxyuridine; TFT; 5-propynyl-1 arabinosyluracil; CDG; DAPD; FDOC; d4C; DXG; FEAU; FLG; FLT; FTC; 5-yl-carbocyclic 2'deoxyguanosine; oxetanocin A; oxetanocin G; Cyclobut A, Cyclobut G; dFdC; araC; bromodeoxyuridine; IDU; CdA; FaraA; Coformycin, 2'-deoxycoformycin; araT; tiazofurin; ddAPR; 9-(arabinofuranosyl)-2,6 diaminopurine; 9-(2'-deoxyribofuranosyl)-2,6 diaminopurine; 9-(2'-deoxy 2'fluororibofuranosyl)-2,6-diaminopurine; 9 (arabinofuranosyl)guanine; 9-(2' deoxyribofuranosyl)guanine; 9-(2'-deoxy 2'fluororibofuranosyl)guanine; FMdC; 5,6 dihydro-5-azacytidine; 5-azacytidine; 5-aza 2'deoxycytidine; AICAR; ACV, GCV; penciclovir; (R)-9-(3,4 dihydroxybutyl)guanine; cytallene; PMEA, PMEDAP, HPMPC, HPMPA, FPMPA, and PMPA.

Preferred antiviral drugs include:

araA; AZT; d4T; ddI; ddA; ddC; L-ddC; L FddC; L-d4C; L-Fd4C; 3TC; ribavirin; FIAU; FIAC; BHCG; L-FMAU; BvaraU; E-5-(2 bromovinyl-2'-deoxyuridine; TFT; 5-propynyl 1-arabinosyluracil; CDG; DAPD; FDOC; d4C; DXG; FEAU; FLG; FLT; FTC; 5-yl-carbocyclic 2'deoxyguanosine; cytallene; oxetanocin A; oxetanocin G; Cyclobut A, Cyclobut G; bromodeoxyuridine; IDU; araT; tiazofurin; ddAPR; 9-(arabinofuranosyl)-2,6 diaminopurine; 9-(2'-deoxyribofuranosyl)-2,6 diaminopurine; 9-(2'-deoxy 2'fluororibofuranosyl)-2,6-diaminopurine; 9 (arabinofuranosyl) guanine; 9-(2' deoxyribofuranosyl)guanine; 9-(2'-deoxy 2'fluororibofuranosyl)guanine; FMdC; 5,6 dihydro-5-azacytidine; 5-azacytidine; 5-aza 2'deoxycytidine; ACV, GCV; penciclovir; (R) 9-(3,4-dihydroxybutyl)guanine; cytallene; PMEA; PMEDAP; HPMPC; HPMPA; FPMPA; PMPA; foscarnet; and phosphonoformic acid.

More preferred antiviral drugs include:

araA; AZT; d4T; ddI; ddA; ddC; L-ddC; L FddC; L-d4C; L-Fd4C; 3TC; ribavirin; FIAU; FIAC; L-FMAU; TFT; CDG; DAPD; FDOC; d4C; DXG; FEAU; FLG; FLT; FTC; 5-yl carbocyclic 2'deoxyguanosine; cytallene; oxetanocin A; oxetanocin G; Cyclobut A, Cyclobut G; araT; ACV, GCV; penciclovir; PMEA; PMEDAP; HPMPC; HPMPA; PMPA; foscarnet; araA.

Most preferred antiviral drugs include:
3TC;
penciclovir;
FMAU;
DAPD;
FTC;
Cyclobut G;
ACV;
GCV;
PMEA;
HPMPA;
5-yl-carbocyclic 2'deoxyguanosine;
ribavirin Preferred anticancer drugs include:
dFdC; 2',2'-difluorodeoxycytidine (gemcitabine);
araC; arabinosylcytosine (cytarabine);
F-ara-A; 2-fluoroarabinosyladenosine (fludarabine); and
CdA; 2-chlorodeoxyadenosine (cladribine).
2'-deoxy-5-iodouridine
Coformycin
2'-deoxycoformycin
Tiazofurin
Ribavirin
5-fluoro-2'deoxyuridine
9-(arabinofuranosyl)-2,6-diaminopurine
9-(2'-deoxyribofuranosyl)-2,6-diaminopurine
9-(2'-deoxy-2'-fluororibofuranosyl)-2,6-diaminopurine
9-(arabinofuranosyl)-guanine
9-(2'-deoxyribofuranosyl)-guanine
9-(2'-deoxy-2'-fluororibofuranosyl)-guanine
5,6-dihydro-5-azacytidine;
5-azacytidine; and
5-aza-2'-deoxycytidine.

More preferred anticancer drugs include:
dFdC;
araC;
FaraA;
CdA;
5-fluoro 2'deoxyuridine; and
GCV.

Drugs containing a phosphonic acid ($C-PO_3^{2-}$) moiety are also suitable parent drugs advantageously used in the present invention. These drugs are biologically active either in the form of $MPO_3^{2-}$; $MP_2O_6^{3-}$, or $MP_3O_9^{4-}$. Phosphonic acids that are also suitable for this prodrug delivery strategy include protease inhibitors that are useful for example as antihypertensives, anticancer or antiinflammatory agents. The novel prodrug methodology can be applied to NEP inhibitors, (DeLambert et al. *J. Med. Chem*. 37:498 (1994)), ACE inhibitors, endothelin converting enzyme inhibitors, purine nucleoside phosphorylase inhibitors of metalloproteases, involved in tumor metastasis, and inhibitors of collagenase (Bird et al., J. Med. Chem. 37, 158-169 (1994). Moreover, phosphonic acids useful as NMDA antagonists which are useful for treating a variety of conditions, including stroke, head trauma, pain, and epilepsy. Other phosphonic acids that could benefit from the prodrug strategies are phosphonic acids reported by Squibb that inhibit squalene synthase by Hoechst that are immunomodulators, by Merck that are antidepressants, by Ciba-Geigy and Marion Merrel Dow that are immunosuppressants via inhibition of purine nucleoside phosphorylase, and by Bristol-Myers Squibb, Gilead that are antivirals. Certain antibiotics might be suitable, especially antibiotics such as D-alanine racemase inhibitors and fosfomycin and associated analogs.

The following compounds and their analogs can be used in the prodrug methodology of the present invention:

NEP Inhibitors
(S)-3-[N-[2-[(phosphonomethyl)amino]-3-(4-biphenylyl) propionyl]amino]propionic acid by DeLombaert et al in J Med Chem. Feb. 18, 1994; 37(4):498-511

Collagenase Inhibitors
N,[N-((R)-1-phosphonopropyl(-(S)-leucyl]-(S)-phenylalanine N-methyl amide by Bird et al. in *J Med Chem* Jan. 7, 1994; 37(1):158-69

Angiotensin Coverting Enzyme Inhibitors
(IR)-1-(N-(N-acetyl-L-isoleucyl)-L-tyrosyl)amino-2-(4-hydroxyphenyl)ethy 1-phosphonic acid by Hirayama et al. in *Int J Pept Protein Res* July 1991; 38(1):20-4.

Endothelin Inhibitor
CGS 26303 by DeLombaert et al. *Biochem Biophys Res Commun* Oct. 14, 1994; 204(1):407-12
(S,S)-3-Cyclohexyl-2-[[5-(2,4-difluorophenyl)-2-[(phosphonomethyl)amino]pent-4-ynoyl]amino]propionic acid by Wallace et al. *J Med Chem* Apr. 23, 1998; 41(9):1513-23
(S,S)-2-[[5-(2-fluorophenyl)-2-[(phosphonomethyl)amino] pent-4-ynoyl]amino]-4-methylpentanoic acid
(S,S)-2-[[5-(3-fluorophenyl)-2-[(phosphonomethyl)amino] pent-4-ynoyl]+++amino]-4-methylpentanoic acid NMDA/AMPA Antagonists
N-phosphonoalkyl-5-aminomethylquinoxaline-2,3-diones as described in Bioorg Med Chem Lett. Jan. 18, 1999; 9(2):249-54
3-(2-carboxypiperazin-4-yl)-1-propenyl-1-phosphonic acid by Bespalov et al. in *Eur J Pharmacol* Jun. 26, 1998; 351(3):299-305
[2-(8,9-dioxo-2,6-diazabicyclo[5.2.0]non-1(7)-en-2-yl)-ethyl]phosphonic acid D,L-(E)-2-amino-4-[3H]-propyl-5-phosphono-3-pentenoic acid
6,7-dichloro-2(1H)-oxoquinoline-3-phosphonic acid by Desos et al in J Med Chem. Jan. 5, 1996; 39(1):197-206.
cis-4-(phosphonomethyl)piperidine-2-carboxylic acid (CGS 19755)

Purine Nucleoside Phosphorylase Inhibitors

[7-(2-amino-1,6-dihydro-6-chloro-9H-purin-9-yl)-1,1-difluoroheptyl]phosphonic acid and
[4-(5-amino-6,7-dihydro-7-oxo-3H-1,2,3,-triazolo[4,5-d]-pyrimidin-3-yl)butyl]phosphonic acid.
[[[5-(2-amino-1,6-dihydro-6-oxo-9H-purin-9-yl)pentyl]phosphinico]methyl]phosphonic acid by Kelly et al. in *J Med Chem* Mar. 17, 1995; 38(6):1005-14
(2-[2-[(2-amino-1,6-dihydro-6-oxo-9H-purin-9-yl)methyl]-phenyl]ethenyl)-phosphonic acid by Weibel et al in Biochem Pharmacol. Jul. 19, 1994; 48(2):245-52.
9-(3,3-Dimethyl-5-phosphonopentyl)guanine by Guida et al. in *J Med Chem* Apr. 15, 1994; 37(8):1109-14.

Alanine Racemase Inhibitors

DL-(1-Amino-2-propenyl)phosphonic acid by Vo-Quang et al. in *J Med Chem* April 1986; 29(4):579-81

Squalene Synthase Inhibitors

1-Hydroxy-3-(methylpentylamino)-propylidene-1,1-bis-phosphonic acid by Amin et al. in Arzneimittelforschung. August 1996; 46(8):759-62.
BMS188494 is POM prodrug of BMS 187745 by Dickson et al. in J Med Chem. Feb. 2, 1996; 39(3):661-4.

Treatment of Cancer:

The prodrug strategy in the current invention encompasses several features that are advantageously used in cancer therapies. Many of the known anticancer drugs are nucleosides that undergo phosphorylation to the monophosphate which frequently is further converted to the triphosphate. The prodrug strategy increases the effectiveness of these drugs because the prodrug is cleaved by liver-abundant enzymes and therefore higher levels of the active metabolite are achieved in the liver relative to extrahepatic tissues. The net effect is greater efficacy and/or a greater therapeutic index. In some cases, the prodrug strategy also increases the effectiveness of these drugs by bypassing well-known resistance mechanisms including mechanisms involved in the uptake, intracellular biosynthesis of the active metabolite, export and metabolism of the monophosphate. Examples of preferred drug candidates that are specifically amenable to the strategy include, e.g. dFdC, araC, F-ara, CdA, and 5-fluoro-2'-deoxyuridine.

Some prodrugs may result in some accumulation of the monophosphate in cells. Certain monophosphates are useful for the treatment of cancers, e.g. monophosphates that are potent inhibitors of thymidylate synthase (TS) and IMP dehydrogenase. Some TS inhibitors are reported to be moderately effective in treating liver cancers. For example, 5-FU and 5-FdUMP are effective. These drugs, however, are plagued by drug resistance and severe side effects. To avoid the latter, 5-FU analogs are often delivered via the portal artery to achieve the highest possible liver levels. Drug resistance is also very common. Accordingly, 5-FdUMP and associated analogs are suitable targets for the prodrug strategy. Other nucleosides such as ribavirin, tiazofurin and coformycin can and analogs thereof are also suitable targets for prodrug strategy.

Liver cancers are also very resistant to radiotherapy. One method for enhancing radiotherapy is to administer radiosensitizers. Radiosensitizers such as 2'-deoxy-5-iodouridine are nucleosides suitable for the prodrug technology since the prodrugs will be cleaved by only P450 containing cells. After cleavage the monophosphate can be further phosphorylated to the triphosphate and trapped inside the cell making the cell more sensitive to radiotherapy.

Treatment of Viral Infections:

Drugs useful for treating viruses that infect the liver and cause liver damage, e.g. hepatitis virus strains, exhibit similar properties to the anticancer nucleoside drugs in terms of efficacy, side effects and resistance. Prodrugs of these nucleosides would therefore be useful in treating hepatitis. In some cases, the drugs are already targeted for hepatitis (e.g. araA, 3TC, L-FMAU, FTC, BMS 200,975). The prodrugs of these compounds could enhance the efficacy, increase the therapeutic index, improve the pharmacodynamic half-life and/or bypass drug resistance. Prodrugs of other agents used to treat viral infections other than hepatitis may also be made useful by administration of the prodrugs of this invention since these drugs are good antivirals (e.g. acyclovir, but useful for other viral infections because they are phosphorylated to the monophosphate by a viral kinase. The monophosphate is converted to the biologically active triphosphate by mammalian kinases. Accordingly, delivery of the monophosphate using this clan of prodrugs enables treatment of hepatitis by drugs normally used to treat other viral infections.

Agents Used to Modulate CYP Activity

A variety of methods may be used to enhance the in vivo activity of compounds of formula I. For example, various drugs are known that enhance cytochrome P450 (CYP) activity. Enhancement frequently entails increased gene transcription. Four families of CYPs are particularly susceptible to induction, namely CYP1-4. Induction is purportedly via receptors that are activated by various xenobiotics. For example, CYP1 gene activation frequently involves activation of the Ah receptor by polycyclic aromatic hydrocarbons. CYP2-4 are activated via orphan nuclear receptors. Data suggests that the nuclear receptor CAR (constitutively Active Receptor) is responsible for phenobarbital CYP activation, especially CYP2 genes. The pregnane nuclear receptors (PXR or PAR or SXR) are thought to activate CYP3A genes whereas the PPAR (peroxisome proliferator activate receptor) is linked to CYP4 gene activation. All three xenobiotic receptors are highly expressed in the liver which accounts for the liver specificity of the P450 gene induction.

Xenobiotics known to induce CYP3 genes include phenobarbital, a variety of steroids, e.g. dexamethasone, antibiotics, e.g. rifampicin, and compounds such as pregnenolone-16a carbonitrile, phenytoin, carbamazepine, phenylbutazone, etc. A variety of methods are known that enable identification of xenobiotics that induce P450s, including a reporter gene assay in HepG2 cells (Ogg et al., *Xenobiotica* 29, 269-279 (1999). Other inducers of the CYP3A subfamily are known that act at the post-transcriptional level either by mRNA or protein stabilization, e.g. clotrimazole, TA and erythromycin. Compounds known to induce CYPs or identified in in vitro assays are then used to enhance CYP activity in vivo. For example, CYP activity is monitored in rats pre-treated with CYP modulators by e.g. evaluating liver microsomes over a period of time to determine the optimal pre-treatment period, dose and dosing frequency. Rats with enhanced CYP activity, especially the CYP activity responsible for activation of the prodrugs (e.g. CYP3A4), are then treated with compounds of formula 1. Enhanced CYP activity can then lead to enhanced prodrug conversion and liver specificity. For example, enhanced metabolism of cyclophosphamide was found with pre-treatment with phenobarbital (Yu et al., *J. Pharm. Exp. Ther.* 288, 928-937 (1999).

In some cases, enhanced CYP activity may lead to unwanted drug metabolism. For example, enhanced activity of CYPs not involved in prodrug activation can result in increased drug metabolism and therefore decreased efficacy. In addition, increased CYP activity in other tissues, e.g. CYP3A4 in the gastrointestinal tract, could result in decreased prodrug absorption and liver drug levels. Inhibitors of CYP activity are known that might be useful in minimizing unwanted drug metabolism. For example, grapefruit juice is known to inactivate gastrointestinal. CYP3A4 and to result in enhanced absorption of numerous drugs metabolized by CYP3A4. CYP inhibitors are also known for many of the CYP subfamilies that can be useful for attenuating unwanted drug metabolism while maintaining CYP activity important for prodrug cleavage. For example, the CYP3A inhibitor TAO was used to modulate cyclophosphamide metabolism in vivo in a manner that decreased the formation of toxic metabolites that do not contribute to its antitumor activity.

Use for Treating Hepatocellular Carcinomas (HCC)

Oncolytic drugs such as etoposide, topotecan, taxol, etc. that contain a biologically important hydroxyl or oncolytic drugs such as mitomycin, anthracyclin antibiotics (e.g. dioxorubicin) that contain a biologically important amino group or oncolytic drugs that contain a sulfhydryl moiety are suitable drugs for conversion to compounds of formula 1. These compounds are especially useful for the treatment of HCC since transformed cells contain abundant CYP3A4 activity. Furthermore it is known that delivery of 5-FU, taxol and other oncolytic agents to the liver via portal vein or intra-arterial infusion has shown significant success with response rates as high as 50% (normal rate is less than 20%). However, the complexity, expense and high incidence of secondary complications associated with long-term percutaneous catheterization or infusion devices diminishes the likelihood that local drug administration will become the standard therapy for liver cancer. (Venook, A. P. *J. Clin. Oncol.* 12, 1323-1334 (1994); b) Atiq, O. T.; Kemeny, N.; Niedzwiecki, D.; et al. *Cancer*, 69, 920-924 (1992).)

Use for Treating Extra-Hepatic Carcinomas

Oncolytic drugs such as etoposide, topotecan, taxol, etc. that contain a biologically important hydroxyl or oncolytic drugs such as mitomycin, methotrexate, anthracyclin antibiotics (e.g. dioxorubicin) that contain a biologically important amino group or oncolytic drugs that contain a sulfhydryl moiety are suitable drugs for conversion to compounds of formula 1. In general, the CYP3 family of genes is expressed in normal tissues predominantly in the liver and gastrointestinal tract. CYP activity, however, is also known to be expressed in various soft tissue sarcomas and other cancers, possibly as part of a drug resistance mechanism. To date, CYP3 activity has been found in renal cancer, lung cancer, stomach cancer, breast cancer. Little tumor heterogeneity is observed (Murray et al., *J. Pathology*, 171, 49-52 (1993); Murray et al., *British J. Cancer*, 79, 1836-1842 (1999)). Accordingly, the prodrugs of formula 1 are useful for treating cancers in which CYP activity, particularly CYP3A, is present.

Methods for Monitoring Patient P450 Activity

CYP activity is known to exhibit significant differences across individuals. The range for CYP3A4 is 5- to 20-fold although most individuals are within a 3-fold range. Modest decreases are noted for individuals with liver disease (30-50%) or advanced age (25-50%). Differences for gender are even more modest (<25%). Methods for phenotyping an individual's CYP activity are known and could be useful in predicting who should receive drugs that modulate CYP activity. Evasive procedures include liver biopsy. Non evasive procedures have been reported, including an "erythromycin breath test" which is based on the exhalation of 14CO2 generated from the CYP3A-mediated N-demethylation of radiolabeled erythromycin (iv). (Watkins, *Pharmacogenetics* 4, 171-184 (1994)).

Gene Therapy

Introduction into tumor cells genes that encode for enzymes not normally expressed represents a new therapeutic strategy for increasing the therapeutic effectiveness of anticancer chemotherapies. The general strategy entails expression of an enzyme that catalyzes the breakdown of a prodrug of an anticancer drug thereby localizing the drug in or near the tumor mass and limiting exposure elsewhere. The strategy has been demonstrated using the HSV-TK gene wherein the thymidylate kinase specifically expressed in the transfected cells activates ganciclovir to the monophosphate which is then converted by other kinases to the tumor cell killing triphosphate. A similar strategy uses the bacterial cytosine deaminase gene for conversion of 5-fluorouracil to 5-fluorocytosine. Other genes have been considered including carboxypeptidase G2, nitro reductase, purine nucleoside phosphorylation, etc. In addition, CYP gene transfer has been explored as a way to enhance the chemotherapeutic effect of cyclophosphamide and ifosfamide, two drugs known to be activated by CYPs. For example, human breast cancer cells were sensitized by transfection with the CYP2B1 gene (Chen et al., *Cancer Research*, 56, 1331 1340 (1996)). The advantage of this strategy relative to the HSV-TK gene strategy is that the product of the CYP catalyzed oxidation readily diffuses outside of the tumor cell and into nearby cells. In contrast to monophosphate products of the HSV-TK strategy, the product can enter cells that are not in cell-cell contact and therefore produce a more widespread tumor killing effect (Chen and Waxman, *Cancer Research*, 55, 581-589 (1995)).

Compounds of formula 1 can be made more effective by using gene therapy to introduce the gene that encodes the CYP specifically involved in prodrug cleavage. The specific CYP that breaks down the prodrug is readily determined using some or all of the following steps: 1) demonstrate prodrug cleavage using human microsomes; 2) classify the subfamily by comparing activity with microsomes induced with various subfamily specific inducers (e.g. CYP3 enzymes are induced with a variety of steroids, e.g. dexamethasone, antibiotics, e.g. rifampicin, and compounds such as pregnenolone-16a carbonitrile, phenytoin, carbamazepine, phenylbutazone, etc.; 3) identify the CYP or CYPs responsible for prodrug activation by using known CYP subfamily specific inhibitors (e.g. troleandomycin, erythromycin, ketoconazole and gestodene) and/or by using neutralizing antibodies; 4) confirm CYP subfamily by demonstrating turnover via the recombinant enzyme.

Genes are introduced to the tumor using a suitable vector (e.g. retroviral vectors, adenoviral vectors) or via direct DNA injection. In theory genes could be introduced into cells which are transplanted into the tumor mass. The compounds of formula 1 are then introduced following significant enhancement of the CYP activity in the tumor.

Use for the Delivery of Diagnostic Agents:

Nucleoside diagnostic agents, e.g. uridine analogs with the 5H substituted with Tc, are useful as the prodrugs of this invention as liver diagnostic agents. These compounds are converted first to the monophosphate and then onto the triphosphate in cells that contain P450 activity, specifically CYP3A4 activity. Since nearly all of the activity is in the liver, diagnostic agents of this type will primarily be metabolized in the liver and accumulate in cells that metabolize the prodrug. Accordingly, liver tumors that have no CYP3A4 activity or tumors such as hepatocellular carcinomas which have approximately 50% of the normal activity may be differentiated from normal liver tissue.

Treatment of Diabetes:

A variety of phosphonic acids have been described that are useful in inhibiting the enzyme fructose 1,6-bisphosphatase (FBPase) and flux through the pathway that uses FBPase activity, namely gluconeogenesis. Inhibition of gluconeogenesis results in significant blood glucose lowering in diabetic animals. As with other phosphonic acids, these compounds are poorly orally bioavailable and exhibit short plasma half-lives. Prodrugs of compounds from the following structural classes are cleaved by cytochrome p450 CYP3A4, rat and human liver microsomes, rat hepatocytes. The prodrugs exhibit enhanced oral bioavailability and good liver drug levels.

The phosphate and phosphonate compounds may be inhibitors of FBPase activity, preferably with IC50s of about 10 μM on the human liver enzyme, or are other compounds with a biological activity such that they are useful in preventing or treating diseases or conditions, e.g., viral infections, cancer, hyperlipidemia, liver fibrosis, and parasitic infections such as malaria. The esters increase oral bioavailability of the parent compound and preferably achieve an oral bioavailability of greater than 5%.

Compounds that exhibit glucose lowering activity in vivo and bind to the AMP site of FBPase as the corresponding 5'-mono-phosphate are compounds represented by formula A where Y is hydroxy, acyloxy or alkoxycarbonyloxy; E is selected from group consisting of hydrogen, alkyl, amino or halogen;

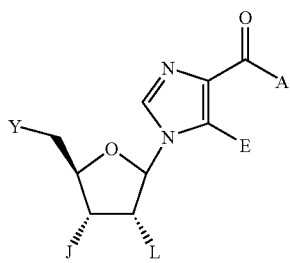

A

L and J are independently selected from the group consisting of hydrogen, hydroxy, acyloxy or when taken together form a lower cyclic ring containing at least one oxygen; and A is selected from the group consisting of amino and lower alkyl amino; and pharmaceutically acceptable salts thereof.

Phosphonates containing a purine, benzimidazole, indole or imidazopyridine also bind to the AMP site of FBPase and lower glucose in diabetic animal models. WO 98/39344, WO 98/39343, and WO 98/39342. These compounds are represented by formulae B-D. Prodrugs of these compounds are considered of potential use in oral delivery.

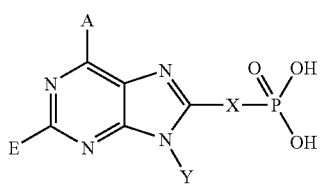

B

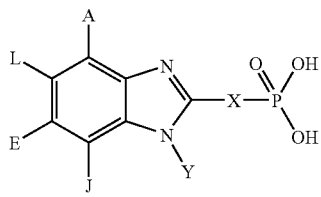

C

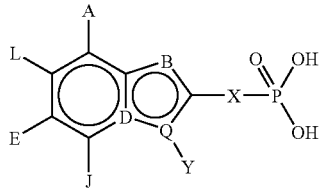

D

Esters disclosed in the invention are converted to the parent phosph(on)ate in cells and tissues, especially hepatocytes and liver, as indicated by measurement of the intracellular drug metabolites in hepatocytes using the procedure described in Example I and by the inhibition of glucose production by rat hepatocytes when M-$PO_3^{2-}$ is an FBPase inhbitor (Example J).

Treatment of Hyperlipidemia:

Phosphonic acids are known to produce an antihyperlipidemic effect in animals. The antihyperlipidemic activity is associated with inhibition of squalene synthase. The drugs exhibit poor oral bioavailability. For example BMS 188494 exhibited <2% oral bioavailability in rodents. The bisPOM diester provided modest improvement. 1-Hydroxy-3-(methylpentylamino)-propylidene-1,1-bisphosphonic acid and BMS 187745 are preferred squalene synthetase inhibitors for use in the present invention.

Treatment of Liver Fibrosis:

A variety of compounds are reported to be useful in treating liver fibrosis that are also compounds suitable for the prodrug strategy described in this invention. For example, N,[N-(CR)-1-phosphonopropyl(1-(S)-lencyl]-(S)-phenylalanine N-methyl amide was described that inhibit collagenase (Bird et al. *J. Med. Chem.* 37:158-169 (1994)).

Delivery of Diagnostic Agents

Use for the delivery of diagnostic agents: Nucleoside diagnostic agents, e.g. uridine analogs with the 5H substituted with Tc, are useful as the prodrugs of this invention as liver diagnostic agents. These compounds are converted first to the monophosphate and then onto the triphosphate in cells that contain P450 activity, specifically CYP3A4 activity. Since nearly all of the activity is in the liver, diagnostic agents of this type will primarily be metabolized in the liver and accumulate in cells that metabolize the prodrug. Accordingly, liver tumors that have no CYP3A4 activity or tumors such as hepatocellular carcinomas which have approximately 50% of the normal activity may be differentiated from normal liver tissue.

Preferred Compounds

The compounds of the invention are substituted 6-membered cyclic 1,3-propane diester prodrugs of certain phosphates, phosphonates and phosphoramidates (M-$PO_3^{2-}$) as represented by Formula I:

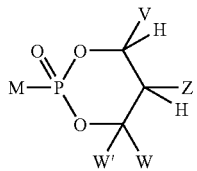

wherein:

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and Z are connected via an additional 3-5 atoms to form a cyclic group containing 5-7 atoms, optionally 1 heteroatom, substituted with hydroxy, acyloxy, alkoxycarbonyloxy, or aryloxycarbonyloxy attached to a carbon atom that is three atoms from both O groups attached to the phosphorus; or together V and Z are connected via an additional 3-5 atoms to form a cyclic group, optionally containing 1 heteroatom, that is fused to an aryl group at the beta and gamma position to the O attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from an O attached to the phosphorus;

together Z and W are connected via an additional 3-5 atoms to form a cyclic group, optionally containing one heteroatom, and V must be aryl, substituted aryl, heteroaryl, or substituted heteroaryl;

together W and W' are connected via an additional 2-5 atoms to form a cyclic group, optionally containing 0-2 heteroatoms, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{12}$, and —(CH$_2$)$_p$—SR$^{12}$;

p is an integer 2 or 3;

with the provisos that:

a) V, Z, W, W' are not all —H; and b) when Z is —R$^2$, then at least one of V, W, and W' is not —H, alkyl, aralkyl, or alicyclic;

R$^2$ is selected from the group consisting of R$^3$ and —H;

R$^3$ is selected from the group consisting of alkyl, aryl, alicyclic, and aralkyl;

R$^{12}$ is selected from the group consisting of —H, and lower acyl;

M is selected from the group that attached to PO$_3$$^{2-}$, P$_2$O$_6$$^{3-}$, or P$_3$O$_9$$^{4-}$ is the biologically active agent, and that is attached to the phosphorus in formula I via a carbon, oxygen, sulfur or nitrogen atom;

and pharmaceutically acceptable prodrugs and salts thereof.

In general, preferred substituents, V, Z, W, and W' of formula I are chosen such that they exhibit one or more of the following properties:

(1) enhance the oxidation reaction since this reaction is likely to be the rate determining step and therefore must compete with drug elimination processes.

(2) enhance stability in aqueous solution and in the presence of other non-P450 enzymes;

(3) enhance cell penetration, e.g. substituents are not charged or of high molecular weight since both properties can limit oral bioavailability as well as cell penetration;

(4) promote the β-elimination reaction following the initial oxidation by producing ring-opened products that have one or more of the following properties:

a) fail to recyclize;

b) undergo limited covalent hydration;

c) promote β-elimination by assisting in the proton abstraction;

d) impede addition reactions that form stable adducts, e.g. thiols to the initial hydroxylated product or nucleophilic addition to the carbonyl generated after ring opening; and e) limit metabolism of reaction intermediates (e.g. ring-opened ketone);

(5) lead to a non-toxic and non-mutagenic by-product with one or more of the following characteristics. Both properties can be minimized by using substituents that limit Michael additions, e.g.:

a) electron donating Z groups that decrease double bond polarization;

b) W groups that sterically block nucleophilic addition to the β-carbon;

c) Z groups that eliminate the double bond after the elimination reaction either through retautomerization (enol->keto) or hydrolysis (e.g. enamine);

d) V groups that contain groups that add to the α,β-unsaturated ketone to form a ring;

e) Z groups that form a stable ring via Michael addition to double bond; and f) groups that enhance detoxification of the by-product by one or more of the following characteristics:

(i) confine to liver; and (ii) make susceptible to detoxification reactions (e.g. ketone reduction); and (6) capable of generating a pharmacologically active product.

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having 3 to about 20 carbon atoms. Suitable heteroaryl groups include groups having from 1 to about 20 carbon atoms and from 1 to 4 heteroatoms, preferably independently selected from nitrogen, oxygen, and sulfur. Suitable heteroalicyclic groups include groups having from 2 to about twenty carbon atoms and from 1 to 5 heteroatoms, preferably independently selected from nitrogen, oxygen, phosphorous, and sulfur.

More preferred are compounds wherein together R¹ and R¹ are

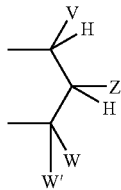

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3-5 atoms to form a cyclic group, optionally containing one heteroatom, and V must be aryl, substituted aryl, heteroaryl, or substituted heteroaryl;

together W and W' are connected via an additional 2-5 atoms to form a cyclic group, optionally containing 0-2 heteroatoms, and V must be aryl, substituted aryl, heteroaryl, or substituted heteroaryl;

Z is selected from the group consisting of —CHR²OH, —CHR²OC(O)R³, —CHR²OC(S)R³, —CHR²OC(S)OR³, —CHR²OC(O)SR³, —CHR²OCO₂R³, —OR², —SR², —R², —NHCOR², —NHCO₂R³, —(CH₂)$_p$—OR¹², and —(CH₂)$_p$—SR¹²;

p is an integer 2 or 3;

with the provisos that:

a) V, Z, W, W' are not all —H; and b) when Z is —R², then at least one of V, W, and W' is not —H, alkyl, aralkyl, or alicyclic;

R² is selected from the group consisting of R³ and —H;

R³ is selected from the group consisting of alkyl, aryl, alicyclic, and aralkyl;

R⁶ is selected from the group consisting of —H, and lower alkyl; and

R¹² is selected from the group consisting of —H, and lower acyl.

More preferred is when V is selected from the group consisting of aryl, substitued aryl, heteroaryl, and substituted heteroaryl.

More preferred V groups of formula VI are aryl, substituted aryl, heteroaryl, and substituted heteoaryl. Particularly preferred aryl and substituted aryl groups include phenyl, and phenyl substituted with 1-3 halogens. Especially preferred are 3,5-dichlorophenyl, 3-bromo-4-fluorophenyl, 3-chlorophenyl, and 3-bromophenyl.

It is also especially preferred when V is selected from the group consisting of monocyclic heteroaryl and monocyclic substituted heteroaryl containing at least one nitrogen atom. Most preferred is when such heteroaryl and substituted heteroaryl is 4-pyridyl, and 3-bromopyridyl, respectively.

In another particularly preferred aspect, R¹ and R¹ together are

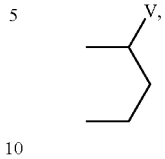

and V is phenyl substituted with 1-3 halogens. Especially preferred are 3,5-dichlorophenyl, 3-bromo-4-fluorophenyl, 3-chlorophenyl, and 3-bromophenyl.

It is also especially preferred when V is selected from the group consisting of heteroaryl and substituted heteroaryl.

Most preferred is when such heteroaryl is 4-pyridyl.

In another aspect, it is preferred when together V and W are connected via an additional 3 carbon atoms to form an optionally substituted cyclic group containing 6 carbon atoms and monosubstituted with one substituent selected from the group consisting of hydroxy, acyloxy, alkoxycarbonyloxy, alkylthiocarbonyloxy, and aryloxycarbonyloxy attached to one of said additional carbon atoms that is three atoms from a Y attached to the phosphorus. In such compounds, it is more preferred when together V and W form a cyclic group selected from the group consisting of —CH₂—CH(OH)—CH₂—, CH₂CH(OCOR³)—CH₂—, and —CH₂CH(OCO₂)R³)—CH₂—

Another preferred V group is 1-alkene. Oxidation by P450 enzymes is known to occur at benzylic and allylic carbons.

In one aspect, preferred V groups include —H, when Z is —CHR²OH, —CH₂OCOR³, or —CH₂OCO₂R³.

In another aspect, when V is aryl, substituted aryl, heteroaryl, or substituted heteroaryl, preferred Z groups include —OR², —SR², —CHR²N₃, —R², —NR²₂, —OCOR³, —OCO₂R³, —SCOR³, —SCO₂R³, —NHCOR², —NHCO₂R³, —CH₂NHaryl, —(CH₂)$_p$ OR¹², and —(CH₂)$_p$—SR¹². More preferred Z groups include —OR², —R², —OCOR³, —OCO₂R³, —CH₃, —NHCOR², —NHCO₂R³, —(CH₂)$_p$—OR², and —(CH₂)$_p$—SR². Most preferred Z groups include —OR², —H, —OCOR², —OCO₂R³, and —NHCOR².

Preferred W and W' groups include H, R³, aryl, substituted aryl, heteroaryl, and substituted aryl. Preferably, W and W' are the same group. More preferred is when W and W' are H.

In one aspect, prodrugs of formula VI are preferred:

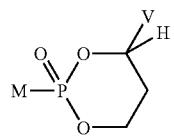

wherein

V is selected from the group consisting of aryl, substituted aryl, heteroaryl, and substituted heteroaryl, aryl, 1-alkenyl, and 1-alkynyl. More preferred V groups of formula VI are aryl, substituted aryl, heteroaryl, and substituted heteoaryl. Particularly preferred aryl and substituted aryl groups include phenyl and substituted phenyl. Particularly preferred heteroaryl groups include monocyclic substituted and unsubstituted heteroaryl groups. Especially preferred are 4-pyridyl and 3-bromopyridyl.

In one aspect, the compounds of formula VI preferably have a group Z which is H, alkyl, alicyclic, hydroxy, alkoxy, OC(O)R³, OC(O)OR³, or NHC(O)R². Preferred are such groups in which Z decreases the propensity of the by-product, vinylaryl ketone to undergo Michael additions. Preferred Z groups are groups that donate electrons to the vinyl group which is a known strategy for decreasing the propensity of α,β-unsaturated carbonyl compounds to undergo a Michael addition. For example, a methyl group in a similar position on acrylamide results in no mutagenic activity whereas the unsubstituted vinyl analog is highly mutagenic. Other groups could serve a similar function, e.g. Z=OR¹², NHAc, etc. Other groups may also prevent the Michael addition especially groups that result in removal of the double bond altogether such as Z=—OH, —OC(O)R³, —OCO₂R³, and NH₂, which will rapidly undergo retautomerization after the elimination reaction. Certain W and W' groups are also advantageous in this role since the group(s) impede the addition reaction to the β-carbon or destabilize the product. Another preferred Z group is one that contains a nucleophilic group capable of adding to the α,β-unsaturated double bond after the elimination reaction i.e. $(CH_2)_pSH$ or $(CH_2)_pOH$ where p is 2 or 3. Yet another preferred group is a group attached to V which is capable of adding to the α,β-unsaturated double bond after the elimination reaction:

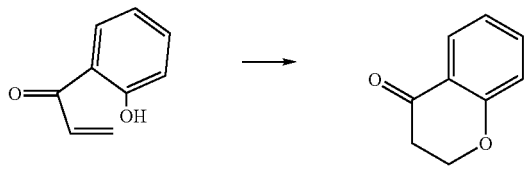

In another aspect, prodrugs of formula VII are preferred:

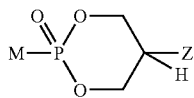

wherein

Z is selected from the group consisting of: —CHR²OH, —CHR²OCOR³, —CHR²OC(S)R³, —CHR²OCO₂R³, —CHR²OC(O)SR³, —CHR²OC(S)OR³, —SR², and —CH₂aryl. More preferred groups include —CHR²OH, —CHR²OC(O)R³, and —CHR²OCO₂R³.

In another aspect, prodrugs of formula VIII are preferred:

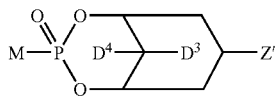

wherein

Z' is selected from the group consisting of —OH, —OC(O)R³, —OCO₂ R³, and —OC(O)S R³;

D⁴ and D³ are independently selected from the group consisting of —H, alkyl, OR², —OH, and —OC(O)R³; with the proviso that at least one of D⁴ and D³ are —H. An especially preferred Z group is OH.

In one preferred embodiment, W' and Z are —H, W and V are both the same aryl, substituted aryl, heteroaryl, or substituted heteroaryl such that the phosphonate prodrug moiety:

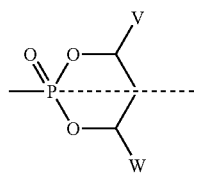

has a plane of symmetry.

In another preferred embodiment, W and W' are H, V is selected from the group consisting of aryl, substituted aryl, heteroaryl, substituted heteroaryl, and Z is selected from the group consisting of —H, OR², and —NHCOR². More preferred are such compounds where Z is —H. Preferably, such compound have M attached via oxygen. Most preferred are such compounds where oxygen is in a primary hydroxyl group. Also more preferred, are those compounds where V is phenyl or substituted phenyl.

Also more preferred, are those compounds where V is an optionally substituted monocyclic heteroaryl containing at least one nitrogen atom. Preferably such compounds have M attached via oxygen. Most preferred are such compounds where said oxygen is in a primary hydroxyl group. Especially preferred are such compounds where V is 4-pyridyl.

Preferably, oral bioavailability is at least 5%. More preferably, oral bioavailability is at least 10%.

P450 oxidation can be sensitive to stereochemistry which might either be at phosphorus or at the carbon bearing the aromatic group. The prodrugs of the present invention have two isomeric forms around the phosphorus. Preferred is the stereochemistry that enables both oxidation and the elimination reaction. Preferred is the cis-stereochemistry. In contrast, the reaction is relatively insensitive to the group M since cleavage occurred with a variety of phosphonate, phosphate and phosphoramidates. The atom in M attached to phosphorus may be O, S or N. The active drug is $M\text{-}PO_3^{2-}$, $MP_2O_6^{3-}$, or $MP_3O_9^{4-}$ useful for treatment of diseases in which the liver is a target organ, including diabetes, hepatitis, liver cancer, liver fibrosis, malaria and metabolic diseases where the liver is responsible for the overproduction of a biochemical end products such as glucose (diabetes), cholesterol, fatty acids and triglycerides (atherosclerosis). Moreover, $M\text{-}PO_3^{2-}$, $MP_2O_6^{3-}$, or $MP_3O_9^{4-}$ may be useful in treating diseases where the target is outside the liver in tissues or cells that can oxidize the prodrug.

Other preferred M groups include drugs useful in treating diabetes, viral infections, liver fibrosis, parasitic infections, hypertension, and hyperlipidemia.

The preferred compounds of formula VIII utilize a Z' group that is capable of undergoing an oxidative reaction that yields an unstable intermediate which via elimination reactions breaks down to the corresponding $M\text{-}PO_3^{2-}$. An especially preferred Z' group is OH. Groups D⁴ and D³ are preferably hydrogen, alkyl, —OR², —OCOR³, but at least one of D⁴ or D³ must be H.

The following compounds and their analogs can be used in the prodrug methodology of the present invention.

In one preferred aspect, M is attached to the phosphorus in formula I via an oxygen atom. Preferably, M is a nucleoside. Preferably, M is attached via an oxygen that is in a primary hydroxyl group on a ribofuranosyl or an arabinofuranosyl group. Preferably such compounds include araA; AZT; d4T; ddI; ddA; ddC; L-ddC; L FddC; L-d4C; L-Fd4C; 3TC; ribavirin; 5-fluoro 2'deoxyuridine; FIAU; FIAC; BHCG; L FMAU; BvaraU; E-5-(2-bromovinyl-2' deoxyuridine; TFT; 5-propynyl-1 arabinosyluracil; CDG; DAPD; FDOC; d4C; DXG; FEAU; FLG; FLT; FTC; 5-yl-carbocyclic 2'deoxyguanosine; oxetanocin A; oxetanocin G; Cyclobut A, Cyclobut G; dFdC; araC; bromodeoxyuridine; IDU; CdA; FaraA; Coformycin, 2'-deoxycoformycin; araT; tiazofurin; ddAPR; 9-(arabinofuranosyl)-2,6 diaminopurine; 9-(2'-deoxyribofuranosyl)-2,6 diaminopurine; 9-(2'-deoxy 2'fluororibofuranosyl)-2,6-diaminopurine; 9 (arabinofuranosyl)guanine; 9-(2' deoxyribofuranosyl)guanine; 9-(2'-deoxy 2'fluororibofuranosyl)guanine; FMdC; 5,6 dihydro-5-azacytidine; 5-azacytidine; 5-aza 2'deoxycytidine; or AICAR. In another aspect, it is preferred when M is attached via an oxygen in a hydroxyl on an acyclic sugar it is preferred when such NH is ACV, GCV; penciclovir; (R)-9-(3,4 dihydroxybutyl)guanine; or cytallene.

In general, it is preferred that when M is attached via an oxygen, said oxygen is in a primary hydroxy group. In such an instance, it is preferred that MH is araA; AZT; d4T; ddI; ddA; ddC; L-ddC; L FddC; L-d4C; L-Fd4C; 3TC; ribavirin; 5-fluoro 2'deoxyuridine; FIAU; FIAC; BHCG; L FMAU; BvaraU; E-5-(2-bromovinyl-2' deoxyuridine; TFT; 5-propynyl-1 arabinosyluracil; CDG; DAPD; FDOC; d4C; DXG; FEAU; FLG; FLT; FTC; 5-yl-carbocyclic 2'deoxyguanosine; oxetanocin A; oxetanocin G; Cyclobut A, Cyclobut G; dFdC; araC; bromodeoxyuridine; IDU; CdA; FaraA; Coformycin, 2'-deoxycoformycin; araT; tiazofurin; ddAPR; 9-(arabinofuranosyl)-2,6 diaminopurine; 9-(2'-deoxyribofuranosyl)-2,6 diaminopurine; 9-(2'-deoxy 2'fluororibofuranosyl)-2,6-diaminopurine; 9 (arabinofuranosyl)guanine; 9-(2' deoxyribofuranosyl)guanine; 9-(2'-deoxy 2'fluororibofuranosyl)guanine; FMdC; 5,6 dihydro-5-azacytidine; 5-azacytidine; 5-aza 2'deoxycytidine; AICAR; ACV, GCV; penciclovir; (R)-9-(3,4 dihydroxybutyl)guanine; or cytallene.

Another preferred group of compounds with M attached via oxygen are M as a compound of formula II:

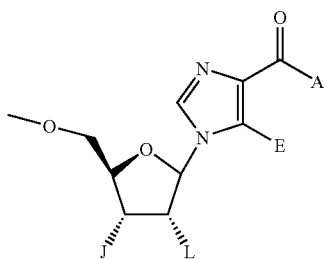

II wherein

E is selected from the group consisting of alkyl, amino or halogen;

L and J are independently selected from the group consisting of hydrogen, hydroxy, acyloxy, alkoxycarbonyloxy, or when taken together form a lower cyclic ring containing at least one oxygen; and A is selected from the group consisting of amino and lower alkylamino; and pharmaceutically acceptable salts thereof.

In another aspect, compounds of formula I wherein M is attached to the phosphorus in formula I via a carbon atom are preferred. In such compounds, preferably M-PO$_3^{2-}$ is phosphohonoformic acid, or phosphonoacetic acid.

For compounds where M is attached via a carbon atom, it is also preferred when M is a compound of formula III:

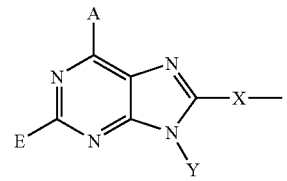

wherein

A is selected from the group consisting of —NR$^8_2$, NHSO$_2$R$^3$, —OR$^5$, —SR$^5$, halogen, lower alkyl, —CON (R$^4$)$_2$, guanidine, amidine, —H, and perhaloalkyl;

E is selected from the group consisting of —H, halogen, lower alkylthio, lower perhaloalkyl, lower alkyl, lower alkenyl, lower alkynyl, lower alkoxy, —CN, and —NR$^7_2$;

X is selected from the group consisting of alkylamino, alkyl, alkenyl, alkynyl, alkyl(carboxyl), alkyl(hydroxy), alkyl(phosphonate), alkyl(sulfonate), aryl, alkylaminoalkyl, alkoxyalkyl, alkylthioalkyl, alkylthio, alicyclic, 1,1-dihaloalkyl, carbonylalkyl, alkylaminocarbonyl, alkylcarbonylamino, aralkyl, and alkylaryl, all optionally substituted; or together with Y forms a cyclic group including cyclic alkyl, heterocyclic, and aryl;

Y is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—OR$^3$, —CONHR$^3$, —NR$^2_2$, and —OR$^3$, all except H are optionally substituted; or together with X forms a cyclic group including aryl, cyclic alkyl, and heterocyclic;

R$^4$ is independently selected from the group consisting of —H, lower alkyl, lower alicyclic, lower aralkyl, and lower aryl;

R$^5$ is selected from the group consisting of lower alkyl, lower aryl, lower aralkyl, and lower alicyclic;

R$^6$ is independently selected from the group consisting of —H, and lower alkyl;

R$^7$ is independently selected from the group consisting of —H, lower alkyl, lower alicyclic, lower aralkyl, lower aryl, and —C(O)R$^{10}$;

R$^8$ is independently selected from the group consisting of —H, lower alkyl, lower aralkyl, lower aryl, lower alicyclic, —C(O)R$^{10}$, or together they form a bidentate alkyl;

R$^{10}$ is selected from the group consisting of —H, lower alkyl, —NH$_2$, lower aryl, and lower perhaloalkyl;

R$^{11}$ is selected from the group consisting of alkyl, aryl, —OH, —NH$_2$ and —OR$^3$; and pharmaceutically acceptable prodrugs and salts thereof.

For compounds where M is attached via a carbon atom, it is also preferred when M is a compound of formula IV:

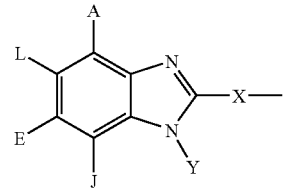

wherein:

A, E, and L are selected from the group consisting of —NR$^8_2$, —NO$_2$, —H, —OR$^7$, —SR$^7$, —C(O)NR$^4_2$, halo, —COR$^{11}$, —SO$_2$R$^3$, guanidine, amidine, —NHSO$_2$R$^5$, —SO$_2$NR$^4_2$, —CN, sulfoxide, perhaloacyl, perhaloalkyl, perhaloalkoxy, C1-C5 alkyl, C2-C5 alkenyl, C2-C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together, with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—OR$^3$, —CONHR$^3$, —NR$^2_2$, and —OR$^3$, all except —H are optionally substituted; or together with X forms a cyclic group including aryl, cyclic alkyl, and heterocyclic;

R$^4$ is independently selected from the group consisting of —H, lower alkyl, lower alicyclic, lower aralkyl, and lower aryl;

R$^5$ is selected from the group consisting of lower alkyl, lower aryl, lower aralkyl, and lower alicyclic;

R$^6$ is independently selected from the group consisting of —H, and lower alkyl;

R$^7$ is independently selected from the group consisting of —H, lower alkyl lower alicyclic, lower aralkyl, lower aryl, and —C(O)R$^{10}$;

R$^8$ is independently selected from the group consisting of —H, lower alkyl, lower aralkyl, lower aryl, lower alicyclic, —C(O)R$^{10}$, or together they form a bidentate alkyl;

R$^{10}$ is selected from the group consisting of —H, lower alkyl, —NH$_2$, lower aryl, and lower perhaloalkyl;

R$^{11}$ is selected from the group consisting of alkyl, aryl, —OH, —NH$_2$ and —OR$^3$; and pharmaceutically acceptable prodrugs and salts thereof, with the provisos that:

a) when X is alkyl or alkene, then A is —NR$^8_2$;

b) X is not alkylamine and alkylaminoalkyl when an alkyl moiety is substituted with phosphonic esters and acids; and c) A, L, E, J, Y, and X together may only form 0-2 cyclic groups.

Preferred A, L, and E groups include —H, —NR$^8_2$, —NO$_2$, hydroxy, alkylaminocarbonyl, halogen, —OR$^7$, —SR$^7$, lower perhaloalkyl, and C1-C5 alkyl or together E and J form a cyclic group. Such a cyclic group may be aromatic, cyclic alkyl, or heterocyclic alkyl, and may be optionally substituted. Suitable aromatic groups include thiazolidine. Particularly preferred A, L and E groups are —NR$^8_2$, —H, hydroxy, halogen, lower alkoxy, lower perhaloalkyl, and lower alkyl.

Preferred A groups include, —NR$^8_2$, —H, halogen, lower perhaloalkyl, and lower alkyl.

Preferred L and E groups include —H, lower alkoxy, lower alkyl, and halogen.

Preferred J groups include —H, halogen, lower alkyl, lower hydroxylalkyl, —NR$_{8 2}$, lower R$^8_2$N-alkyl, lower haloalkyl, lower perhaloalkyl, lower alkenyl, lower alkynyl, lower aryl, heterocyclic, and alicyclic, or together with Y forms a cyclic group. Such a cyclic group may be aromatic, cyclic alkyl, or heterocyclic, and may be optionally substituted. Particularly preferred J groups include —H, halogen, and lower alkyl, lower hydroxyalkyl, —NR$^8_2$, lower R$^8_2$N-alkyl, lower haloalkyl, lower alkenyl, alicyclic, and aryl. Especially preferred are alicyclic and lower alkyl.

Preferred X groups include alkyl, alkynyl, aryl, alkoxyalkyl, alkylthio, alkylaminocarbonyl, alkylcarbonylamino, 1,1-dihaloalkyl, carbonylalkyl, alkyl(OH), and alkyl(sulfonate). Particularly preferred is heteroaryl, alkylaminocarbonyl, 1,1-dihaloalkyl, alkyl(sulfonate), and alkoxyalkyl. Also particularly preferred are heteroaryl, alkylaminocarbonyl, and alkoxyalkyl. Especially preferred are methylaminocarbonyl, methoxymethyl, and furanyl.

In one preferred aspect X is not substituted with a phosphonic acid or ester. In another preferred aspect, when X is substituted with a phosphonic acid or ester, then A is —N(R$_8$)$_2$ and Y is not —H. In another preferred aspect, when X is aryl or alkylaryl, these groups are not linked 1,4 through a 6-membered aromatic ring.

Preferred Y groups include —H, alkyl, aralkyl, aryl, and alicyclic, all except —H may be optionally substituted. Particularly preferred are lower alkyl, and alicyclic.

Preferred R$^4$ and R$^7$ groups include —H, and lower alkyl.

In one preferred aspect A, L, and E are independently —H, lower alkyl, hydroxy, halogen, lower alkoxy, lower perhaloalkyl, and —NR$^8_2$; X is aryl, alkoxyalkyl, alkyl, alkylthio, 1,1-dihaloalkyl, carbonylalkyl, alkyl(hydroxy), alkyl(sulfonate), alkylaminocarbonyl, and alkylcarbonylamino; and each R$^4$ and R$^7$ is independently —H, and lower alkyl. Particularly preferred are such compounds where A, L, and E are independently —H, lower alkyl, halogen, and —NR$^8_2$; J is —H, halogen, haloalkyl, hydroxyalkyl, R$^8_2$N-alkyl, lower alkyl, lower aryl, heterocyclic, and alicyclic, or together with Y forms a cyclic group; and X is heteroaryl, alkylaminocarbonyl, 1,1-dihaloalkyl, and alkoxyalkyl. Especially preferred are such compounds where A is —H, —NH$_2$, —F, and —CH$_3$, L is —H, —F, —OCH$_3$, —Cl, and —CH$_3$, E is —H and —Cl, J is —H, halo, C1-C5 hydroxyalkyl, C1-C5 haloalkyl, C1-C5 R$^8_2$N-alkyl, C1-C5 alicyclic, and C1-C5 alkyl, X is —CH$_2$OCH$_2$—, and 2,5-furanyl, and Y is lower alkyl. Most preferred are the following such compounds and their salts, and prodrug and their salts:

1) A is —NH$_2$, L is —F, E is —H, J is —H, Y is isobutyl; and X is 2,5-furanyl;

2) A, L, and J are —H, E is —Cl, Y is isobutyl, and X is 2,5-furanyl;

3) A is —NH$_2$, L is —F, E and J are —H, Y is cyclopropylmethyl, and X is 2,5-furanyl;

4) A is —NH$_2$, L is —F, E is —H, J is ethyl, Y is isobutyl, and X is 2,5-furanyl;

5) A is —CH$_3$, L is —Cl, E and J are —H, Y is isobutyl, and X is 2,5-furanyl;

6) A is —NH$_2$, L is —F, E is —H, J is —Cl, Y is isobutyl, and X is 2,5-furanyl;

7) A is —NH$_2$, L is —F, E is —H, J is —Br, Y is isobutyl, and X is —CH$_2$OCH$_2$; and 8) A, L, E, and J are —CH$_3$, Y is cyclopropylmethyl, and X is 2,5-furanyl.

Also especially preferred are compounds where A is —NH$_2$, L is —F, E is —H, J is bromopropyl, bromobutyl, chlorobutyl, cyclopropyl, hydroxypropyl, or N,N-dimethylaminopropyl, and X is 2,5-furanyl.

Indole and 9-Azaindole compounds of formula V are another preferred aspect:

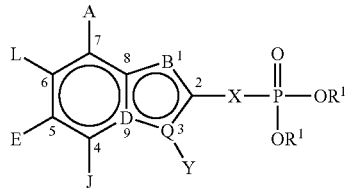

wherein:

B is selected from the group consisting of —NH—, —N= and —CH=;

D is selected from the group consisting of

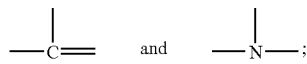

Q is selected from the group consisting of —C= and —N— with the proviso that when B is —NH— then

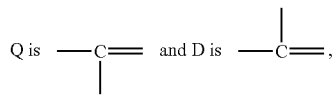

when B is —CH= then Q is —N— and

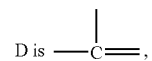

when B is —N=, then D is —N— and Q is —C=;

A, E, and L are selected from the group consisting of —NR$^8_2$, —NO$_2$, —H, —OR$^7$, —SR$^7$, —C(O)NR$^4_2$, halo, —COR$^{11}$, —SO$_2$R$^3$, guanidine, amidine, —NHSO$_2$R$^5$, —SO$_2$NR$^4_2$, —CN, sulfoxide, perhaloacyl, perhaloalkyl, perhaloalkoxy, C1-C5 alkyl, C2-C5 alkenyl, C2-C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;

Y is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—OR$^3$, —CONHR$^3$, —NR$^2_2$, and —OR$^3$, all except H are optionally substituted; or together with X forms a cyclic group including aryl, cyclic alkyl, and heterocyclic;

Preferred A, L, and E groups include —H, —NR$^8_2$, —NO$_2$, hydroxy, halogen, —OR$^7$, alkylaminocarbonyl, —SR$^7$, lower perhaloalkyl, and C1-C5 alkyl, or together E and J form a cyclic group. Such a cyclic group may be aromatic or cyclic alkyl, and may be optionally substituted. Suitable aromatic groups include thiazole. Particularly preferred A, L and E groups are —NR$^8_2$, —H, hydroxy, halogen, lower alkoxy, lower perhaloalkyl, and lower alkyl.

Preferred A groups include —NR$^8_2$, lower alkyl, —H, halogen, and lower perhaloalkyl.

Preferred L and E groups include —H, lower alkoxy, lower alkyl, and halogen.

Preferred J groups include —H, halogen, lower alkyl, lower hydroxyalkyl, —NR$^8_2$, lower R$^8_2$N-alkyl, lower haloalkyl, lower perhaloalkyl, lower alkenyl, lower alkynyl, lower aryl, heterocyclic, and alicyclic or together with Y forms a cyclic group. Such a cyclic group may be aromatic or cyclic alkyl, and may be optionally substituted. Particularly preferred J groups —H, halogen, lower alkyl, lower hydroxyalkyl, —NR$^8_2$, lower R$^8_2$N-alkyl, lower haloalkyl, lower alkenyl, alicyclic, and aryl.

Preferred X groups include alkyl, alkynyl, alkoxyalkyl, alkylthio, aryl, alkylaminocarbonyl, alkylcarbonylamino, 1,1-dihaloalkyl, carbonylalkyl, alkyl(OH), and alkyl(sulfonate). Particularly preferred is 1,1-dihaloalkyl, alkyl(sulfonate), alkylaminocarbonyl, alkoxyalkyl, and heteroaryl. Such compounds that are especially preferred are heteroaryl, alkylaminocarbonyl, and alkoxyalkyl. Most preferred is methylaminocarbonyl, methoxymethyl, and furanyl.

In one preferred aspect, X is not (C2-C3 alkyl)aminocarbonyl.

In one preferred aspect, when X is alkyl and alkene substituted with a phosphonic acid or ester, then A is —N(R$_8$)$_2$ and Y is not —H. In another preferred aspect, X is not substituted with a phosphonic acid or ester.

Preferred Y groups include —H, alkyl, aryl, aralkyl, and alicyclic, all except —H may be optionally substituted. Particularly preferred Y groups include lower alkyl, and alicyclic. Preferred R$^4$ and R$^7$ groups include —H, and lower alkyl.

In one preferred aspect, B is NH,

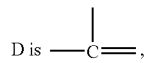

and Q is —C=. In another preferred aspect, B is —N=,

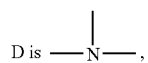

and Q is —C=.

In another preferred aspect, A, L, and E are independently —NR$^8_2$, lower alkyl, lower perhaloalkyl, lower alkoxy, halogen, —OH, or —H, X is aryl, alkoxyalkyl, alkyl, alkylthio, 1,1-dihaloalkyl, carbonylalkyl, alkyl(hydroxy), alkyl(sulfonate), alkylaminocarbonyl, and alkylcarbonylamino, and each R$^4$ and R$^7$ is independently —H, or lower alkyl. Particularly preferred are such compounds where A, L, and E are independently —H, lower alkyl, halogen, and —NR$^8_2$; J is —H, halogen, haloalkyl, hydroxyalkyl, —R$^8_2$N-alkyl, lower alkyl, lower aryl, heterocyclic, and alicyclic, or together with Y forms a cyclic group; and X is heteroaryl, alkylaminocarbonyl, 1,1-dihaloalkyl, and alkoxyalkyl. Especially preferred are such compounds where A is —H, —NH$_2$, —F, or —CH$_3$, L is —H, —F, —OCH$_3$, or —CH$_3$, E is —H, or —Cl, J is —H, halo, C1-C5 hydroxyalkyl, C1-C5 haloalkyl, C1-C5 R$^8_2$N-alkyl, C1-C5 alicyclic or C1-C5 alkyl, X is —CH$_2$OCH$_2$—, or 2,5-furanyl; and Y is lower alkyl. Preferred are such compounds where B is NH,

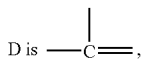

and Q is —C= or where B is —N=,

and Q is —C=.

Most preferred are compounds where:
1) A is —NH$_2$, L is —F, E is —H, J is —H, Y is isobutyl, and X is 2,5-furanyl;
2) A is —NH$_2$, L is —F, E is —H, J is —Cl, Y is isobutyl, and X is 2,5-furanyl.
3) A is —H, L is —H, E is —Cl, J is —H, B is —NH,

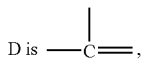

Q is —C=, and Y is isobutyl; and
4) A is —CH$_3$, L is —H, E is —H, J is —H, B is —N=,

Q is —C=, and Y is isobutyl.

Particularly preferred are such compounds where R$^1$ is —CH$_2$OC(O)—C(CH$_3$)$_3$.

Another especially preferred aspect are such compounds where A, L, and E are —H, lower alkyl, halogen, or —NR$^8_2$, J is —H, halogen, lower alkyl, lower aryl, heterocyclic, or alicyclic, or together with Y forms a cyclic group, and X is heteroaryl, alkylaminocarbonyl, or alkoxyalkyl.

For compounds where M is attached via a carbon atom it is also preferred when MH is selected from the group consisting of PMEA, PMEDAP, HPMPC, HPMPA, FPMPA, and PMPA.

In another preferred aspect, MPO$_3^{2-}$, MP$_2$O$_6^{3-}$, or MP$_3$O$_9^{4-}$ is useful for the treatment of diseases of the liver or metabolic diseases where the liver is responsible for the overproduction of a biochemical end product. Preferably, such disease of the liver is selected from the group consisting of hepatitis, cancer, fibrosis, malaria, gallstones, and chronic cholecystalithiasis. It is more preferred when treating such diseases that MH, MPO$_3^{2-}$, MP$_2$O$_6^{3-}$, or MP$_3$O$_9^{4-}$ is an antiviral or anticancer agent.

Preferably, the metabolic disease that MPO$_3^{2-}$, MP$_2$O$_6^{3-}$, or MP$_3$O$_9^{4-}$ are useful for diabetes, atherosclerosis, and obesity.

In another aspect, it is preferred when the biochemical end product is selected from the group consisting of glucose, cholesterol, fatty acids, and triglycerides. More preferred is when MH or MPO$_3^{2-}$ is an AMP activated protein kinase activator.

In another aspect, it is preferred when M-PO$_3^{2-}$ is a compound that inhibits human liver FBPase. It is more preferred when such FBPase inhibitor inhibits human liver FBPase with an IC$_{50}$ of less than 10 μM. More preferred are such FBPase inhibitors wherein M is a group T-X wherein T is selected from the group consisting of benzimidazole, indole, purine, and 9-azaindole, all of which contain at least one substituent;

X is attached at the 2, 2, 8, and 2 positions of said T groups, respectively; and X is selected from the group consisting of alkylamino, alkyl, alkenyl, alkynyl, alkyl(carboxyl), alkyl(hydroxy), alkyl(phosphonate), alkyl(sulfonate), aryl, alkylaminoalkyl, alkoxyalkyl, alkylthioalkyl, alkylthio, alicyclic, 1,1-dihaloalkyl, carbonylalkyl, alkylaminocarbonyl, alkylcarbonylamino, aralkyl, and alkylaryl, all optionally substituted.

Also more preferred, are those compounds where V is phenyl or substituted phenyl. Most preferred are such compounds where said oxygen is in a primary hydroxyl group.

Preferably, such compounds have M attached via oxygen.

Also more preferred, are those compounds where V is an optionally substituted monocyclic heteroaryl containing at least one nitrogen atom. Preferably such compounds have M attached via oxygen. Most preferred are such compounds where said oxygen is in a primary hydroxyl group.

Especially preferred are such compounds where V is selected from the group consisting of phenyl substituted with 1-3 halogens, and 4-pyridyl. In these compounds it is also preferred when MH is selected from the group consisting of araA; AZT; d4T; ddI; ddA; ddC; L-ddC; L FddC; L-d4C; L-Fd4C; 3TC; ribavirin; 5-fluoro 2'deoxyuridine; FIAU; FIAC; BHCG; L FMAU; BvaraU; E-5-(2-bromovinyl-2' deoxyuridine; TFT; 5-propynyl-1 arabinosyluracil; CDG; DAPD; FDOC; d4C; DXG; FEAU; FLG; FLT; FTC; 5-yl-carbocyclic 2'deoxyguanosine; oxetanocin A; oxetanocin G; Cyclobut A, Cyclobut G; dFdC; araC; bromodeoxyuridine; IDU; CdA; FaraA; Coformycin, 2'-deoxycoformycin; araT; tiazofurin; ddAPR; 9-(arabinofuranosyl)-2,6 diaminopurine; 9-(2'-deoxyribofuranosyl)-2,6 diaminopurine; 9-(2'-deoxy 2'fluororibofuranosyl)-2,6-diaminopurine; 9 (arabinofuranosyl)guanine; 9-(2' deoxyribofuranosyl)guanine; 9-(2'-deoxy 2'fluororibofuranosyl)guanine; FMdC; 5,6 dihydro-5-azacytidine; 5-azacytidine; 5-aza 2'deoxycytidine; AICAR; ACV, GCV; penciclovir; (R)-9-(3,4 dihydroxybutyl)guanine; or cytallene. Particularly preferred are such compounds where V is selected from the group consisting of phenyl substituted with 1-3 halogens and 4-pyridyl and MH is selected from the group consisting of araA; AZT; d4T; 3TC; ribavirin; 5 fluoro-2'deoxyuridine; FMAU; DAPD; FTC; 5-yl-carbocyclic 2'deoxyguanosine; Cyclobut G; dFdC; araC; IDU; FaraA; ACV; GCV; or penciclovir.

Also preferred is when MH is selected from the group consisting of ACV, GCV; penciclovir; (R)-9-(3,4 dihydroxybutyl)guanine; cytallene.

When W' and W are H, V is aryl, substituted aryl, heteroaryl, or substituted heteroaryl, and Z is H, OR$^2$, or —NHCOR$^2$, it is also preferred when M is attached to the phosphorus via a carbon atom. Preferred are such compounds wherein $MPO_3^{2-}$ is selected from the group consisting of phosphonoformic acid, and phosphonoacetic acid. Also preferred are MH is selected from the group consisting of PMEA, PMEDAP, HPMPC, HPMPA, FPMPA, and PMPA.

In these compounds it is also preferred when M is selected from the group consisiting of:

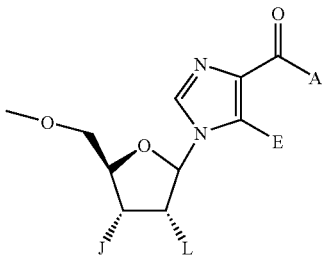

II wherein

E is selected from the group consisting of alkyl, amino or halogen;

L and J are independently selected from the group consisting of hydrogen, hydroxy, acyloxy, alkoxycarbonyloxy, or when taken together form a lower cyclic ring containing at least one oxygen; and A is selected from the group consisting of amino and lower alkylamino; and pharmaceutically acceptable prodrugs and salts thereof.

In another preferred aspect, these compounds where M is selected from the group consisiting of:

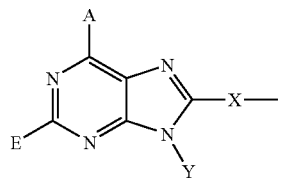

III wherein

A is selected from the group consisting of $-NR^8_2$, $NHSO_2R^3$, $-OR^5$, $-SR^5$, halogen, lower alkyl, $-CON(R^4)_2$, guanidine, amidine, $-H$, and perhaloalkyl;

E is selected from the group consisting of $-H$, halogen, lower alkylthio, lower perhaloalkyl, lower alkyl, lower alkenyl, lower alkynyl, lower alkoxy, $-CN$, and $-NR^7_2$;

X is selected from the group consisting of alkylamino, alkyl, alkenyl, alkynyl, alkyl(carboxyl), alkyl(hydroxy), alkyl(phosphonate), alkyl(sulfonate), aryl, alkylaminoalkyl, alkoxyalkyl, alkylthioalkyl, alkylthio, alicyclic, 1,1-dihaloalkyl, carbonylalkyl, aminocarbonylamino, alkylaminocarbonyl, alkylcarbonylamino, aralkyl, and alkylaryl, all optionally substituted; or together with Y forms a cyclic group including cyclic alkyl, heterocyclic, and aryl;

Y is selected from the group consisting of $-H$, alkyl, alkenyl, alkynyl, aryl, alicyclic, aralkyl, aryloxyalkyl, alkoxyalkyl, $-C(O)R^3$, $-S(O)_2R^3$, $-C(O)-OR^3$, $-CONHR^3$, $-NR^2_2$, and $-OR^3$, all except $-H$ are optionally substituted; or together with X forms a cyclic group including aryl, cyclic alkyl, and heterocyclic;

$R^4$ is independently selected from the group consisting of $-H$, lower alkyl, lower alicyclic, lower aralkyl, and lower aryl;

$R^5$ is selected from the group consisting of lower alkyl, lower aryl, lower aralkyl, and lower alicyclic;

$R^6$ is independently selected from the group consisting of $-H$, and lower alkyl;

$R^7$ is independently selected from the group consisting of $-H$, lower alkyd lower alicyclic, lower aralkyl, lower aryl, and $-C(O)R^{10}$;

$R^8$ is independently selected from the group consisting of $-H$, lower alkyl, lower aralkyl, lower aryl, lower alicyclic, $-C(O)R^{10}$, or together they form a bidentate alkyl;

$R^{10}$ is selected from the group consisting of $-H$, lower alkyl $-NH_2$, lower aryl, and lower perhaloalkyl;

$R^{11}$ is selected from the group consisting of alkyl, aryl, $-OH$, $-NH_2$ and $-OR^3$; and pharmaceutically acceptable prodrugs and salts thereof.

In another preferred aspect, those compounds where M is a compound of formula IV:

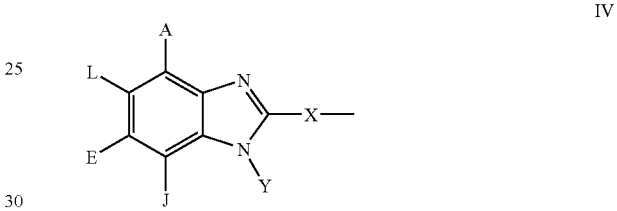

IV wherein:

A, E, and L are selected from the group consisting of $-NR^8_2$, $-NO_2$, $-H$, $-OR^7$, $-SR^7$, $-C(O)NR^4_2$, halo, $-COR^{11}$, $-SO_2R^3$, guanidine, amidine, $-NHSO_2R^5$, $-SO_2NR^4_2$, $-CN$, sulfoxide, perhaloacyl, perhaloalkyl, perhaloalkoxy, C1-C5 alkyl, C2-C5 alkenyl, C2-C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of $-NR^8_2$, $-NO_2$, $-H$, $-OR^7$, $-SR^7$, $-C(O)NR^4_2$, halo, $-C(O)R^{11}$, $-CN$, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X is selected from the group consisting of alkylamino, alkyl(hydroxy), alkyl(carboxyl), alkyl(phosphonate), alkyl, alkenyl, alkynyl, alkyl(sulfonate), aryl, carbonylalkyl, 1,1-dihaloalkyl, aminocarbonylamino, alkylaminoalkyl, alkoxyalkyl, alkylthioalkyl, alkylthio, alkylaminocarbonyl, alkylcarbonylamino, alicyclic, aralkyl, and alkylaryl, all optionally substituted; or together with Y forms a cyclic group including aryl, cyclic alkyl, and heterocyclic;

Y is selected from the group consisting of $-H$, alkyl, alkenyl, alkynyl, aryl, alicyclic, aralkyl, aryloxyalkyl, alkoxyalkyl, $-C(O)R^3$, $-S(O)_2R^3$, $-C(O)-OR^3$, $-CONHR^3$, $-NR^2_2$, and $-OR^3$, all except $-H$ are optionally substituted; or together with X forms a cyclic group including aryl, cyclic alkyl, and heterocyclic;

$R^4$ is independently selected from the group consisting of $-H$, lower alkyl, lower alicyclic, lower aralkyl, and lower aryl;

$R^5$ is selected from the group consisting of lower alkyl, lower aryl, lower aralkyl, and lower alicyclic;

$R^6$ is independently selected from the group consisting of —H, and lower alkyl;

$R^7$ is independently selected from the group consisting of —H, lower alkyl, lower alicyclic, lower aralkyl, lower aryl, and —C(O)$R^{10}$;

$R^8$ is independently selected from the group consisting of —H, lower alkyl, lower aralkyl, lower aryl, lower alicyclic, —C(O)$R^{10}$, or together they form a bidentate alkyl;

$R^{10}$ is selected from the group consisting of —H, lower alkyl, —NH$_2$, lower aryl, and lower perhaloalkyl;

$R^{11}$ is selected from the group consisting of alkyl, aryl, —OH, —NH$_2$ and —OR$^3$; and pharmaceutically acceptable prodrugs and salts thereof; with the provisos that:

a) when X is alkyl or alkene, then A is —NR$^8{}_2$;

b) X is not alkylamine and alkylaminoalkyl when an alkyl moiety is substituted with phosphonic esters and acids; and c) A, L, E, J, Y, and X together may only form 0-2 cyclic groups.

Preferably, oral bioavailability is at least 5%. More preferably, oral bioavailability is at least 10%.

Preferred A groups include —NR$^8{}_2$, lower alkyl, lower perhaloalkyl, lower alkoxy, and halogen. Particularly preferred are —NR$^8{}_2$, and halogen. Especially preferred is —NR$^8{}_2$. Most preferred is —NH$_2$.

Preferred E groups include —H, halogen, lower perhaloalkyl, —CN, lower alkyl, lower alkoxy, and lower alkylthio. Particularly preferred E groups include —H, —SMe, -Et, and —Cl. Especially preferred is —H and —SCH$_3$.

Preferred X groups include alkylamino, alkyl, alkynyl, alkoxyalkyl, alkylthio, aryl, 1,1-dihaloalkyl, carbonylalkyl, heteroaryl, alkylcarbonylamino, and alkylaminocarbonyl. Particularly preferred is alkyl substituted with 1 to 3 substituents selected from halogen, phosphonate, —CO$_2$H, —SO$_3$H, and —OH. Particularly preferred are alkylaminocarbonyl, alkoxyalkyl, and heteroaryl. Preferred alkoxyalkyl groups include methoxymethyl. Preferred heteroaryl groups include furanyl, optionally substituted.

Preferred Y groups include aralkyl, alicyclic, alkyl, and aryl, all optionally substituted. Particularly preferred is lower alkyl. Particularly preferred Y groups include (2-naphthyl)methyl, cyclohexylethyl, phenylethyl, nonyl, cyclohexylpropyl, ethyl, cyclopropylmethyl, cyclobutytmethylphenyl, (2-methyl)propyl, neopentyl, cyclopropyl, cyclopentyl, (1-imidozolyl)propyl, 2-ethoxybenzyl, 1-hydroxy-2,2-dimethylpropyl, 1-chloro-2,2-dimethylpropyl, 2,2-dimethylbutyl, 2-(spiro-3,3-dimethylcyclohex-4-enyl) propyl, and 1-methylneopentyl. Especially preferred is neopentyl and isobutyl.

Preferred $R^4$ and $R^7$ groups are —H, and lower alkyl. Particularly preferred are —H, and methyl.

In another preferred aspect, A is —NR$^8{}_2$ or halogen, E is —H, halogen, —CN, lower alkyl, lower perhaloalkyl, lower alkoxy, or lower alkylthio, X is alkylamino, alkyl, alkoxyalkyl, alkynyl, 1,1-dihaloalkyl, carbonylakyl, alkyl(OH), alkyl(sulfonate), alkylcarbonylamino, alkylaminocarbonyl, alkylthio, aryl, or heteroaryl, and $R^4$ and $R^7$ is —H or lower alkyl. Particularly preferred are such compounds where Y is aralkyl, aryl, alicyclic, or alkyl.

In another preferred aspect, A is —NR$^8{}_2$, E is —H, Cl—, or methylthio, and X is optionally substituted furanyl, or alkoxyalkyl. Particularly preferred are such compounds where A is —NH$_2$, X is 2,5-furanyl, or methoxymethyl, and Y is lower alkyl. Most preferred are such compounds where E is H, X is 2,5-furanyl, and Y is neopentyl; those where E is —SCH$_3$, X is 2,5-furanyl, and Y is isobutyl; and those where E is —H, X is 2,5-furanyl, and Y is 1-(3-chloro-2,2-dimethyl)-propyl.

In one aspect, the compounds of formula VI preferably have a group Z which is H, alkyl, alicyclic, hydroxy, alkoxy, OC(O)$R^3$, OC(O)O$R^3$, amino, or —NHC(O)$R^2$. Preferred are such groups in which Z decreases the propensity of the byproduct, vinyl aryl ketone to undergo Michael reactions. Preferred Z groups are groups that donate electrons to the vinyl group which is a known strategy for decreasing the propensity of α,β-unsaturated carbonyl compounds to undergo a Michael addition. For example, a methyl group in a similar position on acrylamide results in no mutagenic activity whereas the unsubstituted vinyl analog is highly mutagenic. Other groups could serve a similar function, e.g. Z=O$R^3$, NHAc, etc. Other groups may also prevent the Michael addition especially groups that result in removal of the double bond altogether-such as Z=OH, O$R^{12}$, NH$_2$, which will rapidly undergo retautomerization after the elimination reaction. Certain W and W' groups are also advantageous in this role since the group(s) impede the addition reaction to the β-carbon or destabilize the product. Another preferred Z group is one that contains a nucleophilic group capable of adding to the α,β-unsaturated double bond after the elimination reaction i.e. (CH$_2$)$_p$SH or (CH$_2$)$_p$OH where p is 2 or 3.

P450 oxidation can be sensitive to stereochemistry which might either be at phosphorus or at the carbon bearing the aromatic group. The prodrugs of the present invention have two isomeric forms-around the phosphorus. Preferred is the stereochemistry that enables both oxidation and the elimination reaction. Preferred is the cis stereochemistry. In contrast, the reaction is relatively insensitive to the group M since cleavage occurred with a variety of phosphonate, phosphate and phosphoramidates. Accordingly, the group M represents a group that as part of a compound of formula 1 enables generation of a biologically active compound in vivo via conversion to the corresponding M-PO$_3{}^{2-}$. The atom in M attached to phosphorus may be O, C or N. The active drug may be M-PO$_3{}^{2-}$ or a metabolite of M-PO$_3{}^{2-}$ such as the triphosphate useful for treatment of diseases in which the liver is a target organ, including diabetes, hepatitis, liver cancer, liver fibrosis, malaria and metabolic diseases where the liver is responsible for the overproduction of a biochemical end products such as glucose (diabetes), cholesterol, fatty acids and triglycerides (atherosclerosis). Moreover, M-PO$_3{}^{2-}$ may be useful in treating diseases where the target is outside the liver but accessible to a phosph(on)ate.

Preferred M groups are groups in which M is a nucleoside and the phosphate is attached to a hydroxyl, preferably a primary hydroxyl on a sugar or sugar-analog. Especially preferred M groups include araA; AZT; d4T; ddI; ddA; ddC; L-ddC; L FddC; L-d4C; L-Fd4C; 3TC; ribavirin; 5-fluoro 2'deoxyuridine; FIAU; FIAC; BHCG; L FMAU; BvaraU; E-5-(2-bromovinyl-2' deoxyuridine; TFT; 5-propynyl-1 arabinosyluracil; CDG; DAPD; FDOC; d4C; DXG; FEAU; FLG; FLT; FTC; 5-yl-carbocyclic 2'deoxyguanosine; oxetanocin A; oxetanocin G; Cyclobut A, Cyclobut G; dFdC; araC; bromodeoxyuridine; IDU; CdA; FaraA; Coformycin, 2'-deoxycoformycin; araT; tiazofurin; ddAPR; 9-(arabinofuranosyl)-2,6 diaminopurine; 9-(2'-deoxyribofuranosyl)-2,6 diaminopurine; 9-(2'-deoxy 2'fluororibofuranosyl)-2,6-diaminopurine; 9 (arabinofuranosyl)guanine; 9-(2' deoxyribofuranosyl)guanine; 9-(2'-deoxy 2'fluororibofuranosyl)guanine; FMdC; 5,6 dihydro-5-azacytidine; 5-azacytidine; 5-aza 2'deoxycytidine; AICAR; ACV, GCV; penciclovir; (R)-9-(3,4 dihydroxybutyl)guanine; or cytallene.

The preferred M groups include phosphonic acids useful for treating viral infections. Such preferred antivirals include PMEA; PMEDAP; HPMPC; HPMPA; FPMPA; PMPA; foscarnet; phosphonoformic acid. More preferred are PMEA, HPMPC, and HPMPA.

Other preferred M groups include phosphonic acids useful in treating diabetes, liver fibrosis, e.g. collagenase inhibitors such as reported in Bird et al., *J. Med. Chem.* 37, 158-169 (1994), parasitic infections, diseases responsive to metalloprotease inhibition (e.g. hypertension, liver, cancer), and hyperlipidemia.

In one aspect, preferred MH groups are acyclic nucleosides. Preferred acyclic nucleosides include ACV, GCV; penciclovir; (R)-9-(3,4 dihydroxybutyl)guanine; and cytallene. More preferred are ACV; GCV, and penciclovir.

In another aspect, preferred MH groups include dideoxy nucleosides. Preferred dideoxy nucleosides include AZT; d4T; ddI; ddA; ddC; L-ddC; L-FddC; L d4C; L-Fd4C; d4C; and ddAPR. More preferred are AZT; d4T; ddI; and ddC.

In another aspect, preferred MH groups include arabinofuranosyl nucleosides. Preferred are araA; araT; 5-propynyl-1-arabinosyluracil; araC; FaraA; 9-(arabinofurranosyl)-2,6 diaminopurine; and 9-(arabinofuranosyl)guanine. More preferred are araA; araC; and FaraA.

In another aspect, preferred MH groups include carbocyclic nucleosides. Preferred are 5-yl-carbocyclic 2'deoxyguanosine; CDG; cyclobut A; cyclobut G; and BHCG. More preferred are 5-yl-carbocyclic 2'deoxyguanosine; and cyclobut G.

In another aspect, preferred MH groups include fluorinated sugars on the nucleosides. Preferred fluorinated sugars include FLT; FLG; FIAC; FIAU; FMAU; FEAU; dFdC; 9-(2'-deoxy-2'fluororibofuranosyl) 2,6-diaminopurine; and 9-(2'-deoxy 2'fluororibofuranosyl)guanine. More preferred are L-FMAU; and dFdC.

In another aspect, preferred MH groups include dioxolane nucleosides. Preferred dioxolane nucleosides include DAPD; DXG; and FDOC. More preferred is DAPD.

In another aspect, preferred MH groups include L-nucleosides. Preferred L-nucleosides include L-ddC, L-FddC, L-d4C, L-Fd4C, 3TC, FTC, L-FMAU. More preferred are 3TC, FTC, L-FMAU.

The following prodrugs are preferred compounds of the invention. The compounds are shown without depiction of stereochemistry since the compounds are biologically active as the diastereomeric mixture or as a single stereoisomer. Compounds named in Table 1 are designated by numbers assigned to the variables of formula using the following convention: $M^1.V.L1.L2$. $M^1$ is a variable that represents compounds of the formula M-H which have a specific hydroxyl group that is phosphorylated with a group P(O)(O—CH(V)CH2CH2-O) to make compounds of formula VI or $M^1$ is a variable that represents phosphonic acids of the formula $M-PO_3^{2-}$ which are transformed to compounds of formula VI by replacing two oxygens in the $PO_3^{2-}$ group with O—CH(V)CH2CH2-O. V is an aryl or heteroaryl group that has 2 substituents, L1 and L2, at the designated positions.

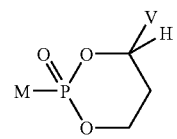

VI

Variable $M^1$ is divided into three groups with the structures assigned to each group listed below:

| Variable $M^1$: Group $M^1$1: | |
|---|---|
| 1) | 3TC where —P(O)(O—CH(V)CH2CH2—O) is attached to the primary hydroxyl. |
| 2) | (−)FTC where —P(O)(O—CH(V)CH2CH2—O) is attached to the primary hydroxyl. |
| 3) | L-FMAU where —P(O)(O—CH(V)CH2CH2—O) is attached to the primary hydroxyl. |
| 4) | Penciclovir where —P(O)(O—CH(V)CH2CH2—O) is attached to the primary hydroxyl that is phosphorylated in cells. |
| 5) | BMS 200,475 where —P(O)(O—CH(V)CH2CH2—O) is attached to the primary hydroxyl. |
| 6) | L(−)Fd4C where —P(O)(O—CH(V)CH2CH2—O) is attached to the primary hydroxyl. |
| 7) | Lobucavir where —P(O)(O—CH(V)CH2CH2—O) is attached to the primary hydroxyl that is phosphorylated in cells. |
| 8) | DXG where —P(O)(O—CH(V)CH2CH2—O) is attached to the primary hydroxyl. |
| 9) | araA where —P(O)(O—CH(V)CH2CH2—O) is attached to the primary hydroxyl. |

| Variable $M^1$: Group $M^1$2: | |
|---|---|
| 1) | ddI where —P(O)(O—CH(V)CH2CH2—O) is attached to the primary hydroxyl. |
| 2) | ddA where —P(O)(O—CH(V)CH2CH2—O) is attached to the primary hydroxyl. |

-continued

| Variable M¹: | Group M¹2: |
|---|---|
| 3) | ddC where —P(O)(O—CH(V)CH2CH2—O) is attached to the primary hydroxyl. |
| 4) | AZT where —P(O)(O—CH(V)CH2CH2—O) is attached to the primary hydroxyl. |
| 5) | d4T where —P(O)(O—CH(V)CH2CH2—O) is attached to the primary hydroxyl. |
| 6) | DAPD where —P(O)(O—CH(V)CH2CH2—O) is attached to the primary hydroxyl. |
| 7) | L-FddC where —P(O)(O—CH(V)CH2CH2—O) is attached to the primary hydroxyl. |
| 8) | Ribavirin where —P(O)(O—CH(V)CH2CH2—O) is attached to the primary hydroxyl. |
| 9) | FMdC where —P(O)(O—CH(V)CH2CH2—O) is attached to the primary hydroxyl |

| Variable M¹: | Group M¹3: |
|---|---|
| 1) | Ganciclovir where —P(O)(O—CH(V)CH2CH2—O) is attached to the primary hydroxyl that is phosphorylated in cells. |
| 2) | Acyclovir where —P(O)(O—CH(V)CH2CH2—O) is attached to the primary hydroxyl. |
| 3) | Cytarabine where —P(O)(O—CH(V)CH2CH2—O) is attached to the primary hydroxyl. |
| 4) | Gemcitabine where —P(O)(O—CH(V)CH2CH2—O) is attached to the primary hydroxyl |
| 5) | Fludarabine where —P(O)(O—CH(V)CH2CH2—O) is attached to the primary hydroxyl |
| 6) | Floxuridine where —P(O)(O—CH(V)CH2CH2—O) is attached to the primary hydroxyl |
| 7) | HPMPC where —P(O)(O—CH(V)CH2CH2—O) replaces the $PO_3^{2-}$ group. |
| 8) | PMEA where —P(O)(O-CH(V)CH2CH2-O) replaces the $PO_3^{2-}$ group. |
| 9) | PMPA where —P(O)(O—CH(V)CH2CH2—O) replaces the $PO_3^{2-}$ group. |

| Variable V: | Group V1 |
|---|---|
| 1) | 2-(L1)-3(L2) phenyl |
| 2) | 2-(L1)-4(L2) phenyl |
| 3) | 2-(L1)-5(L2) phenyl |
| 4) | 2-(L1)-6(L2) phenyl |
| 5) | 3-(L1)-4(L2) phenyl |
| 6) | 3-(L1)-5(L2) phenyl |
| 7) | 3-(L1)-6(L2) phenyl |
| 8) | 2-(L1)-6(L2)-4-chlorophenyl |
| 9) | 3-(L1)-5(L2) 4-chlorophenyl |

| Variable V: | Group V2 |
|---|---|
| 1) | 2-(L1)-3(L2) 4-pyridyl |
| 2) | 2-(L1)-5(L2) 4-pyridyl |
| 3) | 2-(L1)-6(L2) 4-pyridyl |
| 4) | 3-(L1)-5(L2) 4-pyridyl |
| 5) | 3-(L1)-6(L2) 4-pyridyl |
| 6) | 2-(L1)-4(L2) 3-pyridyl |
| 7) | 2-(L1)-5(L2) 3-pyridyl |
| 8) | 2-(L1)-6(L2) 3-pyridyl |
| 9) | 4-(L1)-5(L2) 3-pyridyl |

| Variable V: | Group V3 |
|---|---|
| 1) | 4-(L1)-6(L2) 3-pyridyl |
| 2) | 5-(L1)-6(L2) 3-pyridyl |
| 3) | 3-(L1)-4(L2) 2-pyridyl |
| 4) | 3-(L1)-5(L2) 2-pyridyl |
| 5) | 3-(L1)-6(L2) 2-pyridyl |
| 6) | 4-(L1)-5(L2) 2-pyridyl |
| 7) | 4-(L1)-6(L2) 2-pyridyl |
| 8) | 3-(L1)-4(L2)-2-thienyl |
| 9) | 2-(L1)-5(L2) 3-furnayl |

| | Variable L1 |
|---|---|
| 1) | hydrogen |
| 2) | chloro |
| 3) | bromo |
| 4) | fluoro |
| 5) | methyl |
| 6) | isopropyl |
| 7) | methoxy |
| 8) | dimethylamino |
| 9) | acyloxy |

| Variable L2 | |
| --- | --- |
| 1) | hydrogen |
| 2) | chloro |
| 3) | bromo |
| 4) | fluoro |
| 5) | methyl |
| 6) | isopropyl |
| 7) | methoxy |
| 8) | dimethylamino |
| 9) | acyloxy |

Preferred compounds are compounds listed in Table 1 using groups $M^1 1$ and V1. For example, compound 1.3.6.7 represents structure 1 of group $M^1 1$, i.e. 3TC; structure 3 of group V1, i.e. 2-(L1)-5-(L2) phenyl; structure 6 of variable L1, i.e. isopropyl; and structure 7 of variable L2, i.e. methoxy. The compound 1.3.6.7. therefore is 3TC with the P(O)(O—CH(V)CH2CH2O) attached to the primary hydroxyl group being {[1-(2-I-propyl-5-methoxyphenyl)-1,3-propyl]phosphoryl.

Preferred compounds are also compounds listed in Table 1 using groups $M^1 1$ and V2.

Preferred compounds are also compounds listed in Table 1 using groups $M^1 1$ and V3.

Preferred compounds are also compounds listed in Table 1 using groups $M^1 2$ and V3.

Preferred compounds are also compounds listed in Table 1 using groups $M^1 2$ and V2.

Preferred compounds are also compounds listed in Table 1 using groups $M^1 2$ and V3.

Preferred compounds are also compounds listed in Table 1 using groups $M^1 3$ and V3.

Preferred compounds are also compounds listed in Table 1 using groups $M^1 3$ and V2.

Preferred compounds are also compounds listed in Table 1 using groups $M^1 3$ and V3.

TABLE 1

| | | | | | | | | | |
| --- | --- | --- | --- | --- | --- | --- | --- | --- | --- |
| 1.1.1.1 | 1.1.1.2 | 1.1.1.3 | 1.1.1.4 | 1.1.1.5 | 1.1.1.6 | 1.1.1.7 | 1.1.1.8 | 1.1.1.9 | 1.1.2.1 |
| 1.1.2.2 | 1.1.2.3 | 1.1.2.4 | 1.1.2.5 | 1.1.2.6 | 1.1.2.7 | 1.1.2.8 | 1.1.2.9 | 1.1.3.1 | 1.1.3.2 |
| 1.1.3.3 | 1.1.3.4 | 1.1.3.5 | 1.1.3.6 | 1.1.3.7 | 1.1.3.8 | 1.1.3.9 | 1.1.4.1 | 1.1.4.2 | 1.1.4.3 |
| 1.1.4.4 | 1.1.4.5 | 1.1.4.6 | 1.1.4.7 | 1.1.4.8 | 1.1.4.9 | 1.1.5.1 | 1.1.5.2 | 1.1.5.3 | 1.1.5.4 |
| 1.1.5.5 | 1.1.5.6 | 1.1.5.7 | 1.1.5.8 | 1.1.5.9 | 1.1.6.1 | 1.1.6.2 | 1.1.6.3 | 1.1.6.4 | 1.1.6.5 |
| 1.1.6.6 | 1.1.6.7 | 1.1.6.8 | 1.1.6.9 | 1.1.7.1 | 1.1.7.2 | 1.1.7.3 | 1.1.7.4 | 1.1.7.5 | 1.1.7.6 |
| 1.1.7.7 | 1.1.7.8 | 1.1.7.9 | 1.1.8.1 | 1.1.8.2 | 1.1.8.3 | 1.1.8.4 | 1.1.8.5 | 1.1.8.6 | 1.1.8.7 |
| 1.1.8.8 | 1.1.8.9 | 1.1.9.1 | 1.1.9.2 | 1.1.9.3 | 1.1.9.4 | 1.1.9.5 | 1.1.9.6 | 1.1.9.7 | 1.1.9.8 |
| 1.1.9.9 | 1.2.1.1 | 1.2.1.2 | 1.2.1.3 | 1.2.1.4 | 1.2.1.5 | 1.2.1.6 | 1.2.1.7 | 1.2.1.8 | 1.2.1.9 |
| 1.2.2.1 | 1.2.2.2 | 1.2.2.3 | 1.2.2.4 | 1.2.2.5 | 1.2.2.6 | 1.2.2.7 | 1.2.2.8 | 1.2.2.9 | 1.2.3.1 |
| 1.2.3.2 | 1.2.3.3 | 1.2.3.4 | 1.2.3.5 | 1.2.3.6 | 1.2.3.7 | 1.2.3.8 | 1.2.3.9 | 1.2.4.1 | 1.2.4.2 |
| 1.2.4.3 | 1.2.4.4 | 1.2.4.5 | 1.2.4.6 | 1.2.4.7 | 1.2.4.8 | 1.2.4.9 | 1.2.5.1 | 1.2.5.2 | 1.2.5.3 |
| 1.2.5.4 | 1.2.5.5 | 1.2.5.6 | 1.2.5.7 | 1.2.5.8 | 1.2.5.9 | 1.2.6.1 | 1.2.6.2 | 1.2.6.3 | 1.2.6.4 |
| 1.2.6.5 | 1.2.6.6 | 1.2.6.7 | 1.2.6.8 | 1.2.6.9 | 1.2.7.1 | 1.2.7.2 | 1.2.7.3 | 1.2.7.4 | 1.2.7.5 |
| 1.2.7.6 | 1.2.7.7 | 1.2.7.8 | 1.2.7.9 | 1.2.8.1 | 1.2.8.2 | 1.2.8.3 | 1.2.8.4 | 1.2.8.5 | 1.2.8.6 |
| 1.2.8.7 | 1.2.8.8 | 1.2.8.9 | 1.2.9.1 | 1.2.9.2 | 1.2.9.3 | 1.2.9.4 | 1.2.9.5 | 1.2.9.6 | 1.2.9.7 |
| 1.2.9.8 | 1.2.9.9 | 1.3.1.1 | 1.3.1.2 | 1.3.1.3 | 1.3.1.4 | 1.3.1.5 | 1.3.1.6 | 1.3.1.7 | 1.3.1.8 |
| 1.3.1.9 | 1.3.2.1 | 1.3.2.2 | 1.3.2.3 | 1.3.2.4 | 1.3.2.5 | 1.3.2.6 | 1.3.2.7 | 1.3.2.8 | 1.3.2.9 |
| 1.3.3.1 | 1.3.3.2 | 1.3.3.3 | 1.3.3.4 | 1.3.3.5 | 1.3.3.6 | 1.3.3.7 | 1.3.3.8 | 1.3.3.9 | 1.3.4.1 |
| 1.3.4.2 | 1.3.4.3 | 1.3.4.4 | 1.3.4.5 | 1.3.4.6 | 1.3.4.7 | 1.3.4.8 | 1.3.4.9 | 1.3.5.1 | 1.3.5.2 |
| 1.3.5.3 | 1.3.5.4 | 1.3.5.5 | 1.3.5.6 | 1.3.5.7 | 1.3.5.8 | 1.3.5.9 | 1.3.6.1 | 1.3.6.2 | 1.3.6.3 |
| 1.3.6.4 | 1.3.6.5 | 1.3.6.6 | 1.3.6.7 | 1.3.6.8 | 1.3.6.9 | 1.3.7.1 | 1.3.7.2 | 1.3.7.3 | 1.3.7.4 |
| 1.3.7.5 | 1.3.7.6 | 1.3.7.7 | 1.3.7.8 | 1.3.7.9 | 1.3.8.1 | 1.3.8.2 | 1.3.8.3 | 1.3.8.4 | 1.3.8.5 |
| 1.3.8.6 | 1.3.8.7 | 1.3.8.8 | 1.3.8.9 | 1.3.9.1 | 1.3.9.2 | 1.3.9.3 | 1.3.9.4 | 1.3.9.5 | 1.3.9.6 |
| 1.3.9.7 | 1.3.9.8 | 1.3.9.9 | 1.4.1.1 | 1.4.1.2 | 1.4.1.3 | 1.4.1.4 | 1.4.1.5 | 1.4.1.6 | 1.4.1.7 |
| 1.4.1.8 | 1.4.1.9 | 1.4.2.1 | 1.4.2.2 | 1.4.2.3 | 1.4.2.4 | 1.4.2.5 | 1.4.2.6 | 1.4.2.7 | 1.4.2.8 |
| 1.4.2.9 | 1.4.3.1 | 1.4.3.2 | 1.4.3.3 | 1.4.3.4 | 1.4.3.5 | 1.4.3.6 | 1.4.3.7 | 1.4.3.8 | 1.4.3.9 |
| 1.4.4.1 | 1.4.4.2 | 1.4.4.3 | 1.4.4.4 | 1.4.4.5 | 1.4.4.6 | 1.4.4.7 | 1.4.4.8 | 1.4.4.9 | 1.4.5.1 |
| 1.4.5.2 | 1.4.5.3 | 1.4.5.4 | 1.4.5.5 | 1.4.5.6 | 1.4.5.7 | 1.4.5.8 | 1.4.5.9 | 1.4.6.1 | 1.4.6.2 |
| 1.4.6.3 | 1.4.6.4 | 1.4.6.5 | 1.4.6.6 | 1.4.6.7 | 1.4.6.8 | 1.4.6.9 | 1.4.7.1 | 1.4.7.2 | 1.4.7.3 |
| 1.4.7.4 | 1.4.7.5 | 1.4.7.6 | 1.4.7.7 | 1.4.7.8 | 1.4.7.9 | 1.4.8.1 | 1.4.8.2 | 1.4.8.3 | 1.4.8.4 |
| 1.4.8.5 | 1.4.8.6 | 1.4.8.7 | 1.4.8.8 | 1.4.8.9 | 1.4.9.1 | 1.4.9.2 | 1.4.9.3 | 1.4.9.4 | 1.4.9.5 |
| 1.4.9.6 | 1.4.9.7 | 1.4.9.8 | 1.4.9.9 | 1.5.1.1 | 1.5.1.2 | 1.5.1.3 | 1.5.1.4 | 1.5.1.5 | 1.5.1.6 |
| 1.5.1.7 | 1.5.1.8 | 1.5.1.9 | 1.5.2.1 | 1.5.2.2 | 1.5.2.3 | 1.5.2.4 | 1.5.2.5 | 1.5.2.6 | 1.5.2.7 |
| 1.5.2.8 | 1.5.2.9 | 1.5.3.1 | 1.5.3.2 | 1.5.3.3 | 1.5.3.4 | 1.5.3.5 | 1.5.3.6 | 1.5.3.7 | 1.5.3.8 |
| 1.5.3.9 | 1.5.4.1 | 1.5.4.2 | 1.5.4.3 | 1.5.4.4 | 1.5.4.5 | 1.5.4.6 | 1.5.4.7 | 1.5.4.8 | 1.5.4.9 |
| 1.5.5.1 | 1.5.5.2 | 1.5.5.3 | 1.5.5.4 | 1.5.5.5 | 1.5.5.6 | 1.5.5.7 | 1.5.5.8 | 1.5.5.9 | 1.5.6.1 |
| 1.5.6.2 | 1.5.6.3 | 1.5.6.4 | 1.5.6.5 | 1.5.6.6 | 1.5.6.7 | 1.5.6.8 | 1.5.6.9 | 1.5.7.1 | 1.5.7.2 |
| 1.5.7.3 | 1.5.7.4 | 1.5.7.5 | 1.5.7.6 | 1.5.7.7 | 1.5.7.8 | 1.5.7.9 | 1.5.8.1 | 1.5.8.2 | 1.5.8.3 |
| 1.5.8.4 | 1.5.8.5 | 1.5.8.6 | 1.5.8.7 | 1.5.8.8 | 1.5.8.9 | 1.5.9.1 | 1.5.9.2 | 1.5.9.3 | 1.5.9.4 |
| 1.5.9.5 | 1.5.9.6 | 1.5.9.7 | 1.5.9.8 | 1.5.9.9 | 1.6.1.1 | 1.6.1.2 | 1.6.1.3 | 1.6.1.4 | 1.6.1.5 |
| 1.6.1.6 | 1.6.1.7 | 1.6.1.8 | 1.6.1.9 | 1.6.2.1 | 1.6.2.2 | 1.6.2.3 | 1.6.2.4 | 1.6.2.5 | 1.6.2.6 |
| 1.6.2.7 | 1.6.2.8 | 1.6.2.9 | 1.6.3.1 | 1.6.3.2 | 1.6.3.3 | 1.6.3.4 | 1.6.3.5 | 1.6.3.6 | 1.6.3.7 |
| 1.6.3.8 | 1.6.3.9 | 1.6.4.1 | 1.6.4.2 | 1.6.4.3 | 1.6.4.4 | 1.6.4.5 | 1.6.4.6 | 1.6.4.7 | 1.6.4.8 |
| 1.6.4.9 | 1.6.5.1 | 1.6.5.2 | 1.6.5.3 | 1.6.5.4 | 1.6.5.5 | 1.6.5.6 | 1.6.5.7 | 1.6.5.8 | 1.6.5.9 |
| 1.6.6.1 | 1.6.6.2 | 1.6.6.3 | 1.6.6.4 | 1.6.6.5 | 1.6.6.6 | 1.6.6.7 | 1.6.6.8 | 1.6.6.9 | 1.6.7.1 |
| 1.6.7.2 | 1.6.7.3 | 1.6.7.4 | 1.6.7.5 | 1.6.7.6 | 1.6.7.7 | 1.6.7.8 | 1.6.7.9 | 1.6.8.1 | 1.6.8.2 |
| 1.6.8.3 | 1.6.8.4 | 1.6.8.5 | 1.6.8.6 | 1.6.8.7 | 1.6.8.8 | 1.6.8.9 | 1.6.9.1 | 1.6.9.2 | 1.6.9.3 |
| 1.6.9.4 | 1.6.9.5 | 1.6.9.6 | 1.6.9.7 | 1.6.9.8 | 1.6.9.9 | 1.7.1.1 | 1.7.1.2 | 1.7.1.3 | 1.7.1.4 |
| 1.7.1.5 | 1.7.1.6 | 1.7.1.7 | 1.7.1.8 | 1.7.1.9 | 1.7.2.1 | 1.7.2.2 | 1.7.2.3 | 1.7.2.4 | 1.7.2.5 |
| 1.7.2.6 | 1.7.2.7 | 1.7.2.8 | 1.7.2.9 | 1.7.3.1 | 1.7.3.2 | 1.7.3.3 | 1.7.3.4 | 1.7.3.5 | 1.7.3.6 |
| 1.7.3.7 | 1.7.3.8 | 1.7.3.9 | 1.7.4.1 | 1.7.4.2 | 1.7.4.3 | 1.7.4.4 | 1.7.4.5 | 1.7.4.6 | 1.7.4.7 |
| 1.7.4.8 | 1.7.4.9 | 1.7.5.1 | 1.7.5.2 | 1.7.5.3 | 1.7.5.4 | 1.7.5.5 | 1.7.5.6 | 1.7.5.7 | 1.7.5.8 |

TABLE 1-continued

| | | | | | | | | |
|---|---|---|---|---|---|---|---|---|
| 1.7.5.9 | 1.7.6.1 | 1.7.6.2 | 1.7.6.3 | 1.7.6.4 | 1.7.6.5 | 1.7.6.6 | 1.7.6.7 | 1.7.6.8 | 1.7.6.9 |
| 1.7.7.1 | 1.7.7.2 | 1.7.7.3 | 1.7.7.4 | 1.7.7.5 | 1.7.7.6 | 1.7.7.7 | 1.7.7.8 | 1.7.7.9 | 1.7.8.1 |
| 1.7.8.2 | 1.7.8.3 | 1.7.8.4 | 1.7.8.5 | 1.7.8.6 | 1.7.8.7 | 1.7.8.8 | 1.7.8.9 | 1.7.9.1 | 1.7.9.2 |
| 1.7.9.3 | 1.7.9.4 | 1.7.9.5 | 1.7.9.6 | 1.7.9.7 | 1.7.9.8 | 1.7.9.9 | 1.8.1.1 | 1.8.1.2 | 1.8.1.3 |
| 1.8.1.4 | 1.8.1.5 | 1.8.1.6 | 1.8.1.7 | 1.8.1.8 | 1.8.1.9 | 1.8.2.1 | 1.8.2.2 | 1.8.2.3 | 1.8.2.4 |
| 1.8.2.5 | 1.8.2.6 | 1.8.2.7 | 1.8.2.8 | 1.8.2.9 | 1.8.3.1 | 1.8.3.2 | 1.8.3.3 | 1.8.3.4 | 1.8.3.5 |
| 1.8.3.6 | 1.8.3.7 | 1.8.3.8 | 1.8.3.9 | 1.8.4.1 | 1.8.4.2 | 1.8.4.3 | 1.8.4.4 | 1.8.4.5 | 1.8.4.6 |
| 1.8.4.7 | 1.8.4.8 | 1.8.4.9 | 1.8.5.1 | 1.8.5.2 | 1.8.5.3 | 1.8.5.4 | 1.8.5.5 | 1.8.5.6 | 1.8.5.7 |
| 1.8.5.8 | 1.8.5.9 | 1.8.6.1 | 1.8.6.2 | 1.8.6.3 | 1.8.6.4 | 1.8.6.5 | 1.8.6.6 | 1.8.6.7 | 1.8.6.8 |
| 1.8.6.9 | 1.8.7.1 | 1.8.7.2 | 1.8.7.3 | 1.8.7.4 | 1.8.7.5 | 1.8.7.6 | 1.8.7.7 | 1.8.7.8 | 1.8.7.9 |
| 1.8.8.1 | 1.8.8.2 | 1.8.8.3 | 1.8.8.4 | 1.8.8.5 | 1.8.8.6 | 1.8.8.7 | 1.8.8.8 | 1.8.8.9 | 1.8.9.1 |
| 1.8.9.2 | 1.8.9.3 | 1.8.9.4 | 1.8.9.5 | 1.8.9.6 | 1.8.9.7 | 1.8.9.8 | 1.8.9.9 | 1.9.1.1 | 1.9.1.2 |
| 1.9.1.3 | 1.9.1.4 | 1.9.1.5 | 1.9.1.6 | 1.9.1.7 | 1.9.1.8 | 1.9.1.9 | 1.9.2.1 | 1.9.2.2 | 1.9.2.3 |
| 1.9.2.4 | 1.9.2.5 | 1.9.2.6 | 1.9.2.7 | 1.9.2.8 | 1.9.2.9 | 1.9.3.1 | 1.9.3.2 | 1.9.3.3 | 1.9.3.4 |
| 1.9.3.5 | 1.9.3.6 | 1.9.3.7 | 1.9.3.8 | 1.9.3.9 | 1.9.4.1 | 1.9.4.2 | 1.9.4.3 | 1.9.4.4 | 1.9.4.5 |
| 1.9.4.6 | 1.9.4.7 | 1.9.4.8 | 1.9.4.9 | 1.9.5.1 | 1.9.5.2 | 1.9.5.3 | 1.9.5.4 | 1.9.5.5 | 1.9.5.6 |
| 1.9.5.7 | 1.9.5.8 | 1.9.5.9 | 1.9.6.1 | 1.9.6.2 | 1.9.6.3 | 1.9.6.4 | 1.9.6.5 | 1.9.6.6 | 1.9.6.7 |
| 1.9.6.8 | 1.9.6.9 | 1.9.7.1 | 1.9.7.2 | 1.9.7.3 | 1.9.7.4 | 1.9.7.5 | 1.9.7.6 | 1.9.7.7 | 1.9.7.8 |
| 1.9.7.9 | 1.9.8.1 | 1.9.8.2 | 1.9.8.3 | 1.9.8.4 | 1.9.8.5 | 1.9.8.6 | 1.9.8.7 | 1.9.8.8 | 1.9.8.9 |
| 1.9.9.1 | 1.9.9.2 | 1.9.9.3 | 1.9.9.4 | 1.9.9.5 | 1.9.9.6 | 1.9.9.7 | 1.9.9.8 | 1.9.9.9 | 2.1.1.1 |
| 2.1.1.2 | 2.1.1.3 | 2.1.1.4 | 2.1.1.5 | 2.1.1.6 | 2.1.1.7 | 2.1.1.8 | 2.1.1.9 | 2.1.2.1 | 2.1.2.2 |
| 2.1.2.3 | 2.1.2.4 | 2.1.2.5 | 2.1.2.6 | 2.1.2.7 | 2.1.2.8 | 2.1.2.9 | 2.1.3.1 | 2.1.3.2 | 2.1.3.3 |
| 2.1.3.4 | 2.1.3.5 | 2.1.3.6 | 2.1.3.7 | 2.1.3.8 | 2.1.3.9 | 2.1.4.1 | 2.1.4.2 | 2.1.4.3 | 2.1.4.4 |
| 2.1.4.5 | 2.1.4.6 | 2.1.4.7 | 2.1.4.8 | 2.1.4.9 | 2.1.5.1 | 2.1.5.2 | 2.1.5.3 | 2.1.5.4 | 2.1.5.5 |
| 2.1.5.6 | 2.1.5.7 | 2.1.5.8 | 2.1.5.9 | 2.1.6.1 | 2.1.6.2 | 2.1.6.3 | 2.1.6.4 | 2.1.6.5 | 2.1.6.6 |
| 2.1.6.7 | 2.1.6.8 | 2.1.6.9 | 2.1.7.1 | 2.1.7.2 | 2.1.7.3 | 2.1.7.4 | 2.1.7.5 | 2.1.7.6 | 2.1.7.7 |
| 2.1.7.8 | 2.1.7.9 | 2.1.8.1 | 2.1.8.2 | 2.1.8.3 | 2.1.8.4 | 2.1.8.5 | 2.1.8.6 | 2.1.8.7 | 2.1.8.8 |
| 2.1.8.9 | 2.1.9.1 | 2.1.9.2 | 2.1.9.3 | 2.1.9.4 | 2.1.9.5 | 2.1.9.6 | 2.1.9.7 | 2.1.9.8 | 2.1.9.9 |
| 2.2.1.1 | 2.2.1.2 | 2.2.1.3 | 2.2.1.4 | 2.2.1.5 | 2.2.1.6 | 2.2.1.7 | 2.2.1.8 | 2.2.1.9 | 2.2.2.1 |
| 2.2.2.2 | 2.2.2.3 | 2.2.2.4 | 2.2.2.5 | 2.2.2.6 | 2.2.2.7 | 2.2.2.8 | 2.2.2.9 | 2.2.3.1 | 2.2.3.2 |
| 2.2.3.3 | 2.2.3.4 | 2.2.3.5 | 2.2.3.6 | 2.2.3.7 | 2.2.3.8 | 2.2.3.9 | 2.2.4.1 | 2.2.4.2 | 2.2.4.3 |
| 2.2.4.4 | 2.2.4.5 | 2.2.4.6 | 2.2.4.7 | 2.2.4.8 | 2.2.4.9 | 2.2.5.1 | 2.2.5.2 | 2.2.5.3 | 2.2.5.4 |
| 2.2.5.5 | 2.2.5.6 | 2.2.5.7 | 2.2.5.8 | 2.2.5.9 | 2.2.6.1 | 2.2.6.2 | 2.2.6.3 | 2.2.6.4 | 2.2.6.5 |
| 2.2.6.6 | 2.2.6.7 | 2.2.6.8 | 2.2.6.9 | 2.2.7.1 | 2.2.7.2 | 2.2.7.3 | 2.2.7.4 | 2.2.7.5 | 2.2.7.6 |
| 2.2.7.7 | 2.2.7.8 | 2.2.7.9 | 2.2.8.1 | 2.2.8.2 | 2.2.8.3 | 2.2.8.4 | 2.2.8.5 | 2.2.8.6 | 2.2.8.7 |
| 2.2.8.8 | 2.2.8.9 | 2.2.9.1 | 2.2.9.2 | 2.2.9.3 | 2.2.9.4 | 2.2.9.5 | 2.2.9.6 | 2.2.9.7 | 2.2.9.8 |
| 2.2.9.9 | 2.3.1.1 | 2.3.1.2 | 2.3.1.3 | 2.3.1.4 | 2.3.1.5 | 2.3.1.6 | 2.3.1.7 | 2.3.1.8 | 2.3.1.9 |
| 2.3.2.1 | 2.3.2.2 | 2.3.2.3 | 2.3.2.4 | 2.3.2.5 | 2.3.2.6 | 2.3.2.7 | 2.3.2.8 | 2.3.2.9 | 2.3.3.1 |
| 2.3.3.2 | 2.3.3.3 | 2.3.3.4 | 2.3.3.5 | 2.3.3.6 | 2.3.3.7 | 2.3.3.8 | 2.3.3.9 | 2.3.4.1 | 2.3.4.2 |
| 2.3.4.3 | 2.3.4.4 | 2.3.4.5 | 2.3.4.6 | 2.3.4.7 | 2.3.4.8 | 2.3.4.9 | 2.3.5.1 | 2.3.5.2 | 2.3.5.3 |
| 2.3.5.4 | 2.3.5.5 | 2.3.5.6 | 2.3.5.7 | 2.3.5.8 | 2.3.5.9 | 2.3.6.1 | 2.3.6.2 | 2.3.6.3 | 2.3.6.4 |
| 2.3.6.5 | 2.3.6.6 | 2.3.6.7 | 2.3.6.8 | 2.3.6.9 | 2.3.7.1 | 2.3.7.2 | 2.3.7.3 | 2.3.7.4 | 2.3.7.5 |
| 2.3.7.6 | 2.3.7.7 | 2.3.7.8 | 2.3.7.9 | 2.3.8.1 | 2.3.8.2 | 2.3.8.3 | 2.3.8.4 | 2.3.8.5 | 2.3.8.6 |
| 2.3.8.7 | 2.3.8.8 | 2.3.8.9 | 2.3.9.1 | 2.3.9.2 | 2.3.9.3 | 2.3.9.4 | 2.3.9.5 | 2.3.9.6 | 2.3.9.7 |
| 2.3.9.8 | 2.3.9.9 | 2.4.1.1 | 2.4.1.2 | 2.4.1.3 | 2.4.1.4 | 2.4.1.5 | 2.4.1.6 | 2.4.1.7 | 2.4.1.8 |
| 2.4.1.9 | 2.4.2.1 | 2.4.2.2 | 2.4.2.3 | 2.4.2.4 | 2.4.2.5 | 2.4.2.6 | 2.4.2.7 | 2.4.2.8 | 2.4.2.9 |
| 2.4.3.1 | 2.4.3.2 | 2.4.3.3 | 2.4.3.4 | 2.4.3.5 | 2.4.3.6 | 2.4.3.7 | 2.4.3.8 | 2.4.3.9 | 2.4.4.1 |
| 2.4.4.2 | 2.4.4.3 | 2.4.4.4 | 2.4.4.5 | 2.4.4.6 | 2.4.4.7 | 2.4.4.8 | 2.4.4.9 | 2.4.5.1 | 2.4.5.2 |
| 2.4.5.3 | 2.4.5.4 | 2.4.5.5 | 2.4.5.6 | 2.4.5.7 | 2.4.5.8 | 2.4.5.9 | 2.4.6.1 | 2.4.6.2 | 2.4.6.3 |
| 2.4.6.4 | 2.4.6.5 | 2.4.6.6 | 2.4.6.7 | 2.4.6.8 | 2.4.6.9 | 2.4.7.1 | 2.4.7.2 | 2.4.7.3 | 2.4.7.4 |
| 2.4.7.5 | 2.4.7.6 | 2.4.7.7 | 2.4.7.8 | 2.4.7.9 | 2.4.8.1 | 2.4.8.2 | 2.4.8.3 | 2.4.8.4 | 2.4.8.5 |
| 2.4.8.6 | 2.4.8.7 | 2.4.8.8 | 2.4.8.9 | 2.4.9.1 | 2.4.9.2 | 2.4.9.3 | 2.4.9.4 | 2.4.9.5 | 2.4.9.6 |
| 2.4.9.7 | 2.4.9.8 | 2.4.9.9 | 2.5.1.1 | 2.5.1.2 | 2.5.1.3 | 2.5.1.4 | 2.5.1.5 | 2.5.1.6 | 2.5.1.7 |
| 2.5.1.8 | 2.5.1.9 | 2.5.2.1 | 2.5.2.2 | 2.5.2.3 | 2.5.2.4 | 2.5.2.5 | 2.5.2.6 | 2.5.2.7 | 2.5.2.8 |
| 2.5.2.9 | 2.5.3.1 | 2.5.3.2 | 2.5.3.3 | 2.5.3.4 | 2.5.3.5 | 2.5.3.6 | 2.5.3.7 | 2.5.3.8 | 2.5.3.9 |
| 2.5.4.1 | 2.5.4.2 | 2.5.4.3 | 2.5.4.4 | 2.5.4.5 | 2.5.4.6 | 2.5.4.7 | 2.5.4.8 | 2.5.4.9 | 2.5.5.1 |
| 2.5.5.2 | 2.5.5.3 | 2.5.5.4 | 2.5.5.5 | 2.5.5.6 | 2.5.5.7 | 2.5.5.8 | 2.5.5.9 | 2.5.6.1 | 2.5.6.2 |
| 2.5.6.3 | 2.5.6.4 | 2.5.6.5 | 2.5.6.6 | 2.5.6.7 | 2.5.6.8 | 2.5.6.9 | 2.5.7.1 | 2.5.7.2 | 2.5.7.3 |
| 2.5.7.4 | 2.5.7.5 | 2.5.7.6 | 2.5.7.7 | 2.5.7.8 | 2.5.7.9 | 2.5.8.1 | 2.5.8.2 | 2.5.8.3 | 2.5.8.4 |
| 2.5.8.5 | 2.5.8.6 | 2.5.8.7 | 2.5.8.8 | 2.5.8.9 | 2.5.9.1 | 2.5.9.2 | 2.5.9.3 | 2.5.9.4 | 2.5.9.5 |
| 2.5.9.6 | 2.5.9.7 | 2.5.9.8 | 2.5.9.9 | 2.6.1.1 | 2.6.1.2 | 2.6.1.3 | 2.6.1.4 | 2.6.1.5 | 2.6.1.6 |
| 2.6.1.7 | 2.6.1.8 | 2.6.1.9 | 2.6.2.1 | 2.6.2.2 | 2.6.2.3 | 2.6.2.4 | 2.6.2.5 | 2.6.2.6 | 2.6.2.7 |
| 2.6.2.8 | 2.6.2.9 | 2.6.3.1 | 2.6.3.2 | 2.6.3.3 | 2.6.3.4 | 2.6.3.5 | 2.6.3.6 | 2.6.3.7 | 2.6.3.8 |
| 2.6.3.9 | 2.6.4.1 | 2.6.4.2 | 2.6.4.3 | 2.6.4.4 | 2.6.4.5 | 2.6.4.6 | 2.6.4.7 | 2.6.4.8 | 2.6.4.9 |
| 2.6.5.1 | 2.6.5.2 | 2.6.5.3 | 2.6.5.4 | 2.6.5.5 | 2.6.5.6 | 2.6.5.7 | 2.6.5.8 | 2.6.5.9 | 2.6.6.1 |
| 2.6.6.2 | 2.6.6.3 | 2.6.6.4 | 2.6.6.5 | 2.6.6.6 | 2.6.6.7 | 2.6.6.8 | 2.6.6.9 | 2.6.7.1 | 2.6.7.2 |
| 2.6.7.3 | 2.6.7.4 | 2.6.7.5 | 2.6.7.6 | 2.6.7.7 | 2.6.7.8 | 2.6.7.9 | 2.6.8.1 | 2.6.8.2 | 2.6.8.3 |
| 2.6.8.4 | 2.6.8.5 | 2.6.8.6 | 2.6.8.7 | 2.6.8.8 | 2.6.8.9 | 2.6.9.1 | 2.6.9.2 | 2.6.9.3 | 2.6.9.4 |
| 2.6.9.5 | 2.6.9.6 | 2.6.9.7 | 2.6.9.8 | 2.6.9.9 | 2.7.1.1 | 2.7.1.2 | 2.7.1.3 | 2.7.1.4 | 2.7.1.5 |
| 2.7.1.6 | 2.7.1.7 | 2.7.1.8 | 2.7.1.9 | 2.7.2.1 | 2.7.2.2 | 2.7.2.3 | 2.7.2.4 | 2.7.2.5 | 2.7.2.6 |
| 2.7.2.7 | 2.7.2.8 | 2.7.2.9 | 2.7.3.1 | 2.7.3.2 | 2.7.3.3 | 2.7.3.4 | 2.7.3.5 | 2.7.3.6 | 2.7.3.7 |
| 2.7.3.8 | 2.7.3.9 | 2.7.4.1 | 2.7.4.2 | 2.7.4.3 | 2.7.4.4 | 2.7.4.5 | 2.7.4.6 | 2.7.4.7 | 2.7.4.8 |
| 2.7.4.9 | 2.7.5.1 | 2.7.5.2 | 2.7.5.3 | 2.7.5.4 | 2.7.5.5 | 2.7.5.6 | 2.7.5.7 | 2.7.5.8 | 2.7.5.9 |
| 2.7.6.1 | 2.7.6.2 | 2.7.6.3 | 2.7.6.4 | 2.7.6.5 | 2.7.6.6 | 2.7.6.7 | 2.7.6.8 | 2.7.6.9 | 2.7.7.1 |
| 2.7.7.2 | 2.7.7.3 | 2.7.7.4 | 2.7.7.5 | 2.7.7.6 | 2.7.7.7 | 2.7.7.8 | 2.7.7.9 | 2.7.8.1 | 2.7.8.2 |
| 2.7.8.3 | 2.7.8.4 | 2.7.8.5 | 2.7.8.6 | 2.7.8.7 | 2.7.8.8 | 2.7.8.9 | 2.7.9.1 | 2.7.9.2 | 2.7.9.3 |
| 2.7.9.4 | 2.7.9.5 | 2.7.9.6 | 2.7.9.7 | 2.7.9.8 | 2.7.9.9 | 2.8.1.1 | 2.8.1.2 | 2.8.1.3 | 2.8.1.4 |
| 2.8.1.5 | 2.8.1.6 | 2.8.1.7 | 2.8.1.8 | 2.8.1.9 | 2.8.2.1 | 2.8.2.2 | 2.8.2.3 | 2.8.2.4 | 2.8.2.5 |
| 2.8.2.6 | 2.8.2.7 | 2.8.2.8 | 2.8.2.9 | 2.8.3.1 | 2.8.3.2 | 2.8.3.3 | 2.8.3.4 | 2.8.3.5 | 2.8.3.6 |

TABLE 1-continued

| | | | | | | | | | |
|---|---|---|---|---|---|---|---|---|---|
| 2.8.3.7 | 2.8.3.8 | 2.8.3.9 | 2.8.4.1 | 2.8.4.2 | 2.8.4.3 | 2.8.4.4 | 2.8.4.5 | 2.8.4.6 | 2.8.4.7 |
| 2.8.4.8 | 2.8.4.9 | 2.8.5.1 | 2.8.5.2 | 2.8.5.3 | 2.8.5.4 | 2.8.5.5 | 2.8.5.6 | 2.8.5.7 | 2.8.5.8 |
| 2.8.5.9 | 2.8.6.1 | 2.8.6.2 | 2.8.6.3 | 2.8.6.4 | 2.8.6.5 | 2.8.6.6 | 2.8.6.7 | 2.8.6.8 | 2.8.6.9 |
| 2.8.7.1 | 2.8.7.2 | 2.8.7.3 | 2.8.7.4 | 2.8.7.5 | 2.8.7.6 | 2.8.7.7 | 2.8.7.8 | 2.8.7.9 | 2.8.8.1 |
| 2.8.8.2 | 2.8.8.3 | 2.8.8.4 | 2.8.8.5 | 2.8.8.6 | 2.8.8.7 | 2.8.8.8 | 2.8.8.9 | 2.8.9.1 | 2.8.9.2 |
| 2.8.9.3 | 2.8.9.4 | 2.8.9.5 | 2.8.9.6 | 2.8.9.7 | 2.8.9.8 | 2.8.9.9 | 2.9.1.1 | 2.9.1.2 | 2.9.1.3 |
| 2.9.1.4 | 2.9.1.5 | 2.9.1.6 | 2.9.1.7 | 2.9.1.8 | 2.9.1.9 | 2.9.2.1 | 2.9.2.2 | 2.9.2.3 | 2.9.2.4 |
| 2.9.2.5 | 2.9.2.6 | 2.9.2.7 | 2.9.2.8 | 2.9.2.9 | 2.9.3.1 | 2.9.3.2 | 2.9.3.3 | 2.9.3.4 | 2.9.3.5 |
| 2.9.3.6 | 2.9.3.7 | 2.9.3.8 | 2.9.3.9 | 2.9.4.1 | 2.9.4.2 | 2.9.4.3 | 2.9.4.4 | 2.9.4.5 | 2.9.4.6 |
| 2.9.4.7 | 2.9.4.8 | 2.9.4.9 | 2.9.5.1 | 2.9.5.2 | 2.9.5.3 | 2.9.5.4 | 2.9.5.5 | 2.9.5.6 | 2.9.5.7 |
| 2.9.5.8 | 2.9.5.9 | 2.9.6.1 | 2.9.6.2 | 2.9.6.3 | 2.9.6.4 | 2.9.6.5 | 2.9.6.6 | 2.9.6.7 | 2.9.6.8 |
| 2.9.6.9 | 2.9.7.1 | 2.9.7.2 | 2.9.7.3 | 2.9.7.4 | 2.9.7.5 | 2.9.7.6 | 2.9.7.7 | 2.9.7.8 | 2.9.7.9 |
| 2.9.8.1 | 2.9.8.2 | 2.9.8.3 | 2.9.8.4 | 2.9.8.5 | 2.9.8.6 | 2.9.8.7 | 2.9.8.8 | 2.9.8.9 | 2.9.9.1 |
| 2.9.9.2 | 2.9.9.3 | 2.9.9.4 | 2.9.9.5 | 2.9.9.6 | 2.9.9.7 | 2.9.9.8 | 2.9.9.9 | 3.1.1.1 | 3.1.1.2 |
| 3.1.1.3 | 3.1.1.4 | 3.1.1.5 | 3.1.1.6 | 3.1.1.7 | 3.1.1.8 | 3.1.1.9 | 3.1.2.1 | 3.1.2.2 | 3.1.2.3 |
| 3.1.2.4 | 3.1.2.5 | 3.1.2.6 | 3.1.2.7 | 3.1.2.8 | 3.1.2.9 | 3.1.3.1 | 3.1.3.2 | 3.1.3.3 | 3.1.3.4 |
| 3.1.3.5 | 3.1.3.6 | 3.1.3.7 | 3.1.3.8 | 3.1.3.9 | 3.1.4.1 | 3.1.4.2 | 3.1.4.3 | 3.1.4.4 | 3.1.4.5 |
| 3.1.4.6 | 3.1.4.7 | 3.1.4.8 | 3.1.4.9 | 3.1.5.1 | 3.1.5.2 | 3.1.5.3 | 3.1.5.4 | 3.1.5.5 | 3.1.5.6 |
| 3.1.5.7 | 3.1.5.8 | 3.1.5.9 | 3.1.6.1 | 3.1.6.2 | 3.1.6.3 | 3.1.6.4 | 3.1.6.5 | 3.1.6.6 | 3.1.6.7 |
| 3.1.6.8 | 3.1.6.9 | 3.1.7.1 | 3.1.7.2 | 3.1.7.3 | 3.1.7.4 | 3.1.7.5 | 3.1.7.6 | 3.1.7.7 | 3.1.7.8 |
| 3.1.7.9 | 3.1.8.1 | 3.1.8.2 | 3.1.8.3 | 3.1.8.4 | 3.1.8.5 | 3.1.8.6 | 3.1.8.7 | 3.1.8.8 | 3.1.8.9 |
| 3.1.9.1 | 3.1.9.2 | 3.1.9.3 | 3.1.9.4 | 3.1.9.5 | 3.1.9.6 | 3.1.9.7 | 3.1.9.8 | 3.1.9.9 | 3.2.1.1 |
| 3.2.1.2 | 3.2.1.3 | 3.2.1.4 | 3.2.1.5 | 3.2.1.6 | 3.2.1.7 | 3.2.1.8 | 3.2.1.9 | 3.2.2.1 | 3.2.2.2 |
| 3.2.2.3 | 3.2.2.4 | 3.2.2.5 | 3.2.2.6 | 3.2.2.7 | 3.2.2.8 | 3.2.2.9 | 3.2.3.1 | 3.2.3.2 | 3.2.3.3 |
| 3.2.3.4 | 3.2.3.5 | 3.2.3.6 | 3.2.3.7 | 3.2.3.8 | 3.2.3.9 | 3.2.4.1 | 3.2.4.2 | 3.2.4.3 | 3.2.4.4 |
| 3.2.4.5 | 3.2.4.6 | 3.2.4.7 | 3.2.4.8 | 3.2.4.9 | 3.2.5.1 | 3.2.5.2 | 3.2.5.3 | 3.2.5.4 | 3.2.5.5 |
| 3.2.5.6 | 3.2.5.7 | 3.2.5.8 | 3.2.5.9 | 3.2.6.1 | 3.2.6.2 | 3.2.6.3 | 3.2.6.4 | 3.2.6.5 | 3.2.6.6 |
| 3.2.6.7 | 3.2.6.8 | 3.2.6.9 | 3.2.7.1 | 3.2.7.2 | 3.2.7.3 | 3.2.7.4 | 3.2.7.5 | 3.2.7.6 | 3.2.7.7 |
| 3.2.7.8 | 3.2.7.9 | 3.2.8.1 | 3.2.8.2 | 3.2.8.3 | 3.2.8.4 | 3.2.8.5 | 3.2.8.6 | 3.2.8.7 | 3.2.8.8 |
| 3.2.8.9 | 3.2.9.1 | 3.2.9.2 | 3.2.9.3 | 3.2.9.4 | 3.2.9.5 | 3.2.9.6 | 3.2.9.7 | 3.2.9.8 | 3.2.9.9 |
| 3.3.1.1 | 3.3.1.2 | 3.3.1.3 | 3.3.1.4 | 3.3.1.5 | 3.3.1.6 | 3.3.1.7 | 3.3.1.8 | 3.3.1.9 | 3.3.2.1 |
| 3.3.2.2 | 3.3.2.3 | 3.3.2.4 | 3.3.2.5 | 3.3.2.6 | 3.3.2.7 | 3.3.2.8 | 3.3.2.9 | 3.3.3.1 | 3.3.3.2 |
| 3.3.3.3 | 3.3.3.4 | 3.3.3.5 | 3.3.3.6 | 3.3.3.7 | 3.3.3.8 | 3.3.3.9 | 3.3.4.1 | 3.3.4.2 | 3.3.4.3 |
| 3.3.4.4 | 3.3.4.5 | 3.3.4.6 | 3.3.4.7 | 3.3.4.8 | 3.3.4.9 | 3.3.5.1 | 3.3.5.2 | 3.3.5.3 | 3.3.5.4 |
| 3.3.5.5 | 3.3.5.6 | 3.3.5.7 | 3.3.5.8 | 3.3.5.9 | 3.3.6.1 | 3.3.6.2 | 3.3.6.3 | 3.3.6.4 | 3.3.6.5 |
| 3.3.6.6 | 3.3.6.7 | 3.3.6.8 | 3.3.6.9 | 3.3.7.1 | 3.3.7.2 | 3.3.7.3 | 3.3.7.4 | 3.3.7.5 | 3.3.7.6 |
| 3.3.7.7 | 3.3.7.8 | 3.3.7.9 | 3.3.8.1 | 3.3.8.2 | 3.3.8.3 | 3.3.8.4 | 3.3.8.5 | 3.3.8.6 | 3.3.8.7 |
| 3.3.8.8 | 3.3.8.9 | 3.3.9.1 | 3.3.9.2 | 3.3.9.3 | 3.3.9.4 | 3.3.9.5 | 3.3.9.6 | 3.3.9.7 | 3.3.9.8 |
| 3.3.9.9 | 3.4.1.1 | 3.4.1.2 | 3.4.1.3 | 3.4.1.4 | 3.4.1.5 | 3.4.1.6 | 3.4.1.7 | 3.4.1.8 | 3.4.1.9 |
| 3.4.2.1 | 3.4.2.2 | 3.4.2.3 | 3.4.2.4 | 3.4.2.5 | 3.4.2.6 | 3.4.2.7 | 3.4.2.8 | 3.4.2.9 | 3.4.3.1 |
| 3.4.3.2 | 3.4.3.3 | 3.4.3.4 | 3.4.3.5 | 3.4.3.6 | 3.4.3.7 | 3.4.3.8 | 3.4.3.9 | 3.4.4.1 | 3.4.4.2 |
| 3.4.4.3 | 3.4.4.4 | 3.4.4.5 | 3.4.4.6 | 3.4.4.7 | 3.4.4.8 | 3.4.4.9 | 3.4.5.1 | 3.4.5.2 | 3.4.5.3 |
| 3.4.5.4 | 3.4.5.5 | 3.4.5.6 | 3.4.5.7 | 3.4.5.8 | 3.4.5.9 | 3.4.6.1 | 3.4.6.2 | 3.4.6.3 | 3.4.6.4 |
| 3.4.6.5 | 3.4.6.6 | 3.4.6.7 | 3.4.6.8 | 3.4.6.9 | 3.4.7.1 | 3.4.7.2 | 3.4.7.3 | 3.4.7.4 | 3.4.7.5 |
| 3.4.7.6 | 3.4.7.7 | 3.4.7.8 | 3.4.7.9 | 3.4.8.1 | 3.4.8.2 | 3.4.8.3 | 3.4.8.4 | 3.4.8.5 | 3.4.8.6 |
| 3.4.8.7 | 3.4.8.8 | 3.4.8.9 | 3.4.9.1 | 3.4.9.2 | 3.4.9.3 | 3.4.9.4 | 3.4.9.5 | 3.4.9.6 | 3.4.9.7 |
| 3.4.9.8 | 3.4.9.9 | 3.5.1.1 | 3.5.1.2 | 3.5.1.3 | 3.5.1.4 | 3.5.1.5 | 3.5.1.6 | 3.5.1.7 | 3.5.1.8 |
| 3.5.1.9 | 3.5.2.1 | 3.5.2.2 | 3.5.2.3 | 3.5.2.4 | 3.5.2.5 | 3.5.2.6 | 3.5.2.7 | 3.5.2.8 | 3.5.2.9 |
| 3.5.3.1 | 3.5.3.2 | 3.5.3.3 | 3.5.3.4 | 3.5.3.5 | 3.5.3.6 | 3.5.3.7 | 3.5.3.8 | 3.5.3.9 | 3.5.4.1 |
| 3.5.4.2 | 3.5.4.3 | 3.5.4.4 | 3.5.4.5 | 3.5.4.6 | 3.5.4.7 | 3.5.4.8 | 3.5.4.9 | 3.5.5.1 | 3.5.5.2 |
| 3.5.5.3 | 3.5.5.4 | 3.5.5.5 | 3.5.5.6 | 3.5.5.7 | 3.5.5.8 | 3.5.5.9 | 3.5.6.1 | 3.5.6.2 | 3.5.6.3 |
| 3.5.6.4 | 3.5.6.5 | 3.5.6.6 | 3.5.6.7 | 3.5.6.8 | 3.5.6.9 | 3.5.7.1 | 3.5.7.2 | 3.5.7.3 | 3.5.7.4 |
| 3.5.7.5 | 3.5.7.6 | 3.5.7.7 | 3.5.7.8 | 3.5.7.9 | 3.5.8.1 | 3.5.8.2 | 3.5.8.3 | 3.5.8.4 | 3.5.8.5 |
| 3.5.8.6 | 3.5.8.7 | 3.5.8.8 | 3.5.8.9 | 3.5.9.1 | 3.5.9.2 | 3.5.9.3 | 3.5.9.4 | 3.5.9.5 | 3.5.9.6 |
| 3.5.9.7 | 3.5.9.8 | 3.5.9.9 | 3.6.1.1 | 3.6.1.2 | 3.6.1.3 | 3.6.1.4 | 3.6.1.5 | 3.6.1.6 | 3.6.1.7 |
| 3.6.1.8 | 3.6.1.9 | 3.6.2.1 | 3.6.2.2 | 3.6.2.3 | 3.6.2.4 | 3.6.2.5 | 3.6.2.6 | 3.6.2.7 | 3.6.2.8 |
| 3.6.2.9 | 3.6.3.1 | 3.6.3.2 | 3.6.3.3 | 3.6.3.4 | 3.6.3.5 | 3.6.3.6 | 3.6.3.7 | 3.6.3.8 | 3.6.3.9 |
| 3.6.4.1 | 3.6.4.2 | 3.6.4.3 | 3.6.4.4 | 3.6.4.5 | 3.6.4.6 | 3.6.4.7 | 3.6.4.8 | 3.6.4.9 | 3.6.5.1 |
| 3.6.5.2 | 3.6.5.3 | 3.6.5.4 | 3.6.5.5 | 3.6.5.6 | 3.6.5.7 | 3.6.5.8 | 3.6.5.9 | 3.6.6.1 | 3.6.6.2 |
| 3.6.6.3 | 3.6.6.4 | 3.6.6.5 | 3.6.6.6 | 3.6.6.7 | 3.6.6.8 | 3.6.6.9 | 3.6.7.1 | 3.6.7.2 | 3.6.7.3 |
| 3.6.7.4 | 3.6.7.5 | 3.6.7.6 | 3.6.7.7 | 3.6.7.8 | 3.6.7.9 | 3.6.8.1 | 3.6.8.2 | 3.6.8.3 | 3.6.8.4 |
| 3.6.8.5 | 3.6.8.6 | 3.6.8.7 | 3.6.8.8 | 3.6.8.9 | 3.6.9.1 | 3.6.9.2 | 3.6.9.3 | 3.6.9.4 | 3.6.9.5 |
| 3.6.9.6 | 3.6.9.7 | 3.6.9.8 | 3.6.9.9 | 3.7.1.1 | 3.7.1.2 | 3.7.1.3 | 3.7.1.4 | 3.7.1.5 | 3.7.1.6 |
| 3.7.1.7 | 3.7.1.8 | 3.7.1.9 | 3.7.2.1 | 3.7.2.2 | 3.7.2.3 | 3.7.2.4 | 3.7.2.5 | 3.7.2.6 | 3.7.2.7 |
| 3.7.2.8 | 3.7.2.9 | 3.7.3.1 | 3.7.3.2 | 3.7.3.3 | 3.7.3.4 | 3.7.3.5 | 3.7.3.6 | 3.7.3.7 | 3.7.3.8 |
| 3.7.3.9 | 3.7.4.1 | 3.7.4.2 | 3.7.4.3 | 3.7.4.4 | 3.7.4.5 | 3.7.4.6 | 3.7.4.7 | 3.7.4.8 | 3.7.4.9 |
| 3.7.5.1 | 3.7.5.2 | 3.7.5.3 | 3.7.5.4 | 3.7.5.5 | 3.7.5.6 | 3.7.5.7 | 3.7.5.8 | 3.7.5.9 | 3.7.6.1 |
| 3.7.6.2 | 3.7.6.3 | 3.7.6.4 | 3.7.6.5 | 3.7.6.6 | 3.7.6.7 | 3.7.6.8 | 3.7.6.9 | 3.7.7.1 | 3.7.7.2 |
| 3.7.7.3 | 3.7.7.4 | 3.7.7.5 | 3.7.7.6 | 3.7.7.7 | 3.7.7.8 | 3.7.7.9 | 3.7.8.1 | 3.7.8.2 | 3.7.8.3 |
| 3.7.8.4 | 3.7.8.5 | 3.7.8.6 | 3.7.8.7 | 3.7.8.8 | 3.7.8.9 | 3.7.9.1 | 3.7.9.2 | 3.7.9.3 | 3.7.9.4 |
| 3.7.9.5 | 3.7.9.6 | 3.7.9.7 | 3.7.9.8 | 3.7.9.9 | 3.8.1.1 | 3.8.1.2 | 3.8.1.3 | 3.8.1.4 | 3.8.1.5 |
| 3.8.1.6 | 3.8.1.7 | 3.8.1.8 | 3.8.1.9 | 3.8.2.1 | 3.8.2.2 | 3.8.2.3 | 3.8.2.4 | 3.8.2.5 | 3.8.2.6 |
| 3.8.2.7 | 3.8.2.8 | 3.8.2.9 | 3.8.3.1 | 3.8.3.2 | 3.8.3.3 | 3.8.3.4 | 3.8.3.5 | 3.8.3.6 | 3.8.3.7 |
| 3.8.3.8 | 3.8.3.9 | 3.8.4.1 | 3.8.4.2 | 3.8.4.3 | 3.8.4.4 | 3.8.4.5 | 3.8.4.6 | 3.8.4.7 | 3.8.4.8 |
| 3.8.4.9 | 3.8.5.1 | 3.8.5.2 | 3.8.5.3 | 3.8.5.4 | 3.8.5.5 | 3.8.5.6 | 3.8.5.7 | 3.8.5.8 | 3.8.5.9 |
| 3.8.6.1 | 3.8.6.2 | 3.8.6.3 | 3.8.6.4 | 3.8.6.5 | 3.8.6.6 | 3.8.6.7 | 3.8.6.8 | 3.8.6.9 | 3.8.7.1 |
| 3.8.7.2 | 3.8.7.3 | 3.8.7.4 | 3.8.7.5 | 3.8.7.6 | 3.8.7.7 | 3.8.7.8 | 3.8.7.9 | 3.8.8.1 | 3.8.8.2 |
| 3.8.8.3 | 3.8.8.4 | 3.8.8.5 | 3.8.8.6 | 3.8.8.7 | 3.8.8.8 | 3.8.8.9 | 3.8.9.1 | 3.8.9.2 | 3.8.9.3 |
| 3.8.9.4 | 3.8.9.5 | 3.8.9.6 | 3.8.9.7 | 3.8.9.8 | 3.8.9.9 | 3.9.1.1 | 3.9.1.2 | 3.9.1.3 | 3.9.1.4 |

TABLE 1-continued

| | | | | | | | | | |
|---|---|---|---|---|---|---|---|---|---|
| 3.9.1.5 | 3.9.1.6 | 3.9.1.7 | 3.9.1.8 | 3.9.1.9 | 3.9.2.1 | 3.9.2.2 | 3.9.2.3 | 3.9.2.4 | 3.9.2.5 |
| 3.9.2.6 | 3.9.2.7 | 3.9.2.8 | 3.9.2.9 | 3.9.3.1 | 3.9.3.2 | 3.9.3.3 | 3.9.3.4 | 3.9.3.5 | 3.9.3.6 |
| 3.9.3.7 | 3.9.3.8 | 3.9.3.9 | 3.9.4.1 | 3.9.4.2 | 3.9.4.3 | 3.9.4.4 | 3.9.4.5 | 3.9.4.6 | 3.9.4.7 |
| 3.9.4.8 | 3.9.4.9 | 3.9.5.1 | 3.9.5.2 | 3.9.5.3 | 3.9.5.4 | 3.9.5.5 | 3.9.5.6 | 3.9.5.7 | 3.9.5.8 |
| 3.9.5.9 | 3.9.6.1 | 3.9.6.2 | 3.9.6.3 | 3.9.6.4 | 3.9.6.5 | 3.9.6.6 | 3.9.6.7 | 3.9.6.8 | 3.9.6.9 |
| 3.9.7.1 | 3.9.7.2 | 3.9.7.3 | 3.9.7.4 | 3.9.7.5 | 3.9.7.6 | 3.9.7.7 | 3.9.7.8 | 3.9.7.9 | 3.9.8.1 |
| 3.9.8.2 | 3.9.8.3 | 3.9.8.4 | 3.9.8.5 | 3.9.8.6 | 3.9.8.7 | 3.9.8.8 | 3.9.8.9 | 3.9.9.1 | 3.9.9.2 |
| 3.9.9.3 | 3.9.9.4 | 3.9.9.5 | 3.9.9.6 | 3.9.9.7 | 3.9.9.8 | 3.9.9.9 | 4.1.1.1 | 4.1.1.2 | 4.1.1.3 |
| 4.1.1.4 | 4.1.1.5 | 4.1.1.6 | 4.1.1.7 | 4.1.1.8 | 4.1.1.9 | 4.1.2.1 | 4.1.2.2 | 4.1.2.3 | 4.1.2.4 |
| 4.1.2.5 | 4.1.2.6 | 4.1.2.7 | 4.1.2.8 | 4.1.2.9 | 4.1.3.1 | 4.1.3.2 | 4.1.3.3 | 4.1.3.4 | 4.1.3.5 |
| 4.1.3.6 | 4.1.3.7 | 4.1.3.8 | 4.1.3.9 | 4.1.4.1 | 4.1.4.2 | 4.1.4.3 | 4.1.4.4 | 4.1.4.5 | 4.1.4.6 |
| 4.1.4.7 | 4.1.4.8 | 4.1.4.9 | 4.1.5.1 | 4.1.5.2 | 4.1.5.3 | 4.1.5.4 | 4.1.5.5 | 4.1.5.6 | 4.1.5.7 |
| 4.1.5.8 | 4.1.5.9 | 4.1.6.1 | 4.1.6.2 | 4.1.6.3 | 4.1.6.4 | 4.1.6.5 | 4.1.6.6 | 4.1.6.7 | 4.1.6.8 |
| 4.1.6.9 | 4.1.7.1 | 4.1.7.2 | 4.1.7.3 | 4.1.7.4 | 4.1.7.5 | 4.1.7.6 | 4.1.7.7 | 4.1.7.8 | 4.1.7.9 |
| 4.1.8.1 | 4.1.8.2 | 4.1.8.3 | 4.1.8.4 | 4.1.8.5 | 4.1.8.6 | 4.1.8.7 | 4.1.8.8 | 4.1.8.9 | 4.1.9.1 |
| 4.1.9.2 | 4.1.9.3 | 4.1.9.4 | 4.1.9.5 | 4.1.9.6 | 4.1.9.7 | 4.1.9.8 | 4.1.9.9 | 4.2.1.1 | 4.2.1.2 |
| 4.2.1.3 | 4.2.1.4 | 4.2.1.5 | 4.2.1.6 | 4.2.1.7 | 4.2.1.8 | 4.2.1.9 | 4.2.2.1 | 4.2.2.2 | 4.2.2.3 |
| 4.2.2.4 | 4.2.2.5 | 4.2.2.6 | 4.2.2.7 | 4.2.2.8 | 4.2.2.9 | 4.2.3.1 | 4.2.3.2 | 4.2.3.3 | 4.2.3.4 |
| 4.2.3.5 | 4.2.3.6 | 4.2.3.7 | 4.2.3.8 | 4.2.3.9 | 4.2.4.1 | 4.2.4.2 | 4.2.4.3 | 4.2.4.4 | 4.2.4.5 |
| 4.2.4.6 | 4.2.4.7 | 4.2.4.8 | 4.2.4.9 | 4.2.5.1 | 4.2.5.2 | 4.2.5.3 | 4.2.5.4 | 4.2.5.5 | 4.2.5.6 |
| 4.2.5.7 | 4.2.5.8 | 4.2.5.9 | 4.2.6.1 | 4.2.6.2 | 4.2.6.3 | 4.2.6.4 | 4.2.6.5 | 4.2.6.6 | 4.2.6.7 |
| 4.2.6.8 | 4.2.6.9 | 4.2.7.1 | 4.2.7.2 | 4.2.7.3 | 4.2.7.4 | 4.2.7.5 | 4.2.7.6 | 4.2.7.7 | 4.2.7.8 |
| 4.2.7.9 | 4.2.8.1 | 4.2.8.2 | 4.2.8.3 | 4.2.8.4 | 4.2.8.5 | 4.2.8.6 | 4.2.8.7 | 4.2.8.8 | 4.2.8.9 |
| 4.2.9.1 | 4.2.9.2 | 4.2.9.3 | 4.2.9.4 | 4.2.9.5 | 4.2.9.6 | 4.2.9.7 | 4.2.9.8 | 4.2.9.9 | 4.3.1.1 |
| 4.3.1.2 | 4.3.1.3 | 4.3.1.4 | 4.3.1.5 | 4.3.1.6 | 4.3.1.7 | 4.3.1.8 | 4.3.1.9 | 4.3.2.1 | 4.3.2.2 |
| 4.3.2.3 | 4.3.2.4 | 4.3.2.5 | 4.3.2.6 | 4.3.2.7 | 4.3.2.8 | 4.3.2.9 | 4.3.3.1 | 4.3.3.2 | 4.3.3.3 |
| 4.3.3.4 | 4.3.3.5 | 4.3.3.6 | 4.3.3.7 | 4.3.3.8 | 4.3.3.9 | 4.3.4.1 | 4.3.4.2 | 4.3.4.3 | 4.3.4.4 |
| 4.3.4.5 | 4.3.4.6 | 4.3.4.7 | 4.3.4.8 | 4.3.4.9 | 4.3.5.1 | 4.3.5.2 | 4.3.5.3 | 4.3.5.4 | 4.3.5.5 |
| 4.3.5.6 | 4.3.5.7 | 4.3.5.8 | 4.3.5.9 | 4.3.6.1 | 4.3.6.2 | 4.3.6.3 | 4.3.6.4 | 4.3.6.5 | 4.3.6.6 |
| 4.3.6.7 | 4.3.6.8 | 4.3.6.9 | 4.3.7.1 | 4.3.7.2 | 4.3.7.3 | 4.3.7.4 | 4.3.7.5 | 4.3.7.6 | 4.3.7.7 |
| 4.3.7.8 | 4.3.7.9 | 4.3.8.1 | 4.3.8.2 | 4.3.8.3 | 4.3.8.4 | 4.3.8.5 | 4.3.8.6 | 4.3.8.7 | 4.3.8.8 |
| 4.3.8.9 | 4.3.9.1 | 4.3.9.2 | 4.3.9.3 | 4.3.9.4 | 4.3.9.5 | 4.3.9.6 | 4.3.9.7 | 4.3.9.8 | 4.3.9.9 |
| 4.4.1.1 | 4.4.1.2 | 4.4.1.3 | 4.4.1.4 | 4.4.1.5 | 4.4.1.6 | 4.4.1.7 | 4.4.1.8 | 4.4.1.9 | 4.4.2.1 |
| 4.4.2.2 | 4.4.2.3 | 4.4.2.4 | 4.4.2.5 | 4.4.2.6 | 4.4.2.7 | 4.4.2.8 | 4.4.2.9 | 4.4.3.1 | 4.4.3.2 |
| 4.4.3.3 | 4.4.3.4 | 4.4.3.5 | 4.4.3.6 | 4.4.3.7 | 4.4.3.8 | 4.4.3.9 | 4.4.4.1 | 4.4.4.2 | 4.4.4.3 |
| 4.4.4.4 | 4.4.4.5 | 4.4.4.6 | 4.4.4.7 | 4.4.4.8 | 4.4.4.9 | 4.4.5.1 | 4.4.5.2 | 4.4.5.3 | 4.4.5.4 |
| 4.4.5.5 | 4.4.5.6 | 4.4.5.7 | 4.4.5.8 | 4.4.5.9 | 4.4.6.1 | 4.4.6.2 | 4.4.6.3 | 4.4.6.4 | 4.4.6.5 |
| 4.4.6.6 | 4.4.6.7 | 4.4.6.8 | 4.4.6.9 | 4.4.7.1 | 4.4.7.2 | 4.4.7.3 | 4.4.7.4 | 4.4.7.5 | 4.4.7.6 |
| 4.4.7.7 | 4.4.7.8 | 4.4.7.9 | 4.4.8.1 | 4.4.8.2 | 4.4.8.3 | 4.4.8.4 | 4.4.8.5 | 4.4.8.6 | 4.4.8.7 |
| 4.4.8.8 | 4.4.8.9 | 4.4.9.1 | 4.4.9.2 | 4.4.9.3 | 4.4.9.4 | 4.4.9.5 | 4.4.9.6 | 4.4.9.7 | 4.4.9.8 |
| 4.4.9.9 | 4.5.1.1 | 4.5.1.2 | 4.5.1.3 | 4.5.1.4 | 4.5.1.5 | 4.5.1.6 | 4.5.1.7 | 4.5.1.8 | 4.5.1.9 |
| 4.5.2.1 | 4.5.2.2 | 4.5.2.3 | 4.5.2.4 | 4.5.2.5 | 4.5.2.6 | 4.5.2.7 | 4.5.2.8 | 4.5.2.9 | 4.5.3.1 |
| 4.5.3.2 | 4.5.3.3 | 4.5.3.4 | 4.5.3.5 | 4.5.3.6 | 4.5.3.7 | 4.5.3.8 | 4.5.3.9 | 4.5.4.1 | 4.5.4.2 |
| 4.5.4.3 | 4.5.4.4 | 4.5.4.5 | 4.5.4.6 | 4.5.4.7 | 4.5.4.8 | 4.5.4.9 | 4.5.5.1 | 4.5.5.2 | 4.5.5.3 |
| 4.5.5.4 | 4.5.5.5 | 4.5.5.6 | 4.5.5.7 | 4.5.5.8 | 4.5.5.9 | 4.5.6.1 | 4.5.6.2 | 4.5.6.3 | 4.5.6.4 |
| 4.5.6.5 | 4.5.6.6 | 4.5.6.7 | 4.5.6.8 | 4.5.6.9 | 4.5.7.1 | 4.5.7.2 | 4.5.7.3 | 4.5.7.4 | 4.5.7.5 |
| 4.5.7.6 | 4.5.7.7 | 4.5.7.8 | 4.5.7.9 | 4.5.8.1 | 4.5.8.2 | 4.5.8.3 | 4.5.8.4 | 4.5.8.5 | 4.5.8.6 |
| 4.5.8.7 | 4.5.8.8 | 4.5.8.9 | 4.5.9.1 | 4.5.9.2 | 4.5.9.3 | 4.5.9.4 | 4.5.9.5 | 4.5.9.6 | 4.5.9.7 |
| 4.5.9.8 | 4.5.9.9 | 4.6.1.1 | 4.6.1.2 | 4.6.1.3 | 4.6.1.4 | 4.6.1.5 | 4.6.1.6 | 4.6.1.7 | 4.6.1.8 |
| 4.6.1.9 | 4.6.2.1 | 4.6.2.2 | 4.6.2.3 | 4.6.2.4 | 4.6.2.5 | 4.6.2.6 | 4.6.2.7 | 4.6.2.8 | 4.6.2.9 |
| 4.6.3.1 | 4.6.3.2 | 4.6.3.3 | 4.6.3.4 | 4.6.3.5 | 4.6.3.6 | 4.6.3.7 | 4.6.3.8 | 4.6.3.9 | 4.6.4.1 |
| 4.6.4.2 | 4.6.4.3 | 4.6.4.4 | 4.6.4.5 | 4.6.4.6 | 4.6.4.7 | 4.6.4.8 | 4.6.4.9 | 4.6.5.1 | 4.6.5.2 |
| 4.6.5.3 | 4.6.5.4 | 4.6.5.5 | 4.6.5.6 | 4.6.5.7 | 4.6.5.8 | 4.6.5.9 | 4.6.6.1 | 4.6.6.2 | 4.6.6.3 |
| 4.6.6.4 | 4.6.6.5 | 4.6.6.6 | 4.6.6.7 | 4.6.6.8 | 4.6.6.9 | 4.6.7.1 | 4.6.7.2 | 4.6.7.3 | 4.6.7.4 |
| 4.6.7.5 | 4.6.7.6 | 4.6.7.7 | 4.6.7.8 | 4.6.7.9 | 4.6.8.1 | 4.6.8.2 | 4.6.8.3 | 4.6.8.4 | 4.6.8.5 |
| 4.6.8.6 | 4.6.8.7 | 4.6.8.8 | 4.6.8.9 | 4.6.9.1 | 4.6.9.2 | 4.6.9.3 | 4.6.9.4 | 4.6.9.5 | 4.6.9.6 |
| 4.6.9.7 | 4.6.9.8 | 4.6.9.9 | 4.7.1.1 | 4.7.1.2 | 4.7.1.3 | 4.7.1.4 | 4.7.1.5 | 4.7.1.6 | 4.7.1.7 |
| 4.7.1.8 | 4.7.1.9 | 4.7.2.1 | 4.7.2.2 | 4.7.2.3 | 4.7.2.4 | 4.7.2.5 | 4.7.2.6 | 4.7.2.7 | 4.7.2.8 |
| 4.7.2.9 | 4.7.3.1 | 4.7.3.2 | 4.7.3.3 | 4.7.3.4 | 4.7.3.5 | 4.7.3.6 | 4.7.3.7 | 4.7.3.8 | 4.7.3.9 |
| 4.7.4.1 | 4.7.4.2 | 4.7.4.3 | 4.7.4.4 | 4.7.4.5 | 4.7.4.6 | 4.7.4.7 | 4.7.4.8 | 4.7.4.9 | 4.7.5.1 |
| 4.7.5.2 | 4.7.5.3 | 4.7.5.4 | 4.7.5.5 | 4.7.5.6 | 4.7.5.7 | 4.7.5.8 | 4.7.5.9 | 4.7.6.1 | 4.7.6.2 |
| 4.7.6.3 | 4.7.6.4 | 4.7.6.5 | 4.7.6.6 | 4.7.6.7 | 4.7.6.8 | 4.7.6.9 | 4.7.7.1 | 4.7.7.2 | 4.7.7.3 |
| 4.7.7.4 | 4.7.7.5 | 4.7.7.6 | 4.7.7.7 | 4.7.7.8 | 4.7.7.9 | 4.7.8.1 | 4.7.8.2 | 4.7.8.3 | 4.7.8.4 |
| 4.7.8.5 | 4.7.8.6 | 4.7.8.7 | 4.7.8.8 | 4.7.8.9 | 4.7.9.1 | 4.7.9.2 | 4.7.9.3 | 4.7.9.4 | 4.7.9.5 |
| 4.7.9.6 | 4.7.9.7 | 4.7.9.8 | 4.7.9.9 | 4.8.1.1 | 4.8.1.2 | 4.8.1.3 | 4.8.1.4 | 4.8.1.5 | 4.8.1.6 |
| 4.8.1.7 | 4.8.1.8 | 4.8.1.9 | 4.8.2.1 | 4.8.2.2 | 4.8.2.3 | 4.8.2.4 | 4.8.2.5 | 4.8.2.6 | 4.8.2.7 |
| 4.8.2.8 | 4.8.2.9 | 4.8.3.1 | 4.8.3.2 | 4.8.3.3 | 4.8.3.4 | 4.8.3.5 | 4.8.3.6 | 4.8.3.7 | 4.8.3.8 |
| 4.8.3.9 | 4.8.4.1 | 4.8.4.2 | 4.8.4.3 | 4.8.4.4 | 4.8.4.5 | 4.8.4.6 | 4.8.4.7 | 4.8.4.8 | 4.8.4.9 |
| 4.8.5.1 | 4.8.5.2 | 4.8.5.3 | 4.8.5.4 | 4.8.5.5 | 4.8.5.6 | 4.8.5.7 | 4.8.5.8 | 4.8.5.9 | 4.8.6.1 |
| 4.8.6.2 | 4.8.6.3 | 4.8.6.4 | 4.8.6.5 | 4.8.6.6 | 4.8.6.7 | 4.8.6.8 | 4.8.6.9 | 4.8.7.1 | 4.8.7.2 |
| 4.8.7.3 | 4.8.7.4 | 4.8.7.5 | 4.8.7.6 | 4.8.7.7 | 4.8.7.8 | 4.8.7.9 | 4.8.8.1 | 4.8.8.2 | 4.8.8.3 |
| 4.8.8.4 | 4.8.8.5 | 4.8.8.6 | 4.8.8.7 | 4.8.8.8 | 4.8.8.9 | 4.8.9.1 | 4.8.9.2 | 4.8.9.3 | 4.8.9.4 |
| 4.8.9.5 | 4.8.9.6 | 4.8.9.7 | 4.8.9.8 | 4.8.9.9 | 4.9.1.1 | 4.9.1.2 | 4.9.1.3 | 4.9.1.4 | 4.9.1.5 |
| 4.9.1.6 | 4.9.1.7 | 4.9.1.8 | 4.9.1.9 | 4.9.2.1 | 4.9.2.2 | 4.9.2.3 | 4.9.2.4 | 4.9.2.5 | 4.9.2.6 |
| 4.9.2.7 | 4.9.2.8 | 4.9.2.9 | 4.9.3.1 | 4.9.3.2 | 4.9.3.3 | 4.9.3.4 | 4.9.3.5 | 4.9.3.6 | 4.9.3.7 |
| 4.9.3.8 | 4.9.3.9 | 4.9.4.1 | 4.9.4.2 | 4.9.4.3 | 4.9.4.4 | 4.9.4.5 | 4.9.4.6 | 4.9.4.7 | 4.9.4.8 |
| 4.9.4.9 | 4.9.5.1 | 4.9.5.2 | 4.9.5.3 | 4.9.5.4 | 4.9.5.5 | 4.9.5.6 | 4.9.5.7 | 4.9.5.8 | 4.9.5.9 |
| 4.9.6.1 | 4.9.6.2 | 4.9.6.3 | 4.9.6.4 | 4.9.6.5 | 4.9.6.6 | 4.9.6.7 | 4.9.6.8 | 4.9.6.9 | 4.9.7.1 |
| 4.9.7.2 | 4.9.7.3 | 4.9.7.4 | 4.9.7.5 | 4.9.7.6 | 4.9.7.7 | 4.9.7.8 | 4.9.7.9 | 4.9.8.1 | 4.9.8.2 |

TABLE 1-continued

| | | | | | | | | | |
|---|---|---|---|---|---|---|---|---|---|
| 4.9.8.3 | 4.9.8.4 | 4.9.8.5 | 4.9.8.6 | 4.9.8.7 | 4.9.8.8 | 4.9.8.9 | 4.9.9.1 | 4.9.9.2 | 4.9.9.3 |
| 4.9.9.4 | 4.9.9.5 | 4.9.9.6 | 4.9.9.7 | 4.9.9.8 | 4.9.9.9 | 5.1.1.1 | 5.1.1.2 | 5.1.1.3 | 5.1.1.4 |
| 5.1.1.5 | 5.1.1.6 | 5.1.1.7 | 5.1.1.8 | 5.1.1.9 | 5.1.2.1 | 5.1.2.2 | 5.1.2.3 | 5.1.2.4 | 5.1.2.5 |
| 5.1.2.6 | 5.1.2.7 | 5.1.2.8 | 5.1.2.9 | 5.1.3.1 | 5.1.3.2 | 5.1.3.3 | 5.1.3.4 | 5.1.3.5 | 5.1.3.6 |
| 5.1.3.7 | 5.1.3.8 | 5.1.3.9 | 5.1.4.1 | 5.1.4.2 | 5.1.4.3 | 5.1.4.4 | 5.1.4.5 | 5.1.4.6 | 5.1.4.7 |
| 5.1.4.8 | 5.1.4.9 | 5.1.5.1 | 5.1.5.2 | 5.1.5.3 | 5.1.5.4 | 5.1.5.5 | 5.1.5.6 | 5.1.5.7 | 5.1.5.8 |
| 5.1.5.9 | 5.1.6.1 | 5.1.6.2 | 5.1.6.3 | 5.1.6.4 | 5.1.6.5 | 5.1.6.6 | 5.1.6.7 | 5.1.6.8 | 5.1.6.9 |
| 5.1.7.1 | 5.1.7.2 | 5.1.7.3 | 5.1.7.4 | 5.1.7.5 | 5.1.7.6 | 5.1.7.7 | 5.1.7.8 | 5.1.7.9 | 5.1.8.1 |
| 5.1.8.2 | 5.1.8.3 | 5.1.8.4 | 5.1.8.5 | 5.1.8.6 | 5.1.8.7 | 5.1.8.8 | 5.1.8.9 | 5.1.9.1 | 5.1.9.2 |
| 5.1.9.3 | 5.1.9.4 | 5.1.9.5 | 5.1.9.6 | 5.1.9.7 | 5.1.9.8 | 5.1.9.9 | 5.2.1.1 | 5.2.1.2 | 5.2.1.3 |
| 5.2.1.4 | 5.2.1.5 | 5.2.1.6 | 5.2.1.7 | 5.2.1.8 | 5.2.1.9 | 5.2.2.1 | 5.2.2.2 | 5.2.2.3 | 5.2.2.4 |
| 5.2.2.5 | 5.2.2.6 | 5.2.2.7 | 5.2.2.8 | 5.2.2.9 | 5.2.3.1 | 5.2.3.2 | 5.2.3.3 | 5.2.3.4 | 5.2.3.5 |
| 5.2.3.6 | 5.2.3.7 | 5.2.3.8 | 5.2.3.9 | 5.2.4.1 | 5.2.4.2 | 5.2.4.3 | 5.2.4.4 | 5.2.4.5 | 5.2.4.6 |
| 5.2.4.7 | 5.2.4.8 | 5.2.4.9 | 5.2.5.1 | 5.2.5.2 | 5.2.5.3 | 5.2.5.4 | 5.2.5.5 | 5.2.5.6 | 5.2.5.7 |
| 5.2.5.8 | 5.2.5.9 | 5.2.6.1 | 5.2.6.2 | 5.2.6.3 | 5.2.6.4 | 5.2.6.5 | 5.2.6.6 | 5.2.6.7 | 5.2.6.8 |
| 5.2.6.9 | 5.2.7.1 | 5.2.7.2 | 5.2.7.3 | 5.2.7.4 | 5.2.7.5 | 5.2.7.6 | 5.2.7.7 | 5.2.7.8 | 5.2.7.9 |
| 5.2.8.1 | 5.2.8.2 | 5.2.8.3 | 5.2.8.4 | 5.2.8.5 | 5.2.8.6 | 5.2.8.7 | 5.2.8.8 | 5.2.8.9 | 5.2.9.1 |
| 5.2.9.2 | 5.2.9.3 | 5.2.9.4 | 5.2.9.5 | 5.2.9.6 | 5.2.9.7 | 5.2.9.8 | 5.2.9.9 | 5.3.1.1 | 5.3.1.2 |
| 5.3.1.3 | 5.3.1.4 | 5.3.1.5 | 5.3.1.6 | 5.3.1.7 | 5.3.1.8 | 5.3.1.9 | 5.3.2.1 | 5.3.2.2 | 5.3.2.3 |
| 5.3.2.4 | 5.3.2.5 | 5.3.2.6 | 5.3.2.7 | 5.3.2.8 | 5.3.2.9 | 5.3.3.1 | 5.3.3.2 | 5.3.3.3 | 5.3.3.4 |
| 5.3.3.5 | 5.3.3.6 | 5.3.3.7 | 5.3.3.8 | 5.3.3.9 | 5.3.4.1 | 5.3.4.2 | 5.3.4.3 | 5.3.4.4 | 5.3.4.5 |
| 5.3.4.6 | 5.3.4.7 | 5.3.4.8 | 5.3.4.9 | 5.3.5.1 | 5.3.5.2 | 5.3.5.3 | 5.3.5.4 | 5.3.5.5 | 5.3.5.6 |
| 5.3.5.7 | 5.3.5.8 | 5.3.5.9 | 5.3.6.1 | 5.3.6.2 | 5.3.6.3 | 5.3.6.4 | 5.3.6.5 | 5.3.6.6 | 5.3.6.7 |
| 5.3.6.8 | 5.3.6.9 | 5.3.7.1 | 5.3.7.2 | 5.3.7.3 | 5.3.7.4 | 5.3.7.5 | 5.3.7.6 | 5.3.7.7 | 5.3.7.8 |
| 5.3.7.9 | 5.3.8.1 | 5.3.8.2 | 5.3.8.3 | 5.3.8.4 | 5.3.8.5 | 5.3.8.6 | 5.3.8.7 | 5.3.8.8 | 5.3.8.9 |
| 5.3.9.1 | 5.3.9.2 | 5.3.9.3 | 5.3.9.4 | 5.3.9.5 | 5.3.9.6 | 5.3.9.7 | 5.3.9.8 | 5.3.9.9 | 5.4.1.1 |
| 5.4.1.2 | 5.4.1.3 | 5.4.1.4 | 5.4.1.5 | 5.4.1.6 | 5.4.1.7 | 5.4.1.8 | 5.4.1.9 | 5.4.2.1 | 5.4.2.2 |
| 5.4.2.3 | 5.4.2.4 | 5.4.2.5 | 5.4.2.6 | 5.4.2.7 | 5.4.2.8 | 5.4.2.9 | 5.4.3.1 | 5.4.3.2 | 5.4.3.3 |
| 5.4.3.4 | 5.4.3.5 | 5.4.3.6 | 5.4.3.7 | 5.4.3.8 | 5.4.3.9 | 5.4.4.1 | 5.4.4.2 | 5.4.4.3 | 5.4.4.4 |
| 5.4.4.5 | 5.4.4.6 | 5.4.4.7 | 5.4.4.8 | 5.4.4.9 | 5.4.5.1 | 5.4.5.2 | 5.4.5.3 | 5.4.5.4 | 5.4.5.5 |
| 5.4.5.6 | 5.4.5.7 | 5.4.5.8 | 5.4.5.9 | 5.4.6.1 | 5.4.6.2 | 5.4.6.3 | 5.4.6.4 | 5.4.6.5 | 5.4.6.6 |
| 5.4.6.7 | 5.4.6.8 | 5.4.6.9 | 5.4.7.1 | 5.4.7.2 | 5.4.7.3 | 5.4.7.4 | 5.4.7.5 | 5.4.7.6 | 5.4.7.7 |
| 5.4.7.8 | 5.4.7.9 | 5.4.8.1 | 5.4.8.2 | 5.4.8.3 | 5.4.8.4 | 5.4.8.5 | 5.4.8.6 | 5.4.8.7 | 5.4.8.8 |
| 5.4.8.9 | 5.4.9.1 | 5.4.9.2 | 5.4.9.3 | 5.4.9.4 | 5.4.9.5 | 5.4.9.6 | 5.4.9.7 | 5.4.9.8 | 5.4.9.9 |
| 5.5.1.1 | 5.5.1.2 | 5.5.1.3 | 5.5.1.4 | 5.5.1.5 | 5.5.1.6 | 5.5.1.7 | 5.5.1.8 | 5.5.1.9 | 5.5.2.1 |
| 5.5.2.2 | 5.5.2.3 | 5.5.2.4 | 5.5.2.5 | 5.5.2.6 | 5.5.2.7 | 5.5.2.8 | 5.5.2.9 | 5.5.3.1 | 5.5.3.2 |
| 5.5.3.3 | 5.5.3.4 | 5.5.3.5 | 5.5.3.6 | 5.5.3.7 | 5.5.3.8 | 5.5.3.9 | 5.5.4.1 | 5.5.4.2 | 5.5.4.3 |
| 5.5.4.4 | 5.5.4.5 | 5.5.4.6 | 5.5.4.7 | 5.5.4.8 | 5.5.4.9 | 5.5.5.1 | 5.5.5.2 | 5.5.5.3 | 5.5.5.4 |
| 5.5.5.5 | 5.5.5.6 | 5.5.5.7 | 5.5.5.8 | 5.5.5.9 | 5.5.6.1 | 5.5.6.2 | 5.5.6.3 | 5.5.6.4 | 5.5.6.5 |
| 5.5.6.6 | 5.5.6.7 | 5.5.6.8 | 5.5.6.9 | 5.5.7.1 | 5.5.7.2 | 5.5.7.3 | 5.5.7.4 | 5.5.7.5 | 5.5.7.6 |
| 5.5.7.7 | 5.5.7.8 | 5.5.7.9 | 5.5.8.1 | 5.5.8.2 | 5.5.8.3 | 5.5.8.4 | 5.5.8.5 | 5.5.8.6 | 5.5.8.7 |
| 5.5.8.8 | 5.5.8.9 | 5.5.9.1 | 5.5.9.2 | 5.5.9.3 | 5.5.9.4 | 5.5.9.5 | 5.5.9.6 | 5.5.9.7 | 5.5.9.8 |
| 5.5.9.9 | 5.6.1.1 | 5.6.1.2 | 5.6.1.3 | 5.6.1.4 | 5.6.1.5 | 5.6.1.6 | 5.6.1.7 | 5.6.1.8 | 5.6.1.9 |
| 5.6.2.1 | 5.6.2.2 | 5.6.2.3 | 5.6.2.4 | 5.6.2.5 | 5.6.2.6 | 5.6.2.7 | 5.6.2.8 | 5.6.2.9 | 5.6.3.1 |
| 5.6.3.2 | 5.6.3.3 | 5.6.3.4 | 5.6.3.5 | 5.6.3.6 | 5.6.3.7 | 5.6.3.8 | 5.6.3.9 | 5.6.4.1 | 5.6.4.2 |
| 5.6.4.3 | 5.6.4.4 | 5.6.4.5 | 5.6.4.6 | 5.6.4.7 | 5.6.4.8 | 5.6.4.9 | 5.6.5.1 | 5.6.5.2 | 5.6.5.3 |
| 5.6.5.4 | 5.6.5.5 | 5.6.5.6 | 5.6.5.7 | 5.6.5.8 | 5.6.5.9 | 5.6.6.1 | 5.6.6.2 | 5.6.6.3 | 5.6.6.4 |
| 5.6.6.5 | 5.6.6.6 | 5.6.6.7 | 5.6.6.8 | 5.6.6.9 | 5.6.7.1 | 5.6.7.2 | 5.6.7.3 | 5.6.7.4 | 5.6.7.5 |
| 5.6.7.6 | 5.6.7.7 | 5.6.7.8 | 5.6.7.9 | 5.6.8.1 | 5.6.8.2 | 5.6.8.3 | 5.6.8.4 | 5.6.8.5 | 5.6.8.6 |
| 5.6.8.7 | 5.6.8.8 | 5.6.8.9 | 5.6.9.1 | 5.6.9.2 | 5.6.9.3 | 5.6.9.4 | 5.6.9.5 | 5.6.9.6 | 5.6.9.7 |
| 5.6.9.8 | 5.6.9.9 | 5.7.1.1 | 5.7.1.2 | 5.7.1.3 | 5.7.1.4 | 5.7.1.5 | 5.7.1.6 | 5.7.1.7 | 5.7.1.8 |
| 5.7.1.9 | 5.7.2.1 | 5.7.2.2 | 5.7.2.3 | 5.7.2.4 | 5.7.2.5 | 5.7.2.6 | 5.7.2.7 | 5.7.2.8 | 5.7.2.9 |
| 5.7.3.1 | 5.7.3.2 | 5.7.3.3 | 5.7.3.4 | 5.7.3.5 | 5.7.3.6 | 5.7.3.7 | 5.7.3.8 | 5.7.3.9 | 5.7.4.1 |
| 5.7.4.2 | 5.7.4.3 | 5.7.4.4 | 5.7.4.5 | 5.7.4.6 | 5.7.4.7 | 5.7.4.8 | 5.7.4.9 | 5.7.5.1 | 5.7.5.2 |
| 5.7.5.3 | 5.7.5.4 | 5.7.5.5 | 5.7.5.6 | 5.7.5.7 | 5.7.5.8 | 5.7.5.9 | 5.7.6.1 | 5.7.6.2 | 5.7.6.3 |
| 5.7.6.4 | 5.7.6.5 | 5.7.6.6 | 5.7.6.7 | 5.7.6.8 | 5.7.6.9 | 5.7.7.1 | 5.7.7.2 | 5.7.7.3 | 5.7.7.4 |
| 5.7.7.5 | 5.7.7.6 | 5.7.7.7 | 5.7.7.8 | 5.7.7.9 | 5.7.8.1 | 5.7.8.2 | 5.7.8.3 | 5.7.8.4 | 5.7.8.5 |
| 5.7.8.6 | 5.7.8.7 | 5.7.8.8 | 5.7.8.9 | 5.7.9.1 | 5.7.9.2 | 5.7.9.3 | 5.7.9.4 | 5.7.9.5 | 5.7.9.6 |
| 5.7.9.7 | 5.7.9.8 | 5.7.9.9 | 5.8.1.1 | 5.8.1.2 | 5.8.1.3 | 5.8.1.4 | 5.8.1.5 | 5.8.1.6 | 5.8.1.7 |
| 5.8.1.8 | 5.8.1.9 | 5.8.2.1 | 5.8.2.2 | 5.8.2.3 | 5.8.2.4 | 5.8.2.5 | 5.8.2.6 | 5.8.2.7 | 5.8.2.8 |
| 5.8.2.9 | 5.8.3.1 | 5.8.3.2 | 5.8.3.3 | 5.8.3.4 | 5.8.3.5 | 5.8.3.6 | 5.8.3.7 | 5.8.3.8 | 5.8.3.9 |
| 5.8.4.1 | 5.8.4.2 | 5.8.4.3 | 5.8.4.4 | 5.8.4.5 | 5.8.4.6 | 5.8.4.7 | 5.8.4.8 | 5.8.4.9 | 5.8.5.1 |
| 5.8.5.2 | 5.8.5.3 | 5.8.5.4 | 5.8.5.5 | 5.8.5.6 | 5.8.5.7 | 5.8.5.8 | 5.8.5.9 | 5.8.6.1 | 5.8.6.2 |
| 5.8.6.3 | 5.8.6.4 | 5.8.6.5 | 5.8.6.6 | 5.8.6.7 | 5.8.6.8 | 5.8.6.9 | 5.8.7.1 | 5.8.7.2 | 5.8.7.3 |
| 5.8.7.4 | 5.8.7.5 | 5.8.7.6 | 5.8.7.7 | 5.8.7.8 | 5.8.7.9 | 5.8.8.1 | 5.8.8.2 | 5.8.8.3 | 5.8.8.4 |
| 5.8.8.5 | 5.8.8.6 | 5.8.8.7 | 5.8.8.8 | 5.8.8.9 | 5.8.9.1 | 5.8.9.2 | 5.8.9.3 | 5.8.9.4 | 5.8.9.5 |
| 5.8.9.6 | 5.8.9.7 | 5.8.9.8 | 5.8.9.9 | 5.9.1.1 | 5.9.1.2 | 5.9.1.3 | 5.9.1.4 | 5.9.1.5 | 5.9.1.6 |
| 5.9.1.7 | 5.9.1.8 | 5.9.1.9 | 5.9.2.1 | 5.9.2.2 | 5.9.2.3 | 5.9.2.4 | 5.9.2.5 | 5.9.2.6 | 5.9.2.7 |
| 5.9.2.8 | 5.9.2.9 | 5.9.3.1 | 5.9.3.2 | 5.9.3.3 | 5.9.3.4 | 5.9.3.5 | 5.9.3.6 | 5.9.3.7 | 5.9.3.8 |
| 5.9.3.9 | 5.9.4.1 | 5.9.4.2 | 5.9.4.3 | 5.9.4.4 | 5.9.4.5 | 5.9.4.6 | 5.9.4.7 | 5.9.4.8 | 5.9.4.9 |
| 5.9.5.1 | 5.9.5.2 | 5.9.5.3 | 5.9.5.4 | 5.9.5.5 | 5.9.5.6 | 5.9.5.7 | 5.9.5.8 | 5.9.5.9 | 5.9.6.1 |
| 5.9.6.2 | 5.9.6.3 | 5.9.6.4 | 5.9.6.5 | 5.9.6.6 | 5.9.6.7 | 5.9.6.8 | 5.9.6.9 | 5.9.7.1 | 5.9.7.2 |
| 5.9.7.3 | 5.9.7.4 | 5.9.7.5 | 5.9.7.6 | 5.9.7.7 | 5.9.7.8 | 5.9.7.9 | 5.9.8.1 | 5.9.8.2 | 5.9.8.3 |
| 5.9.8.4 | 5.9.8.5 | 5.9.8.6 | 5.9.8.7 | 5.9.8.8 | 5.9.8.9 | 5.9.9.1 | 5.9.9.2 | 5.9.9.3 | 5.9.9.4 |
| 5.9.9.5 | 5.9.9.6 | 5.9.9.7 | 5.9.9.8 | 5.9.9.9 | 6.1.1.1 | 6.1.1.2 | 6.1.1.3 | 6.1.1.4 | 6.1.1.5 |
| 6.1.1.6 | 6.1.1.7 | 6.1.1.8 | 6.1.1.9 | 6.1.2.1 | 6.1.2.2 | 6.1.2.3 | 6.1.2.4 | 6.1.2.5 | 6.1.2.6 |
| 6.1.2.7 | 6.1.2.8 | 6.1.2.9 | 6.1.3.1 | 6.1.3.2 | 6.1.3.3 | 6.1.3.4 | 6.1.3.5 | 6.1.3.6 | 6.1.3.7 |
| 6.1.3.8 | 6.1.3.9 | 6.1.4.1 | 6.1.4.2 | 6.1.4.3 | 6.1.4.4 | 6.1.4.5 | 6.1.4.6 | 6.1.4.7 | 6.1.4.8 |
| 6.1.4.9 | 6.1.5.1 | 6.1.5.2 | 6.1.5.3 | 6.1.5.4 | 6.1.5.5 | 6.1.5.6 | 6.1.5.7 | 6.1.5.8 | 6.1.5.9 |

TABLE 1-continued

| | | | | | | | | |
|---|---|---|---|---|---|---|---|---|
| 6.1.6.1 | 6.1.6.2 | 6.1.6.3 | 6.1.6.4 | 6.1.6.5 | 6.1.6.6 | 6.1.6.7 | 6.1.6.8 | 6.1.6.9 | 6.1.7.1 |
| 6.1.7.2 | 6.1.7.3 | 6.1.7.4 | 6.1.7.5 | 6.1.7.6 | 6.1.7.7 | 6.1.7.8 | 6.1.7.9 | 6.1.8.1 | 6.1.8.2 |
| 6.1.8.3 | 6.1.8.4 | 6.1.8.5 | 6.1.8.6 | 6.1.8.7 | 6.1.8.8 | 6.1.8.9 | 6.1.9.1 | 6.1.9.2 | 6.1.9.3 |
| 6.1.9.4 | 6.1.9.5 | 6.1.9.6 | 6.1.9.7 | 6.1.9.8 | 6.1.9.9 | 6.2.1.1 | 6.2.1.2 | 6.2.1.3 | 6.2.1.4 |
| 6.2.1.5 | 6.2.1.6 | 6.2.1.7 | 6.2.1.8 | 6.2.1.9 | 6.2.2.1 | 6.2.2.2 | 6.2.2.3 | 6.2.2.4 | 6.2.2.5 |
| 6.2.2.6 | 6.2.2.7 | 6.2.2.8 | 6.2.2.9 | 6.2.3.1 | 6.2.3.2 | 6.2.3.3 | 6.2.3.4 | 6.2.3.5 | 6.2.3.6 |
| 6.2.3.7 | 6.2.3.8 | 6.2.3.9 | 6.2.4.1 | 6.2.4.2 | 6.2.4.3 | 6.2.4.4 | 6.2.4.5 | 6.2.4.6 | 6.2.4.7 |
| 6.2.4.8 | 6.2.4.9 | 6.2.5.1 | 6.2.5.2 | 6.2.5.3 | 6.2.5.4 | 6.2.5.5 | 6.2.5.6 | 6.2.5.7 | 6.2.5.8 |
| 6.2.5.9 | 6.2.6.1 | 6.2.6.2 | 6.2.6.3 | 6.2.6.4 | 6.2.6.5 | 6.2.6.6 | 6.2.6.7 | 6.2.6.8 | 6.2.6.9 |
| 6.2.7.1 | 6.2.7.2 | 6.2.7.3 | 6.2.7.4 | 6.2.7.5 | 6.2.7.6 | 6.2.7.7 | 6.2.7.8 | 6.2.7.9 | 6.2.8.1 |
| 6.2.8.2 | 6.2.8.3 | 6.2.8.4 | 6.2.8.5 | 6.2.8.6 | 6.2.8.7 | 6.2.8.8 | 6.2.8.9 | 6.2.9.1 | 6.2.9.2 |
| 6.2.9.3 | 6.2.9.4 | 6.2.9.5 | 6.2.9.6 | 6.2.9.7 | 6.2.9.8 | 6.2.9.9 | 6.3.1.1 | 6.3.1.2 | 6.3.1.3 |
| 6.3.1.4 | 6.3.1.5 | 6.3.1.6 | 6.3.1.7 | 6.3.1.8 | 6.3.1.9 | 6.3.2.1 | 6.3.2.2 | 6.3.2.3 | 6.3.2.4 |
| 6.3.2.5 | 6.3.2.6 | 6.3.2.7 | 6.3.2.8 | 6.3.2.9 | 6.3.3.1 | 6.3.3.2 | 6.3.3.3 | 6.3.3.4 | 6.3.3.5 |
| 6.3.3.6 | 6.3.3.7 | 6.3.3.8 | 6.3.3.9 | 6.3.4.1 | 6.3.4.2 | 6.3.4.3 | 6.3.4.4 | 6.3.4.5 | 6.3.4.6 |
| 6.3.4.7 | 6.3.4.8 | 6.3.4.9 | 6.3.5.1 | 6.3.5.2 | 6.3.5.3 | 6.3.5.4 | 6.3.5.5 | 6.3.5.6 | 6.3.5.7 |
| 6.3.5.8 | 6.3.5.9 | 6.3.6.1 | 6.3.6.2 | 6.3.6.3 | 6.3.6.4 | 6.3.6.5 | 6.3.6.6 | 6.3.6.7 | 6.3.6.8 |
| 6.3.6.9 | 6.3.7.1 | 6.3.7.2 | 6.3.7.3 | 6.3.7.4 | 6.3.7.5 | 6.3.7.6 | 6.3.7.7 | 6.3.7.8 | 6.3.7.9 |
| 6.3.8.1 | 6.3.8.2 | 6.3.8.3 | 6.3.8.4 | 6.3.8.5 | 6.3.8.6 | 6.3.8.7 | 6.3.8.8 | 6.3.8.9 | 6.3.9.1 |
| 6.3.9.2 | 6.3.9.3 | 6.3.9.4 | 6.3.9.5 | 6.3.9.6 | 6.3.9.7 | 6.3.9.8 | 6.3.9.9 | 6.4.1.1 | 6.4.1.2 |
| 6.4.1.3 | 6.4.1.4 | 6.4.1.5 | 6.4.1.6 | 6.4.1.7 | 6.4.1.8 | 6.4.1.9 | 6.4.2.1 | 6.4.2.2 | 6.4.2.3 |
| 6.4.2.4 | 6.4.2.5 | 6.4.2.6 | 6.4.2.7 | 6.4.2.8 | 6.4.2.9 | 6.4.3.1 | 6.4.3.2 | 6.4.3.3 | 6.4.3.4 |
| 6.4.3.5 | 6.4.3.6 | 6.4.3.7 | 6.4.3.8 | 6.4.3.9 | 6.4.4.1 | 6.4.4.2 | 6.4.4.3 | 6.4.4.4 | 6.4.4.5 |
| 6.4.4.6 | 6.4.4.7 | 6.4.4.8 | 6.4.4.9 | 6.4.5.1 | 6.4.5.2 | 6.4.5.3 | 6.4.5.4 | 6.4.5.5 | 6.4.5.6 |
| 6.4.5.7 | 6.4.5.8 | 6.4.5.9 | 6.4.6.1 | 6.4.6.2 | 6.4.6.3 | 6.4.6.4 | 6.4.6.5 | 6.4.6.6 | 6.4.6.7 |
| 6.4.6.8 | 6.4.6.9 | 6.4.7.1 | 6.4.7.2 | 6.4.7.3 | 6.4.7.4 | 6.4.7.5 | 6.4.7.6 | 6.4.7.7 | 6.4.7.8 |
| 6.4.7.9 | 6.4.8.1 | 6.4.8.2 | 6.4.8.3 | 6.4.8.4 | 6.4.8.5 | 6.4.8.6 | 6.4.8.7 | 6.4.8.8 | 6.4.8.9 |
| 6.4.9.1 | 6.4.9.2 | 6.4.9.3 | 6.4.9.4 | 6.4.9.5 | 6.4.9.6 | 6.4.9.7 | 6.4.9.8 | 6.4.9.9 | 6.5.1.1 |
| 6.5.1.2 | 6.5.1.3 | 6.5.1.4 | 6.5.1.5 | 6.5.1.6 | 6.5.1.7 | 6.5.1.8 | 6.5.1.9 | 6.5.2.1 | 6.5.2.2 |
| 6.5.2.3 | 6.5.2.4 | 6.5.2.5 | 6.5.2.6 | 6.5.2.7 | 6.5.2.8 | 6.5.2.9 | 6.5.3.1 | 6.5.3.2 | 6.5.3.3 |
| 6.5.3.4 | 6.5.3.5 | 6.5.3.6 | 6.5.3.7 | 6.5.3.8 | 6.5.3.9 | 6.5.4.1 | 6.5.4.2 | 6.5.4.3 | 6.5.4.4 |
| 6.5.4.5 | 6.5.4.6 | 6.5.4.7 | 6.5.4.8 | 6.5.4.9 | 6.5.5.1 | 6.5.5.2 | 6.5.5.3 | 6.5.5.4 | 6.5.5.5 |
| 6.5.5.6 | 6.5.5.7 | 6.5.5.8 | 6.5.5.9 | 6.5.6.1 | 6.5.6.2 | 6.5.6.3 | 6.5.6.4 | 6.5.6.5 | 6.5.6.6 |
| 6.5.6.7 | 6.5.6.8 | 6.5.6.9 | 6.5.7.1 | 6.5.7.2 | 6.5.7.3 | 6.5.7.4 | 6.5.7.5 | 6.5.7.6 | 6.5.7.7 |
| 6.5.7.8 | 6.5.7.9 | 6.5.8.1 | 6.5.8.2 | 6.5.8.3 | 6.5.8.4 | 6.5.8.5 | 6.5.8.6 | 6.5.8.7 | 6.5.8.8 |
| 6.5.8.9 | 6.5.9.1 | 6.5.9.2 | 6.5.9.3 | 6.5.9.4 | 6.5.9.5 | 6.5.9.6 | 6.5.9.7 | 6.5.9.8 | 6.5.9.9 |
| 6.6.1.1 | 6.6.1.2 | 6.6.1.3 | 6.6.1.4 | 6.6.1.5 | 6.6.1.6 | 6.6.1.7 | 6.6.1.8 | 6.6.1.9 | 6.6.2.1 |
| 6.6.2.2 | 6.6.2.3 | 6.6.2.4 | 6.6.2.5 | 6.6.2.6 | 6.6.2.7 | 6.6.2.8 | 6.6.2.9 | 6.6.3.1 | 6.6.3.2 |
| 6.6.3.3 | 6.6.3.4 | 6.6.3.5 | 6.6.3.6 | 6.6.3.7 | 6.6.3.8 | 6.6.3.9 | 6.6.4.1 | 6.6.4.2 | 6.6.4.3 |
| 6.6.4.4 | 6.6.4.5 | 6.6.4.6 | 6.6.4.7 | 6.6.4.8 | 6.6.4.9 | 6.6.5.1 | 6.6.5.2 | 6.6.5.3 | 6.6.5.4 |
| 6.6.5.5 | 6.6.5.6 | 6.6.5.7 | 6.6.5.8 | 6.6.5.9 | 6.6.6.1 | 6.6.6.2 | 6.6.6.3 | 6.6.6.4 | 6.6.6.5 |
| 6.6.6.6 | 6.6.6.7 | 6.6.6.8 | 6.6.6.9 | 6.6.7.1 | 6.6.7.2 | 6.6.7.3 | 6.6.7.4 | 6.6.7.5 | 6.6.7.6 |
| 6.6.7.7 | 6.6.7.8 | 6.6.7.9 | 6.6.8.1 | 6.6.8.2 | 6.6.8.3 | 6.6.8.4 | 6.6.8.5 | 6.6.8.6 | 6.6.8.7 |
| 6.6.8.8 | 6.6.8.9 | 6.6.9.1 | 6.6.9.2 | 6.6.9.3 | 6.6.9.4 | 6.6.9.5 | 6.6.9.6 | 6.6.9.7 | 6.6.9.8 |
| 6.6.9.9 | 6.7.1.1 | 6.7.1.2 | 6.7.1.3 | 6.7.1.4 | 6.7.1.5 | 6.7.1.6 | 6.7.1.7 | 6.7.1.8 | 6.7.1.9 |
| 6.7.2.1 | 6.7.2.2 | 6.7.2.3 | 6.7.2.4 | 6.7.2.5 | 6.7.2.6 | 6.7.2.7 | 6.7.2.8 | 6.7.2.9 | 6.7.3.1 |
| 6.7.3.2 | 6.7.3.3 | 6.7.3.4 | 6.7.3.5 | 6.7.3.6 | 6.7.3.7 | 6.7.3.8 | 6.7.3.9 | 6.7.4.1 | 6.7.4.2 |
| 6.7.4.3 | 6.7.4.4 | 6.7.4.5 | 6.7.4.6 | 6.7.4.7 | 6.7.4.8 | 6.7.4.9 | 6.7.5.1 | 6.7.5.2 | 6.7.5.3 |
| 6.7.5.4 | 6.7.5.5 | 6.7.5.6 | 6.7.5.7 | 6.7.5.8 | 6.7.5.9 | 6.7.6.1 | 6.7.6.2 | 6.7.6.3 | 6.7.6.4 |
| 6.7.6.5 | 6.7.6.6 | 6.7.6.7 | 6.7.6.8 | 6.7.6.9 | 6.7.7.1 | 6.7.7.2 | 6.7.7.3 | 6.7.7.4 | 6.7.7.5 |
| 6.7.7.6 | 6.7.7.7 | 6.7.7.8 | 6.7.7.9 | 6.7.8.1 | 6.7.8.2 | 6.7.8.3 | 6.7.8.4 | 6.7.8.5 | 6.7.8.6 |
| 6.7.8.7 | 6.7.8.8 | 6.7.8.9 | 6.7.9.1 | 6.7.9.2 | 6.7.9.3 | 6.7.9.4 | 6.7.9.5 | 6.7.9.6 | 6.7.9.7 |
| 6.7.9.8 | 6.7.9.9 | 6.8.1.1 | 6.8.1.2 | 6.8.1.3 | 6.8.1.4 | 6.8.1.5 | 6.8.1.6 | 6.8.1.7 | 6.8.1.8 |
| 6.8.1.9 | 6.8.2.1 | 6.8.2.2 | 6.8.2.3 | 6.8.2.4 | 6.8.2.5 | 6.8.2.6 | 6.8.2.7 | 6.8.2.8 | 6.8.2.9 |
| 6.8.3.1 | 6.8.3.2 | 6.8.3.3 | 6.8.3.4 | 6.8.3.5 | 6.8.3.6 | 6.8.3.7 | 6.8.3.8 | 6.8.3.9 | 6.8.4.1 |
| 6.8.4.2 | 6.8.4.3 | 6.8.4.4 | 6.8.4.5 | 6.8.4.6 | 6.8.4.7 | 6.8.4.8 | 6.8.4.9 | 6.8.5.1 | 6.8.5.2 |
| 6.8.5.3 | 6.8.5.4 | 6.8.5.5 | 6.8.5.6 | 6.8.5.7 | 6.8.5.8 | 6.8.5.9 | 6.8.6.1 | 6.8.6.2 | 6.8.6.3 |
| 6.8.6.4 | 6.8.6.5 | 6.8.6.6 | 6.8.6.7 | 6.8.6.8 | 6.8.6.9 | 6.8.7.1 | 6.8.7.2 | 6.8.7.3 | 6.8.7.4 |
| 6.8.7.5 | 6.8.7.6 | 6.8.7.7 | 6.8.7.8 | 6.8.7.9 | 6.8.8.1 | 6.8.8.2 | 6.8.8.3 | 6.8.8.4 | 6.8.8.5 |
| 6.8.8.6 | 6.8.8.7 | 6.8.8.8 | 6.8.8.9 | 6.8.9.1 | 6.8.9.2 | 6.8.9.3 | 6.8.9.4 | 6.8.9.5 | 6.8.9.6 |
| 6.8.9.7 | 6.8.9.8 | 6.8.9.9 | 6.9.1.1 | 6.9.1.2 | 6.9.1.3 | 6.9.1.4 | 6.9.1.5 | 6.9.1.6 | 6.9.1.7 |
| 6.9.1.8 | 6.9.1.9 | 6.9.2.1 | 6.9.2.2 | 6.9.2.3 | 6.9.2.4 | 6.9.2.5 | 6.9.2.6 | 6.9.2.7 | 6.9.2.8 |
| 6.9.2.9 | 6.9.3.1 | 6.9.3.2 | 6.9.3.3 | 6.9.3.4 | 6.9.3.5 | 6.9.3.6 | 6.9.3.7 | 6.9.3.8 | 6.9.3.9 |
| 6.9.4.1 | 6.9.4.2 | 6.9.4.3 | 6.9.4.4 | 6.9.4.5 | 6.9.4.6 | 6.9.4.7 | 6.9.4.8 | 6.9.4.9 | 6.9.5.1 |
| 6.9.5.2 | 6.9.5.3 | 6.9.5.4 | 6.9.5.5 | 6.9.5.6 | 6.9.5.7 | 6.9.5.8 | 6.9.5.9 | 6.9.6.1 | 6.9.6.2 |
| 6.9.6.3 | 6.9.6.4 | 6.9.6.5 | 6.9.6.6 | 6.9.6.7 | 6.9.6.8 | 6.9.6.9 | 6.9.7.1 | 6.9.7.2 | 6.9.7.3 |
| 6.9.7.4 | 6.9.7.5 | 6.9.7.6 | 6.9.7.7 | 6.9.7.8 | 6.9.7.9 | 6.9.8.1 | 6.9.8.2 | 6.9.8.3 | 6.9.8.4 |
| 6.9.8.5 | 6.9.8.6 | 6.9.8.7 | 6.9.8.8 | 6.9.8.9 | 6.9.9.1 | 6.9.9.2 | 6.9.9.3 | 6.9.9.4 | 6.9.9.5 |
| 6.9.9.6 | 6.9.9.7 | 6.9.9.8 | 6.9.9.9 | 7.1.1.1 | 7.1.1.2 | 7.1.1.3 | 7.1.1.4 | 7.1.1.5 | 7.1.1.6 |
| 7.1.1.7 | 7.1.1.8 | 7.1.1.9 | 7.1.2.1 | 7.1.2.2 | 7.1.2.3 | 7.1.2.4 | 7.1.2.5 | 7.1.2.6 | 7.1.2.7 |
| 7.1.2.8 | 7.1.2.9 | 7.1.3.1 | 7.1.3.2 | 7.1.3.3 | 7.1.3.4 | 7.1.3.5 | 7.1.3.6 | 7.1.3.7 | 7.1.3.8 |
| 7.1.3.9 | 7.1.4.1 | 7.1.4.2 | 7.1.4.3 | 7.1.4.4 | 7.1.4.5 | 7.1.4.6 | 7.1.4.7 | 7.1.4.8 | 7.1.4.9 |
| 7.1.5.1 | 7.1.5.2 | 7.1.5.3 | 7.1.5.4 | 7.1.5.5 | 7.1.5.6 | 7.1.5.7 | 7.1.5.8 | 7.1.5.9 | 7.1.6.1 |
| 7.1.6.2 | 7.1.6.3 | 7.1.6.4 | 7.1.6.5 | 7.1.6.6 | 7.1.6.7 | 7.1.6.8 | 7.1.6.9 | 7.1.7.1 | 7.1.7.2 |
| 7.1.7.3 | 7.1.7.4 | 7.1.7.5 | 7.1.7.6 | 7.1.7.7 | 7.1.7.8 | 7.1.7.9 | 7.1.8.1 | 7.1.8.2 | 7.1.8.3 |
| 7.1.8.4 | 7.1.8.5 | 7.1.8.6 | 7.1.8.7 | 7.1.8.8 | 7.1.8.9 | 7.1.9.1 | 7.1.9.2 | 7.1.9.3 | 7.1.9.4 |
| 7.1.9.5 | 7.1.9.6 | 7.1.9.7 | 7.1.9.8 | 7.1.9.9 | 7.2.1.1 | 7.2.1.2 | 7.2.1.3 | 7.2.1.4 | 7.2.1.5 |
| 7.2.1.6 | 7.2.1.7 | 7.2.1.8 | 7.2.1.9 | 7.2.2.1 | 7.2.2.2 | 7.2.2.3 | 7.2.2.4 | 7.2.2.5 | 7.2.2.6 |
| 7.2.2.7 | 7.2.2.8 | 7.2.2.9 | 7.2.3.1 | 7.2.3.2 | 7.2.3.3 | 7.2.3.4 | 7.2.3.5 | 7.2.3.6 | 7.2.3.7 |

TABLE 1-continued

| | | | | | | | | |
|---|---|---|---|---|---|---|---|---|
| 7.2.3.8 | 7.2.3.9 | 7.2.4.1 | 7.2.4.2 | 7.2.4.3 | 7.2.4.4 | 7.2.4.5 | 7.2.4.6 | 7.2.4.7 | 7.2.4.8 |
| 7.2.4.9 | 7.2.5.1 | 7.2.5.2 | 7.2.5.3 | 7.2.5.4 | 7.2.5.5 | 7.2.5.6 | 7.2.5.7 | 7.2.5.8 | 7.2.5.9 |
| 7.2.6.1 | 7.2.6.2 | 7.2.6.3 | 7.2.6.4 | 7.2.6.5 | 7.2.6.6 | 7.2.6.7 | 7.2.6.8 | 7.2.6.9 | 7.2.7.1 |
| 7.2.7.2 | 7.2.7.3 | 7.2.7.4 | 7.2.7.5 | 7.2.7.6 | 7.2.7.7 | 7.2.7.8 | 7.2.7.9 | 7.2.8.1 | 7.2.8.2 |
| 7.2.8.3 | 7.2.8.4 | 7.2.8.5 | 7.2.8.6 | 7.2.8.7 | 7.2.8.8 | 7.2.8.9 | 7.2.9.1 | 7.2.9.2 | 7.2.9.3 |
| 7.2.9.4 | 7.2.9.5 | 7.2.9.6 | 7.2.9.7 | 7.2.9.8 | 7.2.9.9 | 7.3.1.1 | 7.3.1.2 | 7.3.1.3 | 7.3.1.4 |
| 7.3.1.5 | 7.3.1.6 | 7.3.1.7 | 7.3.1.8 | 7.9.1.9 | 7.3.2.1 | 7.3.2.2 | 7.3.2.3 | 7.3.2.4 | 7.3.2.5 |
| 7.3.2.6 | 7.3.2.7 | 7.3.2.8 | 7.3.2.9 | 7.3.3.1 | 7.3.3.2 | 7.3.3.3 | 7.3.3.4 | 7.3.3.5 | 7.3.3.6 |
| 7.3.3.7 | 7.3.3.8 | 7.3.3.9 | 7.3.4.1 | 7.3.4.2 | 7.3.4.3 | 7.3.4.4 | 7.3.4.5 | 7.3.4.6 | 7.3.4.7 |
| 7.3.4.8 | 7.3.4.9 | 7.3.5.1 | 7.3.5.2 | 7.3.5.3 | 7.3.5.4 | 7.3.5.5 | 7.3.5.6 | 7.3.5.7 | 7.3.5.8 |
| 7.3.5.9 | 7.3.6.1 | 7.3.6.2 | 7.3.6.3 | 7.3.6.4 | 7.3.6.5 | 7.3.6.6 | 7.3.6.7 | 7.3.6.8 | 7.3.6.9 |
| 7.3.7.1 | 7.3.7.2 | 7.3.7.3 | 7.3.7.4 | 7.3.7.5 | 7.3.7.6 | 7.3.7.7 | 7.3.7.8 | 7.3.7.9 | 7.3.8.1 |
| 7.3.8.2 | 7.3.8.3 | 7.3.8.4 | 7.3.8.5 | 7.3.8.6 | 7.3.8.7 | 7.3.8.8 | 7.3.8.9 | 7.3.9.1 | 7.3.9.2 |
| 7.3.9.3 | 7.3.9.4 | 7.3.9.5 | 7.3.9.6 | 7.3.9.7 | 7.3.9.8 | 7.3.9.9 | 7.4.1.1 | 7.4.1.2 | 7.4.1.3 |
| 7.4.1.4 | 7.4.1.5 | 7.4.1.6 | 7.4.1.7 | 7.4.1.8 | 7.4.1.9 | 7.4.2.1 | 7.4.2.2 | 7.4.2.3 | 7.4.2.4 |
| 7.4.2.5 | 7.4.2.6 | 7.4.2.7 | 7.4.2.8 | 7.4.2.9 | 7.4.3.1 | 7.4.3.2 | 7.4.3.3 | 7.4.3.4 | 7.4.3.5 |
| 7.4.3.6 | 7.4.3.7 | 7.4.3.8 | 7.4.3.9 | 7.4.4.1 | 7.4.4.2 | 7.4.4.3 | 7.4.4.4 | 7.4.4.5 | 7.4.4.6 |
| 7.4.4.7 | 7.4.4.8 | 7.4.4.9 | 7.4.5.1 | 7.4.5.2 | 7.4.5.3 | 7.4.5.4 | 7.4.5.5 | 7.4.5.6 | 7.4.5.7 |
| 7.4.5.8 | 7.4.5.9 | 7.4.6.1 | 7.4.6.2 | 7.4.6.3 | 7.4.6.4 | 7.4.6.5 | 7.4.6.6 | 7.4.6.7 | 7.4.6.8 |
| 7.4.6.9 | 7.4.7.1 | 7.4.7.2 | 7.4.7.3 | 7.4.7.4 | 7.4.7.5 | 7.4.7.6 | 7.4.7.7 | 7.4.7.8 | 7.4.7.9 |
| 7.4.8.1 | 7.4.8.2 | 7.4.8.3 | 7.4.8.4 | 7.4.8.5 | 7.4.8.6 | 7.4.8.7 | 7.4.8.8 | 7.4.8.9 | 7.4.9.1 |
| 7.4.9.2 | 7.4.9.3 | 7.4.9.4 | 7.4.9.5 | 7.4.9.6 | 7.4.9.7 | 7.4.9.8 | 7.4.9.9 | 7.5.1.1 | 7.5.1.2 |
| 7.5.1.3 | 7.5.1.4 | 7.5.1.5 | 7.5.1.6 | 7.5.1.7 | 7.5.1.8 | 7.5.1.9 | 7.5.2.1 | 7.5.2.2 | 7.5.2.3 |
| 7.5.2.4 | 7.5.2.5 | 7.5.2.6 | 7.5.2.7 | 7.5.2.8 | 7.5.2.9 | 7.5.3.1 | 7.5.3.2 | 7.5.3.3 | 7.5.3.4 |
| 7.5.3.5 | 7.5.3.6 | 7.5.3.7 | 7.5.3.8 | 7.5.3.9 | 7.5.4.1 | 7.5.4.2 | 7.5.4.3 | 7.5.4.4 | 7.5.4.5 |
| 7.5.4.6 | 7.5.4.7 | 7.5.4.8 | 7.5.4.9 | 7.5.5.1 | 7.5.5.2 | 7.5.5.3 | 7.5.5.4 | 7.5.5.5 | 7.5.5.6 |
| 7.5.5.7 | 7.5.5.8 | 7.5.5.9 | 7.5.6.1 | 7.5.6.2 | 7.5.6.3 | 7.5.6.4 | 7.5.6.5 | 7.5.6.6 | 7.5.6.7 |
| 7.5.6.8 | 7.5.6.9 | 7.5.7.1 | 7.5.7.2 | 7.5.7.3 | 7.5.7.4 | 7.5.7.5 | 7.5.7.6 | 7.5.7.7 | 7.5.7.8 |
| 7.5.7.9 | 7.5.8.1 | 7.5.8.2 | 7.5.8.3 | 7.5.8.4 | 7.5.8.5 | 7.5.8.6 | 7.5.8.7 | 7.5.8.8 | 7.5.8.9 |
| 7.5.9.1 | 7.5.9.2 | 7.5.9.3 | 7.5.9.4 | 7.5.9.5 | 7.5.9.6 | 7.5.9.7 | 7.5.9.8 | 7.5.9.9 | 7.6.1.1 |
| 7.6.1.2 | 7.6.1.3 | 7.6.1.4 | 7.6.1.5 | 7.6.1.6 | 7.6.1.7 | 7.6.1.8 | 7.6.1.9 | 7.6.2.1 | 7.6.2.2 |
| 7.6.2.3 | 7.6.2.4 | 7.6.2.5 | 7.6.2.6 | 7.6.2.7 | 7.6.2.8 | 7.6.2.9 | 7.6.3.1 | 7.6.3.2 | 7.6.3.3 |
| 7.6.3.4 | 7.6.3.5 | 7.6.3.6 | 7.6.3.7 | 7.6.3.8 | 7.6.3.9 | 7.6.4.1 | 7.6.4.2 | 7.6.4.3 | 7.6.4.4 |
| 7.6.4.5 | 7.6.4.6 | 7.6.4.7 | 7.6.4.8 | 7.6.4.9 | 7.6.5.1 | 7.6.5.2 | 7.6.5.3 | 7.6.5.4 | 7.6.5.5 |
| 7.6.5.6 | 7.6.5.7 | 7.6.5.8 | 7.6.5.9 | 7.6.6.1 | 7.6.6.2 | 7.6.6.3 | 7.6.6.4 | 7.6.6.5 | 7.6.6.6 |
| 7.6.6.7 | 7.6.6.8 | 7.6.6.9 | 7.6.7.1 | 7.6.7.2 | 7.6.7.3 | 7.6.7.4 | 7.6.7.5 | 7.6.7.6 | 7.6.7.7 |
| 7.6.7.8 | 7.6.7.9 | 7.6.8.1 | 7.6.8.2 | 7.6.8.3 | 7.6.8.4 | 7.6.8.5 | 7.6.8.6 | 7.6.8.7 | 7.6.8.8 |
| 7.6.8.9 | 7.6.9.1 | 7.6.9.2 | 7.6.9.3 | 7.6.9.4 | 7.6.9.5 | 7.6.9.6 | 7.6.9.7 | 7.6.9.8 | 7.6.9.9 |
| 7.7.1.1 | 7.7.1.2 | 7.7.1.3 | 7.7.1.4 | 7.7.1.5 | 7.7.1.6 | 7.7.1.7 | 7.7.1.8 | 7.7.1.9 | 7.7.2.1 |
| 7.7.2.2 | 7.7.2.3 | 7.7.2.4 | 7.7.2.5 | 7.7.2.6 | 7.7.2.7 | 7.7.2.B | 7.7.2.9 | 7.7.3.1 | 7.7.3.2 |
| 7.7.3.3 | 7.7.3.4 | 7.7.3.5 | 7.7.3.6 | 7.7.3.7 | 7.7.3.8 | 7.7.3.9 | 7.7.4.1 | 7.7.4.2 | 7.7.4.3 |
| 7.7.4.4 | 7.7.4.5 | 7.7.4.6 | 7.7.4.7 | 7.7.4.8 | 7.7.4.9 | 7.7.5.1 | 7.7.5.2 | 7.7.5.3 | 7.7.5.4 |
| 7.7.5.5 | 7.7.5.6 | 7.7.5.7 | 7.7.5.8 | 7.7.5.9 | 7.7.6.1 | 7.7.6.2 | 7.7.6.3 | 7.7.6.4 | 7.7.6.5 |
| 7.7.6.6 | 7.7.6.7 | 7.7.6.8 | 7.7.6.9 | 7.7.7.1 | 7.7.7.2 | 7.7.7.3 | 7.7.7.4 | 7.7.7.5 | 7.7.7.6 |
| 7.7.7.7 | 7.7.7.8 | 7.7.7.9 | 7.7.8.1 | 7.7.8.2 | 7.7.8.3 | 7.7.8.4 | 7.7.8.5 | 7.7.8.6 | 7.7.8.7 |
| 7.7.8.8 | 7.7.8.9 | 7.7.9.1 | 7.7.9.2 | 7.7.9.3 | 7.7.9.4 | 7.7.9.5 | 7.7.9.6 | 7.7.9.7 | 7.7.9.8 |
| 7.7.9.9 | 7.8.1.1 | 7.8.1.2 | 7.8.1.3 | 7.8.1.4 | 7.8.1.5 | 7.8.1.6 | 7.8.1.7 | 7.8.1.8 | 7.8.1.9 |
| 7.8.2.1 | 7.8.2.2 | 7.8.2.3 | 7.8.2.4 | 7.8.2.5 | 7.8.2.6 | 7.8.2.7 | 7.8.2.8 | 7.8.2.9 | 7.8.3.1 |
| 7.8.3.2 | 7.8.3.3 | 7.8.3.4 | 7.8.3.5 | 7.8.3.6 | 7.8.3.7 | 7.8.3.8 | 7.8.3.9 | 7.8.4.1 | 7.8.4.2 |
| 7.8.4.3 | 7.8.4.4 | 7.8.4.5 | 7.8.4.6 | 7.8.4.7 | 7.8.4.8 | 7.8.4.9 | 7.8.5.1 | 7.8.5.2 | 7.8.5.3 |
| 7.8.5.4 | 7.8.5.5 | 7.8.5.6 | 7.8.5.7 | 7.8.5.8 | 7.8.5.9 | 7.8.6.1 | 7.8.6.2 | 7.8.6.3 | 7.8.6.4 |
| 7.8.6.5 | 7.8.6.6 | 7.8.6.7 | 7.8.6.8 | 7.8.6.9 | 7.8.7.1 | 7.8.7.2 | 7.8.7.3 | 7.8.7.4 | 7.8.7.5 |
| 7.8.7.6 | 7.8.7.7 | 7.8.7.8 | 7.8.7.9 | 7.8.8.1 | 7.8.8.2 | 7.8.8.3 | 7.8.8.4 | 7.8.8.5 | 7.8.8.6 |
| 7.8.8.7 | 7.8.8.8 | 7.8.8.9 | 7.8.9.1 | 7.8.9.2 | 7.8.9.3 | 7.8.9.4 | 7.8.9.5 | 7.8.9.6 | 7.8.9.7 |
| 7.8.9.8 | 7.8.9.9 | 7.9.1.1 | 7.9.1.2 | 7.9.1.3 | 7.9.1.4 | 7.9.1.5 | 7.9.1.6 | 7.9.1.7 | 7.9.1.8 |
| 7.9.1.9 | 7.9.2.1 | 7.9.2.2 | 7.9.2.3 | 7.9.2.4 | 7.9.2.5 | 7.9.2.6 | 7.9.2.7 | 7.9.2.8 | 7.9.2.9 |
| 7.9.3.1 | 7.9.3.2 | 7.9.3.3 | 7.9.3.4 | 7.9.3.5 | 7.9.3.6 | 7.9.3.7 | 7.9.3.8 | 7.9.3.9 | 7.9.4.1 |
| 7.9.4.2 | 7.9.4.3 | 7.9.4.4 | 7.9.4.5 | 7.9.4.6 | 7.9.4.7 | 7.9.4.8 | 7.9.4.9 | 7.9.5.1 | 7.9.5.2 |
| 7.9.5.3 | 7.9.5.4 | 7.9.5.5 | 7.9.5.6 | 7.9.5.7 | 7.9.5.8 | 7.9.5.9 | 7.9.6.1 | 7.9.6.2 | 7.9.6.3 |
| 7.9.6.4 | 7.9.6.5 | 7.9.6.6 | 7.9.6.7 | 7.9.6.8 | 7.9.6.9 | 7.9.7.1 | 7.9.7.2 | 7.9.7.3 | 7.9.7.4 |
| 7.9.7.5 | 7.9.7.6 | 7.9.7.7 | 7.9.7.8 | 7.9.7.9 | 7.9.8.1 | 7.9.8.2 | 7.9.8.3 | 7.9.8.4 | 7.9.8.5 |
| 7.9.8.6 | 7.9.8.7 | 7.9.8.8 | 7.9.8.9 | 7.9.9.1 | 7.9.9.2 | 7.9.9.3 | 7.9.9.4 | 7.9.9.5 | 7.9.9.6 |
| 7.9.9.7 | 7.9.9.8 | 7.9.9.9 | 8.1.1.1 | 8.1.1.2 | 8.1.1.3 | 8.1.1.4 | 8.1.1.5 | 8.1.1.6 | 8.1.1.7 |
| 8.1.1.8 | 8.1.1.9 | 8.1.2.1 | 8.1.2.2 | 8.1.2.3 | 8.1.2.4 | 8.1.2.5 | 8.1.2.6 | 8.1.2.7 | 8.1.2.8 |
| 8.1.2.9 | 8.1.3.1 | 8.1.3.2 | 8.1.3.3 | 8.1.3.4 | 8.1.3.5 | 8.1.3.6 | 8.1.3.7 | 8.1.3.8 | 8.1.3.9 |
| 8.1.4.1 | 8.1.4.2 | 8.1.4.3 | 8.1.4.4 | 8.1.4.5 | 8.1.4.6 | 8.1.4.7 | 8.1.4.8 | 8.1.4.9 | 8.1.5.1 |
| 8.1.5.2 | 8.1.5.3 | 8.1.5.4 | 8.1.5.5 | 8.1.5.6 | 8.1.5.7 | 8.1.5.8 | 8.1.5.9 | 8.1.6.1 | 8.1.6.2 |
| 8.1.6.3 | 8.1.6.4 | 8.1.6.5 | 8.1.6.6 | 8.1.6.7 | 8.1.6.8 | 8.1.6.9 | 8.1.7.1 | 8.1.7.2 | 8.1.7.3 |
| 8.1.7.4 | 8.1.7.5 | 8.1.7.6 | 8.1.7.7 | 8.1.7.8 | 8.1.7.9 | 8.1.8.1 | 8.1.8.2 | 8.1.8.3 | 8.1.8.4 |
| 8.1.8.5 | 8.1.8.6 | 8.1.8.7 | 8.1.8.8 | 8.1.8.9 | 8.1.9.1 | 8.1.9.2 | 8.1.9.3 | 8.1.9.4 | 8.1.9.5 |
| 8.1.9.6 | 8.1.9.7 | 8.1.9.8 | 8.1.9.9 | 8.2.1.1 | 8.2.1.2 | 8.2.1.3 | 8.2.1.4 | 8.2.1.5 | 8.2.1.6 |
| 8.2.1.7 | 8.2.1.8 | 8.2.1.9 | 8.2.2.1 | 8.2.2.2 | 8.2.2.3 | 8.2.2.4 | 8.2.2.5 | 8.2.2.6 | 8.2.2.7 |
| 8.2.2.8 | 8.2.2.9 | 8.2.3.1 | 8.2.3.2 | 8.2.3.3 | 8.2.3.4 | 8.2.3.5 | 8.2.3.6 | 8.2.3.7 | 8.2.3.8 |
| 8.2.3.9 | 8.2.4.1 | 8.2.4.2 | 8.2.4.3 | 8.2.4.4 | 8.2.4.5 | 8.2.4.6 | 8.2.4.7 | 8.2.4.8 | 8.2.4.9 |
| 8.2.5.1 | 8.2.5.2 | 8.2.5.3 | 8.2.5.4 | 8.2.5.5 | 8.2.5.6 | 8.2.5.7 | 8.2.5.8 | 8.2.5.9 | 8.2.6.1 |
| 8.2.6.2 | 8.2.6.3 | 8.2.6.4 | 8.2.6.5 | 8.2.6.6 | 8.2.6.7 | 8.2.6.8 | 8.2.6.9 | 8.2.7.1 | 8.2.7.2 |
| 8.2.7.3 | 8.2.7.4 | 8.2.7.5 | 8.2.7.6 | 8.2.7.7 | 8.2.7.8 | 8.2.7.9 | 8.2.8.1 | 8.2.8.2 | 8.2.8.3 |
| 8.2.8.4 | 8.2.8.5 | 8.2.8.6 | 8.2.8.7 | 8.2.8.8 | 8.2.8.9 | 8.2.9.1 | 8.2.9.2 | 8.2.9.3 | 8.2.9.4 |
| 8.2.9.5 | 8.2.9.6 | 8.2.9.7 | 8.2.9.8 | 8.2.9.9 | 8.3.1.1 | 8.3.1.2 | 8.3.1.3 | 8.3.1.4 | 8.3.1.5 |

TABLE 1-continued

| | | | | | | | | | |
|---|---|---|---|---|---|---|---|---|---|
| 8.3.1.6 | 8.3.1.7 | 8.3.1.8 | 8.3.1.9 | 8.3.2.1 | 8.3.2.2 | 8.3.2.3 | 8.3.2.4 | 8.3.2.5 | 8.3.2.6 |
| 8.3.2.7 | 8.3.2.8 | 8.3.2.9 | 8.3.3.1 | 8.3.3.2 | 8.3.3.3 | 8.3.3.4 | 8.3.3.5 | 8.3.3.6 | 8.3.3.7 |
| 8.3.3.8 | 8.3.3.9 | 8.3.4.1 | 8.3.4.2 | 8.3.4.3 | 8.3.4.4 | 8.3.4.5 | 8.3.4.6 | 8.3.4.7 | 8.3.4.8 |
| 8.3.4.9 | 8.3.5.1 | 8.3.5.2 | 8.3.5.3 | 8.3.5.4 | 8.3.5.5 | 8.3.5.6 | 8.3.5.7 | 8.3.5.8 | 8.3.5.9 |
| 8.3.6.1 | 8.3.6.2 | 8.3.6.3 | 8.3.6.4 | 8.3.6.5 | 8.3.6.6 | 8.3.6.7 | 8.3.6.8 | 8.3.6.9 | 8.3.7.1 |
| 8.3.7.2 | 8.3.7.3 | 8.3.7.4 | 8.3.7.5 | 8.3.7.6 | 8.3.7.7 | 8.3.7.8 | 8.3.7.9 | 8.3.8.1 | 8.3.8.2 |
| 8.3.8.3 | 8.3.8.4 | 8.3.8.5 | 8.3.8.6 | 8.3.8.7 | 8.3.8.8 | 8.3.8.9 | 8.3.9.1 | 8.3.9.2 | 8.3.9.3 |
| 8.3.9.4 | 8.3.9.5 | 8.3.9.6 | 8.3.9.7 | 8.3.9.8 | 8.3.9.9 | 8.4.1.1 | 8.4.1.2 | 8.4.1.3 | 8.4.1.4 |
| 8.4.1.5 | 8.4.1.6 | 8.4.1.7 | 8.4.1.8 | 8.4.1.9 | 8.4.2.1 | 8.4.2.2 | 8.4.2.3 | 8.4.2.4 | 8.4.2.5 |
| 8.4.2.6 | 8.4.2.7 | 8.4.2.8 | 8.4.2.9 | 8.4.3.1 | 8.4.3.2 | 8.4.3.3 | 8.4.3.4 | 8.4.3.5 | 8.4.3.6 |
| 8.4.3.7 | 8.4.3.8 | 8.4.3.9 | 8.4.4.1 | 8.4.4.2 | 8.4.4.3 | 8.4.4.4 | 8.4.4.5 | 8.4.4.6 | 8.4.4.7 |
| 8.4.4.8 | 8.4.4.9 | 8.4.5.1 | 8.4.5.2 | 8.4.5.3 | 8.4.5.4 | 8.4.5.5 | 8.4.5.6 | 8.4.5.7 | 8.4.5.8 |
| 8.4.5.9 | 8.4.6.1 | 8.4.6.2 | 8.4.6.3 | 8.4.6.4 | 8.4.6.5 | 8.4.6.6 | 8.4.6.7 | 8.4.6.8 | 8.4.6.9 |
| 8.4.7.1 | 8.4.7.2 | 8.4.7.3 | 8.4.7.4 | 8.4.7.5 | 8.4.7.6 | 8.4.7.7 | 8.4.7.8 | 8.4.7.9 | 8.4.8.1 |
| 8.4.8.2 | 8.4.8.3 | 8.4.8.4 | 8.4.8.5 | 8.4.8.6 | 8.4.8.7 | 8.4.8.8 | 8.4.8.9 | 8.4.9.1 | 8.4.9.2 |
| 8.4.9.3 | 8.4.9.4 | 8.4.9.5 | 8.4.9.6 | 8.4.9.7 | 8.4.9.8 | 8.5.1.1 | 8.5.1.2 | 8.5.1.3 | 8.5.1.4 |
| 8.5.1.4 | 8.5.1.5 | 8.5.1.6 | 8.5.1.7 | 8.5.1.8 | 8.5.1.9 | 8.5.2.1 | 8.5.2.2 | 8.5.2.3 | 8.5.2.4 |
| 8.5.2.5 | 8.5.2.6 | 8.5.2.7 | 8.5.2.8 | 8.5.2.9 | 8.5.3.1 | 8.5.3.2 | 8.5.3.3 | 8.5.3.4 | 8.5.3.5 |
| 8.5.3.6 | 8.5.3.7 | 8.5.3.8 | 8.5.3.9 | 8.5.4.1 | 8.5.4.2 | 8.5.4.3 | 8.5.4.4 | 8.5.4.5 | 8.5.4.6 |
| 8.5.4.7 | 8.5.4.8 | 8.5.4.9 | 8.5.5.1 | 8.5.5.2 | 8.5.5.3 | 8.5.5.4 | 8.5.5.5 | 8.5.5.6 | 8.5.5.7 |
| 8.5.5.8 | 8.5.5.9 | 8.5.6.1 | 8.5.6.2 | 8.5.6.3 | 8.5.6.4 | 8.5.6.5 | 8.5.6.6 | 8.5.6.7 | 8.5.6.8 |
| 8.5.6.9 | 8.5.7.1 | 8.5.7.2 | 8.5.7.3 | 8.5.7.4 | 8.5.7.5 | 8.5.7.6 | 8.5.7.7 | 8.5.7.8 | 8.5.7.9 |
| 8.5.8.1 | 8.5.8.2 | 8.5.8.3 | 8.5.8.4 | 8.5.8.5 | 8.5.8.6 | 8.5.8.7 | 8.5.8.8 | 8.5.8.9 | 8.5.9.1 |
| 8.5.9.2 | 8.5.9.3 | 8.5.9.4 | 8.5.9.5 | 8.5.9.6 | 8.5.9.7 | 8.5.9.8 | 8.5.9.9 | 8.6.1.1 | 8.6.1.2 |
| 8.6.1.3 | 8.6.1.4 | 8.6.1.5 | 8.6.1.6 | 8.6.1.7 | 8.6.1.8 | 8.6.1.9 | 8.6.2.1 | 8.6.2.2 | 8.6.2.3 |
| 8.6.2.4 | 8.6.2.5 | 8.6.2.6 | 8.6.2.7 | 8.6.2.8 | 8.6.2.9 | 8.6.3.1 | 8.6.3.2 | 8.6.3.3 | 8.6.3.4 |
| 8.6.3.5 | 8.6.3.6 | 8.6.3.7 | 8.6.3.8 | 8.6.3.9 | 8.6.4.1 | 8.6.4.2 | 8.6.4.3 | 8.6.4.4 | 8.6.4.5 |
| 8.6.4.6 | 8.6.4.7 | 8.6.4.8 | 8.6.4.9 | 8.6.5.1 | 8.6.5.2 | 8.6.5.3 | 8.6.5.4 | 8.6.5.5 | 8.6.5.6 |
| 8.6.5.7 | 8.6.5.8 | 8.6.5.9 | 8.6.6.1 | 8.6.6.2 | 8.6.6.3 | 8.6.6.4 | 8.6.6.5 | 8.6.6.6 | 8.6.6.7 |
| 8.6.6.8 | 8.6.6.9 | 8.6.7.1 | 8.6.7.2 | 8.6.7.3 | 8.6.7.4 | 8.6.7.5 | 8.6.7.6 | 8.6.7.7 | 8.6.7.8 |
| 8.6.7.9 | 8.6.8.1 | 8.6.8.2 | 8.6.8.3 | 8.6.8.4 | 8.6.8.5 | 8.6.8.6 | 8.6.8.7 | 8.6.8.8 | 8.6.8.9 |
| 8.6.9.1 | 8.6.9.2 | 8.6.9.3 | 8.6.9.4 | 8.6.9.5 | 8.6.9.6 | 8.6.9.7 | 8.6.9.8 | 8.6.9.9 | 8.7.1.1 |
| 8.7.1.2 | 8.7.1.3 | 8.7.1.4 | 8.7.1.5 | 8.7.1.6 | 8.7.1.7 | 8.7.1.8 | 8.7.1.9 | 8.7.2.1 | 8.7.2.2 |
| 8.7.2.3 | 8.7.2.4 | 8.7.2.5 | 8.7.2.6 | 8.7.2.7 | 8.7.2.8 | 8.7.2.9 | 8.7.3.1 | 8.7.3.2 | 8.7.3.3 |
| 8.7.3.4 | 8.7.3.5 | 8.7.3.6 | 8.7.3.7 | 8.7.3.8 | 8.7.3.9 | 8.7.4.1 | 8.7.4.2 | 8.7.4.3 | 8.7.4.4 |
| 8.7.4.5 | 8.7.4.6 | 8.7.4.7 | 8.7.4.8 | 8.7.4.9 | 8.7.5.1 | 8.7.5.2 | 8.7.5.3 | 8.7.5.4 | 8.7.5.5 |
| 8.7.5.6 | 8.7.5.7 | 8.7.5.8 | 8.7.5.9 | 8.7.6.1 | 8.7.6.2 | 8.7.6.3 | 8.7.6.4 | 8.7.6.5 | 8.7.6.6 |
| 8.7.6.7 | 8.7.6.8 | 8.7.6.9 | 8.7.7.1 | 8.7.7.2 | 8.7.7.3 | 8.7.7.4 | 8.7.7.5 | 8.7.7.6 | 8.7.7.7 |
| 8.7.7.8 | 8.7.7.9 | 8.7.8.1 | 8.7.8.2 | 8.7.8.3 | 8.7.8.4 | 8.7.8.5 | 8.7.8.6 | 8.7.8.7 | 8.7.8.8 |
| 8.7.8.9 | 8.7.9.1 | 8.7.9.2 | 8.7.9.3 | 8.7.9.4 | 8.7.9.5 | 8.7.9.6 | 8.7.9.7 | 8.7.9.8 | 8.7.9.9 |
| 8.8.1.1 | 8.8.1.2 | 8.8.1.3 | 8.8.1.4 | 8.8.1.5 | 8.8.1.6 | 8.8.1.7 | 8.8.1.8 | 8.8.1.9 | 8.8.2.1 |
| 8.8.2.2 | 8.8.2.3 | 8.8.2.4 | 8.8.2.5 | 8.8.2.6 | 8.8.2.7 | 8.8.2.8 | 8.8.2.9 | 8.8.3.1 | 8.8.3.2 |
| 8.8.3.3 | 8.8.3.4 | 8.8.3.5 | 8.8.3.6 | 8.8.3.7 | 8.8.3.8 | 8.8.3.9 | 8.8.4.1 | 8.8.4.2 | 8.8.4.3 |
| 8.8.4.4 | 8.8.4.5 | 8.8.4.6 | 8.8.4.7 | 8.8.4.8 | 8.8.4.9 | 8.8.5.1 | 8.8.5.2 | 8.8.5.3 | 8.8.5.4 |
| 8.8.5.5 | 8.8.5.6 | 8.8.5.7 | 8.8.5.8 | 8.8.5.9 | 8.8.6.1 | 8.8.6.2 | 8.8.6.3 | 8.8.6.4 | 8.8.6.5 |
| 8.8.6.6 | 8.8.6.7 | 8.8.6.8 | 8.8.6.9 | 8.8.7.1 | 8.8.7.2 | 8.8.7.3 | 8.8.7.4 | 8.8.7.5 | 8.8.7.6 |
| 8.8.7.7 | 8.8.7.8 | 8.8.7.9 | 8.8.8.1 | 8.8.8.2 | 8.8.8.3 | 8.8.8.4 | 8.8.8.5 | 8.8.8.6 | 8.8.8.7 |
| 8.8.8.8 | 8.8.8.9 | 8.8.9.1 | 8.8.9.2 | 8.8.9.3 | 8.8.9.4 | 8.8.9.5 | 8.8.9.6 | 8.8.9.7 | 8.8.9.8 |
| 8.8.9.9 | 8.9.1.1 | 8.9.1.2 | 8.9.1.3 | 8.9.1.4 | 8.9.1.5 | 8.9.1.6 | 8.9.1.7 | 8.9.1.8 | 8.9.1.9 |
| 8.9.2.1 | 8.9.2.2 | 8.9.2.3 | 8.9.2.4 | 8.9.2.5 | 8.9.2.6 | 8.9.2.7 | 8.9.2.8 | 8.9.2.9 | 8.9.3.1 |
| 8.9.3.2 | 8.9.3.3 | 8.9.3.4 | 8.9.3.5 | 8.9.3.6 | 8.9.3.7 | 8.9.3.8 | 8.9.3.9 | 8.9.4.1 | 8.9.4.2 |
| 8.9.4.3 | 8.9.4.4 | 8.9.4.5 | 8.9.4.6 | 8.9.4.7 | 8.9.4.8 | 8.9.4.9 | 8.9.5.1 | 8.9.5.2 | 8.9.5.3 |
| 8.9.5.4 | 8.9.5.5 | 8.9.5.6 | 8.9.5.7 | 8.9.5.8 | 8.9.5.9 | 8.9.6.1 | 8.9.6.2 | 8.9.6.3 | 8.9.6.4 |
| 8.9.6.5 | 8.9.6.6 | 8.9.6.7 | 8.9.6.8 | 8.9.6.9 | 8.9.7.1 | 8.9.7.2 | 8.9.7.3 | 8.9.7.4 | 8.9.7.5 |
| 8.9.7.6 | 8.9.7.7 | 8.9.7.8 | 8.9.7.9 | 8.9.8.1 | 8.9.8.2 | 8.9.8.3 | 8.9.8.4 | 8.9.8.5 | 8.9.8.6 |
| 8.9.8.7 | 8.9.8.8 | 8.9.8.9 | 8.9.9.1 | 8.9.9.2 | 8.9.9.3 | 8.9.9.4 | 8.9.9.5 | 8.9.9.6 | 8.9.9.7 |
| 8.9.9.8 | 8.9.9.9 | 9.1.1.1 | 9.1.1.2 | 9.1.1.3 | 9.1.1.4 | 9.1.1.5 | 9.1.1.6 | 9.1.1.7 | 9.1.1.8 |
| 9.1.1.9 | 9.1.2.1 | 9.1.2.2 | 9.1.2.3 | 9.1.2.4 | 9.1.2.5 | 9.1.2.6 | 9.1.2.7 | 9.1.2.8 | 9.1.2.9 |
| 9.1.3.1 | 9.1.3.2 | 9.1.3.3 | 9.1.3.4 | 9.1.3.5 | 9.1.3.6 | 9.1.3.7 | 9.1.3.8 | 9.1.3.9 | 9.1.4.1 |
| 9.1.4.2 | 9.1.4.3 | 9.1.4.4 | 9.1.4.5 | 9.1.4.6 | 9.1.4.7 | 9.1.4.8 | 9.1.4.9 | 9.1.5.1 | 9.1.5.2 |
| 9.1.5.3 | 9.1.5.4 | 9.1.5.5 | 9.1.5.6 | 9.1.5.7 | 9.1.5.8 | 9.1.5.9 | 9.1.6.1 | 9.1.6.2 | 9.1.6.3 |
| 9.1.6.4 | 9.1.6.5 | 9.1.6.6 | 9.1.6.7 | 9.1.6.8 | 9.1.6.9 | 9.1.7.1 | 9.1.7.2 | 9.1.7.3 | 9.1.7.4 |
| 9.1.7.5 | 9.1.7.6 | 9.1.7.7 | 9.1.7.8 | 9.1.7.9 | 9.1.8.1 | 9.1.8.2 | 9.1.8.3 | 9.1.8.4 | 9.1.8.5 |
| 9.1.8.6 | 9.1.8.7 | 9.1.8.8 | 9.1.8.9 | 9.1.9.1 | 9.1.9.2 | 9.1.9.3 | 9.1.9.4 | 9.1.9.5 | 9.1.9.6 |
| 9.1.9.7 | 9.1.9.8 | 9.1.9.9 | 9.2.1.1 | 9.2.1.2 | 9.2.1.3 | 9.2.1.4 | 9.2.1.5 | 9.2.1.6 | 9.2.1.7 |
| 9.2.1.8 | 9.2.1.9 | 9.2.2.1 | 9.2.2.2 | 9.2.2.3 | 9.2.2.4 | 9.2.2.5 | 9.2.2.6 | 9.2.2.7 | 9.2.2.8 |
| 9.2.2.9 | 9.2.3.1 | 9.2.3.2 | 9.2.3.3 | 9.2.3.4 | 9.2.3.5 | 9.2.3.6 | 9.2.3.7 | 9.2.3.8 | 9.2.3.9 |
| 9.2.4.1 | 9.2.4.2 | 9.2.4.3 | 9.2.4.4 | 9.2.4.5 | 9.2.4.6 | 9.2.4.7 | 9.2.4.8 | 9.2.4.9 | 9.2.5.1 |
| 9.2.5.2 | 9.2.5.3 | 9.2.5.4 | 9.2.5.5 | 9.2.5.6 | 9.2.5.7 | 9.2.5.8 | 9.2.5.9 | 9.2.6.1 | 9.2.6.2 |
| 9.2.6.3 | 9.2.6.4 | 9.2.6.5 | 9.2.6.6 | 9.2.6.7 | 9.2.6.8 | 9.2.6.9 | 9.2.7.1 | 9.2.7.2 | 9.2.7.3 |
| 9.2.7.4 | 9.2.7.5 | 9.2.7.6 | 9.2.7.7 | 9.2.7.8 | 9.2.7.9 | 9.2.8.1 | 9.2.8.2 | 9.2.8.3 | 9.2.8.4 |
| 9.2.8.5 | 9.2.8.6 | 9.2.8.7 | 9.2.8.8 | 9.2.8.9 | 9.2.9.1 | 9.2.9.2 | 9.2.9.3 | 9.2.9.4 | 9.2.9.5 |
| 9.2.9.6 | 9.2.9.7 | 9.2.9.8 | 9.2.9.9 | 9.3.1.1 | 9.3.1.2 | 9.3.1.3 | 9.3.1.4 | 9.3.1.5 | 9.3.1.6 |
| 9.3.1.7 | 9.3.1.8 | 9.3.1.9 | 9.3.2.1 | 9.3.2.2 | 9.3.2.3 | 9.3.2.4 | 9.3.2.5 | 9.3.2.6 | 9.3.2.7 |
| 9.3.2.8 | 9.3.2.9 | 9.3.3.1 | 9.3.3.2 | 9.3.3.3 | 9.3.3.4 | 9.3.3.5 | 9.3.3.6 | 9.3.3.7 | 9.3.3.8 |
| 9.3.3.9 | 9.3.4.1 | 9.3.4.2 | 9.3.4.3 | 9.3.4.4 | 9.3.4.5 | 9.3.4.6 | 9.3.4.7 | 9.3.4.8 | 9.3.4.9 |
| 9.3.5.1 | 9.3.5.2 | 9.3.5.3 | 9.3.5.4 | 9.3.5.5 | 9.3.5.6 | 9.3.5.7 | 9.3.5.8 | 9.3.5.9 | 9.3.6.1 |
| 9.3.6.2 | 9.3.6.3 | 9.3.6.4 | 9.3.6.5 | 9.3.6.6 | 9.3.6.7 | 9.3.6.8 | 9.3.6.9 | 9.3.7.1 | 9.3.7.2 |
| 9.3.7.3 | 9.3.7.4 | 9.3.7.5 | 9.3.7.6 | 9.3.7.7 | 9.3.7.8 | 9.3.7.9 | 9.3.8.1 | 9.3.8.2 | 9.3.8.3 |

TABLE 1-continued

| | | | | | | | | | |
|---|---|---|---|---|---|---|---|---|---|
| 9.3.8.4 | 9.3.8.5 | 9.3.8.6 | 9.3.8.7 | 9.3.8.8 | 9.3.8.9 | 9.3.9.1 | 9.3.9.2 | 9.3.9.3 | 9.3.9.4 |
| 9.3.9.5 | 9.3.9.6 | 9.3.9.7 | 9.3.9.8 | 9.3.9.9 | 9.4.1.1 | 9.4.1.2 | 9.4.1.3 | 9.4.1.4 | 9.4.1.5 |
| 9.4.1.6 | 9.4.1.7 | 9.4.1.8 | 9.4.1.9 | 9.4.2.1 | 9.4.2.2 | 9.4.2.3 | 9.4.2.4 | 9.4.2.5 | 9.4.2.6 |
| 9.4.2.7 | 9.4.2.8 | 9.4.2.9 | 9.4.3.1 | 9.4.3.2 | 9.4.3.3 | 9.4.3.4 | 9.4.3.5 | 9.4.3.6 | 9.4.3.7 |
| 9.4.3.8 | 9.4.3.9 | 9.4.4.1 | 9.4.4.2 | 9.4.4.3 | 9.4.4.4 | 9.4.4.5 | 9.4.4.6 | 9.4.4.7 | 9.4.4.8 |
| 9.4.4.9 | 9.4.5.1 | 9.4.5.2 | 9.4.5.3 | 9.4.5.4 | 9.4.5.5 | 9.4.5.6 | 9.4.5.7 | 9.4.5.8 | 9.4.5.9 |
| 9.4.6.1 | 9.4.6.2 | 9.4.6.3 | 9.4.6.4 | 9.4.6.5 | 9.4.6.6 | 9.4.6.7 | 9.4.6.8 | 9.4.6.9 | 9.4.7.1 |
| 9.4.7.2 | 9.4.7.3 | 9.4.7.4 | 9.4.7.5 | 9.4.7.6 | 9.4.7.7 | 9.4.7.8 | 9.4.7.9 | 9.4.8.1 | 9.4.8.2 |
| 9.4.8.3 | 9.4.8.4 | 9.4.8.5 | 9.4.8.6 | 9.4.8.7 | 9.4.8.8 | 9.4.8.9 | 9.4.9.1 | 9.4.9.2 | 9.4.9.3 |
| 9.4.9.4 | 9.4.9.5 | 9.4.9.6 | 9.4.9.7 | 9.4.9.8 | 9.4.9.9 | 9.5.1.1 | 9.5.1.2 | 9.5.1.3 | 9.5.1.4 |
| 9.5.1.5 | 9.5.1.6 | 9.5.1.7 | 9.5.1.8 | 9.5.1.9 | 9.5.2.1 | 9.5.2.2 | 9.5.2.3 | 9.5.2.4 | 9.5.2.5 |
| 9.5.2.6 | 9.5.2.7 | 9.5.2.8 | 9.5.2.9 | 9.5.3.1 | 9.5.3.2 | 9.5.3.3 | 9.5.3.4 | 9.5.3.5 | 9.5.3.6 |
| 9.5.3.7 | 9.5.3.8 | 9.5.3.9 | 9.5.4.1 | 9.5.4.2 | 9.5.4.3 | 9.5.4.4 | 9.5.4.5 | 9.5.4.6 | 9.5.4.7 |
| 9.5.4.8 | 9.5.4.9 | 9.5.5.1 | 9.5.5.2 | 9.5.5.3 | 9.5.5.4 | 9.5.5.5 | 9.5.5.6 | 9.5.5.7 | 9.5.5.8 |
| 9.5.5.9 | 9.5.6.1 | 9.5.6.2 | 9.5.6.3 | 9.5.6.4 | 9.5.6.5 | 9.5.6.6 | 9.5.6.7 | 9.5.6.8 | 9.5.6.9 |
| 9.5.7.1 | 9.5.7.2 | 9.5.7.3 | 9.5.7.4 | 9.5.7.5 | 9.5.7.6 | 9.5.7.7 | 9.5.7.8 | 9.5.7.9 | 9.5.8.1 |
| 9.5.8.2 | 9.5.8.3 | 9.5.8.4 | 9.5.8.5 | 9.5.8.6 | 9.5.8.7 | 9.5.8.8 | 9.5.8.9 | 9.5.9.1 | 9.5.9.2 |
| 9.5.9.3 | 9.5.9.4 | 9.5.9.5 | 9.5.9.6 | 9.5.9.7 | 9.5.9.8 | 9.5.9.9 | 9.6.1.1 | 9.6.1.2 | 9.6.1.3 |
| 9.6.1.4 | 9.6.1.5 | 9.6.1.6 | 9.6.1.7 | 9.6.1.8 | 9.6.1.9 | 9.6.2.1 | 9.6.2.2 | 9.6.2.3 | 9.6.2.4 |
| 9.6.2.5 | 9.6.2.6 | 9.6.2.7 | 9.6.2.8 | 9.6.2.9 | 9.6.3.1 | 9.6.3.2 | 9.6.3.3 | 9.6.3.4 | 9.6.3.5 |
| 9.6.3.6 | 9.6.3.7 | 9.6.3.8 | 9.6.3.9 | 9.6.4.1 | 9.6.4.2 | 9.6.4.3 | 9.6.4.4 | 9.6.4.5 | 9.6.4.6 |
| 9.6.4.7 | 9.6.4.8 | 9.6.4.9 | 9.6.5.1 | 9.6.5.2 | 9.6.5.3 | 9.6.5.4 | 9.6.5.5 | 9.6.5.6 | 9.6.5.7 |
| 9.6.5.8 | 9.6.5.9 | 9.6.6.1 | 9.6.6.2 | 9.6.6.3 | 9.6.6.4 | 9.6.6.5 | 9.6.6.6 | 9.6.6.7 | 9.6.6.8 |
| 9.6.6.9 | 9.6.7.1 | 9.6.7.2 | 9.6.7.3 | 9.6.7.4 | 9.6.7.5 | 9.6.7.6 | 9.6.7.7 | 9.6.7.8 | 9.6.7.9 |
| 9.6.8.1 | 9.6.8.2 | 9.6.8.3 | 9.6.8.4 | 9.6.8.5 | 9.6.8.6 | 9.6.8.7 | 9.6.8.8 | 9.6.8.9 | 9.6.9.1 |
| 9.6.9.2 | 9.6.9.3 | 9.6.9.4 | 9.6.9.5 | 9.6.9.6 | 9.6.9.7 | 9.6.9.8 | 9.6.9.9 | 9.7.1.1 | 9.7.1.2 |
| 9.7.1.3 | 9.7.1.4 | 9.7.1.5 | 9.7.1.6 | 9.7.1.7 | 9.7.1.8 | 9.7.1.9 | 9.7.2.1 | 9.7.2.2 | 9.7.2.3 |
| 9.7.2.4 | 9.7.2.5 | 9.7.2.6 | 9.7.2.7 | 9.7.2.8 | 9.7.2.9 | 9.7.3.1 | 9.7.3.2 | 9.7.3.3 | 9.7.3.4 |
| 9.7.3.5 | 9.7.3.6 | 9.7.3.7 | 9.7.3.8 | 9.7.3.9 | 9.7.4.1 | 9.7.4.2 | 9.7.4.3 | 9.7.4.4 | 9.7.4.5 |
| 9.7.4.6 | 9.7.4.7 | 9.7.4.8 | 9.7.4.9 | 9.7.5.1 | 9.7.5.2 | 9.7.5.3 | 9.7.5.4 | 9.7.5.5 | 9.7.5.6 |
| 9.7.5.7 | 9.7.5.8 | 9.7.5.9 | 9.7.6.1 | 9.7.6.2 | 9.7.6.3 | 9.7.6.4 | 9.7.6.5 | 9.7.6.6 | 9.7.6.7 |
| 9.7.6.8 | 9.7.6.9 | 9.7.7.1 | 9.7.7.2 | 9.7.7.3 | 9.7.7.4 | 9.7.7.5 | 9.7.7.6 | 9.7.7.7 | 9.7.7.8 |
| 9.7.7.9 | 9.7.8.1 | 9.7.8.2 | 9.7.8.3 | 9.7.8.4 | 9.7.8.5 | 9.7.8.6 | 9.7.8.7 | 9.7.8.8 | 9.7.8.9 |
| 9.7.9.1 | 9.7.9.2 | 9.7.9.3 | 9.7.9.4 | 9.7.9.5 | 9.7.9.6 | 9.7.9.7 | 9.7.9.8 | 9.7.9.9 | 9.8.1.1 |
| 9.8.1.2 | 9.8.1.3 | 9.8.1.4 | 9.8.1.5 | 9.8.1.6 | 9.8.1.7 | 9.8.1.8 | 9.8.1.9 | 9.8.2.1 | 9.8.2.2 |
| 9.8.2.3 | 9.8.2.4 | 9.8.2.5 | 9.8.2.6 | 9.8.2.7 | 9.8.2.8 | 9.8.2.9 | 9.8.3.1 | 9.8.3.2 | 9.8.3.3 |
| 9.8.3.4 | 9.8.3.5 | 9.8.3.6 | 9.8.3.7 | 9.8.3.8 | 9.8.3.9 | 9.8.4.1 | 9.8.4.2 | 9.8.4.3 | 9.8.4.4 |
| 9.8.4.5 | 9.8.4.6 | 9.8.4.7 | 9.8.4.8 | 9.8.4.9 | 9.8.5.1 | 9.8.5.2 | 9.8.5.3 | 9.8.5.4 | 9.8.5.5 |
| 9.8.5.6 | 9.8.5.7 | 9.8.5.8 | 9.8.5.9 | 9.8.6.1 | 9.8.6.2 | 9.8.6.3 | 9.8.6.4 | 9.8.6.5 | 9.8.6.6 |
| 9.8.6.7 | 9.8.6.8 | 9.8.6.9 | 9.8.7.1 | 9.8.7.2 | 9.8.7.3 | 9.8.7.4 | 9.8.7.5 | 9.8.7.6 | 9.8.7.7 |
| 9.8.7.8 | 9.8.7.9 | 9.8.8.1 | 9.8.8.2 | 9.8.8.3 | 9.8.8.4 | 9.8.8.5 | 9.8.8.6 | 9.8.8.7 | 9.8.8.8 |
| 9.8.8.9 | 9.8.9.1 | 9.8.9.2 | 9.8.9.3 | 9.8.9.4 | 9.8.9.5 | 9.8.9.6 | 9.8.9.7 | 9.8.9.8 | 9.8.9.9 |
| 9.9.1.1 | 9.9.1.2 | 9.9.1.3 | 9.9.1.4 | 9.9.1.5 | 9.9.1.6 | 9.9.1.7 | 9.9.1.8 | 9.9.1.9 | 9.9.2.1 |
| 9.9.2.2 | 9.9.2.3 | 9.9.2.4 | 9.9.2.5 | 9.9.2.6 | 9.9.2.7 | 9.9.2.8 | 9.9.2.9 | 9.9.3.1 | 9.9.3.2 |
| 9.9.3.3 | 9.9.3.4 | 9.9.3.5 | 9.9.3.6 | 9.9.3.7 | 9.9.3.8 | 9.9.3.9 | 9.9.4.1 | 9.9.4.2 | 9.9.4.3 |
| 9.9.4.4 | 9.9.4.5 | 9.9.4.6 | 9.9.4.7 | 9.9.4.8 | 9.9.4.9 | 9.9.5.1 | 9.9.5.2 | 9.9.5.3 | 9.9.5.4 |
| 9.9.5.5 | 9.9.5.6 | 9.9.5.7 | 9.9.5.8 | 9.9.5.9 | 9.9.6.1 | 9.9.6.2 | 9.9.6.3 | 9.9.6.4 | 9.9.6.5 |
| 9.9.6.6 | 9.9.6.7 | 9.9.6.8 | 9.9.6.9 | 9.9.7.1 | 9.9.7.2 | 9.9.7.3 | 9.9.7.4 | 9.9.7.5 | 9.9.7.6 |
| 9.9.7.7 | 9.9.7.8 | 9.9.7.9 | 9.9.8.1 | 9.9.8.2 | 9.9.8.3 | 9.9.8.4 | 9.9.8.5 | 9.9.8.6 | 9.9.8.7 |
| 9.9.8.8 | 9.9.8.9 | 9.9.9.1 | 9.9.9.2 | 9.9.9.3 | 9.9.9.4 | 9.9.9.5 | 9.9.9.6 | 9.9.9.7 | 9.9.9.8 |
| 9.9.9.9 | | | | | | | | | |

Another group of preferred compounds are named in Table 2 and designated by numbers assigned to the variables of formula I using the following convention: $M^1.V/Z/W$. The compounds are shown without, depiction of stereochemistry since the compounds are biologically active as the diastereomeric mixture or as a single stereoisomer. $M^1$ is a variable that represents compounds of the formula M-H which have a specific hydroxyl group that is phosphorylated with a group $P(O)[O—CH(V)CH(Z)CH(W)—O]$ to make compounds of formula I or $M^1$ is a variable that represents phosphonic acids of the formula $M-PO_3^{2-}$ which are transformed to compounds of formula I by replacing two oxygens in the $PO_3^{2-}$ group with $O—CH(V)CH(Z)CH(W)—O$.

The structures for variable $M^1$ are the same as described above.

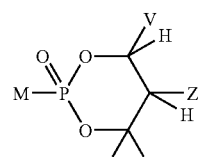

| Variable V/Z/W: | Group V/Z/W1 |
|---|---|
| 1) | V = phenyl; Z = methyl; W = hydrogen |
| 2) | V = 3,5-dichlorophenyl; Z = methyl; W = hydrogen |

-continued

| Variable V/Z/W: | Group V/Z/W1 |
|---|---|
| 3) | V = 4-pyridyl; Z = methyl; W = hydrogen |
| 4) | V = phenyl; Z = methoxy; W = hydrogen |
| 5) | V = 3,5-dichlorophenyl; Z = methoxy; W = hydrogen |
| 6) | V = 4-pyridyl; Z = methoxy; W = hydrogen |
| 7) | V = phenyl; Z = hydrogen; W = phenyl |
| 8) | V = 3,5-dichlorophenyl; Z = hydrogen; W = 3,5-dichlorophenyl |
| 9) | V = 4-pyridyl; Z = hydrogen; W = 4-pyridyl |

| Variable V/Z/W: | Group V/Z/W2 |
|---|---|
| 1) | V = phenyl; Z = NHAc; W = hydrogen |
| 2) | V = 3,5-dichlorophenyl; Z = NHAc; W = hydrogen |
| 3) | V = 4-pyridyl; Z = NHAc; W = hydrogen |
| 4) | V = phenyl; Z = hydrogen; W = methyl |
| 5) | V = 3,5-dichlorophenyl; Z = hydrogen; W = methyl |
| 6) | V = 4-pyridyl; Z = hydrogen; W = methyl |
| 7) | V = phenyl; Z = hydroxy; W = hydrogen |
| 8) | V = 3,5-dichlorophenyl; Z = hydroxy; W = hydrogen |
| 9) | V = 4-pyridyl; Z = hydroxy; W = hydrogen |

| Variable V/Z/W: | Group V/Z/W3 |
|---|---|
| 1) | V = hydrogen; Z = CH2OH; W = hydrogen |
| 2) | V = hydrogen; Z = CH2OC(O)CH3; W = hydrogen |
| 3) | V = hydrogen; Z = CH2OC(O)OCH3; W = hydrogen |
| 4) | V = methyl; Z = CH2OH; W = hydrogen |
| 5) | V = methyl; Z = CH2OC(O)CH3; W = hydrogen |
| 6) | V = methyl; Z = CH2OC(O)OCH3; W = hydrogen |
| 7) | Z = hydrogen; V and W = —CH2—CH(OH)CH2— |
| 8) | Z = hydrogen; V and W = —CH2—CH(OAc)CH2— |
| 9) | Z = hydrogen; V and W = —CH2—CH(OCO2CH2CH3)CH2— |

Preferred compounds are compounds listed in Table 2 using groups $M^1_1$ and V/Z/W1. For example, compound 1.3 represents structure 1 of group $M^1$1, i.e. 3TC; and structure 3 of group V/Z/W1, i.e. V=4-pyridyl, Z=methyl and W=hydrogen. The compound 1.3 therefore is 3TC with the P(O)(O—CH(4-pyridyl)CH(CH3)CH2O) attached to the primary hydroxyl.

Preferred compounds are also compounds listed in Table 2 using groups $M^1$1 and V/Z/W2.

Preferred compounds are also compounds listed in Table 2 using groups $M^1$1 and V/Z/W3.

Preferred compounds are also compounds listed in Table 2 using groups $M^1$2 and V/Z/W 1.

Preferred compounds are also compounds listed in Table 2 using groups $M^1$2 and V/Z/W 2.

Preferred compounds are also compounds listed in Table 2 using groups $M^1$2 and V/Z/W 3.

Preferred compounds are also compounds listed in Table 2 using groups $M^1$3 and V/Z/W 1.

Preferred compounds are also compounds listed in Table 2 using groups $M^1$3 and V/Z/W 2.

Preferred compounds are also compounds listed in Table 2 using groups $M^1$3 and V/Z/W 3.

TABLE 2

| | | | | | | | | | | | | | | | | | | |
|---|---|---|---|---|---|---|---|---|---|---|---|---|---|---|---|---|---|---|
| 1.1 | 1.2 | 1.3 | 1.4 | 1.5 | 1.6 | 1.7 | 1.8 | 1.9 | 2.1 | 2.2 | 2.3 | 2.4 | 2.5 | 2.6 | 2.7 | 2.8 | 2.9 | |
| 3.1 | 3.2 | 3.3 | 3.4 | 3.5 | 3.6 | 3.7 | 3.8 | 3.9 | 4.1 | 4.2 | 4.3 | 4.4 | 4.5 | 4.6 | 4.7 | 4.8 | 4.9 | |
| 5.1 | 5.2 | 5.3 | 5.4 | 5.5 | 5.6 | 5.7 | 5.8 | 5.9 | 6.1 | 6.2 | 6.3 | 6.4 | 6.5 | 6.6 | 6.7 | 6.8 | 6.9 | |
| 7.1 | 7.2 | 7.3 | 7.4 | 7.5 | 7.6 | 7.7 | 7.8 | 7.9 | 8.1 | 8.2 | 8.3 | 8.4 | 8.5 | 8.6 | 8.7 | 8.8 | 8.9 | |
| 9.1 | 9.2 | 9.3 | 9.4 | 9.5 | 9.6 | 9.7 | 9.8 | 9.9 | | | | | | | | | | |

Synthesis of Compounds of Formula I

Synthesis of the compounds encompassed by the present invention includes: I). synthesis of prodrugs; II). synthesis of substituted-1,3-diols; and III). synthesis of FBPase inhibitors.

I) Synthesis of Prodrugs:

The following procedures on the preparation of prodrugs illustrate the general procedures used to prepare the prodrugs of the invention which apply to all phosphate-, phosphonate- and phosphoramidate-containing drugs. Prodrugs can be introduced at different stages of synthesis of a drug. Most often they are made at a later stage, because of the general sensitivity of these groups to various reaction conditions. Optically pure prodrugs containing single isomer at phosphorus centre can be made either by separation of the diastereomers by a combination of column chromatography and/or crytallyzation, or by enantioselective synthesis of chiral activated phosph(on)ate intermediates.

The preparation of prodrugs is further organized into 1) synthesis via activated P(V) intermediates:, 2) synthesis via activated P(III) intermediates, 3) synthesis via phosph(on)ate diacid, and 4) miscellaneous methods.

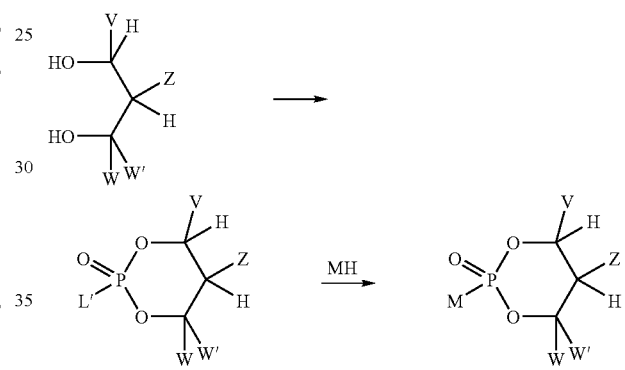

I.1 Synthesis Via Activated P(V) Intermediate:

I.1.a. Synthesis of Activated P(V) Intermediates:

In general, synthesis of phosph(on)ate esters is achieved by coupling the amine or alcohol MH with the corresponding activated phosphonate precursor for example, Chlorophosphate (L'=chloro) addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, *J. Med Chem.*, 1992, 35, 1650). Chlorophosphonates are made by oxidation of the corresponding chlorophospholanes (Anderson, et al, *J. Org. Chem.*, 1984, 49, 1304) which are obtained by reaction of the substituted diol with phosphorus trichloride. Alternatively, the chlorophosphonate agent is made by treating substituted-1,3-diols with phosphorusoxychloride (Patois, et al, *J. Chem. Soc. Perkin Trans. I*, 1990, 1577).

Chlorophosphonate species may also be generated in situ from corresponding cyclic phosphites (Silverburg, et al., Tetrahedron lett., 1996, 37, 771), which in turn can be either made from chlorophospholane or phosphoramidate intermediate. Phosphoroflouridate intermediate prepared either from pyrophosphate or phosphoric acid may also act as precursor in preparation of cyclic prodrugs (Watanabe et al., Tetrahedron lett., 1988, 29, 5763).

Phosphoramidates (L'=NRR') are also well known intermediates for the synthesis of phosphate esters. Monoalkyl or dialkylphosphoramidate (Watanabe, et al, Chem Pharm Bull., 1990, 38, 562), triazolophosphoramidate (Yamakage, et al., Tetrahedron, 1989, 45, 5459) and pyrrolidinophosphoramidate (Nakayama, et al, J. Am. Chem. Soc., 1990, 112, 6936) are some of the known intermediates used for the preparation of phosphate esters. Another effective phosphorylating procedure is a metal catalyzed addition of cyclic chlorophosphonate adduct of 2-oxazolone. This intermediate attains high selectivity in phosphorylation of primary hydroxy group in presence of secondary hydroxyl group (Nagamatsu, et al, Tetrahedron Lett., 1987, 28, 2375). These agents are obtained by reaction of a chlorophosphonate with the amine or alternatively by formation of the corresponding phosphoramidite followed by oxidation.

I.1.b. Synthesis of Chiral Activated Phosph(on)ate:

Phosphorylation of an enantiomerically pure substituted diol with for example, a commercially available phosphorodichloridate R—OP(O)Cl$_2$, where RO is a leaving group, preferably aryl substituted with electron withdrawing groups, such as a nitro or a chloro, produces two diastereomeric intermediates that can be separated by a combination of column chromatography and/or crystallization. Such a method may also be utilized in preparing chiral chloro phosphonates. Chiral phosphoramidate intermediates can be obtained by utilization of optically pure amine as the chiral auxiliary. This type of intermediate are known to undergo stereospecific substitution (Nakayama, et al. J. Am. Chem. Soc., 1990, 112, 6936). The relative configuration of the phosphorus atom is easily determined by comparison of the $^{31}$P NMR spectra. The chemical shift of the equatorial phosphoryloxy moiety (trans-isomer) is always more upfield than the one of the axial isomer (cis-isomer) (Verkade, et al, J. Org. Chem., 1977, 42, 1549).

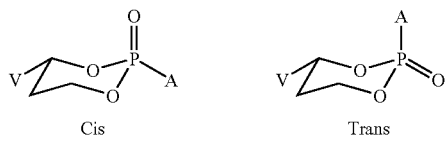

Cis          Trans

I.1.c. Synthesis of Prodrugs Using Activated Phosphates:

Coupling of activated phosphonates with alcohols or amines (MH) is accomplished in the presence of an organic base. For example, Chlorophosphonates synthesized as described in the earlier section react with an alcohol in the presence of a base such as pyridines or N-methylimidazol. In some cases phosphorylation is enhanced by in situ generation of iodophosphonate from chloro (Stomberg, et al, Nucleosides & Nucleotides., 1987, 5: 815). Phosphoroflouridate intermediates have also been used in phosphorylation reactions in the presence of a base such as CsF or n-BuLi to generate cyclic prodrugs (Watanabe et al., Tetrahedron lett., 1988, 29, 5763). Phosphoramidate intermediates are shown to couple in the presence of weak acids (eg., tetrazole) and an oxidising agent (eg., m-chloroperbenzoic acid or t-butyl-hydroperoxide (Watanabe, et al, Chem Pharm Bull., 1990, 38, 562) or by transition metal catalysis (Nagamatsu, et al, Tetrahedron Lett., 1987, 28, 2375).

The phosphonate prodrug esters where spacer group X in formula II-IV is an aryl group, can be prepared by lithiation of aromatic ring using methods well described in literature (Gschwend, Org. React. 1979, 26, 1; Durst, Comprehensive Carbanion Chemistry, Vol. 5, Elsevier, New York, 1984) followed by addition of chlorophosphonate cyclic 1',3'-propanyl ester.

Reaction of the optically pure diastereomer of phosphoramidate intermediate with the hydroxyl of drug in the presence of an acid produces the optically pure phosphate prodrug by direct S$_N$2(P) reaction (Nakayama, et al. J. Am. Chem. Soc., 1990, 112, 6936). Alternatively, reaction of the optically pure phosphate precursor with a fluoride source, preferably cesium fluoride or tetrabutylammonium fluoride, produces the more reactive phosphorofluoridate which reacts with the hydroxyl of the drug to give the optically pure prodrug by overall retention of configuration at the phosphorus atom (Ogilvie, et al, J. Am. Chem. Soc., 1977, 99, 1277). Chiral phosphonate prodrugs can be synthesized by either resolution of phosphonates (Pogatnic, et. al., Tetrahedro Lett., 1997, 38, 3495) or by chirality induction (Taapken, et. al., Tetrahedron Lett., 1995, 36, 6659; J. Org, Chem., 1998, 63, 8284).

I.2 Synthesis Via Phosphite Intermediate:

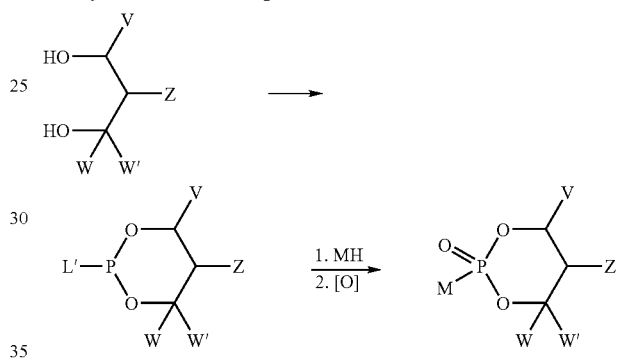

I.2.a. Synthesis of Activated P(III) Intermediates:

Phosphorylation of hydroxy and amino groups is achieved using cyclic 1',3'-propanyl esters of phosphorylating agents where the agent is at the P(III) oxidation state. One preferred phosphorylating agent is a chloro phospholane (L'=chloro). Cyclic chlorophospholanes are prepared under mild conditions by reaction of phosphorus trichloride with substituted 1,3-diols (Wissner, et al, J. Med. Chem., 1992, 35, 1650). Alternatively phosphoramidites can be used as the phosphorylating agent (Beaucage, et al., Tetrahedron, 1993, 49, 6123). Appropriately substituted phoshoramidites can be prepared by reacting cyclic chlorophospholanes with N,N-dialkylamine (Perich, et al., Aust. J. Chem., 1990, 43, 1623. Perich, et al, Synthesis, 1988, 2, 142) or by reaction of commercially available dialkylaminophosphorochloridate with substituted propyl-1,3-diols.

I.2.b. Synthesis of Chiral Activated P(III) Intermediate:

In the cases where unsymmetrical diols are used, the cyclic phosphite is expected to form a mixture of chiral isomers. When an optically active pure diol is used a chromatographically separable mixture of two stable diastereomers with the leaving group (NRR') axial and equatorial on the phosphorous atom is expected. Pure diasteromers can usually be obtained by chromatographic separation.

I.2.c. Synthesis of Prodrugs Using Activated Phosphites:

Chlorophospholanes are used to phosphorylate alcohols on nucleosides in the presence of an organic base (e.g., triethylamine, pyridine). Alternatively, the phosphite can be obtained by coupling the nucleoside with a phosphoramidate in the presence of a coupling promoter such as tetrazole or benzimidazolium triflate (Hayakawa et al., J. Org. Chem., 1996, 61, 7996).

Phosphite diastereomers may be isolated by column chromatography or crystallization (Wang, et al, *Tetrahedron Lett*, 1997, 38, 3797; Bentridge et al., *J. Am. Chem. Soc.*, 1989, 111, 3981). Since condensation of alcohols with chlorophospholanes or phosphoramidites is an $S_N2(P)$ reaction, the product is expected to have an inverted configuration. This allows for the stereoselective synthesis of cyclic phosphites. Isomeric mixtures of phosphorylation reactions can also be equilibrated (e.g. thermal equilbration) to a more thermodynamically stable isomer.

The resulting phosphites are subsequently oxidized to the corresponding phosphate prodrugs using an oxidant such as molecular oxygen or t-butylhydroperoxide (Meier et al., *Bioorg, Med. Chem. Lett.*, 1997, 7, 1577). Oxidation of optically pure phosphites is expected to stereoselectively provide optically active prodrugs (Mikolajczyk, et al., *J. Org. Chem.*, 1978, 43, 2132. Cullis, P. M. *J. Chem. Soc., Chem Commun.*, 1984, 1510, Verfurth; et al., *Chem. Ber.*, 1991, 129, 1627).

I.3 Synthesis of Phosphonate Prodrugs via Phosphonic Acids:

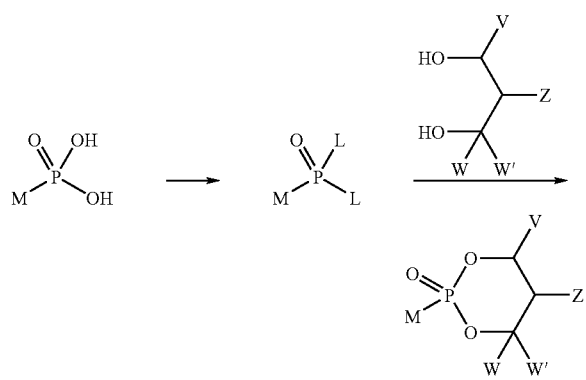

Prodrugs of formula I are synthesized by reaction of the corresponding phosphodichloridate and an alcohol (Khamnei, et. al.,. *J. Med. Chem.*, 1996, 39: 4109). For example, the reaction of a phosphodichloridate with substituted 1,3-diols in the presence of base (such as pyridine, triethylamine, etc) yields compounds of formula I.

Such reactive dichloridate intermediates, can be prepared from the corresponding acids and the chlorinating agents e.g. thionyl chloride (Starrett, et al, *J. Med. Chem.*, 1994, 1857), oxalyl chloride (Stowell, et al, *Tetrahedron Lett.*, 1990, 31: 3261), and phosphorus pentachloride (Quast, et al, *Synthesis*, 1974, 490). Alternatively, these dichlorophosphonates can also be generated from disilyl esters (Bhongle, et al, *Synth. Commun.*, 1987, 17: 1071) and dialkyl esters (Still, et al, *Tetrahedron Lett.*, 1983, 24: 4405; Patois, et al, *Bull. Soc. Chim. Fr.*, 1993, 130: 485).

I.4. Miscellaneous Methods:

Phosph(on)ate prodrugs are also prepared from the free acid by Mitsunobu reactions (Mitsunobu, *Synthesis*, 1981, 1; Campbell, *J. Org. Chem.*, 1992, 52: 6331), and other acid coupling reagents including, but not limited to, carbodiimides (Alexander, et al, *Collect. Czech. Chem. Commun.*, 1994, 59: 1853; Casara, et al, *Bioorg. Med. Chem. Lett.*, 1992, 2: 145; Ohashi, et al, *Tetrahedron Lett.*, 1988, 29: 1189), and benzotriazolyloxytris-(dimethylamino)phosphonium salts (Campagne, et al, *Tetrahedron Lett.*, 1993, 34: 6743).

Phosphorylation of an alcohol or an amine is also achieved under Mitsunobu reaction conditions using the cyclic 1',3'-propanyl ester of phosphoric acid in the presence of triphenylphosphine and diethylazodicarboxylate (Kimura et al., *Bull. Chem. Soc. Jpn.*, 1979, 52, 1191). The procedure can be extended to prepare chiral phosphates from enantiomerically pure phosphoric acids.

Phosph(on)ate prodrugs can be prepared by an alkylation reaction between the phosphonate corresponding tetrabutylammonium salts and substituted-1,3-diiodo propanes made from 1,3-diols (Farquhar, et al, *Tetrahedron Lett.*, 1995 36, 655). Furthermore, phosphate prodrugs can be made by conversion of nucleoside to the dichloridate intermediate with phosphoryl chloride in presence of triethylphosphite and quenching with substituted-1,3-propane diols(Farquhar et al., *J. Org. Chem.*, 1983, 26, 1153).

Phosphorylation can also be achieved by making the mixed anhydride of the cyclic diester of phosphoric acid and a sulfonyl chloride, preferably 8-quinolinesulfonyl chloride, and reacting the hydroxyl of the drug in the presence of a base, preferably methylimidazole (Takaku, et al, *J. Org. Chem.*, 1982, 47, 4937). In addition, starting from a chiral cyclic diester of a phosphoric acid, obtained by chiral resolution (Wynberg, et al., *J. Org. Chem.*, 1985, 50, 4508), one can obtain optically pure phosphates.

Aryl halides undergo $Ni^{2+}$ catalyzed reaction with phosphite derivatives to give aryl phosphonate containing compounds (Balthazar, et al, *J. Org. Chem.*, 1980, 45: 5425). Phosphonates are also prepared from the chlorophosphonate in the presence of a palladium catalyst using aromatic triflates (Petrakis, et al, J. Am. Chem. Soc., 1987, 109: 2831; Lu, et al, *Synthesis*, 1987, 726). In another method, aryl phosphonate esters are prepared from aryl phosphates under anionic rearrangement conditions (Melvin, *Tetrahedron Lett.*, 1981, 22: 3375; Casteel, et al, *Synthesis*, 1991, 691). N-Alkoxy aryl salts with alkali metal derivatives of cyclic alkyl phosphonate provide general synthesis for heteroaryl-2-phosphonate linkers (Redmore, *J. Org. Chem.*, 1970, 35: 4114). These above mentioned methods can also be extended to compounds where the X group is heteroaryl e.g. pyridine, furan, thiophene etc.

Compounds of formulae II-IV, where X is alkyl, substituted alkyl or heteroalkyl are synthesized using well known reactions. For example, when X is substituted with a leaving group (e.g., halogen) an Arbuzov reaction with a phosphite containing cyclic 1',3'-propanyl ester is useful (*Chem. Rev.* 1984, 84: 577). Cyclic alkyl phosphites also attack the lactones at the β-carbon atom, causing the alkyl-oxygen cleavage of the lactone ring, to yield alkyl phosphonate esters. This can be applied to many types of lactones such as β-lactones, γ-lactones etc. as reported by McConnell et al, *J. Am. Chem. Soc.*, 1956, 78, 4453. Alternatively, compounds wherein X is alkyl heteroatom can be prepared by alkylation of hetero atom with an appropriate cyclic phosphonate electrophile $[L(CH_2)_nPO_3R]$ where L is, a leaving group, preferably iodide (Walsh et al, *J. Am. Chem. Soc.*, 1956, 78, 4455). These above mentioned methods can be extended to the heteroalkyl linkers e.g. $—CH_2ZCH_2—$ where Z=O,S etc.

Cyclic-1,3-propanyl prodrugs of phosph(on)ates are also synthesized from diacids (e.g. PMEA) (where L is OH in scheme above) and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethylcarbodiimide hydrochloride (EDCI) can also be utilized for the synthesis of cyclic prodrugs.

II.1) Synthesis of 1,3-Diols:

A variety of synthetic methods are known to prepare the following types of 1,3-diols: a) 1-substituted; b) 2-substituted; and c) 1,2- or 1,3-annulated in their recemic or chiral form. Substitution of V, W, Z groups of formula I, can be introduced or modified either during synthesis of diols or after the synthesis of prodrugs.

II.1) 1-Substituted 1,3-Diols.

1,3-Dihydroxy compounds can be synthesized by several well known methods in literature. Aryl Grignard additions to 1-hydroxy propan-3-al give 1-aryl-substituted propan-1,3-diols (path a). This method will enable conversion of various substituted aryl halides to 1-arylsubstituted-1,3-propane diols (Coppi, et. al., *J. Org. Chem.*, 1988, 53, 911). Aryl 1997, 38 761). Pyridyl, quinoline, isoquinoline propan-3-ol derivatives can be oxygenated to 1-substituted-1,3-diol by N-oxide formation followed by rearrangement in acetic anhydride conditions (path d) (Yamamoto, et. al., *Tetrahedron*, 1981, 37, 1871). Aldol condensation is another well described method for synthesis of the 1,3-oxygenated functionality (Mukaiyama, *Org. React.*, 1982, 28, 203). Chral substituted diols can also be made by enantioselective reduction of carbonyl compounds, by chiral aldol condensation or by enzyme promoted kinetic resolution.

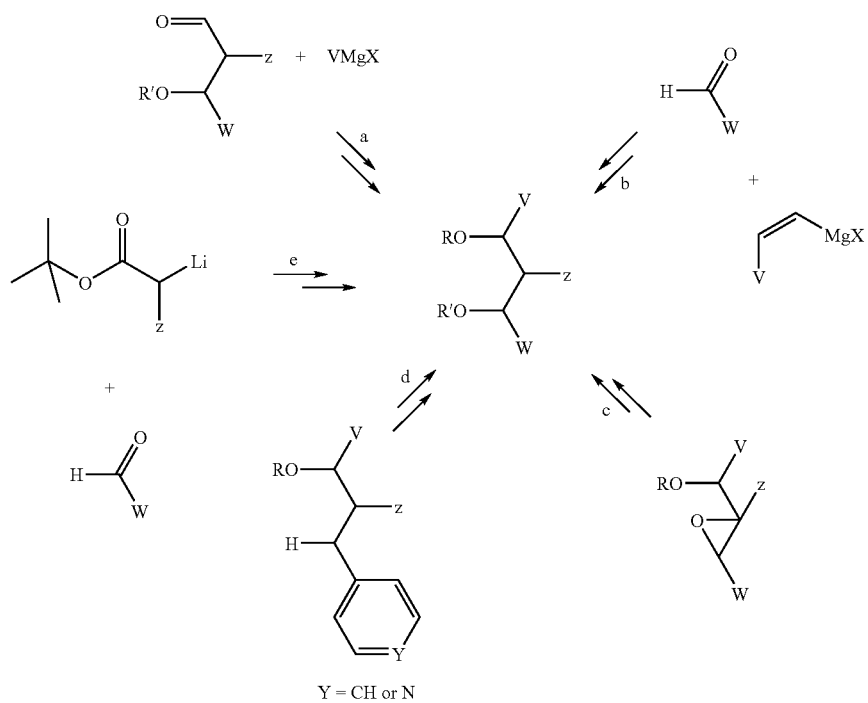

Y = CH or N halides can also be used to synthesize 1-substituted propanediols by Heck coupling of 1,3-diox-4-ene followed by reduction and hydrolysis (Sakamoto, et. al., *Tetrahedron Lett.*, 1992, 33, 6845). Substituted 1,3-diols can be generated enanatioselective reduction of vinyl ketone and hydoboration or by kinetic resolution of allylic alcohol (path b). Variety of aromatic aldehydes can be converted to 1-substituted-1,3-diols by vinyl Grignard addition followed by hydroboration (path b). Substituted aromatic aldehydes are also utilized by lithium-t-butylacetate addition followed by ester reduction (path e) (Turner., *J. Org. Chem.*, 1990, 55 4744). In another method, commercially available cinnamyl alcohols can be converted to epoxy alcohols under catalytic asymmetric epoxidation conditions. These epoxy alcohols are reduced by Red-Al to result in enantiomerically pure 1,3-diols (path c) (Gao, et. al., *J. Org. Chem.*, 1980, 53, 4081). Alternatively, enantiomerically pure 1,3-diols can be obtained by chiral borane reduction of hydroxyethyl aryl ketone derivatives (Ramachandran, et. al., *Tetrahedron Lett.*, II.2) 2-Substituted 1,3-Diols:

Various-2-substituted-1,3-diols can be made from commercially available 2-(hydroxymethyl)-1,3-propane diol. Pentaerythritol can be converted to triol via decarboxylation of diacid followed by reduction (path a) (Werle, et al., *Liebigs. Ann. Chem.*, 1986, 944) or diol-monocarboxylic acid derivatives can also be obtained by decarboxylation under known conditions (Iwata, et. al., *Tetrahedron lett.* 1987, 28, 3131). Nitrotriol is also known to give triol by reductive elimination (path b) (Latour, et. al., *Synthesis*, 1987, 8, 742). The triol can be derivatised by mono acetylation or carbonate formation by treatment with alkanoyl chloride, or alkylchloroformate (path d) (Greene and Wuts, *Protective groups in organic synthesis*, John Wiley, New York, 1990). Aryl substitution can be affected by oxidation to aldehyde and aryl Grignard additions (path c) Aldehydes can also be converted to substituted amines by reductive amination reaction (path e).

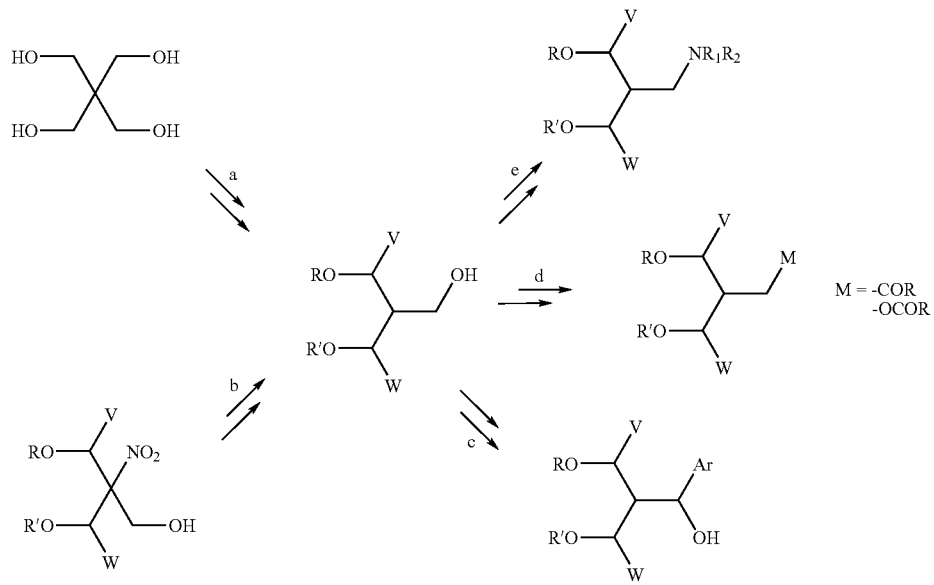

I.3.c) Cyclic-1,3-diols:

Compounds of formula I where V-Z or V-W are fused by four carbons are made from Cyclohexane diol derivatives. Commercially available cis, cis-1,3,5-cyclohexane triol can be used as is or modified as described in case of 2-substituted propan-1,3-diols to give various analogues. These modifications can either be made before or after ester formation. Various 1,3-cyclohexane diols can be made by Diels-Alder methodology using pyrone as diene (Posner, et. al., *Tetrahedron Lett.*, 1991, 32, 5295). Cyclohexyl diol derivatives are also made by nitrile oxide-olefin additions (Curran, et. al., *J. Am. Chem. Soc.*, 1985, 107, 6023). Alternatively, cyclohexyl precursors are also made from commercially available quinic acid (Rao, et. al., *Tetrahedron Lett.*, 1991, 32, 547.)

III. Synthesis of FBPase Inhibitors:

Synthesis of FBPase inhibitors is outlined in four sections: (1) AICA riboside based inhibitors, (2) purine based inhibitors, (3) benzimidazole based inhibitors, (4) Indole and 9-azaindole based inhibitors.

III.1) AICA Riboside Based Inhibitors:

Compounds of AICA riboside may be prepared by a variety of known methods. In general, these compounds are synthesized by the method of Prem C. Srivastava, et al., *J. Med. Chem.*, 1976, 19, 1020-1026 using methodology outlined below. Other methodology is described by Steven G. Wood, et al., J. Med. Chem. 1985, 28, 1198-1203, by G. Sagi, et al., J. Med. Chem. 1992, 35, 4549-4556, by R. Paul, J. Med. Chem. 1985, 28, 1704-1716 and by L. C. Cohen, J. Amer. Chem. Soc. 1973, 95, 4619-4624.

AICA riboside, a commercially readily available starting material, is acetylated, for example, with acetic anhydride and a suitable base such as pyridine or triethylamine, and then optionally dehydrated by treatment, for example with tosyl chloride and pyridine. If esters other than acetate are desired in the final product, other anhydrides or acid chlorides may be employed in the acetylation step, for example use of isobutyryl anhydride gives the appropriate tri-O-isobutyrate. The primary amine function is diazotized, for example with sodium nitrite, and treated with a source of the appropriate nucleophile, for example copper(II) bromide to form corresponding bromide. The product is oxidized with, for example 30% hydrogen peroxide to desired compound.

Alternatively, the optional step of dehydration may be omitted to produce more directly compounds in which the alcohols are acylated. These agents may be deacylated, if desired to give the corresponding alcohols.

Alternatively, the imidazole base may be modified separately and then coupled to the appropriate sugar, using well-known glycoside bond forming reactions.

Further, compounds of the present invention might be prepared from compounds whose synthesis is described above. For example, the 5-thiomethyl analog may be prepared by a, displacement reaction using sodium thiomethoxide and the 5-chloro compound.

Those skilled in the art will recognize that different reagents may be used in place of those listed above to give similar results.

III.2) Purine Based Inhibitors:

Synthesis of intermediates of purine based inhibitors typically includes some or all of the following general steps: (a) deprotection of phosphonate ester (b) modification of C8-substituted purine intermediates; (c) modification of purine at positions other than C8; (d) construction of the purine ring system; (e) preparation of 4,5-diaminopyrimidine; and (f) preparation of functionalized linker (X) phosphonate.

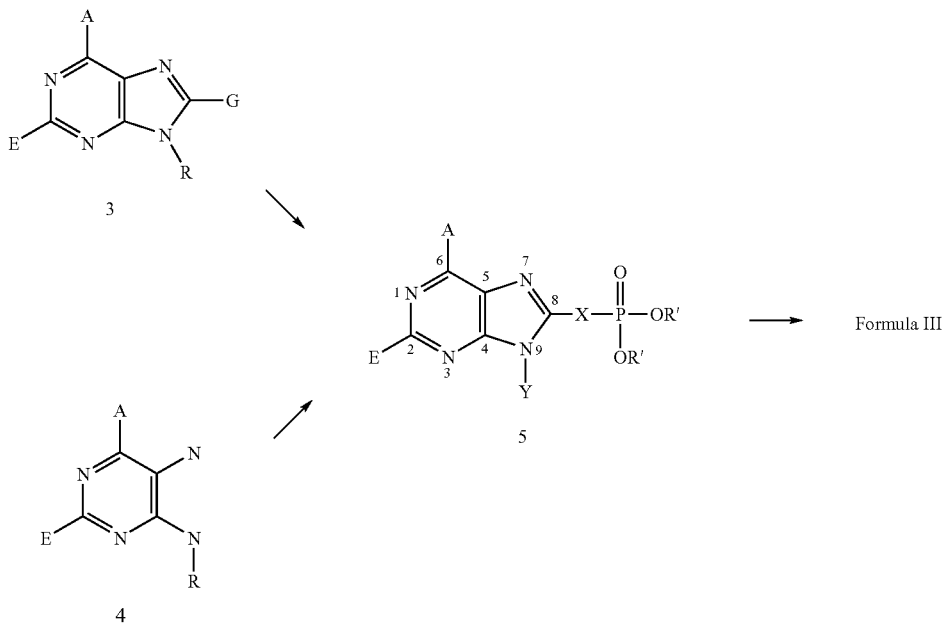

III.2.a) Deprotection of Phosphonate Ester

Phosphonic acids may be prepared from phosphonate esters using known phosphate and phosphonate ester cleavage conditions. For example, alkyl phosphonate esters are generally cleaved by reaction with silyl halides followed by hydrolysis of the intermediate silyl phosphonate esters. Various silyl halides can be used for this transformation, such as chlorotrimethylsilane (Rabinowitz *J. Org. Chem.*, 1963, 28: 2975), bromotrimethylsilane (McKenna et al. *Tetrahedron Lett.*, 1977, 155), iodotrimethylsilane (Blackburn et al. *J. Chem. Soc., Chem. Commun.*, 1978, 870). Phosphonate esters can also be cleaved under strong acidic conditions, such as hydrogen halides in acetic acid or water, and metal halides (Moffatt et al. U.S. Pat. No. 3,524,846, 1970). Phosphonate esters can also be converted to dichlorophosphonates with halogenating agents (e.g. PCl$_5$, and SOCl$_2$, Pelchowicz et al. *J. Chem. Soc.*, 1961, 238) and subsequently hydrolysis to give phosphonic acids. Reductive reactions are useful in cleaving aryl and benzyl phosphonate esters. For example, phenyl phosphonate esters can be cleaved under hydrogenolysis conditions (Lejczak et al. *Synthesis*, 1982, 412) or metal reduction conditions (Shafer et al. *J. Am. Chem. Soc.*, 1977, 99: 5118); benzyl phosphonate esters can also be cleaved similarly (Elliott et al. *J. Med. Chem.*, 1985, 28: 1208). Electrochemical (Shono et al. *J. Org. Chem.*, 1979, 44: 4508) and pyrolysis (Gupta et al. *Synth. Commun.*, 1980, 10: 299) conditions have also been used to cleave various phosphonate esters.

III.2.b) Modification of C8-Substituted Purine Intermediates

8-Substituted purines are useful intermediates in the preparation of compounds of formula III. 8-Halopurines, which are particularly useful intermediates, are readily prepared using chemistry well described in the literature. For example, N$^9$-alkyladenines are halogenated at C8 position using known halogenating agents (e.g. Br$_2$, NBS). 8-Alkylpurine can be prepared through direct lithiation of purine followed by trapping with electrophiles (e.g. alkyl halides, Barton et al. *Tetrahedron Lett.*, 1979, 5877).

Functionaliztion of 8-halopurines can be accomplished under substitution reaction conditions with nucleophiles such as amines, alcohols, azides, sulfides, and alkylthiols. It is advantageous to have the phosphonate moiety as part of the nucleophiles. For example, substitution of 8-bromopurine with aminoalkylphosphonates give compounds of formula III where X are alkylamino groups.

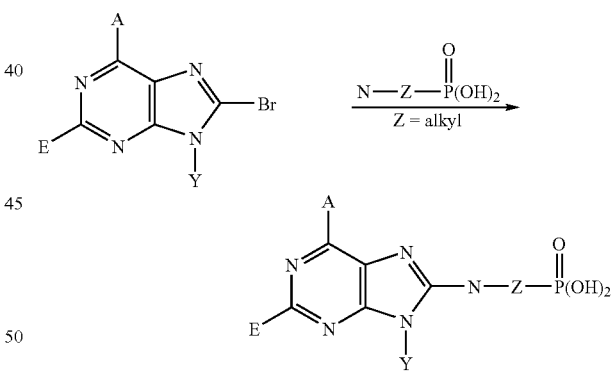

8-Halopurines can also be transformed into other 8-substituted purines using palladium catalyzed reactions (Heck, *Palladium Reagents: in Organic Synthesis*; Academic Press: San Diego, 1985). For example, palladium catalyzed carbonylation reactions of 8-bromopurine in the presence of alcohol give 8-alkoxycarbonylpurines. Using known chemistry the 8-carboxylate group can be converted into other functional groups, such as hydroxymethyl, halomethyl, formyl, carboxylic acid, carbamoyl, thiocarbonyl groups, and these are useful intermediates for the synthesis of compounds of formula III. For example, 8-alkyl and 8-arylpurines can be prepared from 8-halopurines via-palladium catalyzed coupling reactions with organotin (Moriarty et al. *Tetrahedron Lett.*, 1990, 41: 5877), organoborane (Yatagai, *Bull. Chem. Soc. Jpn.*, 1980, 53: 1670), and other reagents known to couple with aryl halides. When the coupling reagents contain the dialkylphosphonate group, the reaction is useful for preparation of compounds of formula 5 where X is alkyl, alkenyl, alkynyl, and aryl. For example, 8-bromopurine can be coupled with diethyl 1-tributylstannyl-3-allylphosphonate to give compounds of formula 5 where X is —CH=CHCH$_2$— and subsequent hydrogenation reaction give compounds of formula 5 where X is —CH$_2$CH$_2$CH$_2$—.

The phosphonate group can also be introduced by further modification of the 8-substituents. Substitutions of 8-haloalkyl or 8-sulfonylalkylpurine with nucleophiles containing the phosphonate group are useful for the preparation of compounds of formula 5 where X is alkylaminoalkyl, alkoxyalkyl, alkylthioalkyl. For example, compounds of formula 5 where X is —CH$_2$OCH$_2$— can be prepared from 8-bromomethylpurine using hydroxymethylphosphonate esters and a suitable base. It is possible to reverse the nature of the nucleophiles and electrophiles for the substitution reactions, i.e. haloalkyl- and/or sulfonylalkylphosphonate esters can be substituted with purines containing a nucleophile at the C8 position (such as 8-hydroxyalkyl, 8-thioalkyl, 8-aminoalkylpurines). For example, diethyl phosphonomethyltriflate can be substituted by alcohols such as 8-hydroxymethylpurine to give compounds of formula 5 where X is —CH$_2$OCH$_2$— (Phillion et al. *Tetrahedron Lett.* 1986, 27: 1477). Known amide formation reactions are useful for the synthesis of compounds of formula 5 where X is alkylaminocarbonyl, alkoxycarbonyl, alkoxythiocarbonyl and alkylthiocarbonyl. For example, coupling of 8-purinecarboxylic acids with aminoalkylphosphonate esters gives compounds of formula 5 where X is alkylaminocarbonyl. For compounds of formula 5 where X is alkyl, the phosphonate group can also be introduced using other common phosphonate formation methods, such as Michaelis-Arbuzov reaction (Bhattacharya et al. *Chem. Rev.*, 1981, 81: 415), Michaelis-Becker reaction (Blackburn et al. *J. Organomet. Chem.*, 1988, 348: 55), addition reactions of phosphorus to electrophiles (such as aldehydes, ketones, acyl halides, imines and other carbonyl derivatives).

Compounds of formula III, where X is carboxypropyl or sulfonopropyl can be prepared from the reaction of 8-(2-iodoethyl)purine and corresponding phosphonomethylcarboxylate or phosphonomethylsulfonate (Carretero et al., *Tetrahedron*, 1987, 43, 5125) in presence of base (eg. NaH) in polar aprotic solvents (eg. DMF). Substituted 8-(2-iodoethyl)purines are prepared using know indole chemistry. For the preparation of a-phosphosulfonic acids see Magnin, D. R. et al. *J. Med. Chem.* 1996, 39, 657.

Following well-reported literature procedures, other modification of 8-substituent of purines can be used to synthesize various compounds of formula III. For example, compounds of formula III where X is carbonylalkyl can be prepared from 8-carboxyalkylpurines via conversion of 8-carboxyalkylpurines to their corresponding acid chloride and followed by Arbuzov reaction (*Chem. Rev.* 1984, 84: 577) with an alkyl phosphite to give 8-(2-dialkylphosphonocarbonylethyl)purines. These a-ketophosphonates can be converted to the a-hydroxyphosphonates and a,a-dihalophosphonates (Smyth, et al. *Tett. Lett.*, 1992, 33, 4137). For another way synthesizing these a,a-dihalophosphonates see Martin et al. *Tett. Lett.*, 1992, 33, 1839.

8-Azidopurines are useful for the preparation for compounds of formula 5 where X is alkylamino and alkylcarbonylamino groups. For example, carboxylic acids (e.g. (RO)$_2$P(O)-alkyl-CO$_2$H) can be directly coupled to 8-azidopurines to give 8-alkylcarbonylaminopurines (Urpi et al. *Tetrahedron Lett.*, 1986, 27: 4623). Alternatively, 8-azidopurines can also be converted to 8-aminopurines under reductive conditions, and subsequently converted to 8-alkylaminocarbonyl- and 8-alkylaminopurines using known chemistry.

III.2.c) Modification of Purines at Positions Other Than C8

Compounds of formula 5 can be further modified to give intermediates useful for the synthesis of compounds of formula III. For example, substitution reactions of 6-chloropurine by ammonia or alkylamines are useful for the preparations of compounds of formula 5 where A is amino and alkylamino groups.

E groups can be introduced by modifying existing 2-substituents of purine. For example, 2-halopurines, readily accessible from 2-aminopurines via chemistry well described in the literature, can be converted to other 2-substituted purines by for example nucleophilic substitution reactions; transition metal catalyzed reactions, etc. (*J. Med. Chem.*, 1993, 36: 2938; *Heterocycles*, 1990, 30: 435).

It is envisioned that N$^9$-substituted purines can be readily prepared from compounds of formula 5 where Y is H using for example standard alkylation reactions (with alkyl halide, or sulfonate), or Mitsunobu reactions. Further elaborations of substituents on Y are also possible.

III.2.d) Construction of the Purine Ring System

Purine ring system of compounds of formula III can be constructed using 4,5-diaminopyrimidines and carboxylates or their derivatives (such as aldehydes, amides, nitrites, ortho esters, imidates, etc.) (Townsend *Chemistry of Nucleosides and Nucleotides, Vol* 1; Plenum Press, New York and London, page 156-158). For example, alkyl and aryl aldehydes can be cyclized with 4,5-diaminopyrimidines as shown below.

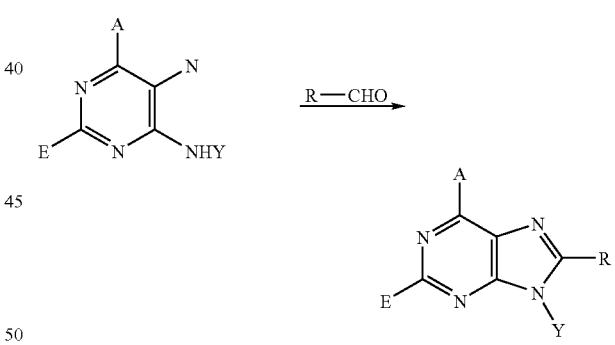

Intramolecular cyclization reactions of pyrimidine derivatives can also be used to construct the purine ring system. For example, 5-acylamino-4-alkylaminopyrimidines are treated with phosphorusoxychloride and cyclized under basic conditions to give purine derivatives. This transformation can also be achieved using other reagents (e.g. SiCl$_4$-Et$_3$N, Desaubry et al. *Tetrahedron Lett.*, 1995, 36: 4249). Imidazole derivatives are also useful for the construction of purine ring system via cyclization reactions to form the pyrimidine ring (Townsend *Chemistry of Nucleosides and Nucleotides, Vol* 1; Plenum Press, New York and London, page 148-156).

III.2.e) Preparation of Diaminopyrimidine

Compounds of formula 4 are useful for the construction of purine ring systems, and such compounds can be readily synthesized using known chemistry. For example, the Y group can be introduced using a nucleophilic substitution reaction involving an amine and 4-halopyrimidines (*Tetrahedron*, 1984, 40: 1433). Alternatively, palladium catalyzed reactions (Wolfe et al. *J. Am. Chem. Soc.*, 1996, 118: 7215) can also be used. Reductive amination reactions (*Synthesis*, 1975, 135) and alkylation with electrophiles (such as halides, sulfonates) are useful for the preparation of compounds of formula 4 from 4-aminopyrimidines. The 5-amino group can be introduced using amine formation reactions such as nitration followed by reduction (Dhainant et al. *J. Med. Chem.*, 1996, 39: 4099), arylazo compound formation followed by reduction (Lopez et al. *Nucleosides & Nucleotides*, 1996, 15: 1335), azide formation followed by reduction, or by rearrangement of carboxylic acid derivatives (e.g. Schmidt, Curtius, and Beckmann reactions).

III.2.f) Preparation of Functionalized Linker (X) Phosphonate.

Coupling of aromatic or aliphatic aldehydes, and carboxylic acid derivatives with attached phosphonate ester are particularly suited for the preparation of compounds of formula III as described in section II.2.d. Such phosphonate esters are prepared by the methods described earlier in section I.2.a.

A second lithiation step can be used to incorporate the aldehyde functionality, although other methods known to generate aromatic aldehydes can be envisioned as well (e.g. Vilsmeier-Hack reaction, Reimar-Teimann reaction etc.). In the second lithiation step, the lithiated aromatic ring is treated with reagents that either directly generate an aldehyde (e.g. DMF, HCO$_2$R, etc.) or with reagents that lead to a-group that subsequently transformed into an aldehyde group using known chemistry (e.g. alcohol, ester, cyano, alkene, etc.). It is also envisioned that sequence of these reactions can be reversed, i.e. the aldehyde moiety can be incorporated first followed by the phosphorylation reaction. The order of the reaction will be dependent on reaction conditions and protecting groups. Prior to the phosphorylation it is also envisioned that it may be advantageous to protect the aldehydes using a number of well-known steps (hemiacetal, hemiaminal, etc.,). The aldehyde is then unmasked after phosphorylation. (*Protective groups in Organic Synthesis*, Greene, T. W., 1991, Wiley, New York).

III.3) Benzimidazole Based Inhibitors

Synthesis of the benzimidazole compounds encompassed by the present invention typically includes some or all of the following general steps: (a) deprotection of phosphonate ester; (b) substitution of the heterocycle; (c) substitution or modification of 2-substituent; (d) cyclization to generate benzimidazole ring system; (e) synthesis of the substituted 1,2-phenylenediamine precursors; and f) preparation of functionalized linker (X) phosphonate. A detailed discussion of each step is given below.

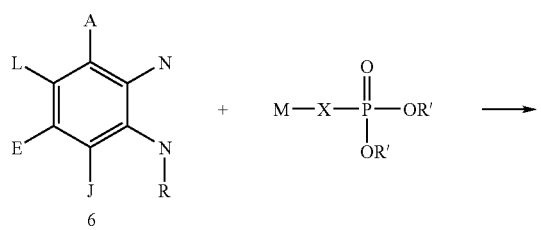

-continued

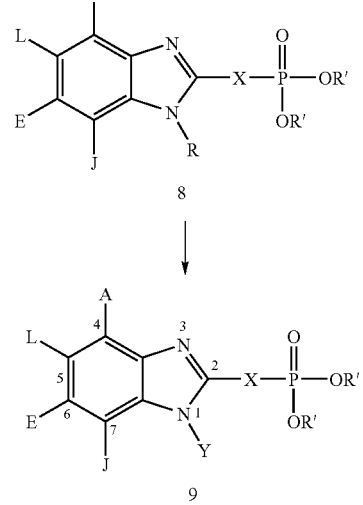

III.3.a) Deprotection of Phosphonate Ester

Deprotection of phosphonate esters is effected as described in section II.2.a.

III.3.b) Substitution of the Heterocycle

The benzimidazole ring system of formula 8, may require further elaboration to provide desired compounds of formula 9.

i) Substitution of the Phenyl Ring

Electrophilic and nucleophilic substitution reactions enable incorporation of the desired substitutions encompassed by the formula 9. (March, *Advanced Organic Chemistry* by, Wiley-Interscience, 1992, 501-521; 641-654). For example treatment of the compounds of formula 8, where A is NH$_2$, L and J are hydrogens with NBS, NCS or NIS in halogenated solvents such as carbon tetrachloride or chloroform gives halo-substituted compounds of formula 9 (L and/or J are halogens). Compounds of formula 9, where A is NO$_2$, L and/or J are alkenyl, alkynyl, alkyl, or aryl groups, and Y is H or alkyl, may be prepared from the formula 8, where A is NO$_2$, R is H or alkyl, and L and/or J are halogens, preferably bromide or iodide, through Stille coupling (Stille, *Angew. Chem. Int. Ed. Engl.* 1986, 25:.508-524). Treatment of the compounds of formula 8, where A is NO$_2$, and L and/or J are bromides, with coupling reagent (e.g. tributyl (vinyl)tin, phenylboronic acid, propargyl alcohol, N,N-propargyl amine etc.) in presence of palladium catalyst [e.g. bis(triphenylphosphine)palladium (II)chloride, tetrakis (triphenylphosphine) palladium(0), etc.] in solvent, such as DMF, toluene, etc. provides the coupling products. The compounds thus obtained can be modified as needed. For example vinyl or propargyl alcohol derivatives can be hydrogenated to give the ethyl or propyl alcohol derivatives respectively. These alcohol can be further modified as required via alkyl halides (ref. Wagner et al. *Tetrahedron Lett.* 1989, 30, 557) or alkyl sulfonates etc. to a number of substituted alkyls such as amino alkyl compounds by subjecting them to nucleophilic substitution reactions (March, *Advanced Organic Chemistry*, Wiley-Interscience, Fourth Edition, 1992, 293-500). Alternately, these substitutions can also be done by metal exchange followed by quenching with an appropriate nucleophile (Jerry March, *Advanced Organic Chemistry*, Wiley-Interscience, 1992, 606-609). Nucleophilic addition reactions can also be useful in preparing compounds of formula 9. For e.g. when A is $NO_2$, L and/or J are halogens nucleophiles such as alkoxides, thiols, etc. provides the halogen displacement products. (March, *Advanced Organic Chemistry*, Wiley-Interscience, Fourth Edition, 1992, 649-676). Another example is the addition reactions for example cyclopropanation (Vorbruggen et al, *Tetrahedron Lett.* 1975, 629) on the olefins (e.g. styryl type) synthesized through Stille coupling.

If required, these substituted compounds can be further modified to the desired products. For example reduction of the $NO_2$ to $NH_2$ may be done in many different ways, e.g. Pd/C, $H_2$, aq. $Na_2S_2O_4$, etc. (Larock, *Comprehensive Organic Transformations*, VCH, 412-415). These primary aromatic amines can also be modified as needed. For example N-acetyl derivatives can be prepared by treatment with acetyl chloride or acetic anhydride in presence of a base such as pyridine and mono-, or di-alkylamines can be synthesized by direct alkylation, using a base such as NaH in polar solvents such as DMF or by reductive alkylation (ref. Abdel-Magid et al. Tetrahedron Lett. 1990, 31, 5595; also see ref. March, Advanced Organic Chemistry, Wiley-Interscience, Fourth Edition, 1992, 898-900 for more methods).

ii) Alkylation of the Imidazole Ring

Alkylation of the heterocycle of formula 8, (where R and J are both H) is obtained through two distinct methods that are amenable to a large number of electrophiles.

Mitsunobu Alkylation

Alkylation of the benzimidazole ring system of formula 8, is achieved by treatment of an alcohol, triphenylphosphine and diethylazodicarboxylate with heterocycle and a non-nucleophilic base such as Hunigs base in polar solvents such as $CH_3CN$ (Zwierzak et al, *Liebigs Ann. Chem.* 1986, 402).

Base Alkylation

Alternately, the berzimidazole ring system of formula 8 can be deprotonated with a suitable base, preferably cesium carbonate in a polar aprotic solvent such as DMF, and the resulting anion is alkylated with an appropriate electrophilic component Y-L', where L' is a leaving group preferably bromide or iodide.

III.3.c) Substitution or Modification of 2-Substituent

Another key intermediate envisioned in the synthesis of compounds of formula 8 are substituted 2-methylbenzimidazoles. These compounds are readily prepared by condensing $Ac_2O$ with the appropriate 1,2-phenylenediamine (Phillips, *J. Chem. Soc.*, 1928, 29: 1305). These compounds are useful in the synthesis of formula IV, wherein X is $CH_2ZCH_2(Z=O,S,NH)$. For example, compounds where Z=O are readily prepared by treatment of the 2-methylbenzimidazole with a halogenating agent such as NBS followed by reaction with the hydroxymethyl phosphonate ester (also see section 6, Synthesis of the Linker-$PO_3R_2$). Alternately, a heterosubstituted methyl phosphonates can also be prepared by displacement reactions on phosphonomethyl halides or sulfonates (Phillion et al., *Tetrahedron Lett.*, 1986, 27: 14774) with an appropriate nucleophile e.g. 2-hydroxylmethyl benzimidazole compound which can be prepared using a variety of methods, including oxidation of the substituted 2-methyl benzimidazoles.

Similarly, compounds of formula IV, where X is carboxypropyl or sulfonopropyl can be prepared from the reaction of 2-(2-iodoethyl) benzimidazole and corresponding phosphonomethylcarboxylate or phosphonomethylsulfonate (Carretero et al., *Tetrahedron*, 1987, 43, 5125) in presence of base such as NaH in polar aprotic solvents such as DMF. The substituted 2-(2-iodoethyl) benzimidazole can be prepared from condensation of the corresponding substituted diamine and 3-halopropanaldehyde. Also see ref. Magnin, D. R. et al. *J. Med. Chem.* 1996, 39, 657 for the preparation of α-phosphosulfonic acids.

The compounds of formula 8 where X is all carbon e.g. —$(CH_2)_3$— can be prepared by Stille coupling (Stille *Angew. Chem. Int. Ed. Engl.* 1986, 25: 508-524) of the dialkylphosphopropenyl tributylstanne (*J. Org. Chem.* 1993, 58:, 1986, 27: 1051).

The compounds of formula 8 where X is an amide linker e.g. —$CONHCH_2$— can be synthesized using the following two steps. Treatment of the appropriate 1,2-phenylenediamine with trihalomethylacetamidate preferably trichloromethylacetamidate in polar solvent such as acetic acid followed by hydrolysis of the trihalomethyl group with strong aqueous base (e.g. KOH) gives the benzimidazole-2-carboxylic acid (*Eur. J. Med. Chem.*, 1993 28: 71). Condensation of the acid with amino phosphonate e.g. diethyl(aminomethyl)phosphonate in presence of condensing agent (e.g. pyBOP) in a polar solvent such as methylene chloride to provide the amide linker phosphonate.

The compounds of formula 8 where X is an amide linker e.g. —$NHCOCH_2$— can be synthesized using the following two steps. Treatment of the appropriate 1,2-phenylenediamine with cyanogen bromide (Johnson, et al, *J. Med. Chem.*, 1993, 36: 3361) in polar solvent such as MeOH gives the 2-amino benzimidazole. Condensation of the 2-aminobenzimidazole with a carboxylic acid e.g. diethyl(carboxymethyl)phosphonate using standard coupling conditions (Klausner, et al, *Synthesis*, 1972, 453) to provide amide linker phosphonate. The 2-aminobenzimidazoles can also be prepared from the 2-bromobenzimidazole via 2-azidobenzimidazole using known methods (*Chem. Rev.* 1988, 88: 297).

III.3.d) Cyclization to Generate Benzimidazole Ring System

The benzimidazole ring systems of formula 8, is preferably assembled by condensation of substituted 1,2-phenylenediamines with an aldehyde (RCHO, where R is e.g. aliphatic, heteroaliphatic, aromatic or heteroaromatic etc.) using known methods; (a) in presence of $Fe^{3+}$ salts preferably $FeCl_3$ in polar solvents such as DMF, EtOH etc., (b) reflux in non polar solvents such as toluene followed by oxidation, preferably with iodine (Bistocchi et al, *Collect. Czech. Chem. C*, 1985, 50(9): 1959.).; (c) in cases of protected aldehydes the first condensation can be achieved in presence of an dilute inorganic acid preferably 10% $H_2SO_4$ in polar solvents such as THF, followed by oxidation with $I_2$. Alternately, this coupling can be achieved with anhydride (RCOOCOR), carboxylic acid (RCOOH) or with the nitrile (RCN) by methods reported by Hein, et al, *J. Am. Chem. Soc.* 1957, 79, 427.; and Applegate, et al, U.S. Pat. No. 5,310,923.

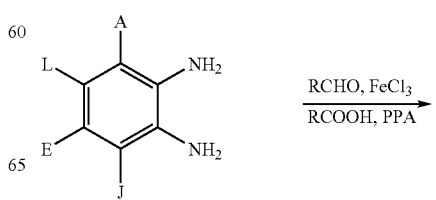

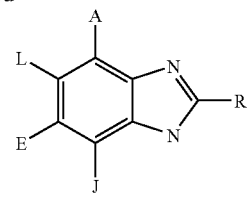

III.3.e) Substituted 1,2-Phenylenediamine 1,2-Phenylenediamines utilized in the preparation of compounds of formula IV, can be synthesized using methods well known in the art.

(a) Compounds of formula 6, where R is H, can be synthesized from simple aromatic compounds. Most aromatic compounds, whether of high or low reactivity can be nitrated, because a wide variety of nitrating agents are available (March, *Advanced Organic Chemistry*, Wiley-Interscience, 1992, 522-525). The primary aromatic amines are often protected as the N-acetyl, before nitration by treatment with acetyl chloride or acetic anhydride. Nitration of the these acetanilides derivatives using 60% $HNO_3$ and $H_2SO_4$ (Monge et al, *J Med. Chem*., 1995, 38: 1786; Ridd *Chem. Soc. Rev.* 1991, 20: 149-165) followed by deprotection, with strong acids (e.g. $H_2SO_4$, HCl, etc.) and hydrogenation (e.g. $H_2$, Pd/C; $Na_2S_2O_4$; etc.) of the resulting 2-nitroanilines to provide the desired substituted 1,2-phenylenediamines. Similarly substituted arylhalides (F,Cl,Br,I) can also be nitrated provides a-halonitroaryl compounds followed by nucleophilic addition (e.g. $NH_3$, $NH_2OH$, etc) and reduction to generate the diamines.

(b) Diamines of formula 6, where A is $NO_2$ and R is H, can be produced using the method of Grivas et. al., *Synthesis* 1992, 1283 and Tian et al *J. Chem. Soc. Perkin Trans 1*, 1993, 257 and an appropriate o-nitroaniline. A variety of reactions can be used to substitute the o-nitroaniline. For example halogenation of the nitroaniline (e.g. $Br_2$, $Cl_2$, etc.) gives the corresponding 4,6-disubstituted or monosubstituted nitroaniline which can be further modified at a later stage. The nitro group can be reduced with number of reagents preferably sodium dithionite to provide the corresponding diamine. This diamine is then subjected to nitration conditions by first generating the 2,1,3-benzoselenadiazole with selenium dioxide followed by nitric acid. Substituted nitro-1,2-phenylenediamines are generated by treatment of the nitro 2,1,3-benzoselenadiazole with aqueous hydrogen iodide or $NH_3/H_2S$ (Nyhammar et al, *Acta, Chem. Scand*. 1986, B40: 583). Other methods to simultaneously protect the diamine are also envisioned.

(c) The compounds of formula 6, where R is alkyl or aryl, can be synthesized using the method of Ohmori et al, *J. Med. Chem*. 1996, 39: 3971. Nucleophilic substitution of the o-halonitrobenzenes by treatment with various alkylamines followed by reduction (e.g. $Na_2S_2O_4$) of the nitro group provides the desired compounds. Alternately, the compounds of formula 6, where R is H, can be synthesized from these o-halonitrobenzenes via o-azidonitrobenzenes followed by reduction of the nitro group to provide the desired compound.

(d) Alternately, diamines of formula 6 where R is not H are prepared by reductive alkylation of the o-nitroanilines with various aldehydes (e.g. aklyl, aryl, etc.) in the presence of a reducing agent preferably $NaB(OAc)_3$ followed by reduction(e.g. $Na_2S_2O_4$; Pd/C, $H_2$, etc.) of the nitro group (Magid et al *Tetrahedron Lett*. 1990, 31: 5595).

III.3.f) Preparation of Functionalized Linker (X) Phosphonate.

Functionalized linker (X) phosphonates are synthesized as described in section II.2.f 11.4) Indole and 9-Azaindole Based Inhibitors:

Synthesis of indole and 9-azaindole compounds encompassed by present invention typically includes some or all of the following steps: (a) deprotection of phosphonate ester; (b) ring substitution of heterocycle; (c) modification of 2-substituent to introduce X group; (d) synthesis of phosphonate substituted heterocycle by ring closure; (e) synthesis of 2-nitro or 2-amino alkylbenzene derivatives; and (f) preparation of functionalized linker (X) phosphonate.

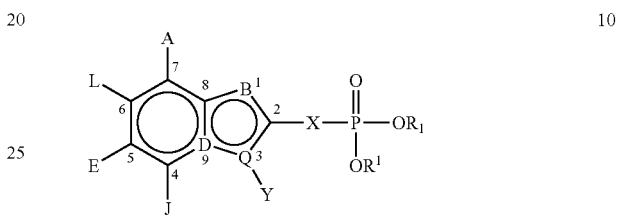

II.4.a) Deprotection of Phosphonate Ester

Deprotection of phosphonate esters is effected as described in section II.2.a.

III.4.b) Ring Substitution of Indole Heterocycle i) Introduction of Y Group on Heterocycle Introduction of Y group on the pyrrole ring of the heterocycle is selectively achieved either at the carbon or on the nitrogen depending on the reaction conditions employed. This selective substitution of the Y group also defines regiochemistry of A, L, E, J substituents on the benzene ring. Substitution at carbon (C-3) of the indole base can be achieved using palladium mediated chemistry (Heck, R. F., *Palladium Reagents in Organic Syntheses*, Academic Press, New York, 1985). In general, these reactions entail coupling C3-iodo or -bromo indoles with boronic acids (*Pure & Appl. Chem*. 1991, 63: 419) and stannanes (Stille, J. K., et al, *J. Am. Chem. Soc*., 1984, 106: 4630) in the presence of a palladium catalyst. Terminal acetylenes also react in the presence of copper (I) chloride and a palladium catalyst in a modified Stephens-Castro reaction (Sonogoshira, K., et al, *Tetrahedron Lett*., 1975, 4467; Sakamoto, T. et al, *Synthesis*, 1983, 312). These alkynyl or alkenyl groups can be further transformed to alkenyl or alkyl substitution in a hydrogenation reaction by selection of a specific catalyst (Hutchins in Patai, *The Chemistry of Functional groups*, Wiley, New York, 1983, 571; Lindlar, H., et al, *Org. Synth. Coll. vol. V*, 1973, 880). Precursors for these coupling reactions can be made by halogenation at C-3 position of indole using reagents such as N-halosuccinimide (Mistry, A. G., et al, *Tetrahedron Lett*., 1986, 27: 1051) or pyridinium bromide perbromide (Erickson, K. L., et al, *Syn. Commun*., 1981, 11: 253).

Introduction of a Y group at the N-1 position of the indole in compounds of formula 10 can be obtained by base-promoted alkylation with halides or sulfonates. Suitable bases include cesium carbonate or sodium hydride in an aprotic solvent (Guida, W. C., et al, *J. Org. Chem.*, 1981, 46: 3172; Kikugawa, Y., *Synthesis*, 1981, 124). Palladium catalyzed N-alkylation of aryl iodides is also an applicable method to introduce Y groups (Wolfe, J. P., et al, *J. org. Chem.*, 1996, 61: 1133). Alternatively, Mitsunobu reaction conditions can be used for N-1 substitution of the heterocycle (Mitsunobu, O., *synthesis*, 1981, 1) using a variety of alcohols.

ii) Substitution of the Benzene Ring of the Heterocycle

Substituents A, L, E and J in formula 10 can be introduced through reactions on indole or indole precursors. For example, substituents can be introduced on the heterocycle by substitution reactions (Hegedus, L. S., Angew. *Chem., Int. Ed. Engl.*, 1988, 27: 113) and further converted to required functional groups at this stage. Functional groups on the benzene ring are transformed after addition of the linker phosphonate and before the deprotection of the phosphonate diester.

Amino groups can be incorporated from nitro groups introduced through nitration reaction of the heterocycle (Masuda, T., et al, *Heterocycles*, 1987, 26, 1475). Nitration reaction of indoles results in a mixture of 4- and 6-regio isomers. Selectivity is obtained based on the other substituents on the benzene ring. The reduction of the nitro functional group is accomplished utilizing methods such as catalytic hydrogenation or a chemical reduction (e.g., Sn/HCl). Alternatively, selective nitro group reduction is obtained by aqueous sodium dithionate reaction. These conditions avoid hydrogenolysis of double bonds or reductive elimination of halogens (*Org. Syn. Coll. vol* 3, 1955, 69). Amines can be used to introduce other groups by diazotization reactions (Wulfman, in Patai *The Chemistry of Diazonium and Diazo Groups*, Wiley, New York, 1978, 286-297). Amine groups are also expected to facilitate other substitution reactions. Halogenation reaction of the heterocycle results in A, L, E, J substitution with 4- and 6-amino indole isomers. Bromo or iodo substituents can be further transformed into various substituents by transition metal chemistry (Heck, R. F., *Palladium Reagents in Organic Syntheses*, Academic Press, New York, 1985). The metallation strategy devised by Mayer et al. (*J. Org. Chem.*, 1986, 51: 5106) can be used to substitute different groups (e.g., CO₂R, COR, SMe, alkyl, aryl) at the 5-position.

III.4.c) Modification of 2-Substituent to Introduce X Group With Phosphonate

2-Substituted indole heterocycles can be converted to intermediates useful for the synthesis of compounds of formula 10. For example, compounds of formula 1 where X is methyleneaminocarbonyl may be obtained through a two-step procedure as shown below. Indole-2-carboxylic esters are hydrolyzed using standard basic conditions (e.g. NaOH, $K_2CO_3$). The resulting carboxylic acids are coupled to form amide linkage (Klausner, et al, *Synthesis*, 1972, 453; Bodansky, *The Practice of Peptide Synthesis*, Springer, New York, 1984) with amino substituted phosphonate utilizing known coupling agents such as Pyr-BOP (*Tetrahedron Lett.*, 1991, 32: 6387). Substituted indole-2-carboxylic esters can be prepared, e.g., by Reissert indole synthesis (Rosenmond, P., et al, *Ber.*, 1966, 99: 2504). The reaction involves condensation of 2-nitro toluene with ethyl acetoacetate in presence of a mild base followed by a reductive cyclization.

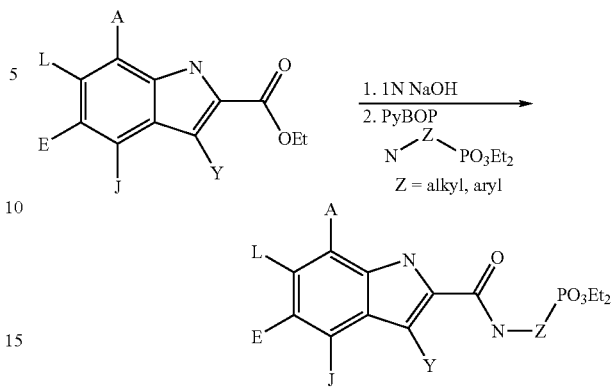

Compounds of formula 10, where X is carboxypropyl or sulfonopropyl can be prepared from the reaction of 2-(2-iodoethyl)indole and corresponding phosphonomethylcarboxylate or phosphonomethylsulfonate (Carretero et al., *Tetrahedron*, 1987, 43, 5125) in presence of base (eg. NaH) in polar aprotic solvents (eg. DMF). Substituted 2-(2-iodoethyl) indoles are prepared using know indole chemistry (eg. Fischer indole synthesis). For the preparation of α-phosphosulfonic acids see Magnin, D. R. et al. *J. Med. Chem.* 1996, 39, 657.

Following well-reported literature procedures, other modification of 2-substituent of indoles can be used to synthesized various compounds of formula 10. For example, compounds of formula 10 where X is carbonylalkyl can be prepared from 2-carboxyalkylindoles via conversion of 2-carboxyalkylindoles to their corresponding acid chloride and followed by Arbuzov reaction (*Chem. Rev.* 1984, 84: 577) with an alkyl phosphite to give 2-(2-dialkylphosphonocarbonylethyl)indoles. These α-ketophosphonates can be converted to the a-hydroxyphosphonates and α,α-dihalophosphonates (Smyth, et al. *Tett. Lett.*, 1992, 33, 4137). For another way synthesizing these α,α-dihalophosphonates see Martin et al. *Tett. Lett.*, 1992, 33, 1839.

3-Substituted indoles can be brominated selectively at the 2-position (Mistry, A. G., et al, *Tetrahedron Lett.*, 1986, 27: 1051). These intermediates are useful in the preparation of compounds where X is alkyl, aryl, alkylamino, arylamino, alkylthio, and arylthio. For example, the bromo can be replaced by such groups through a nucleophilic substitution reaction. Alternatively, phosphonate containing aromatic boronic acids, alkenyl stannanes or alkynyl X groups can be introduced in palladium mediated chemistry (Heck, R. F., *Palladium Reagents in Organic Syntheses*, Academic Press, New York, 1985). In an alternate metallation route, N-substituted or protected indoles undergo lithiation reaction at the 2-position which is useful in reactions with various electrophiles (*Synthesis*, 1991, 1079; *Heterocycles*, 1992, 33:173). Compounds of Formula 10 containing alkoxyalkyl as X group can be synthesized from indole-2-carbinol intermediates obtained from the metallation reaction by quenching with an aldehyde (e.g. formaldehyde). The phosphonate groups are introduced by O-alkylation of hydroxyl with dialkoxy phosphonomethyl halide.

Compounds of formula 10 where X and Y substituents are fused to give annulated indoles can be made in two general methods. Alicyclic fused compounds can be made by Diels-Alder reaction of propargyl phosphonate with 3-vinyl indole derivatives (Pindur, U., *Heterocycles*, 1988, 27, 1253). Heterocyclic annulated indoles are synthesized from Indole-2- methylene amines by Heck type reactions (*Tetrahedron Lett.*, 1996, 37: 2659) and also by ring closure reaction of tryptamine derivatives with aldehydes (Peng, S. Q. et al, *Liebigs. Ann. Chem.*, 1993, 2: 141; Pellegrini, C., et al, *Tetrahedron-Asymmetry*, 1994, 5: 1979). Phosphonate ester on the annulated heterocycle can be substituted by dialkoxyphosphonomethyl triflate (*Tetrahedron lett.*, 1986, 27: 1477).

III.4.d) Synthesis of Phosphonate Substituted Indole by Ring Closure

In another synthetic route, compounds of formula 10 are assembled by a ring closure reaction (Sundberg, R. J., *Indoles*; Academic press: San Diego, 1996).

One of such synthetic sequences involve the use of a phosphonate substituted aryl aldehyde. This aldehyde is condensed with a 2-nitrobenzyl ylide, which is generated in situ by treating 2-nitrobenzyltriphenyl phosphonium chloride with a base, e.g., potassium t-butoxide. The Wittig salt is made under usual conditions by reaction of 2-nitrobenzyl halide with triphenylphosphine (Murphy, P. B., et al, *Chem. Soc. Rev.* 1988, 17: 1: Maryanoff, B. E., et al, *Chem. Rev.* 1989, 89: 863).

compounds of formula 10, where X is an aryl group. Various phosphonate substituted aryl aldehydes can be prepared and used in this condensation.

These types of reductive cyclizations can also be achieved in the presence of a catalytic amount of PdCl$_2$—SnCl$_2$ under carbon monoxide atmosphere (Akazome, M., et al, *Chem. Lett.* 1992, 769). Another transition metal catalyzed synthetic approach by Larock, R. C., et. al, (*J. Am. Chem. Soc.*, 1991, 113, 6689) is also suitable to obtain compounds of formula 1 by a ring closure reaction.

Another ring closure method useful for indole synthesis is the palladium catalyzed cyclization reaction between 2-haloaniline and an alkyne, alkene or ketone (*J. Org. Chem.*, 1997, 62(9), 2676; 62(19), 6464, 6507). More importantly, this approach has been adopted for combinatorial synthesis of indoles on solid-phase which can be applied for the synthesis of indole FBPase inhibitors (*Tetrahedron Lett.*, 1997, 38(13), 2307).

Compounds of formula 10 are also prepared from o-toluidine trisubstituted amide cyclization, known as the Madelung indole synthesis (Brown, R. K., Indoles, Wiley New York 1972 Part 1; Houlihan, W. J., et al, *J. Org. Chem.*, 1981, 46: 4511). The amide is cyclized under modified Madelung reaction conditions in the presence of potassium ethoxide. The cyclization precursor is prepared by N-alkylation of amide followed by treatment with a non-nucleophilic base such as LDA and quenching the heteroaryl anion with chlorodialkylphosphonate. The starting amide is an addition product of substituted o-toluidine and acid chloride.

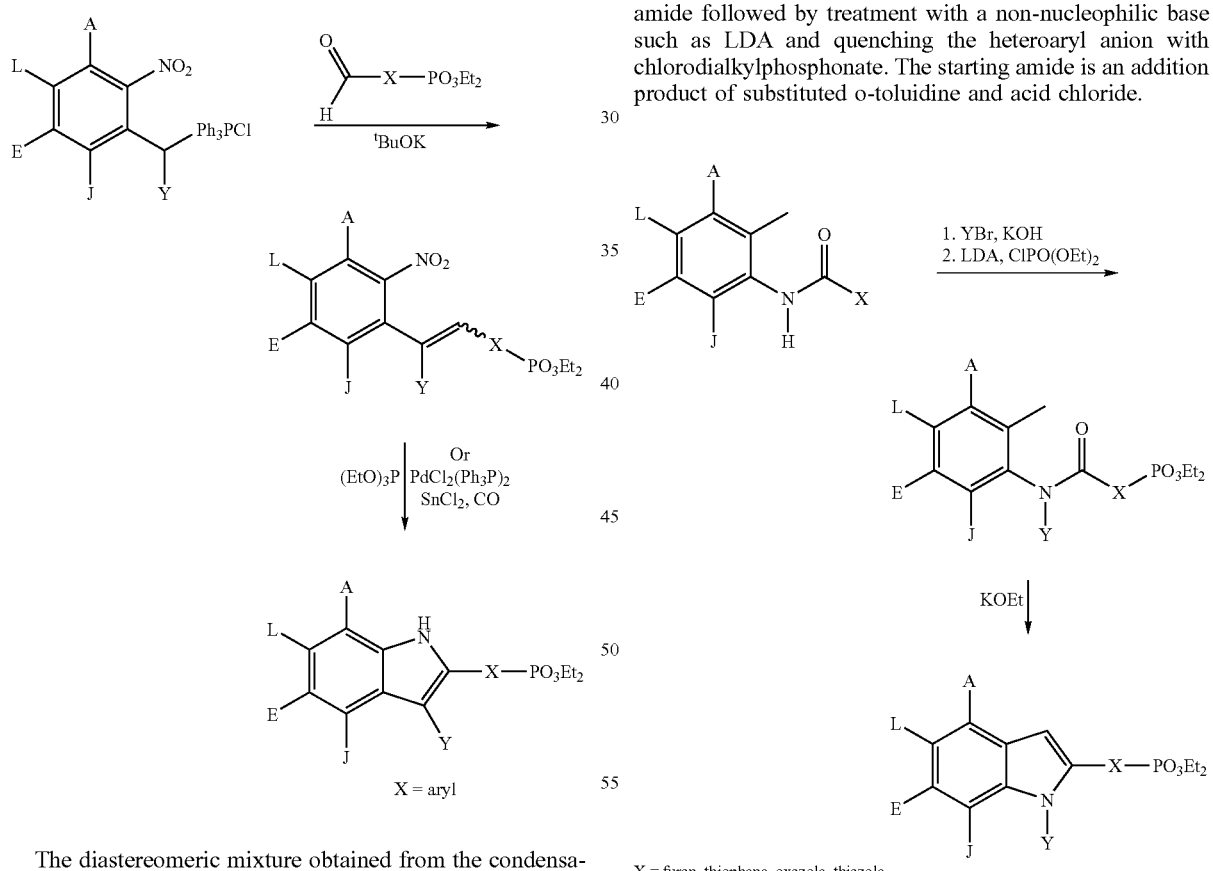

X = aryl

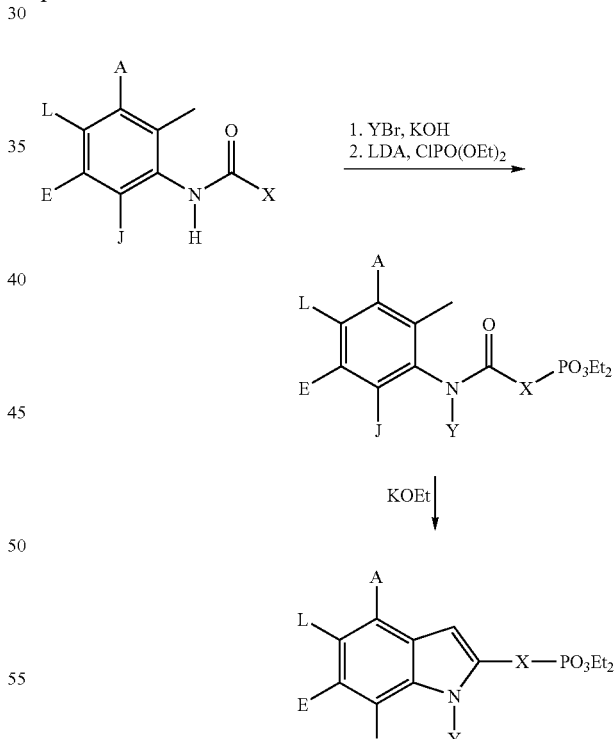

X = furan, thiophene, oxazole, thiazole

The diastereomeric mixture obtained from the condensation is then treated with triethylphosphite under refluxing conditions. This key step involves reduction of the nitro group and consequent addition of nitrene into the styryl double bond resulting in a substituted indole heterocycle as in formula 10 (Gelmi, M. L., et al, *J. Chem. Soc. Perkin I*, 1993, 969). 2-Vinylnitrobenzenes can also be prepared using other known methods, such as transition metal catalyzed coupling reaction between 2-halonitrobenzene and vinyl tin reagents. The above sequence can be used in the synthesis of 2-Acylaminobenzylidenephosphoranes also lead to indoles by an intramolecular Wittig reaction with the amide carbonyl group (Le Corre, M., et al, *Tetrahedron*, 1985, 41: 5313; Capuano, L., et al, *Chem. Ber.*, 1986, 119: 2069).

Alternatively, compounds of formula 10 can be obtained from silylated 2-amino benzylic bromide by treating o-toluidines with 2 equivalents of lithiating agent (e.g. n-BuLi) and TMSCl followed by bromination. Mixed organometallic intermediates are then prepared by reactions with Zn and a soluble copper complex (CuCN.2LiCl). This reactive intermediate undergoes cyclization with an acyl chloride to give highly substituted compounds (Chen, H. G., et al, *Tetrahedron Lett.* 1989, 36: 4795; Bartoli, G., et al, *J. Chem. Soc. Chem Commun.*, 1988, 807).

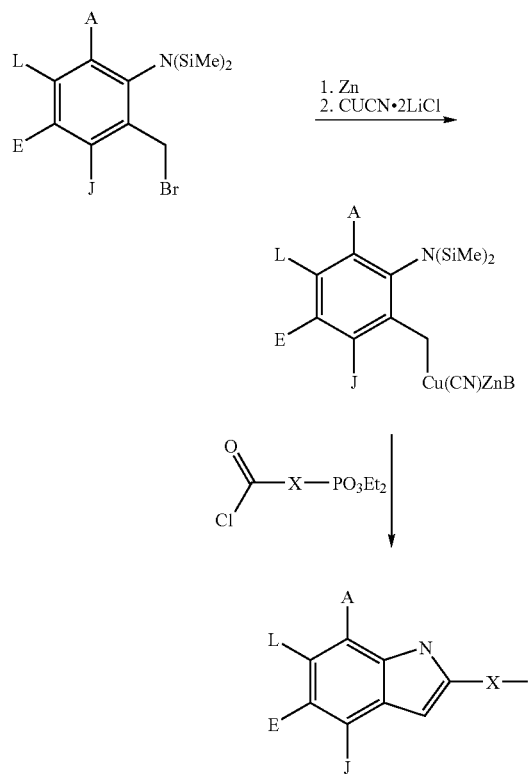

Alternatively, C-2 and C-3 substituted heterocycles of formula 10 can be made by condensation of a carboxylic acid ester with an organo dilithium intermediate of N-trimethylsilyl toluidine. Inverse addition of this organodilithium intermediate to a solution of aryl or alkyl ethyl ester results in a substituted indole heterocycle. (Smith, A, B., et al, *Tetrahedron Lett.* 1985, 26: 3757; Li, J. P., et al, *Synthesis*, 1988, 73).

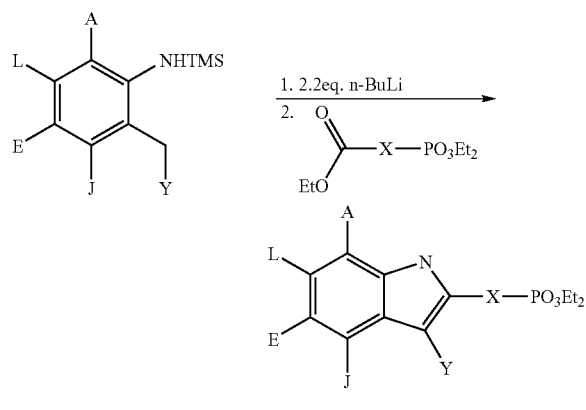

In another classical method known as the Fischer indole synthesis, compounds of formula 10 can be synthesized from aryl hydrazine with an aldehyde or ketone via hydrazone formation. Lewis acid catalyzed [3.3]sigmatropic rearrangement of the hydrazone followed by cyclization of the enamine results in substituted indole (Robinson, *The Fischer indole synthesis*; Wiley: New York, 1983). Zinc chloride is the most frequently used reagent among many known conditions, however, various metal halides or acids (eg. acetic acid, sulfuric acid) also promote the reaction (*Synthesis*, 1980, 2222). Mild acids are used in synthesis of C-2 and C-3 fused indoles known (Simuzu, I., et al, *Chem. Pharm. Bull.*, 1971, 19: 2561).

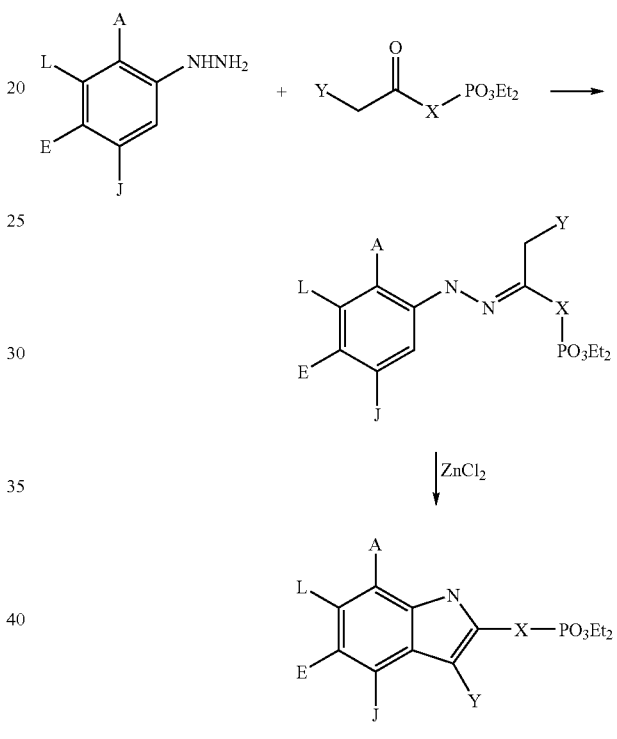

Y = H, alkyl, cycloalkyl, aryl

Phosphonate substituted 9-azaindole (also known as imidazopyridine) can also be synthesized via ring closure reactions (*Heterocycles*, 1997, 45(5), 897; *Synthesis*, 1996, 927). One method useful for 9-azaindole synthesis is the cyclization reaction between 2-aminopyridine and a-haloketones (eg. α-bromoketone, α-chloroketone) and ketone derivatives as shown below (*J. Heterocycl. Chem.*, 1989, 26, 1875).

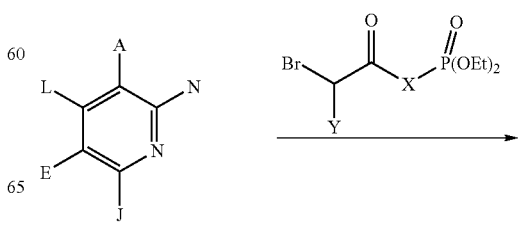

-continued

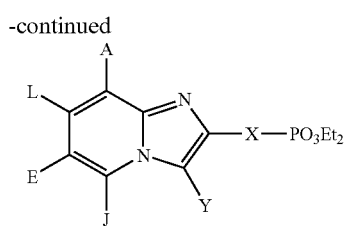

It is advantageous to have phosphonate ester presence in the a-bromoketone segment, however phosphonate can also be introduced to existing 9-azaindole. For example, 2-phosphonomethylaminocarbonyl-9-azaindole can be prepared from 2-ethoxycarbonyl-9-azaindole (available via cyclization reaction between 2-aminopyridine and ethyl bromopyruvate) as described in section II.4.b (Modification of 2-substituent to Introduce X Group with Phosphonate). 2-Phosphonomethoxymethyl-9-azaindole can also be synthesized from 2-ethoxycarbonyl-9-azaindole by the following sequence: reduction of 2-ethoxycarbonyl group to 2-hydroxymethyl group, followed by alkylation with dialkylphosphonomethyl halide (preferably iodide) as described in section II.4.b. Other modifications of 9-azaindole can be conducted as described early.

II.4.e) Synthesis 2-Nitro or 2-Amino Alkyl Benzene Derivatives:

Building blocks for substituted benzene nuclei are obtained by nitration of alkyl benzenes. These-compounds can be further transformed to 2-amino alkyl benzenes. 2-Amino alkyl benzenes can also be obtained from alkylation of aniline derivatives. A variety of substitutions on these groups can be made following known chemistry (March, J., *Advanced Organic Chemistry*, J. Wiley, New York, 1992, 501-568). N-Acyl and N-alkyl precursors can be obtained by methods mentioned earlier.

II.4.f) Synthesis of Linker (X group) Phosphonate Diester

Functionalized linker (X) phosphonates are synthesized as described in section II.2.f Formulations Compounds of the invention are administered orally in a total daily dose of about 0.1 mg/kg/dose to about 100 mg/kg/dose, preferably from about 0.3 mg/kg/dose to about 30 mg/kg/dose. The most preferred dose range is from 0.5 to 10 mg/kg (approximately 1 to 20 nmoles/kg/dose). The use of time-release preparations to control the rate of release of the active ingredient may be preferred. The dose may be administered in as many divided doses as is convenient. When other methods are used (e.g. intravenous administration), compounds are administered to the affected tissue at a rate from 0.3 to 300 nmol/kg/min, preferably from 3 to 100 nmoles/kg/min. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with, a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by, suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 2000 μmol (approximately 10 to 1000 mg) of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 0.05 to about 50 μmol (approximately 0.025 to 25 mg) of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Preferred unit dosage formulations are those containing a daily dose or unit, daily sub-dose, or an appropriate fraction thereof, of a drug.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

EXAMPLES

The prodrug compounds of this invention, their intermediates, and their preparation can be understood further by the examples which illustrate some of the processes by which these compounds are prepared. These examples should not however be construed as specifically limiting the invention and variations of the compounds, now known or later developed, are considered to fall within the scope of the present invention as hereinafter claimed.

Compounds of formula II are prepared according to the literature procedures with modifications and additions well understood by those skilled in the art. In general, these compounds are synthesized by the method of Srivastava, *J. Med. Chem.* 19, 1020 (1976). Other methodology is described by Wood et al. *J. Med. Chem.* 28: 1198-1203 (1985); Sagi et al., *J. Med. Chem.* 35: 4549-4556 (1992); Paul, Jr. *J. Med. Chem.* 28: 1704-1716 (1985); Cohen et al., *J. Am. Chem. Soc.* 95: 4619-4624 (1973).

Compounds of formulae III-V are prepared according to the procedures described in section III, supra.

Compounds of formula I are prepared using procedures detailed in the following examples.

Example 1

General Procedure for 1',3'-cyclohexyl Annulated Prodrugs by Thionyl Chloride Reaction A suspension of 1 mmol of phosphonic acid in 5 mL of thionyl chloride was heated at reflux temperature for 4 h. The reaction mixture was cooled and evaporated to dryness. To the resulting residue was added a solution of 1 mmol of alcohol and 2.5 mmol pyridine in 3 mL of methylene chloride. After stirring at 25° C. for 4 h the reaction was subjected to work up and chromatography.

The following compounds were prepared in this manner:

1.1: 6-Amino-8-(5'-hydroxyl-1',3'-cyclohexyl)phosphono-furanyl-9-phenethyl purine. Anal. Cald. for $C_{23}H_{24}N_5O_5P+0.15 H_2O$: C, 57.06; H, 5.06; N, 14.47. Found: C, 56.84; H, 4.83; N, 14.38.

1.2: 6-Amino-8-(5'-hydroxyl-1',3'-cyclohexyl)phosphono-furanyl-9-neopentyl purine, minor isomer. Rf=0.4 10% MeOH-CH2Cl2. mp 248-250° C.; Anal. Cald. for $C_{20}H_{26}N_5O_5P+0.5 H_2O$: C, 52.63; H, 5.96; N, 15.34. Found: C, 52.62; H, 5.70; N, 15.32.

1.3: 6-Amino-8-(5'-hydroxyl-1',3' cyclohexyl)phosphono-furanyl-9-neopentyl purine, major isomer. Rf=0.35 10% MeOH-CH2Cl2. mp=225-230° C.; Anal. Cald. for $C_{20}H_{26}N_5O_5P+0.5 H_2O$: C, 52.63; H, 5.96; N, 15.34. Found: C, 52.74; H, 5.80; N, 15.32.

1.4: 6-Chloro-4,5-dimethyl-1-cyclopropylmethyl-2-[1'-hydroxy-3',5'-cyclohexylphosphono-5-furanyl]benzimidazole. mp=211-215° C.; Anal. Cald. for $C_{23}H_{26}Cl N_2O_5P+2/3H_2O$: C, 56.50; H, 5.64; N, 5.73. Found: C, 56.65; H, 5.54; N, 5.64.

1.5: 6-Chloro-4,5-dimethyl-1-cyclopropylmethyl-2-[1'-acetylhydroxy-3',5'-cyclohexylphosphono-5-furanyl]benzimidazole, minor isomer. Rf=0.35 in 10% MeOH-CH2Cl2. Anal. Cald. for $C_{25}H_{28}ClN_2O_6P+1.5H_2O$: C, 55.00; H, 5.72; N, 5.13. Found: C, 55.19; H, 5.31; N, 4.65.

1.6: 6-Chloro-4,5-dimethyl-1-cyclopropylmethyl-2-[1'-acetylhydroxy-3',5'-cyclohexylphosphono-5-furanyl]benzimidazole, major isomer. Rf=0.4 in 10% MeOH-CH2Cl2. Anal. Cald. for $C_{25}H_{28}ClN_2O_6P+0.75H_2O+0.1EtOAc$: C, 56.37; H, 5.64; N, 5.18. Found: C, 56.68; H, 5.69; N, 4.80.

1.7: 6-Chloro-1-isobutyl-2-{2-[5-(1'-hydroxy-3',5'-cyclohexyl)phosphono]furanyl}benzimidazole, minor isomer. Rf=0.60 in 10% MeOH-CH2Cl2. mp=>220° C.; Anal. Cald. for $C_{21}H_{24}ClN_2O_5P+1/3H_2O$: C, 55.21; H, 5.44; N, 6.13. Found: C, 55.04; H, 5.50; N, 6.00.

1.8: 6-Chloro-1-isobutyl-2-{2-[5-(1'-hydroxy-3',5'-cyclohexyl)phosphono]furanyl}benzimidazole, major isomer. Rf=0.55 in 10% MeOH-CH2Cl2. mp.=>220° C.; Anal. Cald. for $C_{21}H_{24}ClN_2O_5P$: C, 55.94; H, 5.37; N, 6.21. Found: C, 55.73; H, 5.34; N, 6.13.

Example 2

Preparation of 1'-substituted cyclic-1',3'-propyl esters

The following compounds were prepared by procedure described for Example 1:

2.1: 6-Chloro-1-isobutyl-2-(2-(5-(1'-R-phenyl-1',3'-propyl)phosphono)furanyl)benzimidazole, major isomer. Rf=0.77 in 10% MeOH-CH2Cl2. mp=204-206° C.; Anal. Cald. for $C_{24}H_{24}Cl N_2 O_4 P$: C, 61.22; H, 5.14; N, 5.95. Found: C, 60.95; H, 5.01; N, 5.88.

2.2: 6-Chloro-1-isobutyl-2-(2-(5-(1'-R-phenyl-1',3'-propyl)phosphono)furanyl)benzimidazole, minor isomer. Rf=0.72 in 10% MeOH-CH2Cl2. Anal. Cald. for $C_{24}H_{24}ClN_2O_4P+H_2O$: C, 58.96; H, 5.36; N, 5.73. Found: C, 58.85; H, 5.48; N, 5.55.

2.4: 6-Chloro-1-isobutyl-2-{5-[1S-(4-nitrophenyl)-2R-acetylamino-propan-1,3-yl]phosphono-2-furanyl}benzimidazole, major isomer. Rf=0.35 3% MeOH-CH2Cl2. Mass Cald. for $C_{26}H_{26}ClN_4O_7P$: MH+473: Found: MH+573.

2.5: 6-Chloro-1-isobutyl-2-{5-[1S-(4-nitrophenyl)-2R-acetylamino-propan-1,3-yl]phosphono-2-furanyl}benzimidazole, minor. Rf=0.35 3% MeOH-CH2Cl2. Anal. Cald. for $C_{26}H_{26}ClN_4O_7P+1.6H_2O+0.25CH_2Cl_2$: C, 50;61; H, 4.81; N, 8.99. Found: C, 50.25; H, 4.37; N, 9.01.

2.6: 6-Chloro-1-isobutyl-2-{5-[1S-(4-methylthiophenyl)-2S-acetylamino-propan-1,3-yl]phosphono-2-furanyl}benzimidazole, Anal. Cald. for $C_{27}H_{29}ClN_3O_5PS+1H_2O+0.35CH_2Cl_2$: C, 52.83; H, 5.14; N, 6.76. Found: C, 52.44; H, 4.76; N: 6.59.

Example 3

Preparation of 1'-furan substituted cyclic-1',3'-propyl esters

Step A. To a solution of 2-furaldehyde (3 g, 31.2 mmol) in THF (60 mL) was added 1M vinyl magnesium bromide in THF (34 mL) at 0° C. After stirring for an hour, a solution of 1M $BH_3$. THF complex in THF was added. The reaction was quenched with 3N NaOH (20 mL) and 30% hydrogen peroxide (10 mL) at 0° C. The organic fraction was separated and concentrated. The crude product was chromatographed by eluting with 5% methanol-dichloromethane to give 2-(3-furyl)propane-1,3-diol (1 g, 22%).

Step B. The prodrug was made following the procedure as described in Example 1.

3.1: 6-Chloro-1-isobutyl-2-{5-[1'-(3-furyl)-propan-1',3'-y]phosphono-2-furanyl}benzimidazole. mp 160-162° C. Anal. cald. for $C_{22}H_{22}ClN_2O_5P+0.4H_2O$: C, 56.45; H, 4.91; N, 5.99. Found: C, 56.67; H, 4.82; N, 5.68.

Example 4

Preparation of 1'-pyridyl substituted cyclic-1',3'-propyl esters

Step A: (*J. Org. Chem.*, 1957, 22, 589)

To a solution of 2-pyridine propanol (10 g, 72.9 mmol) in acetic acid (75 mL) was added 30% hydrogen peroxide slowly. The reaction mixture was heated to 80° C. for 16 h. The reaction was concentrated under vacuum and the residue was dissolved in acetic anhydride (100 mL) and heated at 110° C. overnight. Acetic anhydride was evaporated upon completion of the reaction. Chromatography of the mixture by eluting with methanol-methylene chloride (1:9) resulted in 10.5 g (60%) of pure diacetate.

Step B

To a solution of diacetate (5 g, 21.1 mmol) in methanol-water (3:1, 40 mL) was added potassium carbonate (14.6 g, 105.5 mmol). After stirring for 3 h at room temperature, the reaction mixture was concentrated. The residue was chromatographed by eluting with methanol-methylene chloride (1:9) to give 2.2 g (68%) of crystalline diol.

Step C

The procedure for coupling is the same as described in Example 1.

The following compounds were prepared in this manner:

4.1: 6-Amino-9-neopentyl-8-{2-[5-(1'-(2-pyridyl)propane-1',3'-yl)phosphono]furanyl}purine. Anal. Cald. for $C_{22}H_{25}N_6O_4P+0.75H_2O+1HCl$: C, 50.97; H, 5.35; N, 16.21. Found: C, 51.19; H, 5.02; N, 15.91.

4.2: 6-Chloro-1-isobutyl-2-{5-[1'-(2-pyridyl)-propan-1',3'-yl] phosphono-2-furanyl}benzimidazole. Anal. Cald. for $C_{23}H_{23}ClN_3O_4P+1.5H_2O+0.3CH_2Cl_2$: C, 53.37; H, 5.11; N, 8.01. Found: C, 53.23; H, 4.73; N, 7.69.

4.3: 6-Chloro-1-isobutyl-2-{5-[1'-(4-pyridyl)-propan-1',3'-yl]phosphono-2-furanyl}benzimidazole. mp=165.0° C.(dec.); Mass Cald. for $C_{23}H_{23}ClN_3O_4P$: $MH^+454$: Found: $MH^+454$ 4.4: 4,5,6,7-Tetramethyl-1-isobutyl-2-{5-[1-(4-pyridyl)-propan-1,3-yl]phosphono-2-furanyl}benzimidazole. Anal. Cald. for $C_{27}H_{32}N_3O_4P+1.25H_2O$: C, 62.84; H, 6.74; N, 8.14. Found: C, 62.82; H, 6.81; N, 8.48.

4.5: 5-Chloro-4-methyl-1-isobutyl-2-{5-[1-(4-pyridyl)-propan-1,3-yl]phosphono-2-furanyl}benzimidazole. Anal. Cald. for $C_{24}H_{25}ClN_3O_4P+0.5H_2O+0.33HCl$: C, 56.86; H, 5.24; N, 8.29. Found: C, 56.97; H, 5.08; N, 8.26.

Step D

To a solution of 6-chloro-1-isobutyl-2-{5-[1'-(2-pyridyl)-propan-1',3'-yl]phosphono-2-furanyl}benzimidazole (172 mg, 0.36 mmol) in methylene chloride was added 3-chloroperoxybenzoic acid (252 mg, 0.72 mmol) at 0° C. The reaction was warmed to room temperature and allowed stir for 3 h. The solvent was evaporated under reduced pressure. Chromatography by elution with methanol-methylenechloride (5:95) resulted in 100 mg (56%) of pure N-oxide.

The following compound was prepared in this manner:

4.4: 6-Chloro-1-isobutyl-2-{5-[1'-(N-oxo-2-pyridyl)-propan-1',3'-yl]phosphono-2-furanyl}benzimidazole. mp=195.0° C.(dec.); Anal. Cald. for $C_{23}H_{23}ClN_3O_5P+0.25H_2O+0.25CH_2Cl_2$: C, 54.37; H, 4.71; N, 8.18. Found: C, 54.77; H, 4.86; N, 7.76.

Example 5

Preparation of 1'-phenyl substituted cyclic-1,3'-propyl esters

Step A: (*J. Org. Chem.*, 1988, 53, 911)

To a solution of oxalyl chloride (5.7 mL, 97 mmol) in dichloromethane (200 mL) at −78° C. was added dimethyl sulfoxide (9.2 mL, 130 mmol). The reaction mixture was stirred at −78° C. for 20 min before addition of 3-(benzyloxy)propan-1-ol (11 g, 65 mmol) in dichloromethane (25 mL). After an hour at −78 C, reaction was quenched with triethylamine (19 mL, 260 mmol) and warmed to room temperature. Work-up and column chromatography by elution with dichloromethane resulted in 8 g (75%) of 3-(benzyloxy)propan-1-al.

Step B

To a solution of 3-(benzyloxy)propan-1-al (1 g, 6.1 mmol) in THF at 0° C. was added a 1M solution of 4-fluorophenylmagnesium bromide in THF (6.7 mL, 6.7 mmol). The reaction was warmed to room temperature and stirred for 1 h. Work-up and column chromatography by elution with dichloromethane resulted in 0.7 g (44%) of alcohol.

Step C

To a solution of benzyl ether (500 mg) in ethyl acetate (10 mL) was added 10% $Pd(OH)_2$-C (100 mg). The reaction was stirred under hydrogen gas for 16 h. The reaction mixture was filtered through celite and concentrated. Chromatography of the residue by elution with ethyl acetate-dichloromethane (1:1) resulted in 340 mg (79%) of product.

Step D

The procedure for coupling is the same as described in Example 1.

The following compounds were prepared in this manner:

5.1: 6-Chloro-1-isobutyl-2-{5-[1'-(4-fluorophenyl)-propan-1',3'-yl]phosphono-2-furanyl}benzimidazole, minor isomer. Rf=0.45 in 5% MeOH-CH2Cl2. mp=207-208° C.; Anal. Cald. for $C_{24}H_{23}ClFN_2O_4P$: C, 58.96; H, 4.74; N, 5.73. Found: C, 59.20; H, 4.64; N, 5.59.

5.2: 6-Chloro-1-isobutyl-2-{5-[1'-(4-fluorophenyl)-propan-1',3'-yl]phosphono-2-furanyl}benzimidazole, major isomer. Rf=0.4 in 5% MeOH-CH2Cl2. mp 176-179° C.; Anal. Cald. for $C_{24}H_{23}ClFN_2O_4P+0.5H_2O$: C, 57.90; H, 4.86; N, 5.63. Found: C, 57.60; H, 4.68; N, 5.54.

Example 6

Preparation of 1'-phenyl substituted cyclic-1',3'-propyl esters

Step A: (*J. Org. Chem.*, 1990, 55, 4744)

To a solution of diisopropylamine (4.1 mL, 29.4 mmol) in ether (40 mL) at −78° C. was added 2.5M n-butyl lithium (11.8 mL, 29.4 mmol). The reaction was stirred for 15 min before adding t-butyl acetate (4 mL, 29.4 mmol) in ether (10 mL). After 20 min, aldehyde (3 g, 14 mmol) in ether (10 mL) was added and warmed to room temperature where it was stirred for 16 h. Work-up and column chromatography by elution with ethyl acetate-dichloromethane (1:9) resulted in 3.3 g (33%) of addition product.

Step B

To a solution of t-butyl ester (1.5 g, 4.5 mmol) in THF (20 mL) was added 1M lithium aluminum hydride at 0° C. The reaction mixture was warmed to room temperature and stirred for 2 h. The reaction was quenched with ethyl acetate and saturated aqueous sodium sulfate was added to precipitate the salts. Filtration and concentration of solvent resulted in a crude diol. Column chromatography by elution with ethyl acetate-dichloromethane (1:1) gave 970 mg (82%) of pure diol.

Step C

The procedure for coupling is the same as described in Example 1

The following compounds were prepared in this manner:

6.1: 6-Chloro-1-isobutyl-2-{5-[1'-(3-bromo-4-methoxyphenyl)-propan-1',3'-yl]phosphono-2-furanyl}benzimidazole, major isomer. Rf=0.35 in 70%

EtOAc-CH2Cl2. mp=167-169° C.; Anal. Cald. for C25H25BrClN2O5P: C, 51.79; H, 4.35; N, 4.83. Found: C, 51.77; H, 4.25; N, 4.73.

6.2: 6-Chloro-1-isobutyl-2-{5-[1'-(3-Bromo-4-methoxyphenyl)-propan-1',3'-yl]phosphono-2-furanyl}benzimidazole, minor isomer. Rf=0.3 in 70% EtOAc-CH2Cl2. Anal. Cald. for C25H25BrClN2O5P+0.55CHCl3: C, 47.54; H, 3.99; N, 4.34. Found: C, 47.50; H, 3.89; N, 3.99.

Example 7

Preparation of 2'-substituted cyclic-1',3'-propyl esters

Step A

Monoacetylation of 2-(hydroxymethyl)-1,3-propanediol

To a solution of 2-(hydroxymethyl)-1,3-propanediol (1 g, 9.4 mmol) in pyridine (7.5 mL) at 0° C. was added acetic anhydride (0.89 mL, 9.4 mmol) slowly. The resulting solution was warmed to room temperature and stirred for 16 h. The reaction was concentrated under reduced pressure and chromatographed by eluting with methanol-dichloromethane (1:9) to give 510 mg (36%) of pure acetate.

Methylcarbonate formation of 2-(hydroxymethyl)-1,3-propanediol

To a solution of 2-(hydroxymethyl)-1,3-propanediol (1 g, 9.4 mmol) in dichloromethane (20 mL) and pyridine (7.5 mL) at 0° C. was added methyl chloroformate (0.79 mL, 9.4 mmol) slowly. The resulting solution was warmed to room temperature and stirred for 16 h. The reaction was concentrated under reduced pressure and chromatographed by eluting with methanol-dichloromethane (1:4) to give 650 mg (42%) of pure carbonate.

Step B

The procedure for coupling is the same as described in Example 1.

The following compounds were prepared by step B or by step A and B:

7.1: 6-Chloro-1-isobutyl-2-{5-[2'-(hydroxymethyl)-propan-1',3'-yl]phosphono-2-furanyl}benzimidazole. mp=164-165° C.; Anal. Cald. for C19H22ClN2O5P: C, 53.72; H, 5.22; N, 6.59. Found: C, 53.62; H, 5.18; N, 6.42.

7.2: 6-Chloro-1-isobutyl-2-{5-[2'-(acetoxymethyl)-propan-1',3'-yl]phosphono-2-furanyl}benzimidazole. mp=132-134° C.; Anal. Cald. for C21H24ClN2O6P: C, 54.03; H, 5.18; N, 6.00. Found: C, 54.17; H, 4.99; N, 5.81.

7.3: 6-Chloro-1-isobutyl-2-{5-[2'-(methoxycarbonytoxymethyl)-propan-1',3'-yl]phosphono-2-furanyl}benzimidazole. mp=138-140° C.; Anal. Cald. for C21H24ClN2O7P: C, 52.24; H, 5.01; N, 5.80. Found: C, 52.13; H, 5.07; N, 5.51.

7.4: 4-Amino-5-fluoro-7-ethyl-1-isobutyl-2-{5-[2'-(acetoxymethyl)-propan-1',3'-yl]phosphono-2-furanyl}benzimidazole.; Anal. Cald. for C23H29FN3O6P+0.3H2O: C, 55.38; H, 5.98; N, 8.42. Found: C, 55.60; H, 6.31; N, 8.02.

7.5: 6-Amino-9-neopentyl-8-{5-[2'-(acetoxymethyl)-propan-1',3'-yl]phosphono-2-furanyl}purine. mp=164-165° C.; Anal. Cald. for C20H26N5O6P: C, 51.84; H, 5.65; N, 15.11. Found: C, 52.12; H, 5.77 N, 14.59.

7.6: 4-Amino-5-fluoro-7-ethyl-1-isobutyl-2-{5-[2'-(cyclohexanecarbonyloxymethyl)-propan-1',3'-yl]phosphono-2-furanyl}benzimidazole. mp=62-63° C.; Anal. Cald. for C28H37FN3O6P: C, 59.89; H, 6.64; N, 7.48. Found: C, 59.97; H, 6.60; N, 7.33.

7.7: 4-Amino-5-fluoro-7-ethyl-1-isobutyl-2-{5-[2'-(hydroxymethyl)-propan-1',3'-yl]phosphono-2-furanyl}benzimidazole. Anal. Cald. for C21H27N3O5P+0.6 EtOAc: C, 55.73; H, 6.36; N, 8.33. Found: C, 55.81; H, 6.08; N, 8.02.

7.8: 4,5,6,7-Tetramethyl-1-isobutyl-[2-(5-[2-methoxycarbonyloxymethyl)-propan-1,3-yl]phosphono)furanyl]benzimidazole, minor isomer. Rf=0.53 in 5% MeOH-CH2Cl2. Anal. Cald. for C25H33N2O7P+0.25H2O: C, 58.99; H, 6.63; N, 5.50. Found: C, 59.21; H, 6.73; N, 5.48.

7.9: 4,5,6,7-Tetramethyl-1-isobutyl-[2-(5-[2-(methoxycarbonyloxymethyl)-propan-1,3-yl]phosphono)furanyl]benzimidazole, major isomer. Rf=0.54 in 5% MeOH-CH2Cl2. Anal. Cald. for C25H33N27P+H2O: C, 57.47; H, 6.75; N, 5.36. Found: C, 57.72; H, 6.86; N, 5.22.

7.10: 5-Chloro-4-methyl-1-isobutyl-[2-(5-[2-(methoxycarbonyloxymethyl)-propan-1,3-yl]phosphono)furanyl]benzimidazole, minor isomer. Rf=0.59 in 100% EtOAc. Anal. Cald. for C22H26ClN2O7P+0.75H2O: C, 51.77; H, 5.43; N, 5.49. Found: C, 51.80; H, 5.35; N, 5.39.

7.11: 5-Chloro-4-methyl-1-isobutyl-[2-(5-[2-(methoxycarbonyloxymethyl)-propan-1,3-yl]phosphono)furanyl]benzimidazole, major isomer. Rf=0.54 in 100% EtOAc. Anal. Cald. for C22H26ClN2O7P+H2O: C, 51.32; H, 5.48; N, 5.44. Found: C, 51.36; H, 5.25; N, 5.25.

Example 8

8.1: 5-Bromo-1-(B-D-ribofuranosyl)-imidazole-4-carboxamide 8.2: 5-Bromo-1-(2,3,5-tri-O-acetyl-β-D-ribo-furanosyl)imidazole-4-carboxamide A stirred mixture of AICA riboside (200 g, 0.774 mol) in pyridine (1200 mL) was cooled in an ice bath. Acetic anhydride (310 mL, 2.80 mol) was slowly added over 25 minutes. The ice bath was removed and the solution stirred at room temperature for 2½ h. TLC (silica gel, 9/1 methylene chloride/methanol) indicated the reaction was complete. The solvent was evaporated to give a pale orange oil. Diethyl ether (600 mL) was added to the oil and the mixture vigorously stirred. The upper ether phase was decanted. The thickened tar was triturated/decanted three times with 300 mL of ether. The resulting orange tar was dissolved in warm ethanol (600 mL). The solution was stirred overnight at room temperature and the resulting solid filtered, washed with cold ethanol (75 mL) and vacuum dried to yield AICA riboside triacetate, 203 g (68%) [melting point=126.5-128.5° C.; TLC (silica gel, 9/1 methylene chloride/methanol): rf=0.4]. The diethyl ether washings (from above) were combined and stored at room temperature overnight upon which a white crystalline solid formed. The solid was filtered, washed with cold ethanol (50 mL) and vacuum dried to give an additional 26.5 g (8.9%).

AICA riboside triacetate (50.0 g, 130 mmol), CuBr$_2$ (14.5 g, 64.9 mmol), LiBr (45 g, 0.52 mol) and acetonitrile (500 mL) were combined under an atmosphere of argon and cooled to 15° C. Isobutylnitrite (19.3 mL, 162 mmol) was added dropwise over 10 minutes. The cooling bath was removed and the solution stirred for 20 h. The solvent was evaporated and the residue partitioned between methylene chloride (600 mL) and 10% NaHSO$_3$ solution (150 mL). The organic phase was separated, evaporated to 200 mL and diluted with ethyl acetate (250 mL). The solution was extracted twice with 50 mL portions of saturated NaHCO$_3$.

Silica gel (175 g) was added to the organic phase and the mixture stirred for 15 minutes. The mixture was filtered through a pad of Celite and the pad washed with ethyl acetate (400 mL). The combined filtrate was evaporated to give 39.6 g of a tar which was dissolved in warm water (400 mL) and stirred at room temperature overnight. A white precipitate formed and the mixture was refrigerated for several hours. The solid was filtered, washed with cold water (100 mL) and vacuum dried to yield. 20.5 g of an off-white powder (35%) [mp=133-135° C., TLC (silica gel, EtOAc): rf=0.75].

The appropriate chloro and iodo analog were made by using this method with the substitution of copper(II) chloride or copper(II) iodide for the copper(II) bromide.

Example 9

9.1: 5-Bromo-1-(β-D-ribofuranosyl)-imidazole-4-carboxamide-5'-monophosphate

To a cold (0° C.) solution of 5-bromo-1-(β-D-ribofuranosyl)-imidazole-4-carboxamide (0.03 g) (from example 9) in 0.2 mL of triethyl phosphite was added phosphorous oxychloride (0.026 g). The mixture was allow to warm to room temperature over 3 hours and diluted with 1 M aqueous sodium hydroxide solution until the pH reached 8. The mixture was stirred for 1.5 hours and passed through Dowex® ion exchange resin. The resin was washed first with water and then with 6 M formic acid solution eluting the product whose NMR spectra is consistent with its structure and a satisfactory elemental analysis.

Example 10

10.1: 5-Trifluoromethyl-1-(B-D-ribofuranosyl)-imidazole-4-carboxamide

To a solution of 3.5 g of AICA riboside in 65 mL of 50% aqueous tetrafluoroboric acid was added a solution of 1.71 g of sodium nitrite in 2 mL of water. The mixture was irradiated with a medium pressure lamp in a quartz tube for 18 hours and cooled to 0° C. The pH was adjusted to ~5 with sodium hydroxide solution and the mixture extracted with ethyl acetate. The organic layer was dried over magnesium sulfate and the solvent removed under reduced pressure. The residue was chromatographed on silica and eluted with methanol/methylene chloride (3% to 10% MeOH) to give ethyl 5-fluoroimidazole-4-carboxylate, melting point 153-154° C.

This compound was dissolved in methanol and the solution saturated with ammonia in a steel bomb. The bomb was heated a 100° C. for 48 hours. The bomb was carefully opened and the solvent removed under reduced pressure, and the residue chromatographed on silica (1% to 10% methanol in methylene chloride) to give 5-fluoroimidazole-4-carboxamide, melting point 253-254° C.

This compound (500 mg) was dissolved in hexamethyldisilizane (5 mL) and trimethylchlorosilane (0.9 mL) was added. The mixture was heated to 130° C. for 2.5 hours, cooled and the solvent removed under reduced pressure. The residue was dissolved in 2.4 mL of methylene chloride and added to a solution of 1-O-acetyl-2,3,5-tri-O-benzoyl-D-ribose (1.96 g) in methyene chloride. The mixture was cooled to 0° C. and a solution of tin tetrachloride (0.6 mL) in 3.4 mL of methylene chloride was added. The mixture was stirred overnight, diluted with ethyl acetate and extracted with saturated aqueous sodium bicarbonate and with water. The organic layer was dried over magnesium sulfate and the solvent removed. The reside was chromatographed on silica (methylene chloride to 5% methanol/methylene chloride) to give 561 milligrams of coupled product.

The compound was dissolved in methanol and the solution saturated with ammonia and stirred for 18 hours. The solvent was removed under reduced pressure and the residue triturated with ether. The solid was chromatographed on silica (10% methanolvmethylene chloride) to give 0.150 milligrams of final product.

Other 5-substituted analogs were made by this method of coupling the appropriate substituted imidazole with 1-O-acetyl-2,3,5-tri-O-benzoyl-D-ribose. For example, the 5-methyl compound (mp 179-180° C.) and 5-trifluoromethyl compound (mp 255° C. [decomposition]) were prepared in this manner. The substituted imidazoles were made by the general method of R. Paul, *J. Med. Chem.* 1985, 28, 1198-1203.

Example 11

Preparation of $N^9$-neopentyl-8-(2-(5-phosphono) furanyl)adenine

Step A. A solution of 5-amino-4,6-dichloropyrimidine (1 mmol) in nBuOH was treated with $Et_3N$ (1.2 mmol) and neopentylamine (1.05 mmol) at 80° C. After 12 h, the cooled reaction mixture was evaporated under vacuum and the residue was chromatographed to give 6-chloro-5-amino-4-(neopentylamino)-pyrimidine as a yellow solid.

Step B. The 6-chloro-5-amino-4-(2-neopentylamino)pyrimidine (1 mmol) in DMSO was treated with 5-diethylphosphono-2-furaldehyde (1.5 mmol) and $FeCl_3$-silica (2.0 mmol) at 80° C. for 12 h. The cooled reaction mixture was filtered and the filtrate was evaporated under vacuum. Chromatography afforded 6-chloro-$N^9$-neopentyl-8-(2-(5-diethyl-phosphono)furanyl)purine as a yellow solid.

Step C. 6-Chloro-$N^9$-neopentyl-8-(2-(5-diethylphosphono) furanyl)purine (1 mmol) in THF-DMSO was treated with liquid ammonia (2 mL) in a steel bomb. After 12 h, the reaction was evaporated under vacuum and the residue was purified through chromatography to give $N^9$-neopentyl-8-(2-(5-diethylphosphono)furanyl)adenine as a yellow solid.

Step D. A solution of $N^9$-neopentyl-8-(2-(5-diethylphosphono)furanyl)-adenine (1 mmol) in acetonitrile was treated with bromotrimethylsilane (10 mmol). After 12 h, the reaction was evaporated under vacuum and the residue was treated with a mixture of water and acetonitrile. The solid was collected through filtration.

11.1: $N^9$-neopentyl-8-(2-(5-phosphono)furanyl)adenine. mp >230° C.; Anal. calcd. for $C_{14}H_{18}N_5O_4P$: C, 47.87; H, 5.16; N, 19.94. Found: C, 47.59; H, 4.92; N, 19.53.

11.2: 2-{5-[9-(2-Phenylethyl)-8-adeninyl]}furanylphosphonic acid. mp 242-244° C.; Anal. calcd. for C17H16N5O4P+1.37H2O: C, 50.16; H, 4.64; N, 17.21. Found: C, 48.95; H, 4.59; N, 16.80.

Examples 12

Preparation of $N^9$-cyclohexylethyl-8-(phosphonomethoxymethyl)adenine

Step A. A mixture of $N^9$-cyclohexylethyl-8-bromoadenine (1 mmol), tetrakis (triphenylphosphine)palladium (0.05 mmol), and triethylamine (5 mmol) in DMF in a sealed tube was warmed at 110° C. under 50 psi of carbon monoxide. After 24 h the cooled reaction mixture was evaporated and purified through chromatography to give $N^9$-cyclohexylethyl-8-methoxycarbonyladenine as a yellow solid.

Step B. A solution of $N^9$-cyclohexylethyl-8-methoxycarbonyladenine (1 mmol) in tetrahydrofuran was treated with lithium aluminum hydride (1 mmol) at 0° C. for 1 h. Extraction and chromatography give $N^9$-cyclohexylethyl-8-hydroxymethyladernine as a white solid.

Step C. A solution of $N^9$-cyclohexylethyl-8-hydroxymethyladenine (1 mmol) in methylene chloride was treated with $PBr_3$ (1 mmol) at 25° C. for 1 h. Extraction and chromatography give $N^9$-cyclohexylethyl-8-bromomethyl-adenine as a white solid.

Step D. A solution of $N^9$-cyclohexylethyl-8-bromomethyladenine (1 mmol) in DMF was treated with a solution of diethyl hydroxymethylphosphonate sodium salt (1 mmol) in DMF at 25° C. for 1 h. Extraction and chromatography gave $N^9$-cyclohexylethyl-8-diethylphosphonomethoxy-methyladenine as a white solid.

Step E. $N^9$-cyclohexylethyl-8-diethylphosphonomethoxymethyladenine was subjected to Step F in Example 1.

12.1: $N^9$-cyclohexylethyl-8-(phosphonomethoxymethyl)adenine as a white solid. mp>250° C.; Anal. calcd. for C15H24N5O4P+1H2O: C, 46.51; H, 6.76; N, 18.08. Found: C, 46.47; H, 6.71; N, 17.91.

Example 13

Preparation of 2-methylthio-6-amino-$N^9$-isobutyl-8-(2-(5-phosphono)furanyl)purine Step A: 2-Methylthio-4,5,6-triaminopyrimidine and 5-diethylphosphono-2-furaldehyde was subjected to the procedures of Step B in Example 1 to give 6-amino-2-methylthio-8-(2-(5-diethylphosphono)furanyl)purine as a yellow solid. TLC: Rf=0.27, 80% EtOAc-hexane.

Step B: A solution of 6-amino-2-methylthio-8-(2-(5-diethylphosphono)-furanyl)purine (1 mmol) in DMF was treated with cesium carbonate (2 mmol) and isobutyl bromide (1.5 mmol) at 80° C. for 12 h. The cooled reaction mixture was subjected to extraction and chromatography to give 6-amino-$N^9$-isobutyl-2-methylthio-8-(2-(5-diethylphosphono)furanyl)purine as a yellow solid.
TLC: Rf=0.27, 80% EtaAc-hexane.

Step C: 6-Amino-$N^9$-isobutyl-2-methylthio-8-(2-(5-diethylphosphono)-furanyl)purine was subjected to Step F.

13.1: 6-amino-$N^9$-isobutyl-2-methylthio-8-(2-(5-phosphono)-furanyl)purine as a white solid. mp 220° C.; Anal. calcd. for $C_{14}H_{18}N_5O_4PS$+0.25 HBr+0.25 EtOAc: C, 42.33; H, 4.8; N, 16.45. Found: C, 42.42; H, 4.53; N, 16.39.

Example 14

Preparation of 2-Furaldehyde-5-diethylphosohonate

To a solution of 168 g (1.75 mol) 2-furaldehyde in 500 mL toluene was added 215 mL(1.75 mol) of N,N'-dimethylethylene diamine. The solution was refluxed using a Dean Stark trap to remove $H_2O$. After 2 hours of reflux, the solvent was removed under reduced pressure.

The resulting dark mixture was vacuum distilled (3 mm Hg) and the fraction at 59-61° C. was collected yielding 247.8 g(85%) of clear, colorless oil.

A solution of 33.25 g (0.2 mol) furan-2-(N,N'-dimethylimidazolidine) and 30.2 mL (0.2 mol) tetramethylenediamine in 125 mL THF was cooled in a dry ice/IPA bath. A solution of 112 mL n-BuLi in hexane (0.28 mol, 2.5M) was added dropwise, maintaining temperature between −50 and −40° C. during addition. The reaction was allowed to warm to 0° C. over 30 minutes and was maintained at 0° C. for 45 minutes. The reaction was then cooled in a dry ice/IPA bath to −55° C. This cooled solution was transferred to a solution of 34.7 mL (0.24 mol) diethylchlorophosphate in 125 mL THF and cooled in a dry ice/IPA bath over 45 minutes maintaining the reaction temperature between −50° C. and −38° C. The reaction was stirred at rt overnight. The reaction mixture was evaporated under reduced pressure. Ethyl acetate and $H_2O$ were added to the residue and the layers separated. The $H_2O$ layer was washed with ethyl acetate. The ethyl acetate layers were combined, dried over magnesium sulfate and evaporated under reduced pressure yielding 59.6 g (98%) of brown oil.

To a solution of 59.6 g 5-diethylphosphonofuran-2-(N,N'-dimethylimidazolidine) in 30 mL $H_2O$ was added 11.5 mL of conc. $H_2SO_4$ dropwise until pH=1 was obtained. The aqueous reaction mixture was extracted with ethyl acetate. The ethyl acetate layer was washed with saturated sodium bicarbonate, dried over magnesium sulfate and evaporated to a brown oil. The brown oil was added to a silica column and was eluted with hexane/ethyl acetate. Product fractions were pooled and evaporated under reduced pressure yielding a dark yellow oil, 28.2 g(62%).

The following general procedures are used in the synthesis of the benzimidazole parent drugs:

Example 15

General methods for the preparation of substituted 1,2-phenylenediamines

Method A

Step A

Bromination of Nitroanilines

To a solution of 1.0 mmol of substituted nitroaniline in 10 mL of $CHCl_3$ or a mixture of $CHCl_3$ and MeOH(7:1) was added a solution of bromine in 5 mL of $CHCl_3$ over a period of 30 min. After stirring for 2 days at rt, extractive isolation provided the bromination product.

Step B

Reduction of Nitroanilines

To a solution of 1.0 mmol of substituted nitroaniline in 15 mL of MeOH was added 15 mL of saturated solution of sodium dithionite. Filtration followed by removal of solvent and extraction with EtOAc provided the pure diamine.

Step C

Preparation of 2,1,3-benzoselenadiazole

To a solution of 1.0 mmol of substituted diamine in 3 mL of 50% aq. ethanol was added a solution of 1.0 mmol of $SeO_2$ in 1.5 ml of $H_2O$. The mixture quickly thickened to a slurry. The solid separated out, was filtered, washed with water, and dried.

Step D

Nitration of Benzoselenadizoles

To a cold (0° C.) suspension of 1.0 mmol of-substituted 2,1,3-benzoselenadiazole was added dropwise a solution of 2.0 mmol of $HNO_3$ in 1 mL of $H_2SO_4$. The resultant suspension was stirred for 2 h at 15° C. The dark solution was poured onto ice, filtered, washed with water, and dried.

In the case of 5-fluoro-7-bromo-2,1,3-benzoselenadiazole there were two products in 2:1 ratio, major being the required compound, 4-nitro-5-fluoro-7-bromo-2,1,3-benzoselenadiazole. This was extracted with hot toluene from the byproduct, 4-nitro-5-hydroxy-7-bromo-2,1,3-benzoselenadiazole.

Step E

Substituted 3-nitro-1,2-phenylenediamine preparation

A mixture of 1.0 mmol of substituted 4-nitro-2,1,3-benzoselenadiazole in 3 mL of 57% HI was stirred at rt for 2 h. Saturated $NaHSO_3$ was added and the mixture was neutralized with concentrated $NH_3$ solution. The product was extracted with $CHCl_3$(5×10 mL) and the extracts were washed, dried, and evaporated.

Method B

From 2-nitrohalobenzenes

To a solution of 20 mmol of substituted 2-halonitrobenzene in 70 mL of DMF was added 35 mmol of alkyl or arylamine at 0° C. After 0.5 h TLC (ethyl acetate/hexane 2:1) indicated the completion of reaction. The reaction mixture was evaporated under reduced pressure. The residue was dissolved in ethyl acetate and washed with water. The organic layer was dried, and evaporated to yield the displacement products.

Method C

From 2-nitroanilines

To a solution of 10 mmol of substituted 2-nitroaniline, 20 mmol of alkyl or arylaldehyde, and 60 mmol of acetic acid in 30 mL of 1,2-dichloroethane was added 30 mmol sodium triacetoxy borohydride at 0° C. The reaction was stirred overnight under nitrogen atmosphere and was quenched with saturated bicarbonate solution. The product was extracted with EtOAc (3×75 mL) and the extract was washed, dried and evaporated. The residue was chromatographed on a silica gel column eluting with hexane-ethyl acetate (3:1) to yield the product.

These nitroanilines can be reduced to 1,2-phenylenediamines by the procedure given in the Example 2, Method A, Step 2.

Example 16

General Procedures for Alkylation

Method A

A suspension of 1.5 mmol cesium carbonate, 1.0 mmol of substituted benzimidazole-2-(5-diethylphosphonate)furan and 1.0 mmol of electrophile in 5 mL of dry DMF was heated at 80° C. for 1-16 h. Extraction and chromatography provided the alkylation product.

Example 17

General Procedures for Pd Coupling

Method A

A mixture of 1.0 mmol of bromo substituted 2-[(5-diethylphosphonate)furanyl]benzimidazole compound, 2.0 mmol of vinyltributyltin or allyltributyltin, and 0.1 mmol of $Pd(PPh_3)_2Cl_2$ or $Pd(PPh_3)_4$ in 4 mL of DMF was stirred and heated at 90° C. for 1-16 h. Extraction and chromatography provided the coupled compound.

Method B

A mixture of 1.0 mmol of bromo substituted 2-[(5-diethylphosphonate)furanyl]benzimidazole, 2.0 mmol of propargyl alcohol or any terminal acetylenic compound, 0.1 mmol of $Pd(PPh_3)_2Cl_2$, and 0.1 mmol of CuI in 1 mL of $Et_3N$ and 10 mL of $CH_3CN$ was stirred and heated at 50-80° C. for 1-16 h. Extraction and chromatography provided the coupled compound.

Method C

A mixture of 1.0 mmol of bromo substituted 2-[(5-diethylphosphonate)furanyl]benzimidazole, 5.0 mmol of substituted phenylboronic acid, 0.1 mmol of $Pd(PPh_3)_4$, 5 mL of sat. $Na_2CO_3$ and 2 mL of EtOH in 10 mL of diglyme was stirred and heated at 80-90° C. for 1-16 h. Extraction and chromatography provided the coupled compound.

The compounds thus obtained can be modified as needed. For example vinyl or propargyl alcohol derivatives can be hydrogenated (see Example 7, Method A) to give the ethyl or propyl alcohol derivatives respectively. These alcohol can be further modified as required via alkyl halides (see Example 6) or alkyl sulfonates etc. to number of substituted alkyl compounds by subjecting them to nucleophilic substitution reactions (March, *Advanced Organic Chemistry*, Wiley-Interscience, Fourth Edition, 1992, 293-500). See Example 5 for the cyclopropanation of the vinyl derivative.

Example 18

Cyclopropynation of the 4-nitro-7-vinyl-5-fluoro-1-isobutyl-2-(2-diethylphosphono-5-furanyl)benzimidazole To a suspension of 1.0 mmol of 4-nitro-7-vinyl-5-fluoro-1-isobutyl-2-(2-diethylphosphono-5-furanyl)benzimidazole and 0.1 mmol of $Pd(OAc)_2$ in 8 mL of ether was added an ether solution of diazomethane(generated from 3.0 g of 1-methyl-3-nitro-1-nitrosoguanidine) at 0° C. After stirring at rt 20 h. solvent was removed and the residue was subjected to chromatography to give 4-nitro-7-cyclopropyl-5-fluoro-1-isobutyl-2-(2-diethylphosphono-5-furanyl)benzimidazole.

Example 19

Halogenation of the 4-amino-7-(4-hydroxybutyl)-5-fluoro-1-isobutyl-2-(2-diethylphosohono-5-furanyl)benzimidazole To a cold (0° C.) solution of 1.0 mmol of 4-amino-7-(4-hydroxybutyl)-5-fluoro-1-isobutyl-2-(2-diethylphosphono-5-furanyl)benzimidazole in 20 mL of $CH_2Cl_2$ was added 3.0 mmol of $PPh_3$ and 3.0 mmol of $CBr_4$. After 40 min. at rt solvent was removed and the residue was subjected to chromatography to give 4-amino-7-(4-bromobutyl)-5-fluoro-1-isobutyl-2-(2-diethylphosphono-5-furanyl)benzimidazole. $CCl_4$ gave the corresponding chloro compound.

Example 20

General Procedures for Reduction

Method A

A mixture of 1.0 mmol of alkylation product and 20 mg of 10% Pd/C in 5 mL of DMF or MeOH was hydrogenated using H$_2$ in balloon for 0.5-16 h. The reaction mixture was filtered through celite and chromatographed to provide the reduction product as an oil.

Method B

To a solution of 1.0 mmol of substituted nitroaniline in 15 mL of MeOH was added 15 mL of saturated solution of sodium dithionite. Filtration followed by removal of solvent and extraction with EtOAc or CHCl$_3$ provided the pure diamine.

These primary aromatic amines can also be modified as needed. For example N-acetyl derivatives can be prepared by treatment with acetyl chloride or acetic anhydride in presence of a base such as pyridine and mono-, or di-alkylamines can be synthesized by direct alkylation or by reductive alkylation.

General Procedures for Phosphonate Hydrolysis

Example 21

TMSBr Hydrolysis

To a solution of 1.0 mmol of substituted 2-[(5-diethylphosphonate)furanyl]benzimidazole in 5 mL of anhydrous CH$_2$Cl$_2$ was added 10.0 mmol TMSBr at 0° C. After 16 h stirring at rt the solvent and excess TMSBr were removed under reduced pressure. The residue was taken into 15 mL of a 1/5 mixture of acetone/water and was stirred for 16 h at rt. The resulting solid was filtered, washed with water, EtOAc, and MeOH and was dried under vacuum at 50° C.

The following compounds were prepared in this manner:

21.1: 4-Amino-1-(3-carbomethoxybenzyl)-2-[2-(5-phosphono)furanyl]benzimidazole. mp=198-202° C.; Anal. Cald. for C$_{20}$H$_{18}$N$_3$O$_6$P: C, 55.55; H, 4.39; N, 9.63. Found: C, 55.12; H, 4.29; N, 9.18.

21.2: 4-Amino-1-(3-chloropropyl)-2-[2-(5-phosphono)furanyl] benzimidazole. mp>>250° C.; Anal. Cald. for C$_{14}$H$_{15}$N$_3$O$_4$ClP+0.7H$_2$O: C, 44.83; H, 4.61; N, 10.37. Found: C, 44.50; H, 4.29; N, 10.96.

21.3: 4-Amino-1-(3-furanylmethyl)-2-[2-(5-phosphono)furanyl] benzimidazole. mp>>230° C.; Mass. Cald. 358; Obs. 358.

21.4: 4-Amino-5-ethyl-1-isobutyl-2-(2-phosphono-5-furanyl) benzimidazole. mp=220-225° C.; Anal. Cald. for C, 51.34; H, 5.95; N, 10.21.

21.5: 4-Amino-5-fluoro-7-chloro-1-isobutyl-2-(2-phosphono-5-furanyl)benzimidazole. mp=220-225° C.; Anal. Cald. for C$_{15}$H$_{16}$N$_3$O$_4$FClP+0.9HBr; C, 12; H, 3.70; N, 9.12. Found: C, 39.15; H, 3.46; N, 8.77

21.6: 4-Amino-1-[(2-ethyl)pentyl]benzimidazol-2-yl-methylenoxymethyl phosphonic acid. mp=85° C.; Anal. Cald. for C$_{15}$H$_{24}$N$_3$O$_4$P+1/2 H$_2$O+2 HBr+1/3 toluene: C, 38.05; H, 5.49; N, 7.78. Found: C, 38.30; H, 5.45; N, 7.34.

21.7: 4-Amino-5-fluoro-1-cyclopropylmethyl-2-(2-phosphono-5-furanyl)benzimidazole. mp=258-260° C.; Anal. Cald. for C$_{15}$H$_{15}$N$_3$O$_4$PF+0.3H$_2$O: C, 50.51; H, 4.41; N, 11.78. Found: C, 50.21; H, 4.28; N, 11.45.

21.8: 4-Amino-7-ethyl-5-fluoro-1-isobutyl-2-(2-phosphono-5-furanyl)benzimidazole. mp=245-246° C.; Anal. Cald. for C$_{17}$H$_{21}$N$_3$O$_4$FP+0.4H$_2$O: C, 52.55; H, 5.66; N, 10.81. Found: C, 52.40; H, 5.79; N, 10.47.

21.9: 4-Amino-7-(propane-3-ol)-5-fluoro-1-isobutyl-2-(2-phosphono-5-furanyl)benzimidazole. mp=170-173° C.; Anal. Cald. for C$_{18}$H$_{23}$N$_3$O$_5$FP+1.0H$_2$O: C, 50.35; H, 5.87; N, 9.79. Found: C, 50.31; H, 5.80; N, 9.62.

21.10: 4-Amino-5-fluoro-7-(3-bromopropyl)-1-isobutyl-2-(2-phosphono-5-furanyl)benzimidazole. mp=190-195° C.(dec.); Anal. Cald. for C$_{18}$H$_{22}$N$_3$O$_4$FBrP: C, 45.59; H, 4.68; N, 8.86. Found: C, 45.87; H, 4.87; N, 8.70.

21.11: 4-Amino-5-fluoro-7-(4-bromobutyl)-1-isobutyl-2-(2-phosphono-5-furanyl)benzimidazole. mp=200-220° C.(dec.); Anal. Cald. for C$_{19}$H$_{24}$N$_3$O$_4$FBrP+0.5H$_2$O: C, 45.89; H, 5.07; N, 8.45. Found: C, 45.61; H, 5.10; N, 8.20.

21.12: 4-Amino-5-fluoro-7-(3-N,N-dimethylpropylamine)-1-isobutyl-2-(2-phosphono-5-furanyl)benzimidazole hydrobromide salt. mp=208-212° C.(dec.); Anal Cald. for C$_2$OH$_{28}$N$_4$O$_4$FP+1.0 HBr+2.0 H$_2$O: C, 43.25; H, 5.99; N, 10.09. Found: C, 43.39; H, 5.74; N, 9.90.

Example 22

HBr Hydrolysis

A solution of 1.0 mmol of substituted 2-[(5-diethylphosphonate)furanyl]benzimidazole in 10 ml of 30% HBr was heated at 80° C. for 0.5-3 h. The solvent was removed under reduced pressure and the residue was taken into 3 ml of water. The solid precipitated was filtered washed with water and dried under vacuum at 50° C.

The following compounds were prepared in this manner:

22.1: 2-(1,8-Diaza-1,2,3,4-tetrahydroacenaphthen-9-yl)furan-5-phosphonic acid. Anal. Cald. for C$_{14}$H$_{13}$N$_2$PO$_4$+0.5 HBr+0.5H$_2$O: C, 47.54; H, 4.13; N, 7.48. Found: C, 47.33; H, 4.16; N, 7.48.

22.2: 4-Hydroxy-1-isobutyl-2-(2-phosphono-5-furanyl)benzimidazole. mp=244-245° C.; Anal. Cald. for C$_{15}$H$_{17}$N$_2$O$_5$P+1.1H$_2$O: C, 50.59; H, 5.43; N, 7.87. Found: C, 50.33; H, 5.58; N, 7.89.

22.3: 4-Fluoro-1-neopentyl-2-(2-phosphonofuranyl)benzimidazole. Anal. Cald. for C$_{16}$H$_{18}$N$_2$PO$_4$F+0.1 H$_2$O+ 0.3CH$_3$CO$_2$H: C, 53.58; H, 5.25; N, 7.53. Found: C, 53.84; H, 5.12; N, 7.05.

22.4: 5-Phosphonomethylenoxy-1,2,3,4-tetrahydropyrido[1, 2-a] benzimidazole. mp=218-222°°C.; Anal. Cald. for C$_{12}$H$_{15}$N$_2$PO$_4$+H$_2$O+0.9HBr: C, 38.63; H, 4.84; N, 7.51. Found: C, 38.96; H, 4.46; N, 7.41.

22.5: 6-Chloro-1-isobutyl-2-(2-phosphono-5-furanyl) benzimidazole. mp 195-200° C.; Anal. Cald. for C15H16ClN2O4P+0.5HBr: C, 45.59; H, 4.21; N, 7.09; Cl, 8.97; C, 46.02; H, 3.86; N, 7.01; Cl, 8.63.

22.6: 5-Chloro-1-isobutyl-4-methyl-2-(2-phosphono-5-furanyl) benzimidazole". mp=193-196° C. Anal. Cald. for C16 H18 Cl N2 O4P+1.67 H2O: C, 48.19; H, 5.39; N, 7.02; Found: C, 48.24; H, 5.19; N, 6.85.

22.7: N-(Phosphonomethyl)benzimidazole-2-carboxamide. mp=258-260° C. Anal. Cald. for C$_9$H$_{10}$N$_3$O$_4$P+0.15 AcOH; C, 42.28; H, 4.04; N, 15.91; Found. C, 42.60; H, 4.02; N, 15.70.

Example 23

Preparation of 1-isobutyl-4-amino-5-fluoro-7-bromo-2-[3-phospho(methoxymethyl)] benzimidazole Step A Synthesis of Diethylphospho Methyl Acetaldehyde Dimethyl Acetal Ether To a solution of 1.0 mmol diethyl (hydroxymethyl)phosphonate, 1.5 mmol of sodium hydride in 2 mL DMF at 0° C. was added a solution of 1.2 mmol of bromoacetaldehyde dimethyl acetal. After 3 h. at r. t. the mixture was diluted with 5 mL of water and extracted with ether(4×15 mL). The combined ether layers were concentrated. The residue was chromatographed on a silica gel column eluting with hexane-ethyl acetate (8:1) to yield the product.

Step B

Preparation of 1-isobutyl-4-nitro-5-fluoro-7-bromo-2-[3-diethylphospho(methoxymethyl)] benzimidazole To a solution of 1.0 mmol of 2-nitro-3-fluoro-5-bromo-6-isobutylamine aniline and 2.0 mmol of diethylphospho methyl acetaldehyde dimethyl acetal ether in 5 mL THF at 0° C. was added 0.5 mL of 10% H2SO4 and the mixture was heated at 75° C. for 40 min. Solvent was removed under reduced pressure, diluted with water and extracted with EtOAc. The combined EtOAc layers were concentrated. The residue was chromatographed on a silica gel column yield the product.

Step C

A solution of 1.0 mmol of this coupled product and 1.0 mmol of $I_2$ in 5 mL of ethanol was stirred at rt for 1-16 h. Extraction and chromatography provided the title compound as an orange solid.

Step D

Preparation of 1-isobutyl-4-amino-5-fluoro-7-bromo-2-[3-diethylphospho(methoxymethyl)]benzimidazole Followed the procedure given in the Example 20, Method B.

Step E

Followed the procedure given in example 21.

23.1:  4-Amino-5-fluoro-7-bromo-1-isobutyl-2-(1-methoxymethyl-3-phosphono)benzimidazole. mp=200-202° C.(dec.); Anal. Cald. for $C_{13}H_{18}N_3O_4FBrP$: C, 38.07; H, 4.42; N, 10.24. Found: C, 37.87; H, 4.36; N, 10.15.

Example 24

Preparation of diethyl 2-(5-(4-methylvaleryl))furanphosphonate

Step A. A solution of 2-tributylstannylfuran (1 mmol), 4-methylvaleroyl chloride (1.1 mmol), and $PdCl_2(PPh_3)_2$ (0.05 mmol) in THF was stirred at 25° C. for 24 h. Extraction and chromatography gave 2-(4-methylvaleryl)furan.

Step B. A solution of 2-(4-methylvaleryl)furan (1 mmol) and N,N-dimethylhydrazine (1.5 mmol) in EtOH was heated at reflux for 24 h. Evaporation and distilation give 2-(4-methylvaleryl)furan dimethylhydrazone as a brown oil.

Step C. A solution of 2-(4-methylvaleryl)furan dimethylhydrazone (1 mmol) in THF was cooled to −78° C. and treated with LDA (1.2 mmol) dropwisely. After 1h diethyl chlorophosphate (1.2 mmol) was added, and the resulting mixture was stirred at −78° C. for 1 h. The reaction was quenched with brine, and subjected to extraction and chromatography to give diethyl 2-(5-(4-methylvaleryl))furanphosphonate dimethylhydrazone.

Step D. A solution of diethyl 2-(5-(4-methylvaleryl))furanphosphonate dimethylhydrazone (1 mmol) in THF-pH=7 phosphate buffer (1:1) was treated with $CuCl_2$ (1.5 mmol) at 25° C. for 24 h. Extraction and chromatography gave diethyl 2-(5-(4-methylvaleryl))furanphosphonate as a brown oil.

Example 25

Preparation of 5-chloro-3-isobutyl-2-(2-(5-phosphono)furanyl)indole

Step A. A mixture of 4-chlorophenylhydrazine hydrochloride (1.5 mmol), diethyl 2-(5-(4-methylvaleryl))furanphosphonate (1 mmol), and two drops of concentrated sulfuric acid in glacial acetic acid was heated at reflux for 4 h. The cooled reaction mixture was evaporated to dryness, and the residue was subjected to extraction and chromatography to give 5-chloro-3-isobutyl-2-(2-(5-diethylphosphono)furanyl)indole as a yellow sticky solid. TLC: Rf=0.30, 50% EtOAc-hexane.

Step B. A solution of 5-chloro-3-isobutyl-2-(2-(5-diethylphosphono)-furanyl)indole (1 mmol) in acetonitrile was treated with bromotrimethylsilane (10 mmol). After 12 h, the reaction was evaporated under vacuum and the residue was treated with a mixture of water and acetonitrile. The dark green solid was collected through filtration.

25.1:  5-chloro-3-isobutyl-2-(2-(5-phosphono)furanyl)indole. mp 135-139° C.; Anal. cald. for $C_{16}H_{17}NO_4PCl+0.75H_2O$: C, 52.33; H, 5.08; N, 3.83. Found: C, 51.96; H, 4.93; N, 3.81.

Example 26

Preparation of 9-aza-3-isobutyl-7-methyl-2-(2-(5-phosphono) furanyl)indole

Step A. A mixture of diethyl 2-(5-(4-methylvaleryl))furanphosphonate (1 mmol) and $CuBr_2$ (4 mmol) in EtOAc-$CHCl_3$ was stirred at 25° C. for 24 h. The reaction was quenched with saturated ammonium chloride. Extraction and chromatography gave 2-(5-(2-bromo-4-methylvaleryl))furanphosphonate as a yellow oil.

Step B. A solution of 2-amino-6-methylpyridine (1 mmol) and 2-(5-(2-bromo-4-methylvaleryl))furanphosphonate (1.2 mmol) in n-butanol was heated at reflux for 16 h. The cooled reaction mixture was evaporated to dryness, and the residue was subjected to extraction and chromatography to give 9-aza-3-isobutyl-7-methyl-2-(2-(5-diethylphosphono)furanyl)indole as a brown solid.

Step C. 9-Aza-3-isobutyl-7-methyl-2-(2-(5-diethylphosphono)furanyl)-indole was subjected to procedure given in Example 21.

26.1:  9-aza-3-isobutyl-7-methyl-2-(2-(5-phosphono)furanyl)indole. mp 225-227° C. Anal. cald. for $C_{16}H_{19}N_2O_4P+1HBr$: C, 46.28; H, 4.85; N, 6.75. Found: C, 46.23; H, 4.89; N, 6.57.

Example 27

Preparation of 2'-azidomethylene and 2'-aminomethylene substituted cyclic 1',3'-propyl esters Step A. 6-Chloro-1-isobutyl-2-{5-[2'-(hydroxymethyl)-propan-1',3'-yl]phosphono-2-furanyl}benzimidazole was prepared as described in Example 7.

Step B. To a solution of 6-Chloro-1-isobutyl-2-{5-[2'-(hydroxymethyl)-propan-1',3'-yl]phosphono-2-furanyl}benzimidazole (300 mg, 0.70 mmol) in dichloromethane (5 mL) was added pyridine (0.12 mL, 1.4 mmol) and methanesulphonyl chloride (0.066 mL, 0.84 mmol).

The reaction was stirred overnight and concentrated under vacuum. Chromatography by elution with 5% methanol-dichloromethane resulted in 340 mg (95%) of pure mesylated product.

Step C. To a solution of mesylate (100 mg, 0.19 mmol) in DMF (2 mL) was added sodium azide (65 mg, 1 mmol). The mixture was heated to 55° C. for 5 h. The reaction was concentrated and diluted with ethyl acetate (50 mL) washed with water and dried. Chromatography by elution with 5% methanol-dichloromethane gave in 35 mg (39%) of pure product.

27.1: 6-Chloro-1-isobutyl-2-{5-[2'-(azidomethyl)-propan-1',3'-yl]phosphono-2-furanyl}benzimidazole. mp 167-168° C. Anal. calcd. for $C_{19}H_{21}ClN_5O_4P$: C, 50.73; H, 4.71; N, 15.57. Found: C, 50.74; H, 4.72; N, 15.22.

Step D: Azide (100 mg, 0.22 mmol) was dissolved in ethyl acetate (5 mL) and 10% Pd—C (50 mg) was added. The mixture was stirred under hydrogen for 16 h. Catalyst was filtered off through a celite pad. The filterate was concentrated and chromatographed by eluting with 15% methanol-dichloromethane to give pure amine (45 mg, 48%).

27.2: 6-Chloro-1-isobutyl-2-{5-[2'-(aminomethyl)-propan-1',3'-y]phosphono-2-furanyl}benzimidazole. mp 158-160° C. Anal. calcd. for $C_{19}H_{23}ClN_3O_4P+1.25H_2O$: C, 51.13; H, 5.76; N, 9.41. Found: C, 51.35; H, 5.48; N, 9.05.

Example 28

Preparation of cyclic 1',3'-propyl esters of 9-[(2-phosphonomethoxy)ethyl]adenine (PMEA)

Step A: To a solution of cis,cis-1,3,5-cyclohexanetriol (1.68 g, 10 mmol) in DMSO (10 mL) was added 60% sodium hydride mineral oil dispersion (400 mg, 10 mmol). The reaction was stirred at room temperature for 12 h. After work-up, the mixture was chromatographed by eluting with ethyl acetate-methylene chloride (1:1) to yield 800 mg (36%) of monobenzylated product.

Step B: To a suspension of 9-[(2-phosphonomethoxy)ethyl] adenine (Collect. Czech. Chem. Commun., 1990, 55, 808) (1 g, 3.5 mmol) in dichloromethane (10 mL) was added trimethylsilyldiethyl amine (3 mL). The reaction was stirred at room temperature for 2 h and evaporated to dryness. The residue was dissolved in dichloromethane (10 mL). DMF (0.05 mL) followed by oxalyl chloride (0.9 mL) were added at 0° C. The reaction was stirred at 0° C. for 1 h and an additional 1 h at room temperature. The mixture was concentrated under reduced pressure and the residue was dissolved in pyridine (20 mL). Monobenzyl cyclohexyl triol was added and stirred for 16 h at room temperature. The reaction mixture was concentrated and chromatographed by eluting with methanol-methylene chloride (1:9) to give 500 mg (30%) of pure prodrug.

Step C: To a solution of monobenzyl prodrug (500 mg) in DMF (10 mL) was added 10% Pd(OH)2-C (100 mg). The reaction was stirred under hydrogen gas for 16 h. The catalyst was filtered off through celite and the reaction mixture was concentrated. Chromatography of the residue by eluting with aqueous NH3-MeOH-dichloromethane (1:20:80) resulted in 200 mg (50%) of product.

The following compound was prepared in this manner:
28.1: 9-[2-(1'-Hydroxy-3',5'-cyclohexylphosphonomethoxy)ethyl] adenine. mp=171-174° C.; Mass Cald. for C14H20N5O5P: MH$^+$ 370: Found: MH$^+$370

The following compounds were prepared following the procedure of step C:
28.2: 9-[2-(2'-Hydroxymethyl-1',3'-propylphosphonomethoxy)ethyl] adenine. mp 148-151° C.; Mass Cald. for C12H18N5O5P: MH$^+$ 344: Found: MH$^+$344
28.3: 9-[2-(1'-phenyl-1',3'-propylphosphonomethoxy)ethyl] adenine. Mass Cald. for C17H20N5O4P: MH$^+$ 390: Found: MH$^+$390.
28.4: 9-[2-(1-(4-Pyridyl)-1,3-propylphosphonomethoxy) ethyl]adenine. Anal. Cald. for C16H19N6O4P: C, 49.23; H, 4.91; N, 21.53. Found: C, 49.01; H, 5.01; N, 19.37.

Example 29

General Procedure for Formation of Phosphate Prodrugs From Chlorophospholane (Bioorg. Nled, chem. Lett., 1997, 7, 1577)

Step A

Variety of substituted 1,3-diols are commercially available. Diols which are not available are made by procedures described in examples 3 (step A), 4 (step A and B), 5 (step A, B and C), 6 (step A and B) and 7 (step A).

Step B

Cyclic phospholanes are prepared by equimolar addition of 1M phosphorus trichloride in dichloromethane to propane-1,3-diols at 0° C. The resulting mixture was warmed and stirred at room temperature for 3 h The reaction was concentrated under vacuum and dried to give crude chlorophospholane which is used for addition in next step without further purification.

Step C

To a solution of ara-A or other nucleoside or other alcohol containing drug (1 mmol) in DMF (5 mL) was added triethylamine (2 mmol) at −40° C. To this mixture was added crude cyclic chlorophospholane (1.5 mmole) in 2 mL of DMF. The mixture was warmed to room temperature and stirred for two hours. The reaction was cooled back to −40° C. and t-butylhydroperoxide (2 mmol) was added and left at room temperature overnight. The reaction was concentrated and the crude mixture was chromatographed on a silica gel column to give pure cyclic prodrug product.

The following compounds were prepared in this manner:
29.1: Adenine-9-beta-D-arabinofuranoside-5'-[2'-acetoxymethyl-1',3'-propyl]monophosphate. mp=118-120° C.; Anal. Cald. for C16H22N5O9P+1.0H2O: C, 40.26; H, 5.07; N, 14.67. Found: C, 40.08; H, 4.84; N, 14.67.
29.2 Adenine-9-beta-D-arabinofuranoside-5'-[1'-phenyl-1',3'-propyl]monophosphate. mp=122-125° C.; Anal. Cald. for C19H22N5O7P+1.5H2O+0.15CH2Cl2: C, 45.71; H, 5.07; N, 13.92. Found: C, 45.43; H, 4.64; N, 13.92.

Example 30

General Procedure for Formation of Prodrugs by Chlorophosphoramidite Method

Step A

Substituted diols are obtained as described in step A of example 29.

Step B

Preparation of Cyclic Phosphoramidite From Substituted Diols (*Tet.*, 1993, 49, 6123)

To a solution of commercially available diisopropyl phosphoramidous dichloride (1 mmol) in THF (5 mL) was added 1,3-diol (1 mmol) and triethylamine (4 mmol) in THE (5 mL) at −78° C. over 30 min. The reaction was slowly warmed to room temperature and left stirring overnight.

Reaction mixture was filtered to remove salts and filterate was concentrated to give crude product. Silicagel column chromatography provided pure cyclic diisopropyl phosphoramidite of 1,3-diol.

Step C

Addition of Cyclic Phosphoramidite and Oxidation (*J. Org. Chem.*, 1996; 61, 7996).

To a solution of nucleoside (1 mmol) and cyclic phosphoramidite (1 mmol) in DMF (10 mL) was added benzimidazolium triflate (1 mmol). The reaction was stirred for 30 min at room temperature. The mixture was cooled to −40° C. before addition of t-butylhydro peroxide (2 mmol) and left at room temperature overnight. Concentration under reduced pressure and chromatography of crude product resulted in pure cyclic propyl prodrug.

The following compounds were prepared in this manner:

30.1: Adenine-9-beta-D-arabinofuranoside-5'-[1-(4-pyridyl)-1,3-propyl]monophosphate. mp>220° C.; Anal. Cald. for C18H21N6O7P+1H2O+0.25PhCH3: C, 46.93; H, 4.99; N, 16.63. Found: C, 47.42 H, 4.27; N, 16.74.

30.2: 5'-{[1-(4-pyridyl)-1,3-propyl]phosphoryl}-2',3'-dideoxyinosine. mp=133-135° C.; Anal. Cald. for C18H20N5O6P+1H2O: C, 47.90; H, 4.91; N, 15.52. Found: C, 48.06; H, 4.64; N, 15.49.

30.3: 5'-{[1-(4-pyridyl)-1,3-propyl]phosphoryl}ribavirin. mp=162-164° C.; Anal. Cald. for C16H20N5O8P+1.5H2O+0.2CH2Cl2: C, 40.09; H, 4.86; N, 14.43. Found: C, 40.42; H, 4.63; N, 14.63.

30.4: 5'-{[1-(4-pyridyl)-1,3-propyl]phosphoryl}-2-fluoroadenine-9-b-D-arabinofuranoside. mp>210° C.; Anal. Cald. for C18H20FN6O7P+1.5H2O+0.1iPrOH+0.2CH2Cl2: C, 41.74; H, 4.58; N, 15.79. Found: C, 41.55; H, 4.15; N, 15.76.

30.5: 5'-{[1-(4-pyridyl)-1,3-propyl]phosphoryl}-3'-{[1-(4-pyridyl)-1,3-propyl]phosphoryl}-5-fluoro-2'-deoxy uridine. mp=200-204° C.; Anal. Cald. for C25H27FN4O11P2+1.5H2O+0.3CH2Cl2+0.1i-PrOH: C, 43.99; H, 4.53; N, 8.02. Found: C, 43.56; H, 4.06; N, 7.97.

30.6: 5'-{[1-(4-pyridyl)-1,3-propyl]phosphoryl}-2',3'-dideoxyadenosine. mp=98-100° C.; Anal. Cald. for C18H21N6O5P+1.6H2O: C, 46.88; H, 5.29; N, 18.22. Found: C, 47.21; H, 5.11; N, 17.76.

30.7: 5'-{[1-(4-pyridyl)-1,3-propyl]phosphoryl}-5-fluoro-2'-deoxy uridine. mp=120-124° C. Mass. Cald. for C17H19N3O8PF. MNa+: 466. Found: 466.

30.8: 9-{[1-(4-pyridyl)-1,3-propyl]phosphoryl}-[2(methylenoxyethoxy)]-guanine. Mass. Cald. for C16H19N6O6P. MNa+: 445. Found: 445.

Example 31

Step A: (*J. Org. Chem.*, 1990, 55, 4744)

To a solution of diisopropylamine (5.9 mL, 42 mmol) in ether (60 mL) at −78° C. was added 1.6M n-butyllithium (26.2 mL, 42 mmol). The reaction was stirred for 15 min at −78° C. before adding t-butyl acetate (5.7 mL, 42 mmol) in ether (10 mL). After 20 min, aldehyde (2.81 g, 21 mmol) in ether (10 mL) was added and the reaction was warmed to room temperature where it was stirred for 16 h. The reaction was diluted with ether (200 mL), washed, and dried. Evaporation and column chromatography (dichloromethane) resulted in the addition product (5.4 g)

Step B

To a solution of t-butyl ester from Step A (5.4 g, ~20 mmol) in THF (100 mL) was added lithium aluminum hydride (0.83 g, 21 mmol) at 0° C. The reaction mixture was warmed to room temperature and stirred for 2 h. The reaction was quenched with ethyl acetate, and saturated aq.sodium sulfate was added to precipitate the salts. Filtration, concentration of solvent, and column chromatography (3:2 ethyl acetate:hexane) resulted in pure diol (1.1 g).

Step C

To a solution of PMEA (410 mg, 1.5 mmol) in DMF (15 mL) and pyridine (3 mL) was added 1,3-dicyclohexylcarbodiimide (DCC) (925 mg, 4.5 mmol) followed by 1(3-chlorophenyl)propane-1,3-diol from Step B (295 mg, 1.57 mmol). The reaction mixture was heated overnight at 100° C. The mixture was concentrated under reduced pressure and azeotroped with toluene (2×10 mL). Crude compound was chromatographed on a silica gel column (3:97 to 10:90 methanol-dichloromethane) to result in pure cyclic prodrug (310 mg).

31.1: 9-{2-[1-(3-Chlorophenyl)1,3-propylphosphonomethoxy]ethyl}adenine. mp 113-116. Rf=0.32 (silica gel, 1/9 methanol/dichloromethane). Anal. cald. for C17 H19 Cl N5 O4 P+0.75H2O: C, 46.69; H, 4.73; N, 16.01. Found: C, 46.93; H, 4.84; N, 15.60.

46.69 4.73 16.01

46.93 4.84 15.60

C17 H19 Cl N5 O4 P+0,75H2O

Examples of use of the method of the invention includes the following. It will be understood that these examples are exemplary and that the method of the invention is not limited solely to these examples.

For the purposes of clarity and brevity, chemical compounds are referred to as synthetic example numbers in the biological examples below.

Besides the following Examples, assays that may be useful for identifying compounds which inhibit gluconeogenesis include the following animal models of Diabetes:

i. Animals with pancreatic b-cells destroyed by specific chemical cytotoxins such as Alloxan or Streptozotocin (e.g. the Streptozotocin-treated mouse, -rat, dog, and -monkey). Kodama, H., Fujita, M., Yamaguchi, I., *Japanese Journal of Pharmacology* 1994, 66, 331-336 (mouse); Youn, J. H., Kim, J. K., Buchanan, T. A., *Diabetes* 1994, 43, 564-571 (rat); Le Marchand, Y., Loten, E. G., Assimacopoulos-Jannet, F., et al., *Diabetes* 1978, 27, 1182-88 (dog); and Pitkin, R. M., Reynolds, W. A., *Diabetes* 1970, 19, 70-85 (monkey).

ii. Mutant mice such as the C57BL/Ks db/db, C57BL/Ks ob/ob, and C57BL/6J ob/ob strains from Jackson Laboratory, Bar Harbor, and others such as Yellow Obese, T-KK, and New Zealand Obese. Coleman, D. L., Hummel, K. P., *Diabetologia* 1967, 3, 238-248 (C57BL/Ks db/db); Coleman, D. L., *Diabetologia* 1978, 14, 141-148 (C57BL/6J ob/ob); Wolff, G. L., Pitot, H. C., *Genetics* 1973, 73, 109-123 (Yellow Obese); Dulin, W. E., Wyse, B. M., *Diabetologia* 1970, 6, 317-323 (T-KK); and Bielschowsky, M., Bielschowsky, F. *Proceedings of the University of Otago Medical School*, 1953, 31, 29-31 (New Zealand Obese).

iii. Mutant rats such as the Zucker fa/fa Rat rendered diabetic with Streptozotocin or Dexamethasone, the Zucker Diabetic Fatty Rat, and the Wistar Kyoto Fatty Rat. Stolz, K. J., Martin, R. J. *Journal of Nutrition* 1982, 112, 997-1002 (Streptozotocin); Ogawa, A., Johnson, J. H., Ohnbeda, M., McAllister, C. T., Inman, L., Alam, T., Unger, R. H., *The Journal of Clinical Investigation* 1992, 90, 497-504 (Dexamethasane); Clark, J. B., Palmer, C. J., Shaw, W. N., *Proceedings of the Society for Experimental Biology and Medicine* 1983, 173, 68-75 (Zucker Diabetic Fatty Rat); and Idida, H., Shino, A., Matsuo, T., et al., *Diabetes* 1981, 30, 1045-1050 (Wistar Kyoto Fatty Rat).

iv. Animals with spontaneous diabetes such as the Chinese Hanister, the Guinea Pig, the New Zealand White Rabbit, and non-human primates such as the Rhesus rmonkey and Squirrel monkey. Gerritsen, G. C., Connel, M. A., Blanks, M. C., *Proceedings of the Nutrition Society* 1981, 40, 237 245 (Chinese Hamster); Lang, C. M., Munger, B. L., *Diabetes* 1976, 25, 434-443 (Guinea Pig); Conaway, H. H., Brown, C. J., Sanders, L. L. eta l., *Journal of Heredity* 1980, 71, 179-186 (New Zealand White Rabbit); Hansen, B. C., Bodkin, M. L., *Diabetologia* 1986, 29, 713-719 (Rhesus monkey); and Davidson, I. W., Lang, C. M., Blackwell, W. L., *Diabetes* 1967, 16, 395-401 (Squirrel monkey).

V. Animals with nutritionally induced diabetes such as the Sand Rat, the Spiny Mouse, the Mongolian Gerbil, and the Cohen Sucrose-Induced Diabetic Rat. Schmidt-Nielsen, K., Hainess, H. B., Hackel, D. B., *Science* 1964, 143, 689-690 (Sand Rat); Gonet, A. E., Stauffacher, W., Pictet, R., et al., *Diabetologia* 1965, 1, 162-171 (Spiny Mouse); Boquist, L., *Diabetologia* 1972, 8, 274-282 (Mongolian Gerbil); and Cohen, A. M., Teitebaum, A., Saliternik, R., *Metabolism* 1972, 21, 235-240 (Cohen Sucrose-Induced Diabetic Rat).

vi. Any other animal with one of the following or a combination of the following characteristics resulting from a genetic predisposition, genetic engineering, selective breeding, or chemical or nutritional induction: impaired glucose tolerance, insulin resistance, hyperglycemia, obesity, accelerated gluconeogenesis, increased hepatic glucose output.

BIOLOGICAL EXAMPLES

Example A

Chemical Stability

The stability of 30.1 was assessed in isotonic saline and in phosphate buffer (pH 3, 7, and 9), and that of 1.3 in phosphate buffer at pH 7.4.

Methods: Aliquots of a 10 μg/mL solution of 30.1 in isotonic saline and in 100 mM potassium phosphate buffers at pH 3, 7, and 9 were sampled after 1, 2, 5, and 7 days of incubation at room temperature and analyzed by HPLC. A Beckman Ultrasphere C8 column (4.6×150 mm) was employed and eluted with a gradient from 0.1% v/v trifluoroacetic acid to 80% methanol at a flow rate of 1.0 mL/min. Detection was at 254 nm. Using these conditions, the four isomers of 30.1 were readily separated and quantified. 1.3 was incubated at 100 μM in phosphate buffer at pH 7.4 and analyzed by HPLC as described in Example I following 1 hour of incubation at room temperature.

Results: No decomposition of 30.1 was noted either in saline or buffer throughout the 7-day evaluation period. The results demonstrate that 30.1 is stable for a minimum of seven days. 1.3 was found to be fully stable for the-t-hour incubation period tested. Thus, prodrugs of the invention are stable under a broad pH range.

Example B

Stability to Esterases and Phosphatases

The stability of select prodrugs to cleavage by purified esterase and phosphatase preparations is assessed.

Methods: Carboxylesterase (porcine liver) and alkaline phosphatase (calf intestinal mucose) are purchased from Sigma Chemical Co. (St. Louis, Mo.). Carboxyl esterase activity is measured in 0.1 M Tris-HCl buffer at pH 8.0. Activity towards p-nitrophenyl acetate, a known substrate and positive control in the reactions is measured as described for example by Matsushima M., et al. [FEBS Lett. (1991)293(1-2): 37-41]. Alkaline phosphatase activity is measured in a 0.1 M diethanolamine buffer, pH 9.8, containing 0.5 mM MgCl2. Activity towards p-nitrophenyl phosphate, a known substrate and positive control in the reactions, is measured as described [e.g. Brenna O., et al (1975) Biochem J. 151(2): 291-6]. 1.3, 28.4, and 30.1 are incubated at a concentration of, for example, 250 μM in appropriate reaction mixtures containing carboxylesterase or alkaline phosphatase. Parallel reactions are run with known substrates of the enzymes as described above. Aliqouts are removed from the reaction mixture at various time points and the reaction stopped by addition of methanol to 60%. Following centrifugation and filtration, the aliquots are analyzed for generation of parent compound by HPLC. Ara-AMP and PMEA, are analyzed as described in Example G. 6-Amino-9-neopentyl-8-(2-phosphonofuranyl)purine is quantified as described in Example I.

Results: Insusceptibility to cleavage by carboxylesterase or alkaline phosphatase is indicated by the absence of parent compound and presence of intact prodrug in the samples.

Example C

Stability in Plasma

The stability of 30.1, 1.1, and 1.3 was assessed in freshly prepared rat plasma.

Methods: Compounds were incubated in plasma at 37° C., and aliqouts removed at appropriate time points over the course of 5-8 hours. The aliquots were extracted with 1.5 volumes of methanol and clarified by centrifugation. Supernatants were then evaporated to dryness and the residues reconstituted with 100 μL of isoionic saline and then analyzed by reverse phase HPLC.

Results: There was no evidence of metabolism of 30.1, 1.1, or 1.3 during the incubation period. These findings demonstrate that these prodrugs are not susceptible to cleavage by plasma esterases, adenosine deaminase, or other plasma enzymes.

Example D

Activation by Rat Liver Microsomes 7.1 was, and 30.1 and 28.4 are tested for activation to their respective parent compounds in reactions catalyzed by the microsomal fraction of rat liver.

Methods: The microsomal fraction was prepared from fresh, saline-perfused rat liver. Liver tissue was homogenized in three volumes (w/v) of 0.2 M $KH_2PO_4$ buffer pH 7.5, containing 2 mM MgCl$_2$ and 1 mM EGTA. The homogenate was centrifuged at 10,000 g for 1 hour and the supernatant recovered. The supernatant fraction was then recentrifuged at 100,000 g to pellet the microsomal fraction. The pellet was resuspended in homogenization buffer and recentrifuged. This process was repeated twice to ensure complete removal of cytosolic enzyme activities. After the last centrifugation, the microsomal pellet was resuspended in homogenization buffer at a final protein concentration of about 14 mg/ml.

For 7.1, reaction mixtures (0.5 ml) consisted of 0.2 M KH$_2$PO$_4$ pH 7.5, 13 mM glucose-6-phosphate, 2.2 mM NADP$^+$, 1 unit of glucose-6-phosphate dehydrogenase, 0-2.5 mg/ml microsomal protein and 100 µM 7.1. Reactions were carried out at 37° C. Aliquots were removed from the reaction mixtures at appropriate time points, and extracted with 60% methanol. The methanolic extracts were centrifuged at 14,000 rpm, and filtered (0.2 µM) prior to analysis by HPLC as described in Example I. Eluted peaks were quantitated relative to authentic standards of 6-Chloro-1-isobutyl-2-(2-Phosphono-5-furanyl)benzimidazole of known concentration.

28.4 and 30.1 are evaluated essentially as described for 7.1 above. The formation of parent compounds PMEA and ara-AMP is monitored as described in Example G. Alternatively, the activation of 28.4 and 30.1 can be monitored by the depletion of NADPH, an essential cofactor in the reaction. This assay is performed in reactions mixtures consisting of 0.2 M KH$_2$PO$_4$, 0.22 mM NADPH, 0-2.5 mg/ml microsomal protein, and 100 µM 28.4 or 30.1. Reactions are monitored spectrophotometrically at 340 nm. A decrease in absorbance is indicative of cofactor depletion and thus of the enzymatic oxidation of prodrug to parent compound.

Results: 7.1 was converted to parent compound in the presence, but not in the absence of, NADP$^+$ (this cofactor is enzymatically reduced to NADPH by the dehydrogenase present in the reaction mixtures). This result indicates that an oxidative step was involved in the activation of the prodrug. The rate of activation of 7.1 to parent compound was found to be linearly dependent on microsomal protein concentration, confirming that activation occurs by an enzyme-dependent mechanism. Similar results are found for 30.1 and 28.4.

Example E

Activation by Human Liver Microsomes 7.1, 1.3, and 30.1 were tested for conversion to their respective parent compounds by the microsomal fraction of human liver.

Methods: Reaction mixtures (0.5 ml@37° C.) consisted of 0.2 M KH$_2$PO$_4$, 13 mM glucose-6-phosphate, 2.2 mM NADP$^+$, 1 unit of glucose-6-phosphate dehydrogenase, 0-2.5 mg/ml human microsomal protein (In Vitro Technologies, Inc.), and 250 µM of 7.1, 1.3, or 30.1. The activation of 7.1 and 1.3 to parent compound was monitored by HPLC as described in Example I. Ara-AMP generated by activation of 30.1 was detected by reverse-phase, ion-pairing HPLC as follows. Reactions were stopped by addition of methanol to a concentration of 60%, filtered (0.2 µM filter), and lyophilized. Samples were resuspended in HPLC buffer (10 mM phosphate pH 5.5, 2.5 mM octyl-triethyl-ammonium), loaded onto a YMC C8 HPLC column (250×4.6 mm), and eluted with a methanol gradient to 80%. Formation of ara-AMP was confirmed by co-elution with an authentic ara-AMP standard.

Results: The rate of formation of parent compound from 1.3 and 7.1 was determined to be 0.55 and 0.85 nmoles/mg microsomal protein/minute, respectively. The reaction rate observed for the formation of ara-AMP from 30.1 was 0.12 nmoles/min/mg of microsomal protein. All three prodrugs were thus transformed to their respective parent compounds by an NADPH-requiring microsome-catalyzed reaction.

Example F

Identification of the p450 Isozyme Involved in the Activation 30.1, 1.3, and 7.1 were evaluated for human microsome-catalyzed conversion to parent compound in the absence and presence of specific inhibitors of three major p450 isozymes: ketoconazole (CYP3A4), furafylline (CYP1A2), and sulfaphenazole (CYP2C9).

Methods: Reactions (0.5 ml@37° C.) consisted of 0.2 M KH$_2$PO$_4$, 13 mM glucose-6-phosphate, 2.2 mM NADP$^+$, 1 unit of glucose-6-phosphate dehydrogenase, 0-2.5 mg/ml human microsomal protein (In Vitro Technologies,. Inc.), 250 µM prodrug, and 0-100 µM p450 isozyme inhibitor. Ara-AMP, parent compound of 30.1, was detected by reverse-phase, ion-pairing HPLC. Reactions were stopped by addition of methanol to a concentration of 60%, filtered (0.2 µM filter), and lyophilized. Samples were resuspended in HPLC buffer (10 mM phosphate pH 5.5, 2.5 mM octyl-triethyl-ammonium), loaded onto a YMC C8 HPLC column (250×4.6 mm), and eluted with a methanol gradient to 80%. Formation of ara-AMP was confirmed by co-elution with an authentic ara-AMP standard. Generation of parent compound from 1.3 and 7.1 was determined as described in Example I.

Results: 30.1 was converted readily to ara-AMP in human liver microsomes. The reaction rate observed for the formation of ara-AMP was 0.12 nmoles/min/mg of microsomal protein. Ketoconazole inhibited the formation of ara-AMP in a dose-dependent fashion; 95% inhibition was observed at 1 µM, a concentration known to specifically inhibit CYP3A4. The other inhibitors, furafylline and sulfaphenazole, showed no significant inhibition. The results indicated that CYP3A4 is the primary p450 isoform responsible for 30.1 activation in human liver. Similar results were obtained with 1.3 and 7.1 in human microsomes.

Example G

Activation of 30.1 and 28.4 by Recombinant CYP3A4

Activation of 30.1 and 28.4 was evaluated in reactions containing microsomes from baculovirus-infected insect cells co-expressing recombinant CYP3A4 and cytochrome p450 reductase (Panvera Corp., Madison, Wis.).

Methods: Reaction mixture composition was similar to that described in Example E. Reactions were terminated by addition of methanol to a final concentration of 60%, and products typically analyzed by HPLC with use of a YMC reverse phase C8 column (250×4.6 mm). Samples were loaded onto the column in mobile phase A (10 mM phosphate pH 5.5, 2.5 mM octyl-triethyl-ammonium) and eluted with a gradient of mobile phase B (methanol) to 60% over 10 minutes. The effluent was monitored at 254 nm.

Results: Activation of 30.1 and 28.4 to their respective parent compounds was found to be dependent upon the presence of NADPH, and to be linear for 30 minutes at 37°

C. The rate of formation of ara-AMP from 30.1 (250 μM) was 3.3±0.5 nmoles/min/nmole CYP3A4, whereas the rate of formation of PMEA from 28.4 (100 μM) was 3.1±0.1 nmoles/min/nmole CYP3A4. These studies confirmed that p450 isoform CYP3A4 catalyzed the oxidation of 30.1 and 28.4.

Example H

Identification of Active Diastereomers

P450 enzyme-catalyzed oxidation of the four isomers of 30.1 was evaluated in reactions containing microsomes from baculovirus-infected insect cells co-expressing recombinant CYP3A4 and cytochrome p450 reductase (Panvera Corp., Madison, Wis). Methods: Reaction mixtures were similar to those described in Example E. Prodrug stock solutions were prepared in methanol and added to the reaction mixture to a final concentration of 100 μM. Reactions were terminated by addition of methanol to 60% (v/v), evaporated, and redissolved in methanol. The 30.1 isomers were separated and quantified by HPLC with use of a YMC reverse phase C8 column (250×4.6 min) equilibrated with mobile phase A (0.1% TFA) and eluted with a gradient to 80% mobile phase B (methanol) over 15 minutes. Isomers 1, 2, 3, and 4 had retention times of 11.4, 12, 12.1, and 12.4 minutes, respectively.

Results: Reaction rates were linear over the 30 minute reaction period. Oxidation rates for each isomer are shown below (Isomer numbers refer to their elution order from the HPLC column):

| Isomer | nmoles oxidized/min/nmole CYP3A4 |
|---|---|
| 1 | 0.31 |
| 2 | 0.54 |
| 3 | 0.70 |
| 4 | 0.75 |

The results indicate that all four isomers of 30.1 were substrates for CYP3A4. Isomer 1 was the poorest substrate while isomer 4 was the best. This is in agreement with in vivo results described in Example N. Selection of single purified isomers may allow for optimization of pharmocokinetic and pharmacodynamic parameters.

Example I

Activation in Isolated Rat Hepatocytes 7.1, 7.2, and 1.3 were evaluated for activation to parent compound in isolated rat hepatocytes.

Methods: Hepatocytes were prepared from fed Sprague-Dawley rats (250-300 g) according to the procedure of Berry and Friend (Berry, M. N., Friend, D. S. *J. Cell Biol.* 43, 506-520 (1969)) as modified by Groen (Groen, A. K. et al. *Eur J. Biochem* 122, 87-93 (1982)). Hepatocytes (75 mg wet weight/ml) were incubated in 1 ml Krebs-bicarbonate buffer containing 10 mM glucose, and 1 mg/ml BSA. Incubations were carried out in a 95% oxygen, 5% carbon dioxide atmosphere in closed, 50-ml Falcon tubes submerged in a rapidly shaking water bath (37° C.). Prodrugs were dissolved in DMSO to yield 10 mM stock solutions, and then diluted into the cell suspension to yield a final concentration of 100 μM. At appropriate time points over the course of one hour, aliquots of the cell suspension were removed and spun through a silicon/mineral oil layer into 10% perchloric acid. The cell extracts in the acid layers were neutralized, and the intracellular prodrug metabolite content analyzed by reverse phase HPLC. An ODS column was used for analysis. It was eluted with a gradient from 10 mM sodium phosphate, pH 5.5 to 75% acetonitrile. Detection was at 310 nm. Peaks on the chromatograms were identified by comparison to the retention times and spectra of standards of prodrug and parent compound.

Results: Both 7.1 and 7.2 generated peak intrahepatocyte levels of 6-Chloro-1-isobutyl-2-(2-Phosphono-5-furanyl) benzimidazole (approximately 700 and 500 nmoles/g cells, respectively) within 15 minutes of addition to the cell suspension. 1.3 generated similarly high levels of its parent compound, 6-Amino-9-neopentyl-8-(2-phosphonofuranyl) purine. The data indicated that the prodrugs diffused rapidly into the cells and that they were readily metabolized to parent compound intracellularly.

Example J

Inhibition of Glucose Production in Rat Hepatocytes

Select prodrugs of FBPase inhibitors were tested for inhibition of glucose production in isolated rat hepatocytes.

Methods: Hepatocytes were prepared from overnight fasted Sprague-Dawley rats (250-300 g) as described in Example I. Hepatocytes (75 mg wet weight/ml) were incubated in 1 ml Krebs-bicarbonate buffer containing 1 mg/ml BSA. Incubations were carried out in a 95% oxygen, 5% carbon dioxide atmosphere in closed, 50-ml Falcon tubes submerged in a rapidly shaking water bath (37° C.). After a 10 minute equilibration period, lactate and pyruvate were added to 10 mM and 1 mM concentrations, respectively. Addition of gluconeogenic substrates was immediately followed by that of appropriate concentrations of test compound. After 1 hour, an aliquot (0.25 ml) was removed, transferred to an Eppendorf tube and centrifuged. The supernatant (50 μl) was then assayed for glucose content using a Glucose Oxidase kit (Sigma Chemical Co.) as per the manufacturer's instructions.

Results: The following table depicts the inhibitory effect on gluconeogenesis for several prodrugs prepared in the Examples. Since none of the prodrugs were found to be inhibitors of FBPase, inhibition of gluconeogenesis in hepatocytes is a measure of the degree of activation of prodrug to the active parent compound. The results indicate that all of the prodrugs were converted to their respective parent compounds in hepatocytes.

| Compound | % inhibition @ 100 μM | IC50, μM |
|---|---|---|
| 1.1 | | 77 |
| 1.3 | | 13 |
| 1.4 | 36 | |
| 7.1 | | 48 |
| 2.4 | 40 | |
| 4.2 | 68 | |
| 5.2 | 36 | |
| 5.2 | 16 | |
| 7.2 | | 90 |
| 4.3 | 55 | |
| 6.1 | 11 | |
| 7.1 | 65 | 48 |
| 7.3 | 61 | |
| 7.4 | | 25 |
| 7.5 | | 13 |

Example K

Biologically Active Drug Metabolites Formed Following Prodrug Activation in Isolated Rat Hepatocytes Metabolism of 28.4 and 30.1 to active antiviral nucleoside phosphates was monitored in isolated rat hepatocytes.

Methods: Hepatocytes were prepared and incubated as described in Example I. 28.4 and 30.1 and their respective parent compounds, PMEA and ara-AMP, were dissolved in DMSO or methanol to yield 10 nM stock solutions, and then diluted into the cell suspension to yield a final concentration of 100 µM. At appropriate time points over the course of 2-4 hours, aliquots of the cell suspension were removed and spun through a silicon/mineral oil layer into 10% perchloric acid. The cell extracts in the acid layers were neutralized by:the addition of 0.3 volumes of 3M KOH/3M KHCO$_3$, and the extract was then centrifuged, filtered (0.2 micron filter) and loaded onto an anion exchange HPLC column equilibrated with 70% A (10 mM ammonium phosphate pH 3.5, 6% ETOH) and 30% B (1 M ammonium phosphate pH 3.5, 6% ETOH). Ara-ATP and PMEApp were eluted with a gradient to 80% B. Detection was at 254 nm.

Results: The Table below clearly demonstrates that both 28.4 and 30.1 were readily converted to PMEA-diphosphate and ara-ATP in hepatocytes.

The lower levels of ara-ATP generated with 30.1 relative to ara-AMP are most likely due to the slow rate of activation of the prodrug to parent compound in cells. In vivo, 30.1 was demonstrated to have a clear advantage over ara-AMP as evidenced by the 2- to 5-fold higher levels of ara-ATP generated in liver (Example O).

| Compound | Dose, µM | Product | Time Point | Product concentration nmoles/g cells |
|---|---|---|---|---|
| 28.4 | 100 | PMEApp | 4 h | 169 |
| PMEA | 250 | PMEApp | 4 h | 120 |
| 30.1 | 100 | ara-ATP | 2 h | 108 ± 4 |
| araAMP | 100 | ara-ATP | 2 h | 212 ± 0.6 |

Example L

Identification of Prodrug Cleavage Products 1.1 was evaluated for microsome-catalyzed conversion to parent compound 2-{5-[9-(2-Phenylethyl)-8-adeninyl]} furanylphosphonic acid and phenol, an expected byproduct of the reaction.

Methods: Rat liver microsomes were prepared as described in Example I. Reaction conditions, sample processing, and HPLC analysis were as described in Example D. Phenol was identified by HPLC by its retention time and spectral characteristics relative to-an authentic standard.

Results: 2-{5-[9-(2-Phenylethyl)-8-adeninyl]} furanylphosphonic acid and phenol were generated in a linear fashion over a 5 hour reaction period at a rate of 15 pmoles/mg microsomal protein/minute. 2-{5-[9-(2-Phenylethyl)-8-adeninyl]} furanylphosphonic acid and phenol were liberated in an equimolar fashion as expected. These results support an oxidative/β-elimination mechanism.

Example M

Oral Bioavailability

The oral bioavailability (OBAV) of 30.1 was estimated by comparison of the area under the curve of ara-ATP generated in liver following oral administration to that generated following intravenous administration. The oral bioavailability of prodrugs of a variety of phosphonic acid FBPase inhibitors was estimated by a urinary excretion method in rat.

Methods: Fasted rats were dosed orally and intravenously with 30.1 at 3 and 10 mg/kg. Liver samples were obtained, processed, and analyzed for ara-ATP content as described in Example P.

Prodrugs of FBPase inhibitors were dissolved in 10% ethanol/90% polyethylene glycol (mw 400) and administered by oral gavage at doses of 20 or 40 mg/kg parent compound equivalents to 6-hour fasted, Sprague Dawley rats (220-240 g). The rats were subsequently placed in metabolic cages and urine was collected for 24 hours. The quantity of parent compound excreted into urine was determined by HPLC analysis. An ODS column eluted with a gradient from potassium phosphate buffer, pH 5.5 to acetonitrile was employed for these measurements. Detection was at 310-325 nm. The percentage oral bioavailability was estimated by comparison of the recovery in urine of the parent compound generated from the prodrug, to that recovered in urine 24 hours after intravenous administration of unsubstituted parent compound at approximately 10 mg/kg. Parent compounds were typically dissolved in dimethyl sulfoxide, and administered via the tail vein in animals that were briefly anesthetized with halothane.

Results: The oral bioavailability of 30.1 was found to be 17.4% and 13.7% by comparison of the 10 mg/kg and 3 mg/kg oral and intravenous doses, respectively. These results suggest that 30.1 may be administered orally for the treatment of viral disease. AraA, the parent compound, has only been useful as a parenteral treatment because of its low oral bioavailability. ["Adenine Arabinoside: An Antiviral Agent" (1975) D. Pavan-Langston, Editor, Raven Press Publishers, New York].

Results for the FBPase inhibitor prodrugs were as follows

| Prodrug | Parent compound | % OBAV Parent | % OBAV Prodrug |
|---|---|---|---|
| 2.4 | 6-Chloro-1-isobutyl-2-(2-Phosphono-5-furanyl)benzimidazole | 0.5 | 8.7 |
| 4.2 | 6-Chloro-1-isobutyl-2-(2-Phosphono-5-furanyl)benzimidazole | 0.5 | 8.5 |
| 5.2 | 6-Chloro-1-isobutyl-2-(2-Phosphono-5-furanyl)benzimidazole | 0.5 | 2.4 |
| 7.2 | 6-Chloro-1-isobutyl-2-(2-Phosphono-5-furanyl)benzimidazole | 0.5 | 12.5 |
| 4.3 | 6-Chloro-1-isobutyl-2-(2-Phosphono-5-furanyl)benzimidazole | 0.5 | 11.6 |
| 7.1 | 6-Chloro-1-isobutyl-2-(2-Phosphono-5-furanyl)benzimidazole | 0.5 | 10.9 |
| 7.3 | 6-Chloro-1-isobutyl-2-(2-Phosphono-5-furanyl)benzimidazole | 0.5 | 14.1 |

As is evident from the above, the prodrugs increased the oral bioavailability of 6-Chloro-1-isobutyl-2-(2-Phosphono-5-furanyl)benzimidazole by 2.5- to 25-fold.

Example N

Pharmacokinetics of 30.1 and Certain Drug Metabolites

The pharmacokinetics of 30.1 were evaluated in the rat.

Methods: 30.1 was administered at 20 mg/kg to fasted rats via the tail vein under light halothane anesthesia. At appropriate time points following drug administration, rats were re-anesthetized with halothane. The peritoneal cavity was then opened and a blood sample was obtained from the abdominal vena cava and the liver freeze-clamped and excised. Blood samples were briefly centrifuged and the plasma fraction was then extracted with 1.5 volumes of methanol, processed, and analyzed by HPLC as described in Example A. Liver samples were excised, frozen in liquid nitrogen, and then homogenized in 100% methanol. Liver extracts were then centrifuged at 14,000 rpm and the methanolic supernatants subsequently filtered and evaporated to dryness. Samples were resuspended in isotonic saline and analyzed by HPLC as described in Example A. Pharmacokinetic parameters were determined with the aid of Win-NonLin version 1.1 (Scientific Consulting, Inc.) software. Renal excretions studies were performed as described in Example Q.

Results: The following pharmocokinetic parameters were calculated for 30.1:

| | |
|---|---|
| clearance | 3.34 L/hr/kg |
| plasma half life | 0.19 hr |
| volume of distribution | 0.70 L/kg |
| mean residence time | 0.21 hr |
| liver half life | 0.90 hr |
| urinary (renal) excretion (24 hr) | (57.7 ± 5.9%) |

The primary route of clearance was renal (~58%). However, the short plasma half life and low volume of distribution of 30.1, coupled with high concentrations of prodrug observed in liver (~20 nmoles/g at 20 minutes), suggest that 30.1 was rapidly extracted from plasma by the liver as well. Hepatic metabolism of 30.1 to ara-ATP and/or other products could potentially account for clearance of the remaining 42% of the dose.

The results also indicated that the four isomers of 30.1 underwent hepatic metabolism at different rates. The isomers were separated according to Example H. Isomer 1, for instance, was cleared in liver significantly slower than isomer 3. The hepatic half-lives for isomers 1 and 3 were 0.98 and 0.54 hours, respectively.

Example O

Enhanced Liver Delivery of ara-ATP and Reduced Generation of Ara-hypoxanthine The temporal profile of ara-hypoxanthine and ara-ATP generation following intravenous administration of 30.1 and free ara-AMP was compared in the rat.

Method: 30.1 and ara-AMP (Sigma) were administered to normal, fasted rats intravenously (in saline) via tail vein catheters. At appropriate time points following drug administration, animals were lightly anesthetized with halothane. The peritoneal cavity was then opened and a blood sample was obtained from the abdominal vena cava and the liver freeze-clamped and excised.

The blood samples were heparinized and plasma was prepared. Plasma samples (100 µL) were mixed with 4 N perchloric acid (40 µL), vortexed, and then clarified by centrifugation. The supernatants were analyzed for ara-hypoxanthine by HPLC with use of a Beckman Ultrasphere ODS column (4.6×150 mm). The column was eluted with 100 mM acetic acid at a flow rate of 1.0 mL/min. The eluent was monitored by UV absorbance at 254 nm.

Livers were immediately homogenized in 3 volumes of 10% perchloric acid (w/w), and the extracts clarified by centrifugation at 2500×g (5 minutes). The resulting supernatants were removed and neutralized with 0.3 volumes of 3M KOH/3M KHCO3. The neutralized liver extracts were then spun in an Eppendorf microfuge at 10,000 rpm (20 minutes, 4° C.). The supernatants were analyzed for ara-ATP content by reverse phase HPLC (HP1050) using a Whatman Partisphere SA column (4.6×125 mm). A gradient from 0.3M ammonium phosphate buffer pH 3.5 to 0.8M ammonium phosphate pH 3.5 was run (1 ml/minute flow rate).

Renal excretion of araH following i.v. administration of 30.1 or ara-AMP was determined as described in Example Q.

Results: Ara-hypoxanthine was not detected following administration of 30.1. Nor was ara-hypoxanthine detected in urine. In contrast, ara-AMP at equivalent doses generated µmolar levels of ara-hypoxanthine in plasma, which persisted for 8 hours. In addition, 19.2% of the 10 mg/kg equivalent ara-AMP dose was excreted in the form of ara-hypoxanthine in urine.

Both 30.1 and ara-AMP readily generated ara-ATP in liver. Based on area under the curve, Ara-ATP levels generated in liver by 30.1 at doses of 10 and 3 mg/kg were 5.2 and 2.1 times higher over 8 hours, respectively, than those generated by a 10 mg/kg equivalent dose of ara-AMP. These studies indicate that 30.1 has an advantage-over ara-AMP in vivo because higher levels of the active antiviral metabolite, ara-ATP, were generated in liver, whereas ara-hypoxanthine, a metabolite associated with the toxicity of ara-AMP, was not detected in plasma or urine.

Example P

Hepatic PMEA-diphosphate and Plasma PMEA Generation Following Intravenous Administration of 28.4 and bisPONI-PMEA to Rats The metabolism of 28.4 and bisPOM-PMEA to the active antiviral nucleoside diphosphate, PMEApp, and parent compound, PMEA, were compared in rat.

Methods. 28.4 and bisPOM-PMEA were dissolved in DMSO/ethanol and administered intravenously (10 mg/kg, PMEA equivalents) to fasted rats via tail vein catheters under light halothane anesthesia. At appropriate time points, blood and liver samples were obtained and processed as described in Example O. PMEA-diphosphate in liver and PMEA in plasma were analyzed by HPLC as described for araATP and ara-hypoxanthine, respectively, in Example O.

Results: Both 28.4 and bisPOM-PMEA, generated readily detectable levels of PMEA-diphosphate in liver. The area under the curve for hepatic PMEA-diphosphate was 3-fold greater for bisPOM-PMEA relative to 28.4. Plasma PMEA levels, however, were greater than 10-fold lower with 28.4 relative to bisPOM-PMEA. The results indicate that peripheral exposure to PMEA can be reduced by using a cyclic prodrug targeted to the liver and, coupled with the findings described in Example Q, suggest that the therapeutic index for PMEA can be increased with 28.4.

Example Q

Renal Excretion of PMEA following Intravenous Administration of 28.4, bisPOM-PMEA, and PMEA in Rats The renal excretion profiles of 28.4, bisPOM-PMEA, and PMEA were compared in rat.

Methods: 28.4, bisPOM-PMEA, and PMEA were dissolved in 56% DMSO/44% isotonic saline and administered intravenously to rats via the tail vein. Rats were subsequently caged in metabolic cages and urine collected over a 24 hour period. Urine samples were extracted with 70% methanol/2% acetic acid, vortexed and clarified by centrifugation. Supernatants were analyzed for PMEA content by reverse phase HPLC. A Beckman Ultrasphere ODS (4.6× 150 mm) column was used with a gradient from 20 mM potassium phosphate pH 6.2 to 50% acetonitrile.

Results: Renal excretion of PMEA and of PMEA generated from bisPOM-PMEA was 83% and 54%, respectively, of the administered dose. In contrast, less than 1% of the 28.4 dose was recovered as PMEA in the urine. This result indicates that the renal exposure and thus the renal toxicity associated with PMEA may be avoided by administration of the compound as the prodrug 28.4.

Example R

Preliminary Toxicological Evaluation of 30.1 in Mice

The toxicity of 30.1 was evaluated in the mouse.

Methods: 30.1 and free Ara-AMP were administered intraperitoneally to normal C57 mice for 22 days at doses of 10 and 100 mg/kg (b.i.d.). Death and other obvious signs of toxicity such as weight loss, tremors, ruffling fur, hunching, prostration, diarrhea, lethargy, and hyperactivity were monitored. On day 22, 3 hours following the final dosing, mice were sacrificed and livers were removed and homogenized in 3 volumes (to liver weight) of 10% perchloric acid. Liver extracts were neutralized and araATP was quantitated by ion-exchange HPLC as in Example K.

Results: There was no mortality during the study nor were significant differences in weight gain observed for any of the drug treated mice relative to saline treated controls. In addition, no abnormal behaviors were observed during the treatment period. AraATP levels measured in liver at the end of the treatment period are shown in the table below:

| Compound | Dose, mg/kg/d | araATP, nmoles/g liver |
| --- | --- | --- |
| araAMP | 20 | 2.5 ± 0.2 |
| 30.1 | 20 | 6.6 ± 1.6 |
| araAMP | 200 | 19.1 ± 4.0 |
| 30.1 | 200 | 23.1 ± 9 |

The results demonstrate that 30.1 can be safely administered to mice over a 22 day period at doses up to 200 mg/kg/d while generating liver ara-ATP levels that are equal to or higher than levels generated by the parent compound, ara-AMP.

Example S

Sustained Drug Levels

As described in Example O, the plasma half-life of 30.1 in rat was 12 minutes, whereas that of free ara-AMP, as judged by our inability to detect the compound in plasma, was considerably shorter. The latter is in accordance with studies reported in woodchucks and in man. In woodchucks administered araAMP intravenously, plasma ara-AMP levels dropped by greater than 90% over 2.5 minutes, suggesting a half-life on the order of seconds [Ponzetto, A. et al. (1991) Hepatology 14: 16-24]. Following intravenous administration to human patients, ara-AMP was not detected in plasma, also indicating an extremely short half-life [e.g. Whitley, R J et al (1980) Antimicrobial Agents and Chemotherapy 18: 709-715]. 30.1, by virtue of its sustained plasma levels, can thus serve as a reservoir of parent compound and can therefore be useful in extending the pharmacokinetic and pharmacodynamic half-life of the parent drug.

The pharmacodynamic half-life of parent compounds may also be extended by selecting prodrugs with a slow rate of activation. In the study described in Example o it was found that the four isomers of 30.1 were activated at different rates in liver. Isomer 1, for instance, had an intrahepatic elimination rate half-life of 0.98 h whereas isomer 3 had a half-life of 0.54 h. This suggests that the intrahepatic half-life of 30.1 and thus presumably that of the active antiviral nucleoside triphosphate, ara-ATP, is dependent on the drug diastereomer. For example, Isomer 1 would have a relatively long half-life, whereas isomer 3 would have a shorter half-life.

Example T

Tissue Distribution 30.1 is tested for activation in homogenates from various tissues to assess the specificity of liver activation.

Methods: Rats are anaesthetized under halothane and tissues including liver, kidney, brain, heart, stomach, spleen, muscle, lung, and testis are excised and frozen in liquid nitrogen. Tissues are then homogenized in 1 to 3 volumes of 50 mM Tris/HCl, 154 mM KCl, 1 mM EGTA pH 7.4. The homogenate is centrifuged at 10,000 rpm and 4° C. for 30 minutes and the supernatant recovered. Liver cytosol is prepared by centrifuging the liver crude extract for 1 hour at 40,000 rpm and 4° C. Reaction mixtures consist of 50 mM $KH_2PO_4$ pH 7.4, 13 mM glucose-6-phosphate, 2 mM $NADP^+$, 10 units of glucose-6-phosphate dehydrogenase, 100 μM 30.1 and tissue homogenate at a protein concentration of 8.5 mg/ml. Reactions are incubated at 37° C. Aliquots are taken after 0 and 1 hour of incubation, and extracted with 60% methanol. The methanolic extracts are centrifuged at 14,000 rpm, and filtered prior to analysis by HPLC. The samples are loaded onto a YMC C8 column equilibrated with 0.1% TFA and eluted with a methanol gradient to 80%. The activation of 30.1 to ara-AMP is monitored at 254 nM Results. Activation of 30.1 is expected in crude rat liver homogenate resulting in depletion of the prodrug and formation of parent compound, ara-AMP. Incubation of 30.1 with liver cytosol, which does not contain microsomes, does not result in activation. Incubation with all of the other tissue homogenates is not expected to result in activation. Results of this nature indicate liver specific activation of 30.1.

Example U

Delivery of 6-Amino-9-neopentyl-8-(2-phosphonofuranyl)purine to liver

The generation of parent compound 6-Amino-9-neopentyl-8-(2-phosphonofuranyl)purine in liver following administration of prodrug 1.3 was evaluated in rat.

139

Methods: 1.3 was dissolved in DMSO and administered intraperitoneally to fasted rats at a dose of 50 mg/kg. At various time points following drug administration, animals were anesthetized with halothane. The peritoneal cavity was then opened and a blood sample was obtained from the abdominal vena cava and the liver freeze-clamped and excised. Blood and liver samples were processed as described in Example P and analyzed for 6-Amino-9-neopentyl-8-(2-phosphonofuranyl)purine content as described in Example I.

Results: 6-Amino-9-neopentyl-8-(2-phosphonofuranyl)purine was detected both in plasma and liver following 1.3 administration. Peak levels measured at the earliest time point of 1 hour were 5.8 µM in plasma and 5 nmoles/g tissue in liver. 6-Amino-9-neopentyl-8-(2-phosphonofuranyl)purine persisted in plasma and liver for 4 hours (the last time point measured).

The data demonstrate that 1.3 is metabolized to 6-Amino-9-neopentyl-8-(2-phosphonofuranyl)purine in vivo and that prodrug administration results in the delivery of 6-Amino-9-neopentyl-8-(2-phosphonofuranyl)purine to the liver.

Example V

Generation of PMEApp from Compound 31.1 and bisPOM-PMEA in Isolated Rat Hepatocytes The intracellular generation of the antiviral PMEApp from two prodrugs of PMEA, compound 31.1 and bisPOM-PMEA, was compared in isolated rat hepatocytes.

Methods: Hepatocytes were prepared from fed rats and incubated as described in Example I. Test compounds were prepared in DMSO and-diluted to 250 µM in the cell suspensions. Reactions were performed in triplicate. After 4 hours of incubation, aliquots of the suspension were removed and processed as described in Example I. Quantitation of PMEApp was performed by anion exchange HPLC also as described in Example I.

Results.

| Compound cells | Dose (µM) | Time Point (h) | PMEApp nmoles/g |
|---|---|---|---|
| compound 31.1 | 250 | 4 | 52.8 ± 1.5 |
| bisPOM-PMEA | 250 | 4 | 200 ± 33 |

Example W

Hepatic PMEA-diphosphate Generation Following Oral Administration of GP6193 and bisPOM-PMEA to Rats The metabolism of compound 31.1 and bisPOM-PMEA to the active antiviral PMEApp was compared following oral administration in the rat.

Methods: compound 31.1 and bisPOM-PMEA were dissolved in polyethylene glycouethanol (90/10) and administered by oral gavage to overnight fasted rats at a dose of 30 mg/kg (PMEA equivalents). Four hours post administration, liver samples were obtained and processed as described in Example O. PMEApp was analyzed by anion exchange HPLC as described for araATP in Example O.

140

Results:

| Compound | Dose (PMEA equiv.) | Time Point (h) | Hepatic PMEApp (nmoles/g/tissue) |
|---|---|---|---|
| compound 31.1 (n = 3) | 30 | 4 | 11.1 ± 1.8 |
| bisPOM-PMEA (n = 3) | 30 | 4 | 4.3 ± 0.3 |

We claim:
1. A pharmaceutical composition comprising a compound of Formula I:

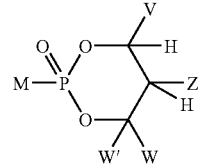

Formula I wherein:
V, W and W' are independently selected from the group consisting of hydrogen, alkyl, aralkyl, alicyclic, aryl, substituted aryl, heteroaryl, substituted heteroaryl, 1-alkenyl, and 1-alkynyl; or together V and Z are connected via an additional 3-5 atoms to form a cyclic group containing 5-7 atoms, wherein the cyclic group optionally contains one heteroatom and is substituted with a hydroxy, acyloxy, alkoxycarbonyloxy, or aryloxycarbonyloxy group attached to a carbon atom that is three atoms away from both oxygen atoms that are attached to the phosphorus atom; or together V and Z are connected via an additional 3-5 atoms to form a cyclic group wherein the cyclic group optionally contains one heteroatom, and is fused to an aryl group, at the beta and gamma position to the oxygen attached to the phosphorus; or together V and W are connected via an additional three carbon atoms to form an optionally substituted cyclic group containing six carbon atoms and is optionally substituted with one substituent selected from the group consisting of hydroxy, acyloxy, alkoxycarbonyloxy, alkylthiocarbonyloxy, and aryloxycarbonyloxy groups, wherein such substituent is attached to one of said carbon atoms that is three atoms away from an oxygen attached to the phosphorus atom; or together Z and W are connected via an additional 3-5 atoms to form a cyclic group, optionally containing one heteroatom, and V must be aryl, substituted aryl, heteroaryl, or substituted heteroaryl; or together W and W' are connected via an additional 2-5 atoms to form a cyclic group, optionally containing 0-2 heteroatoms, and V must be aryl, substituted aryl, heteroaryl, or substituted heteroaryl; or Z is selected from —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$(aryl), —CH(aryl)OH, —CH(CH=CR$^2{}_2$)OH, —CH(C≡CR$^2$)OH, —R$^2$, —NR$^2{}_2$, —OC(O)R$^3$, —OCO$_2$R$^3$, —SC(O)R$^3$, —SCO$_2$R$^3$, —NHC(O)R$^2$, —NHCO$_2$R$^3$, —CH$_2$NH(aryl), —(CH$_2$)$_p$OR$^{12}$, and —CH$_2$)$_p$SR$^{12}$;

R$^2$ is selected from the group consisting of R$^3$ and hydrogen;

R$^3$ is selected from the group consisting of alkyl, aryl, alicyclic, and aralkyl;

R$^{12}$ is selected from the group consisting of hydrogen, and lower acyl; and p is an integer 2 or 3;

with the provisos that:
  a) V, Z, W, and W' are not all hydrogen; and
  b) when Z is —R$^2$, then at least one of V, W, and W' is not hydrogen, alkyl, aralkyl, or alicyclic; and M, attached to PO$_3^{2-}$, is a phosphonic acid selected from the group consisting of (S)-3-[N-[2-[(phosphonomethyl)amino]-3-(4-biphenylyl)propionyl]amino]propionic acid; N,[N-((R)-1-phosphonopropyl((S)-leucyl]-(S)-phenylalanine N-methyl amide; (lR)-1-(N-(N-acetyl-L-isoleucyl)-L-tyrosyl)amino-2-(4-hydroxyphenyl)ethyl-phosphonic acid; CGS 26303; (S,S)-3-Cyclohexyl-2-[[5-(2,4-difluorophenyl)-2-[(phosphonomethyl)amino]pent-4-ynoyl]amino]propionic acid; (S,S)-2-[[5-(2-fluorophenyl)-2-](phosphonomethyl)amino]pent-4-ynoyl]amino]-4-methylpentanoic acid; (S,S)-2-[[5-(3-fluorophenyl)-2-[(phosphonomethyl)amino]pent-4-ynoyl]amino]-4-methylpentanoic acid; N-phosphonoalkyl-5-aminomethylquinoxaline-2,3-diones; 3-(2-carboxypiperazin-4-yl)-1-propenyl-1-phosphonic acid; [2-(8,9-dioxo-2,6-diazabicyclo[5.2.0]non-1(7)-en-2-yl)-ethyl]phosphonic acid; D,L-(E)-2-amino-4-[3H]-propyl-5-phosphono-3-pentenoic acid; 6,7-dichloro-2(1H)-oxoquinoline-3-phosphonic acid; cis-4-(phosphonomethyl)piperidine-2-carboxylic acid; [7-(2-amino-1,6-dihydro-6-chloro-9H-purin-9-yl)-1,1-difluoroheptyl]phosphonic acid; [4-(5-amino-6,7-dihydro-7-oxo-3H-1,2,3-triazolo[4,5-d]-pyrimidin-3-yl)butyl]phosphonic acid; [[[5-(2-amino-1,6-dihydro-6-oxo-9H-purin-9-yl)pentyl]phosphinico]methyl] phosphonic acid; (2-[2-[(2-amino-1,6-dihydro-6-oxo-9H-purin-9-yl)methyl]-phenyl] ethenyl)-phosphonic acid; 9-(3,3-Dimethyl-5-phosphonopentyl)guanine; DL-(1-Amino-2-propenyl)phosphonic acid; and 1-Hydroxy-3-(methylpentylamino)-propylidene-1,1-bisphosphonic acid; that is biologically active in vivo and when in the form of P$_2$O$_6^{3-}$ or P$_3$O$_9^{4-}$ derivatives, and wherein M is attached to the phosphorus atom in Formula I via a carbon, oxygen, or nitrogen atom, with the proviso that M-PO$_3^{2-}$ is not an FBPase inhibitor;

wherein said compound of Formula I is converted to MPO$_3$H$_2$ by human liver microsomes;

or a pharmaceutically acceptable salt of Formula I;

and a pharmaceutically acceptable excipient.

2. The pharmaceutical composition of claim 1, wherein M, attached to PO$_3^{2-}$, is (S)-3-[N-[2-[(phosphonomethyl)amino]-3-(4-biphenylyl)propionyl]amino]-propionic acid.

3. The pharmaceutical composition of claim 1, wherein M, attached to PO$_3^{2-}$, is N,[N-((R)-1-phosphonopropyl((S)-leucyl]-(S)-phenylalanine N-methyl amide.

4. The pharmaceutical composition of claim 1, wherein M, attached to PO$_3^{2-}$, is (lR)-1-(N-(N-acetyl-L-isoleucyl)-L-tyrosyl)amino-2-(4-hydroxyphenyl)ethyl-phosphonic acid.

5. The pharmaceutical composition of claim 1, wherein M, attached to PO$_3^{2-}$, is selected from the group consisting of CGS 26303; (S,S)-3-Cyclohexyl-2-[[5-(2,4-difluorophenyl)-2-[(phosphonomethyl)amino]pent-4-ynoyl]amino]propionic acid; (S,S)-2-[[5-(2-fluorophenyl)-2-[(phosphonomethyl)amino]pent-4-ynoyl]amino]-4-methylpentanoic acid; and (S,S)-2-[[5-(3-fluorophenyl)-2-[(phosphonomethyl)amino]pent-4-ynoyl]amino]-4-methylpentanoic acid.

6. The pharmaceutical composition of claim 1, wherein M, attached to PO$_3^{2-}$, is selected from the group consisting of N-phosphonoalkyl-5-aminomethylquinoxaline-2,3-diones; 3-(2-carboxypiperazin-4-yl)-1-propenyl-1-phosphonic acid; [2-(8,9-dioxo-2,6-diazabicyclo[5.2.0]non-1(7)-en-2-yl)-ethyl]phosphonic acid; D,L-(E)-2-amino-4-[3H]-propyl-5-phosphono-3-pentenoic acid; 6,7-dichioro-2(1H)-oxoquinoline-3-phosphonic acid; and cis-4-(phosphonomethyl)piperidine-2-carboxylic acid.

7. The pharmaceutical composition of claim 1, wherein M, attached to PO$_3^{2-}$, is selected from the group consisting of [7-(2-amino-1,6-dihydro-6-chloro-9H-purin-9-yl)-1,1-difluoroheptyl]phosphonic acid; [4-(5-amino-6,7-dihydro-7-oxo-3H-1,2,3-triazolo[4,5-d]-pyrimidin-3-yl)butyl]phosphonic acid; [[[5-(2-amino-1,6-dihydro-6-oxo-9H-purin-9-yl)pentyl]phosphinico]methyl]phosphonic acid; (2-[2-[(2-amino-1,6-dihydro-6-oxo-9H-purin-9-yl)methyl]-phenyl] ethenyl)-phosphonic acid; and 9-(3,3-Dimethyl-5-phosphonopentyl)guanine.

8. The pharmaceutical composition of claim 1, wherein M, attached to PO$_3^{2-}$, is DL-(1-Amino-2-propenyl)phosphonic acid.

9. The pharmaceutical composition of claim 1, wherein M, attached to PO$_3^{2-}$, is 1-Hydroxy-3-(methylpentylamino)-propylidene-1,1-bisphosphonic acid.

* * * * *